(12) United States Patent
Kukreja et al.

(10) Patent No.: US 12,384,787 B2
(45) Date of Patent: Aug. 12, 2025

(54) FUSED HETEROCYCLIC COMPOUNDS AND THEIR USE AS PEST CONTROL AGENTS

(71) Applicant: PI INDUSTRIES LTD., Udaipur-Rajasthan (IN)

(72) Inventors: Gagan Kukreja, Delhi (IN); Vikas Kumar, Ghaziabad (IN); Lalit Kumar Jena, Belasore (IN); Jeevan Singh Verma, Sehore (IN); Rohit Saxena, Lucknow (IN); Sunil Kumar Mandal, Bangalore (IN); Vishwanath Gade, Thane West (IN); Kiran K C, Davanagere (IN); Ravikumar Suryanarayana Saragur, Bangalore (IN); Alexander G.M. Klausener, Pulheim (DE)

( * ) Notice: Subject to any disclaimer, the term of this patent is extended or adjusted under 35 U.S.C. 154(b) by 802 days.

(21) Appl. No.: 17/618,531

(22) PCT Filed: Jun. 12, 2020

(86) PCT No.: PCT/IB2020/055513
§ 371 (c)(1),
(2) Date: Dec. 13, 2021

(87) PCT Pub. No.: WO2020/250183
PCT Pub. Date: Dec. 17, 2020

(65) Prior Publication Data
US 2022/0251094 A1 Aug. 11, 2022

(30) Foreign Application Priority Data
Jun. 13, 2019 (IN) .............................. 201911023447

(51) Int. Cl.
C07D 487/04 (2006.01)
A01N 43/90 (2006.01)
C07D 471/04 (2006.01)

(52) U.S. Cl.
CPC .......... *C07D 487/04* (2013.01); *A01N 43/90* (2013.01); *C07D 471/04* (2013.01)

(58) Field of Classification Search
CPC ..... C07D 487/04; C07D 471/04; A01N 43/90
See application file for complete search history.

(56) References Cited

U.S. PATENT DOCUMENTS

| | | | |
|---|---|---|---|
| 5,013,659 A | 5/1991 | Bedbrook et al. | |
| 2003/0069257 A1 | 4/2003 | Guiying et al. | |
| 2004/0237395 A1 | 12/2004 | Legro et al. | |
| 2006/0150489 A1 | 7/2006 | Legro et al. | |

FOREIGN PATENT DOCUMENTS

| | | | |
|---|---|---|---|
| CA | 2 083 415 A1 | 5/1993 | |
| CA | 2 940 002 A1 | 8/2015 | |
| EP | D 142 924 A2 | 5/1985 | |
| EP | 0 193 259 A1 | 9/1986 | |
| EP | 0 242 236 A1 | 10/1987 | |
| EP | 0 242 246 A1 | 10/1987 | |
| EP | 0 257 993 A2 | 3/1988 | |
| EP | 1 247 436 A1 | 10/2002 | |
| EP | 1 273 219 A1 | 1/2003 | |
| EP | 1 371 638 A1 | 12/2003 | |
| EP | 1 795 071 A1 | 6/2007 | |
| EP | 2 229 808 A1 | 9/2010 | |
| EP | 2 671 582 A1 | 12/2013 | |
| EP | 2 740 730 A1 | 6/2014 | |
| EP | 3 158 864 A1 | 4/2017 | |
| EP | 3 165 092 A1 | 5/2017 | |
| NL | 1012918 C2 | 2/2001 | |
| WO | 91/13972 A1 | 9/1991 | |
| WO | 91/19806 A1 | 12/1991 | |
| WO | 92/00377 A1 | 1/1992 | |
| WO | 92/11376 A1 | 7/1992 | |
| WO | 92/14827 A1 | 9/1992 | |
| WO | 01/78507 A2 | 10/2001 | |
| WO | 03/086075 A1 | 10/2003 | |
| WO | 2006/065703 A1 | 6/2006 | |
| WO | 2007/067042 A1 | 6/2007 | |
| WO | 2007/113558 A2 | 10/2007 | |

(Continued)

OTHER PUBLICATIONS

Noboru Matsumura et al, "One-Pot Synthesis of N-Heterocyclic Compounds from Cyclopropenethione Derivatives", United States, Jun. 2, 2000 (Jun. 2, 2000), p. 3341-3345, Retrieved from the Internet: URL:https://pubs.acs.org/doi/pdf/10.1021/jo991640r—XP055720147.

(Continued)

*Primary Examiner* — Zohreh A Fay
(74) *Attorney, Agent, or Firm* — Lippes Mathias LLP

(57) ABSTRACT

The present invention discloses a fused heterocyclic compound of formula (I),

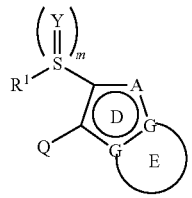

Formula (I)

wherein, $R^1$, Y, Q, A, G, m and E are as defined in the detailed description. The present invention further discloses methods for their preparation and use of the compounds of formula (I) as a pest control agent.

17 Claims, No Drawings

(56) References Cited

FOREIGN PATENT DOCUMENTS

| | | |
|---|---|---|
| WO | 2009/131237 A1 | 10/2009 |
| WO | 2010/065760 A1 | 6/2010 |
| WO | 2010/125985 A1 | 11/2010 |
| WO | 2011/008689 A1 | 1/2011 |
| WO | 2011/028115 A1 | 3/2011 |
| WO | 2011/040629 A1 | 4/2011 |
| WO | 2011/043404 A1 | 4/2011 |
| WO | 2011/075643 A1 | 6/2011 |
| WO | 2011/090122 A1 | 7/2011 |
| WO | 2011/163355 A1 | 12/2011 |
| WO | 2012/086848 A1 | 6/2012 |
| WO | 2012/133607 A1 | 10/2012 |
| WO | 2013/018928 A1 | 2/2013 |
| WO | 2013/041472 A1 | 3/2013 |
| WO | 2014/070978 A1 | 5/2014 |
| WO | 2015/000715 A1 | 1/2015 |
| WO | 2015/071180 A1 | 5/2015 |
| WO | 2015/076800 A1 | 5/2015 |
| WO | 2015/121136 A1 | 8/2015 |
| WO | 2015/168010 A1 | 11/2015 |
| WO | 2015/192923 A1 | 12/2015 |
| WO | 2016/039623 A1 | 3/2016 |
| WO | 2016/091731 A1 | 6/2016 |
| WO | 2016/133838 A1 | 8/2016 |
| WO | 2016/156129 A1 | 10/2016 |
| WO | 2016/162318 A1 | 10/2016 |
| WO | 2016/198644 A1 | 12/2016 |
| WO | 2017/001311 A1 | 1/2017 |
| WO | 2017/061497 A1 | 4/2017 |
| WO | 2017/084879 A1 | 5/2017 |
| WO | 2017/113558 A1 | 7/2017 |
| WO | 2017/125340 A1 | 7/2017 |
| WO | 2017/153200 A1 | 9/2017 |
| WO | 2018/015289 A1 | 1/2018 |
| WO | 2018/081417 A2 | 5/2018 |
| WO | 2018/095953 A1 | 5/2018 |
| WO | 2018/206479 A1 | 11/2018 |
| WO | 2019/038195 A1 | 2/2019 |
| WO | 2019/068572 A1 | 4/2019 |
| WO | 2019/072906 A1 | 4/2019 |

OTHER PUBLICATIONS

Alexander V. Borisov et al, "Parallel Liquid-Phase Synthesis of 5-(1 H-4-Pyrazolyl)-[1,2,4]oxadiazole Libraries", Journal of Combinatorial Chemistry, vol. 11, No. 6, Nov. 9, 2009 (Nov. 9, 2009), p. 1023-1029, XP055158413.

J Ram Vishnu J et al., "Polarized ketene dithioacetals, versatile synthons for the synthesis of bis-heterocycles" Sulfur Letters, Jan. 1, 1993 Taylor & Francis, GB—ISSN 0278-6117, vol. 16, Nr:4, pp. 165-170.

FUSED HETEROCYCLIC COMPOUNDS AND THEIR USE AS PEST CONTROL AGENTS

This application is a National Stage Entry of International Application No. PCT/IB2020/055513, filed Jun. 12, 2020, and entitled "FUSED HETEROCYCLIC COMPOUNDS AND THEIR USE AS PEST CONTROL AGENTS" which claims priority to Indian Application No. 201911023447, filed Jun. 13, 2019, the contents of which are incorporated by reference herein.

FIELD OF THE INVENTION

The present invention relates to fused heterocyclic compounds. More particularly, the present invention relates to fused heterocyclic compounds of formula (I) and to the process for the preparation thereof. The present invention further relates to the use of fused heterocyclic compounds of formula (I) as pest control agents.

BACKGROUND OF THE INVENTION

The currently available modern insecticides and acaricides have to satisfy many requirements, for example regarding level of efficacy, residual activity and spectrum of activity as well as further beneficial effects, and the possible use thereof. Efforts have been made during the past decades to develop selective insecticides that are acting specifically on biochemical modes of action being present only in insects or mites, but additionally showing properties that differ from known insecticides in an advantageous way.

Heterocyclic compounds with pesticidal activity are known and described, for example, in WO2016091731, WO2016162318, WO2017061497, WO2017125340, WO2017001311, WO2018095953, WO2019068572 and WO2019038195.

However, by long term use of such pesticides, many pests acquire resistance and the effective control by existing insecticides and germicides that have been used conventionally over years becomes more and more difficult and this phenomenon is even increasing during recent years. Furthermore, some of those existing pesticides are highly toxic, or remain for along time in the environment because of their residual properties, which may become a growing problem due to the disruption of the ecosystem.

Therefore, there is a continuous need for new compounds which are more effective, less toxic, and environmentally safer and/or have different modes of action.

In view of the above, the present invention envisages such compounds that satisfy or overcome drawbacks associated with the prior art.

It has now surprisingly been found that certain novel pesticidally active fused heterocyclic compounds with sulfur containing substituents being subject of this invention have favorable properties as pesticides, as desired.

SUMMARY OF THE INVENTION

Accordingly, the present invention provides a fused heterocyclic compound of formula (I) or agriculturally acceptable salts, isomers/structural isomers, stereo-isomers, diastereomers, enantiomers, tautomers, metal complexes, polymorphs or N-oxides thereof.

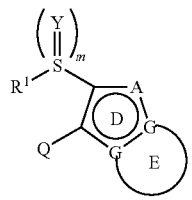

Formula (I)

wherein, $R^1$, Y, Q, A, G, m and E are as defined in the detailed description.

In one embodiment, the present invention provides a process for preparing the compound of formula (I) or agriculturally acceptable salts thereof.

In another embodiment, the present invention provides a composition for controlling or preventing invertebrate pests comprising a biologically effective amount of compound of formula (I), agriculturally acceptable salts, isomers/structural isomers, stereo-isomers, diastereomers, enantiomers, tautomers, metal complexes, polymorphs, or N-oxides thereof and at least one additional component selected from the group consisting of surfactants and auxiliaries.

In yet another embodiment, the composition additionally comprises at least one additional biologically active and compatible compound selected from fungicides, insecticides, nematicides, acaricides, biopesticides, herbicides, plant growth regulators, antibiotics, fertilizers or nutrients.

In still another embodiment, the present invention provides use of the compound of formula (I), agriculturally acceptable salts, isomers/structural isomers, stereo-isomers, diastereomers, enantiomers, tautomers, metal complexes, polymorphs, or N-oxides, composition or combination thereof, for combating invertebrate pests in agricultural crops and/or horticultural crops or parasites on animals.

In yet another embodiment, the present invention provides a method of combating invertebrate pests comprising contacting the invertebrate pests, their habitat, breeding ground, food supply, plant, seed, soil, area, material or environment in which the invertebrate pests are growing or may grow, or the materials, plants, seeds, soils, surfaces or spaces to be protected from pest attack or infestation with a biologically effective amount of the compound of formula (I) or agriculturally acceptable salts, isomers/structural isomers, stereo-isomers, diastereomers, enantiomers, tautomers, metal complexes, polymorphs, or N-oxides, composition or combination thereof.

DETAILED DESCRIPTION OF THE INVENTION

Definitions

The definitions provided herein for the terminologies used in the present disclosure are for illustrative purpose only and in no manner limit the scope of the present invention disclosed in the present disclosure.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B are true (or present).

Also, the indefinite articles "a" and "an" preceding an element or component of the present invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" refers to a living organism of the Phylum Nematoda. The term "helminths" includes roundworms, heartworms, phytophagous nematodes (Nematoda), flukes (Tematoda), acanthocephala and tapeworms (Cestoda).

The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the present invention, typically in the form of a composition formulated for veterinary use, to the animal to be protected. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

The compounds of the present disclosure may be present either in pure form or as mixtures of different possible isomeric forms such as stereoisomers or constitutional isomers. The various stereoisomers include enantiomers, diastereomers, chiral isomers, atropisomers, conformers, rotamers, tautomers, optical isomers, polymorphs, and geometric isomers. Any desired mixtures of these isomers fall within the scope of the claims of the present disclosure. One skilled in the art will appreciate that one stereoisomer may be more active and/or may exhibit beneficial effects when enriched relative to the other isomer(s) or when separated from the other isomer(s). Additionally, the person skilled in the art knows processes or methods or technology to separate, enrich, and/or to selectively prepare said isomers.

The meaning of various terms used in the description shall now be illustrated.

The term "aliphatic compound/s" or "aliphatic group/s" used herein is an organic compound/s whose carbon atoms are linked in straight chains, branched chains, or non-aromatic rings.

The term "alkyl", used either alone or in compound words such as "alkylthio" or "haloalkyl" or —N(alkyl) or alkylcarbonylalkyl or alkylsuphonylamino includes straight-chain or branched $C_1$ to $C_{24}$ alkyl, preferably $C_1$ to $C_{15}$ alkyl, more preferably $C_1$ to $C_{10}$ alkyl, most preferably $C_1$ to $C_6$ alkyl. Representative examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, carbonyl, carbonyloxy and the like, are at the end.

The term "alkenyl", used either alone or in compound words includes straight-chain or branched $C_2$ to $C_{24}$ alkenes, preferably $C_2$ to $C_{15}$ alkenes, more preferably $C_2$ to $C_{10}$ alkenes, most preferably $C_2$ to $C_6$ alkenes. Representative examples of alkenes include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl and the different isomers. "Alkenyl" also includes polyenes such as 1,2-propadienyl and 2,4-hexadienyl. This definition also applies to alkenyl as a part of a composite substituent, for example haloalkenyl and the like, unless defined specifically elsewhere.

The term "alkynyl", used either alone or in compound words includes straight-chain or branched $C_2$ to $C_{24}$ alkynes, preferably $C_2$ to $C_{15}$ alkynes, more preferably $C_2$ to $C_{10}$ alkynes, most preferably $C_2$ to $C_6$ alkynes. Non-limiting examples of alkynes include ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propenyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl and the different isomers. This definition also applies to alkynyl as a part of a composite substituent, for example haloalkynyl etc., unless specifically defined elsewhere. The term "alkynyl" can also include moieties comprised of multiple triple bonds such as 2,5-hexadiynyl.

The term "cycloalkyl" means alkyl closed to form a ring. Non-limiting examples include but are not limited to cyclopropyl, cyclopentyl and cyclohexyl. This definition also applies to cycloalkyl as a part of a composite substituent, for example cycloalkylalkyl etc., unless specifically defined elsewhere.

The term "cycloalkenyl" means alkenyl closed to form a ring including monocyclic, partially unsaturated hydrocarbyl groups. Non-limiting examples include but are not limited to cyclopropenyl, cyclopentenyl and cyclohexenyl. This definition also applies to cycloalkenyl as a part of a composite substituent, for example cycloalkenylalkyl etc., unless specifically defined elsewhere.

The term "cycloalkynyl" means alkynyl closed to form a ring including monocyclic, partially unsaturated groups. Non-limiting examples include but are not limited to cyclopropynyl, cyclopentynyl and cyclohexynyl. This definition also applies to cycloalkynyl as a part of a composite substituent, for example cycloalkynylalkyl etc., unless specifically defined elsewhere.

The terms "cycloalkoxy", "cycloalkenyloxy" and the like are defined analogously. Non limiting examples of cycloalkoxy include cyclopropyloxy, cyclopentyloxy and cyclohexyloxy. This definition also applies to cycloalkoxy as a part of a composite substituent, for example cycloalkoxy alkyl etc., unless specifically defined elsewhere.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Non-limiting examples of "haloalkyl" include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, for example haloalkylaminoalkyl etc., unless specifically defined elsewhere.

The terms "haloalkenyl", "haloalkynyl" are defined analogously except that, instead of alkyl groups, alkenyl and alkynyl groups are present as a part of the substituent.

The term "haloalkoxy" means straight-chain or branched alkoxy groups where some or all of the hydrogen atoms in these groups may be replaced by halogen atoms as specified above. Non-limiting examples of haloalkoxy include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as a part of a composite substituent, for example haloalkoxyalkyl etc., unless specifically defined elsewhere.

The term "haloalkylthio" means straight-chain or branched alkylthio groups where some or all of the hydrogen atoms in these groups may be replaced by halogen atoms as specified above. Non-limiting examples of haloalkylthio include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio. This definition also applies to haloalkylthio as a part of a composite substituent, for example haloalkylthioalkyl etc., unless specifically defined elsewhere.

Non-limiting examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

The term "hydroxy" means —OH, Amino means —NRR, wherein R can be H or any possible substituent such as alkyl. Carbonyl means —C(O)—, carbonyloxy means —OC(O)—, sulfinyl means SO, sulfonyl means $S(O)_2$.

The term "alkoxy" used either alone or in compound words included $C_1$ to $C_{24}$ alkoxy, preferably $C_1$ to $C_{15}$ alkoxy, more preferably $C_1$ to $C_{10}$ alkoxy, most preferably $C_1$ to $C_6$ alkoxy. Examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy and the different isomers. This definition also applies to alkoxy as a part of a composite substituent, for example haloalkoxy, alkynylalkoxy, etc., unless specifically defined elsewhere.

The term "Alkoxyalkyl" denotes alkoxy substitution on alkyl. Non-limiting examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$.

The term "alkoxyalkoxy" denotes alkoxy substitution on alkoxy.

The term "alkylthio" includes branched or straight-chain alkylthio moieties such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio and the different isomers.

Halocycloalkyl, halocycloalkenyl, alkylcycloalkyl, cycloalkylalkyl, cycloalkoxyalkyl, alkylsulfinylalkyl, alkylsulfonylalkyl, haloalkylcarbonyl, cycloalkylcarbonyl, haloalkoxyalkyl, and the like, are defined analogously to the above examples.

The term "alkylthioalkyl" denotes alkylthio substitution on alkyl. Representative examples of "alkylthioalkyl" include $-CH_2SCH_2$, $-CH_2SCH_2CH_2$, $CH_3CH_2SCH_2$, $CH_3CH_2CH_2CH_2SCH_2$ and $CH_3CH_2SCH_2CH_2$. "Alkylthioalkoxy" denotes alkylthio substitution on alkoxy. The term "cycloalkylalkylamino" denotes cycloalkyl substitution on alkyl amino.

The terms alkoxyalkoxyalkyl, alkylaminoalkyl, dialkylaminoalkyl, cycloalkylaminoalkyl, cycloalkylaminocarbonyl and the like, are defined analogously to "alkylthioalkyl" or cycloalkylalkylamino.

The term "alkoxycarbonyl" is an alkoxy group bonded to a skeleton via a carbonyl group (—CO—). This definition also applies to alkoxycarbonyl as a part of a composite substituent, for example cycloalkylalkoxycarbonyl and the like, unless specifically defined elsewhere.

The term "alkoxycarbonylalkylamino" denotes alkoxy carbonyl substitution on alkyl amino. "Alkylcarbonylalkylamino" denotes alkyl carbonyl substitution on alkyl amino. The terms alkylthioalkoxycarbonyl, cycloalkylalkylaminoalkyl and the like are defined analogously.

Non-limiting examples of "alkylsulfinyl" include but are not limited to methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl and the different isomers. The term "arylsulfinyl" includes Ar—S(O), wherein Ar can be any carbocyle or heterocylcle. This definition also applies to alkylsulphinyl as a part of a composite substituent, for example haloalkylsulphinyl etc., unless specifically defined elsewhere.

Non-limiting examples of "alkylsulfonyl" include but are not limited to methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl and the different isomers. The term "arylsulfonyl" includes Ar—S(O)$_2$, wherein Ar can be any carbocyle or heterocylcle. This definition also applies to alkylsulphonyl as a part of a composite substituent, for example alkylsulphonylalkyl etc., unless defined elsewhere.

"Alkylamino", "dialkylamino", and the like, are defined analogously to the above examples.

The term "carbocycle" includes "aromatic carbocyclic ring system" and "nonaromatic carbocylic ring system" or polycyclic or bicyclic (spiro, fused, bridged, nonfused) ring compounds in which ring may be aromatic or non-aromatic (where aromatic indicates that the Huckel rule is satisfied and non-aromatic indicates that the Huckel rule is not satisfied).

The term "hetero" in connection with rings refers to a ring in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs.

The term "aromatic" indicates that the Huckel rule is satisfied and the term "non-aromatic" indicates that the Huckel rule is not satisfied.

The term "heterocycle" or "heterocyclic" or "heterocyclic ring system" includes "aromatic heterocycle" or "heteroaryl bicyclic ring system" and "nonaromatic heterocycle ring system" or polycyclic or bicyclic (spiro, fused, bridged, non-fused) ring compounds in which ring may be aromatic or non-aromatic, wherein the heterocycle ring contains at least one heteroatom selected from N, O, S(O)$_{0-2}$, and or C ring member of the heterocycle may be replaced by C(=O), C(=S), C(=CR*R*) and C=NR*, * indicates integers.

The term "non-aromatic heterocycle" or "non-aromatic heterocyclic" means three- to fifteen-membered, preferably three- to twelve-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxetanyl, oxiranyl, aziridinyl, 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-1-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, pyrrolinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, piperidinyl, 2-piperidinyl, 3-piperidinyl, 4-piperidinyl, pyrazynyl, morpholinyl, thiomorphlinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl, cycloserines, 2,3,4,5-tetrahydro[1H]azepin-1- or -2- or -3- or -4- or -5- or -6- or -7-yl, 3,4,5,6-tetra-hydro[2H]azepin-2- or -3- or -4- or -5- or -6- or -7-yl, 2,3,4,7-tetrahydro[1H]azepin-1- or -2- or -3- or -4- or -5- or -6- or -7-yl, 2,3,6,7-tetrahydro[1H]azepin-1- or -2- or -3- or -4- or -5- or -6- or -7-yl, hexahydroazepin-1- or -2- or -3- or -4-yl, tetra- and hexahydrooxepinyl such as 2,3,4,5-tetrahydro[1H]oxepin-2- or -3- or -4- or -5- or -6- or -7-yl, 2,3,4,7-tetrahydro[1H]oxepin-2- or -3- or -4- or -5- or -6- or -7-yl, 2,3,6,7-tetrahydro[1H]oxepin-2- or -3- or -4- or -5- or -6- or -7-yl, hexahydroazepin-1- or -2- or -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl. This definition also applies to heterocyclyl as a part of a composite substituent, for example heterocyclylalkyl etc., unless specifically defined elsewhere.

The term "heteroaryl" or "aromatic heterocyclic" means 5 or 6-membered, fully unsaturated monocyclic ring system containing one to four heteroatoms from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) furyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl, 1,3,4-oxadiazolyl, 1,3,4-thiadiazolyl, 1,3,4-triazolyl, tetrazolyl; nitrogen-bonded 5-membered heteroaryl containing one to four nitrogen atoms, or benzo fused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl and 1,3,4-triazol-1-yl.

6-membered heteroaryl which contains one to four nitrogen atoms: 6-membered heteroaryl groups which, in addition to carbon atoms, may contain, respectively, one to three and one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl; benzo fused 5-membered heteroaryl containing one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl; benzo fused 6-membered heteroaryl which contains one to three nitrogen atoms: for example (but not limited to) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

This definition also applies to heteroaryl as a part of a composite substituent, for example heteroarylalkyl etc., unless specifically defined elsewhere.

The term "Trialkylsilyl" includes three branched and/or straight-chain alkyl radicals attached to and linked through a silicon atom such as trimethylsilyl, triethylsilyl and t-butyl-dimethylsilyl. "Halotrialkylsilyl" denotes at least one of the three alkyl radicals is partially or fully substituted with halogen atoms which may be the same or different. The term "alkoxytrialkylsilyl" denotes at least one of the three alkyl radicals is substituted with one or more alkoxy radicals which may be the same or different. The term "trialkylsilyloxy" denotes a trialkylsilyl moiety attached through oxygen.

Non-limiting examples of "alkylcarbonyl" include C(O)CH$_3$, C(O)CH$_2$CH$_2$CH$_3$ and C(O)CH(CH$_3$)$_2$. Non-limiting examples of "alkoxycarbonyl" include CH$_3$OC(=O), CH$_3$CH$_2$OC(=O), CH$_3$CH$_2$CH$_2$OC(=O), (CH$_3$)$_2$CHOC(=O) and the different butoxy -or pentoxycarbonyl isomers. Non-limiting examples of "alkylaminocarbonyl" include CH$_3$NHC(=O), CH$_3$CH$_2$NHC(=O), CH$_3$CH$_2$CH$_2$NHC(=O), (CH$_3$)$_2$CHNHC(=O) and the different butylamino -or pentylaminocarbonyl isomers. Non-limiting examples of "dialkylaminocarbonyl" include (CH$_3$)$_2$NC(=O), (CH$_3$CH$_2$)$_2$NC(=O), CH$_3$CH$_2$(CH$_3$)NC(=O), CH$_3$CH$_2$CH$_2$(CH$_3$)NC(=O) and (CH$_3$)$_2$CHN(CH$_3$)C(=O). Non-limiting examples of "alkoxyalkylcarbonyl" include CH$_3$OCH$_2$C(=O), CH$_3$OCH$_2$CH$_2$C(=O), CH$_3$CH$_2$OCH$_2$C(=O), CH$_3$CH$_2$CH$_2$CH$_2$OCH$_2$C(=O) and CH$_3$CH$_2$OCH$_2$CH$_2$C(=O). Non-limiting examples of "alkylthioalkylcarbonyl" include CH$_3$SCH$_2$C(=O), CH$_3$SCH$_2$CH$_2$C(=O), CH$_3$CH$_2$SCH$_2$C(=O), CH$_3$CH$_2$CH$_2$CH$_2$SCH$_2$C(=O) and CH$_3$CH$_2$SCH$_2$CH$_2$C(=O). The term haloalkylsufonylaminocarbonyl, alkylsulfonylaminocarbonyl, alkylthioalkoxycarbonyl, alkoxycarbonylalkyl amino and the like are defined analogously.

Non-limiting examples of "alkylaminoalkylcarbonyl" include CH$_3$NHCH$_2$C(=O), CH$_3$NHCH$_2$CH$_2$C(=O), CH$_3$CH$_2$NHCH$_2$C(=O), CH$_3$CH$_2$CH$_2$NHCH$_2$C(=O) and CH$_3$CH$_2$NHCH$_2$CH$_2$C(=O).

The term "amide" means A-R'C=ONR"—B, wherein R' and R" indicates substituents and A and B indicate any group.

The term "thioamide" means A-R'C=SNR"—B, wherein R' and R" indicates substituents and A and B indicate any group.

The total number of carbon atoms in a substituent group is indicated by the "$C_i$-$C_j$" prefix where i and j are numbers from 1 to 21. For example, $C_1$-$C_3$ alkylsulfonyl designates methylsulfonyl through propylsulfonyl; $C_2$ alkoxyalkyl designates CH$_3$OCH$_2$; $C_3$ alkoxyalkyl designates, for example, CH$_3$CH(OCH$_3$), CH$_3$OCH$_2$CH$_2$ or CH$_3$CH$_2$OCH$_2$; and $C_4$ alkoxyalkyl designates the various isomers of an alkyl group substituted with an alkoxy group containing a total of four carbon atoms, examples including CH$_3$CH$_2$CH$_2$OCH$_2$ and CH$_3$CH$_2$OCH$_2$CH$_2$. In the above recitations, when a compound of formula (I) is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript m in (R)$_m$ indicates an integer ranging from for example 0 to 4 then the number of substituents may be selected from the integers between 0 and 4 inclusive.

When a group contains a substituent which can be hydrogen, then, when this substituent is taken as hydrogen, it is recognized that said group is being un-substituted.

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skilled in the art to practice the embodiments herein. Accordingly, the examples should not be construed as limiting the scope of the embodiments herein.

The description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned in the description and the description/claims though might form a critical part of the present invention of the present invention, any deviation from such numerical values shall still fall within the scope of the present invention if that deviation follows the same scientific principle as that of the present invention disclosed in the present invention. The inventive compound of the present invention may, if appropriate, be present as mixtures of different possible isomeric forms, especially of stereoisomers, for example E and Z, threo and erythro, and also optical isomers, but if appropriate also of tautomers. Both the E and the Z isomers, and also the threo and erythro isomers, and the optical isomers, any desired mixtures of these isomers and the possible tautomeric forms are disclosed and claimed.

The term "pest" for the purpose of the present disclosure includes but is not limited to fungi, stramenopiles (oomycetes), bacteria, nematodes, mites, ticks, insects and rodents. Also pest is an animal or plant detrimental to humans or human concerns including crops, livestock, and forestry.

The term "plant" is understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights.

For the purpose of the present disclosure the term "plant" includes a living organism of the kind exemplified by trees, shrubs, herbs, grasses, ferns, and mosses, typically growing in a site, absorbing water and required substances through its roots, and synthesizing nutrients in its leaves by photosynthesis.

Examples of "plant" for the purpose of the present invention include but are not limited to agricultural crops such as wheat, rye, barley, triticale, oats or rice; beet, e.g. sugar beet or fodder beet; fruits and fruit trees, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit and citrus trees, such as oranges, lemons, grapefruits or mandarins; any horticultural plants, vegetables, such as spinach, lettuce, asparagus, cabbages, carrots, onions, tomatoes, potatoes, cucurbits or paprika; lauraceous plants, such as avocados, cinnamon or camphor; cucurbitaceae; oleaginous plants; energy and raw material plants, such as cereals, corn, soybean, other leguminous plants, rape, sugar cane or oil palm; tobacco; nuts; coffee; tea; cacao; bananas; peppers; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferably, the plant for the purpose of the present invention includes but is not limited to cereals, corn, rice, soybean and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and vegetables, ornamentals, any floricultural plants and other plants for use of human and animals.

The term "plant parts" is understood to mean all parts and organs of plants above and below the ground. For the purpose of the present disclosure the term plant parts includes but is not limited to cuttings, leaves, twigs, tubers, flowers, seeds, branches, roots including taproots, lateral roots, root hairs, root apex, root cap, rhizomes, slips, shoots, fruits, fruit bodies, bark, stem, buds, auxiliary buds, meristems, nodes and internodes.

The term "locus thereof" includes soil, surroundings of plant or plant parts and equipment or tools used before, during or after sowing/planting a plant or a plant part.

Application of the compounds of the present disclosure or the compound of the present disclosure in a composition optionally comprising other compatible compounds to a plant or a plant material or locus thereof include application by a technique known to a person skilled in the art which include but is not limited to spraying, coating, dipping, fumigating, impregnating, injecting and dusting.

The term "applied" means adhered to a plant or plant part either physically or chemically including impregnation.

In one embodiment, the present invention provides a compound of formula (I),

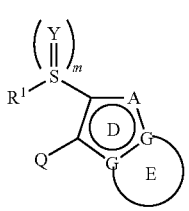

Formula (I)

wherein,
R$^1$ is selected from the group consisting of C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_3$-C$_8$-cycloalkyl and C$_3$-C$_8$-cycloalkyl-C$_1$-C$_6$-alkyl;
Y is independently selected from O or NR$^Y$;
R$^Y$ is selected from the group consisting of hydrogen, cyano, C$_1$-C$_4$-alkyl, C$_2$-C$_4$-alkenyl, C$_2$-C$_4$-alkynyl, C$_1$-C$_4$-haloalkyl, C$_2$-C$_4$-haloalkenyl, C$_3$-C$_5$-cycloalkyl and C$_3$-C$_5$-cycloalkyl-C$_1$-C$_3$-alkyl;
A represents N or CR$^2$;
G represents N or C; provided that both G are not nitrogen simultaneously;
R$^2$ is selected from the group consisting of hydrogen, halogen, cyano, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_3$-C$_8$-cycloalkyl, OR$^4$, CR$^4$=NR$^5$, NR$^5$R$^6$, S(O)$_{0-2}$R$^7$, C(=O)R$^8$, S(O)$_{0-1}$R$^9$=NR$^{10}$, N=S(O)$_{0-1}$(R$^9$)$_2$, P(=O)(OR')$_2$, Si(R')$_3$, C$_6$-C$_{10}$-aryl, C$_7$-C$_{14}$-aralkyl and C$_3$-C$_{10}$-heterocyclyl; wherein each aliphatic group may be optionally substituted with one or more groups of R$^{2a}$ and cyclic groups of R$^2$ may be optionally substituted with one or more groups of R$^{2b}$;
R$^{2a}$ is selected from the group consisting of halogen, cyano, C$_1$-C$_6$-alkyl, C$_2$-C$_6$-alkenyl, C$_2$-C$_6$-alkynyl, C$_1$-C$_6$-haloalkyl, C$_3$-C$_8$-cycloalkyl, OR$^4$, CR$^4$=NR$^5$, NR$^5$R$^6$, S(O)$_{0-2}$R$^7$, C(=O)R$^8$, S(O)$_{0-1}$R$^9$=NR$^{10}$, N=S(O)$_{0-1}$(R$^9$)$_2$, Si(R')$_3$, C$_6$-C$_{10}$-aryl, C$_7$-C$_{14}$-aralkyl and C$_3$-C$_{10}$-heterocyclyl;
R$^{2b}$ is selected from the group consisting of halogen, cyano, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_3$-C$_8$-cycloalkyl, OR$^4$, CR$^4$=NR$^5$, NR$^5$R$^6$, S(O)$_{0-2}$R$^7$, C(=O)R$^8$, Si(R')$_3$, S(O)$_{0-1}$R$^9$=NR$^{10}$ and N=S(O)$_{0-1}$(R$^9$)$_2$; or
two R$^{2a}$ or two R$^{2b}$ substituents together with the atom to which they are attached or together with further atoms selected from the group consisting of C, N, O, S and optionally including 1 to 3 ring members selected from the group consisting of C(=O), C(=S), S(O)$_{0-2}$ and Si(R')$_2$, may form a 3- to 7-membered ring, which for its part may be substituted by one or more groups of R$^{2ab}$;
R$^{2ab}$ is selected from the group consisting of halogen, cyano, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_3$-C$_8$-cycloalkyl, OR$^4$, NR$^5$R$^6$, S(O)$_{0-2}$R$^7$, S(O)$_{0-1}$R$^9$=NR$^{10}$, N=S(O)$_{0-1}$(R$^9$)$_2$, Si(R')$_3$, C$_6$-C$_{10}$-aryl, C$_7$-C$_{14}$-aralkyl and C$_3$-C$_{10}$-heterocyclyl;
Q represents partially saturated or unsaturated, 5 to 12 membered heterocyclic ring system which may optionally be substituted by one or more groups of R$^3$; wherein said heterocyclic ring system does not represent unsubstituted benzothiazolyl and unsubstituted N-methyl benzimidazolyl;
R$^3$ is selected from the group consisting of halogen, cyano, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_3$-C$_8$-cycloalkyl, OR$^4$, CR$^4$=NR$^5$, NR$^5$R$^6$, S(O)$_{0-2}$R$^7$, C(=O)R$^8$, S(O)$_{0-1}$R$^9$=NR$^{10}$, N=S(O)$_{0-1}$(R$^9$)$_2$, P(=O)(OR')$_2$, Si(R')$_3$, C$_6$-C$_{10}$-aryl, C$_7$-C$_{14}$-aralkyl and C$_3$-C$_{10}$-heterocyclyl; wherein each aliphatic group may be optionally substituted with one or more groups of R$^{3a}$ and cyclic groups of R$^3$ may be optionally substituted with one or more groups of R$^{3b}$;
R$^{3a}$ is selected from the group consisting of halogen, cyano, C$_1$-C$_6$-alkyl, C$_2$-C$_6$-alkenyl, C$_2$-C$_6$-alkynyl, C$_1$-C$_6$-haloalkyl, C$_3$-C$_8$-cycloalkyl, OR$^4$, CR$^4$=NR$^5$, NR$^5$R$^6$, S(O)$_{0-2}$R$^7$, C(=O)R$^8$, $S(O)_{0-1}R^9$=$NR^{10}$, N=$S(O)_{0-1}(R^9)_2$, $Si(R')_3$, $C_6$-$C_{10}$-aryl, $C_7$-$C_{14}$-aralkyl and $C_3$-$C_{10}$-heterocyclyl;

$R^{3b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $C(R')_2$—$NR^5R^6$, $C(R')_2$—$OR^4$, $CR^4$=$NR^5$, $NR^5R^6$, $S(O)_{0-2}R^7$, $C(=O)R^8$, $S(O)_{0-1}R^9$=$NR^{10}$, N=$S(O)_{0-1}(R^9)_2$, $Si(R')_3$, $C_6$-$C_{10}$-aryl, $C_7$-$C_{14}$-aralkyl and $C_3$-$C_{10}$-heterocyclyl;

two $R^{3a}$ or two $R^{3b}$ substituents together with the atom to which they are attached or together with further atoms selected from the group consisting of C, N, O, S and optionally including 1 to 3 ring members selected from the group consisting of C(=O), C(=S), $S(O)_m$ and $Si(R')_2$, may form a 3- to 7-membered ring, which for its part may be substituted by one or more groups of $R^{3ab}$; wherein $R^{3ab}$ is selected from the group consisting of hydrogen, halogen, cyano, $C_1$-$C_6$-alkyl, $C_1$-$C_6$-haloalkyl, $C_3$-$C_8$-cycloalkyl, $OR^4$, $NR^5R^6$ and $S(O)_{0-2}R^7$;

two $R^3$ together with the atom to which they are attached or together with further atoms selected from the group consisting of C, N, O, S and optionally including 1 to 3 ring members selected from the group consisting of C(=O), C(=S), $S(O)_m$ and $Si(R')_2$ may form a three to seven membered ring, which for its part may be substituted by one or more groups selected from the group consisting of halogen, cyano, $R^{3c}$, $OR^{3c}$, $SR^{3c}$, $NR^{3c}_2$, $Si(R^{3c})_3$, $COOR^{3c}$ and $CONR^{3c}_2$;

$R^{3c}$ is selected from the group consisting of hydrogen, halogen, straight chain or branched chain $C_1$-$C_6$-alkyl and cyclic $C_{3-8}$-alkyl; wherein each group of $R^{3c}$ is optionally substituted by one or more halogen;

ring E represents a 5 or 6 membered heterocyclic ring fused with ring D; wherein ring E is optionally substituted by one or more groups of $R^{11}$;

$R^{11}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $CR^4$=$NR^5$, $NR^5R^6$, $S(O)_{0-2}R^7$, C(=O)$R^8$, $S(O)_{0-1}R^9$=$NR^{10}$, N=$S(O)_{0-1}(R^9)_2$, P(=O)(OR')$_2$, $Si(R')_3$, $C_6$-$C_{10}$-aryl, $C_7$-$C_{14}$-aralkyl and $C_3$-$C_{10}$-heterocyclyl; wherein each aliphatic group may be optionally substituted with one or more groups of $R^{11a}$ and cyclic groups of $R^{11}$ may be optionally substituted with one or more groups of $R^{11b}$;

$R^{11a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, $OR^4$, $CR^4$=$NR^5$, $NR^5R^6$, $S(O)_{0-2}R^7$, $C(=O)R^8$, $S(O)_{0-1}R^9$=$NR^{10}$, N=$S(O)_{0-1}(R^9)_2$, $Si(R')_3$, $C_6$-$C_{10}$-aryl, $C_7$-$C_{14}$-aralkyl and $C_3$-$C_{10}$-heterocyclyl;

$R^{11b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $C(R')_2$—$NR^5R^6$, $C(R')_2$—$OR^4$, $CR^4$=$NR^5$, $NR^5R^6$, $S(O)_{0-2}R^7$, $C(=O)R^8$, $S(O)_{0-1}R^9$=$NR^{10}$, N=$S(O)_{0-1}(R^9)_2$, $Si(R')_3$, $C_6$-$C_{10}$-aryl, $C_7$-$C_{14}$-aralkyl and $C_3$-$C_{10}$-heterocyclyl;

$R^4$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $S(O)_2R^7$, $Si(R')_3$, $C_6$-$C_{10}$-aryl, $C_7$-$C_{14}$-aralkyl and $C_3$-$C_{10}$-heterocyclyl; wherein each aliphatic group may be optionally substituted with $R^{4a}$ and cyclic groups of $R^4$ may be optionally substituted with one or more groups of $R^{4b}$;

$R^{4a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, OR', NR'R", $S(O)_{0-2}R'$, C(=O)R', $Si(R')_3$, $C_6$-$C_{10}$-aryl, $C_7$-$C_{14}$-aralkyl and $C_3$-$C_{10}$-heterocyclyl;

$R^{4b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, OR', NR'R", $S(O)_{0-2}R'$, C(=O)R', $Si(R')_3$, $C_6$-$C_{10}$-aryl, $C_7$-$C_{14}$-aralkyl and $C_3$-$C_{10}$-heterocyclyl;

$R^5$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, NR'R", $S(O)_{0-2}R^7$, $C(=O)R^8$, $Si(R')_3$, $C_6$-$C_{10}$-aryl, $C_7$-$C_{14}$-aralkyl and $C_3$-$C_{10}$-heterocyclyl; wherein each aliphatic group may be optionally substituted with $R^{5a}$ and cyclic groups of $R^5$ may be optionally substituted with one or more groups of $R^{5b}$;

$R^{5a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, OR', NR'R", $S(O)_{0-2}R'$, C(=O)R', $Si(R')_3$, $C_6$-$C_{10}$-aryl, $C_7$-$C_{14}$-aralkyl and $C_3$-$C_{10}$-heterocyclyl;

$R^{5b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, OR', NR'R", $S(O)_{0-2}R'$, $Si(R')_3$, C(=O)R', $C_6$-$C_{10}$-aryl, $C_7$-$C_{14}$-aralkyl and $C_3$-$C_{10}$-heterocyclyl;

$R^6$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-cycloalkyl and $C(=O)R^8$;

$R^7$ is selected from the group consisting of $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $NR^5R^6$, $C_6$-$C_{10}$-aryl, $C_7$-$C_{14}$-aralkyl and $C_3$-$C_{10}$-heterocyclyl; wherein each aliphatic group may be optionally substituted with one or more groups of $R^{7a}$ and cyclic groups of $R^7$ may be optionally substituted with one or more groups of $R^{7b}$;

$R^{7a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, OR', NR'R", $S(O)_{0-2}R'$, C(=O)R', $C_6$-$C_{10}$-aryl, $C_7$-$C_{14}$-aralkyl and $C_3$-$C_{10}$-heterocyclyl;

$R^{7b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, OR', NR'R", $S(O)_{0-2}R'$, C(=O)R', $C_6$-$C_{10}$-aryl, $C_7$-$C_{14}$-aralkyl and $C_3$-$C_{10}$-heterocyclyl;

$R^8$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $NR^5R^6$, N=$S(O)_{0-1}(R^9)_2$, $C_6$-$C_{10}$-aryl, $C_7$-$C_{14}$-aralkyl and $C_3$-$C_{10}$-heterocyclyl; wherein each aliphatic group may be optionally substituted with one or more groups of $R^{8a}$ and cyclic groups of $R^8$ may be optionally substituted with one or more groups of $R^{8b}$;

$R^{8a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, OR', NR'R'', $S(O)_{0-2}R'$, $C(=O)R'$, $C_6$-$C_{10}$-aryl, $C_7$-$C_{14}$-aralkyl and $C_3$-$C_{10}$-heterocyclyl;

$R^{8b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, OR', NR'R'', $S(O)_{0-2}R'$, $C(=O)R'$, $C_6$-$C_{10}$-aryl, $C_7$-$C_{14}$-aralkyl and $C_3$-$C_{10}$-heterocyclyl;

$R^9$ is selected from the group consisting of $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl and $C(=O)R^8$;

$R^{10}$ is selected from the group consisting of hydrogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $Si(R')_3$, $S(O)_{0-2}R^7$ and $C(=O)R^8$;

R' is selected from the group consisting of halogen, cyano, R'', OR'', N(R'')$_2$, $S(O)_{0-2}R''$, $C(=O)R''$, $C(=O)OR''$ and $C(=O)N(R'')_2R^8$;

R'' is selected from the group consisting of hydrogen, $C_1$-$C_6$-alkyl, $C_2$-$C_6$-alkenyl, $C_2$-$C_6$-alkynyl, $C_1$-$C_6$-haloalkyl and $C_3$-$C_8$-cycloalkyl; wherein each may be optionally substituted with halogen;

each group of $R^1$ to $R^{11}$, $R^{2a}$, $R^{2b}$, $R^{2ab}$, $R^{3a}$, $R^{3b}$, $R^{3ab}$, $R^{3c}$, $R^{4a}$, $R^{4b}$, $R^{5a}$, $R^{5b}$, $R^{7a}$, $R^{7b}$, $R^{8a}$ and $R^{8b}$ may be optionally substituted by one or more groups selected from the group consisting of halogen, cyano, R', OR', SR', N(R')$_2$, COOR' and CON(R')$_2$;

"m" is an integer ranging from 0 to 2;

or agrochemically acceptable salts, isomers/structural isomers, stereo-isomers, diastereoisomers, enantiomers, tautomers, polymorphs, metal complexes or N-oxides thereof.

In another embodiment, the compound of formula (I) is represented by compound of formula (IA);

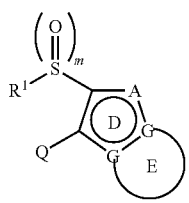

Formula (IA)

In yet another embodiment, the compound of formula (I) is represented by compound of formula (IB);

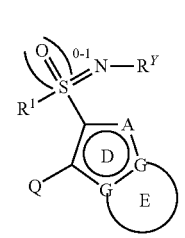

Formula (IB)

In one embodiment, Q is selected from the group consisting of formula $Q_1$ to $Q_{10}$:

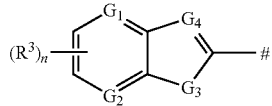
Q1

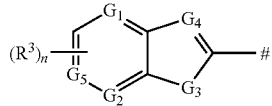
Q2

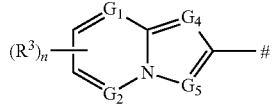
Q3

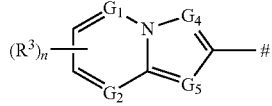
Q4

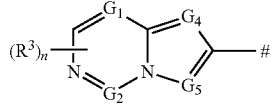
Q5

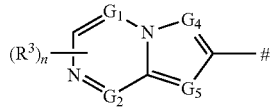
Q6

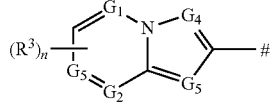
Q7

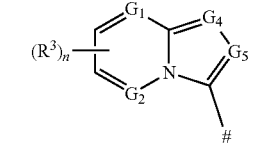
Q8

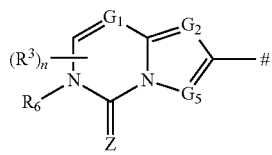
Q9

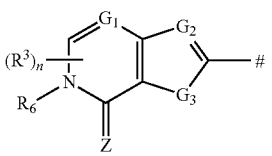
Q10 wherein, $G_1$, $G_2$, $G_4$ and $G_5$ are independently represents N or $CR^3$; $G_3$ is $NR^6$, O or S; Z is O or S; and "n" is an integer ranging from 0 to 4.

In a preferred embodiment, Q is selected from the group consisting of Q1a to Q10b:

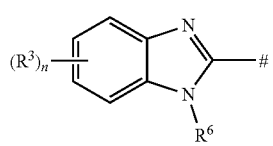 Q1a
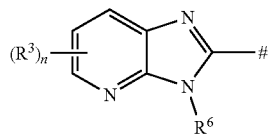 Q1b
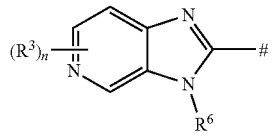 Q1c
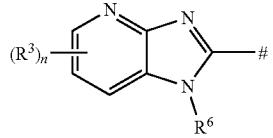 Q1d
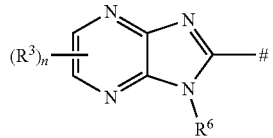 Q1e
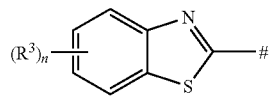 Q1f
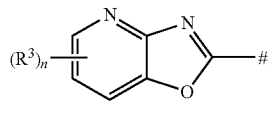 Q1g
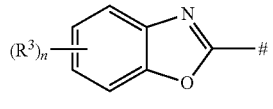 Q1h
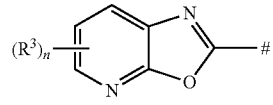 Q1i
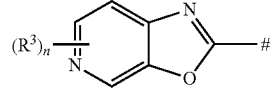 Q1j
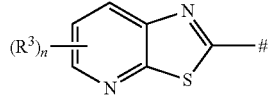 Q1k
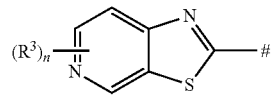 Q1l
-continued
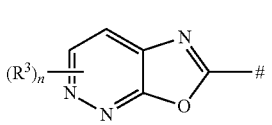 Q2a
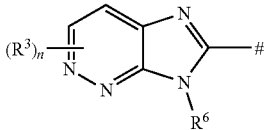 Q2b
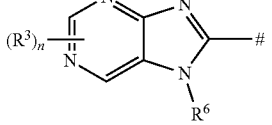 Q2c
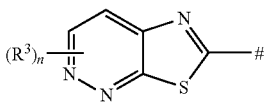 Q2d
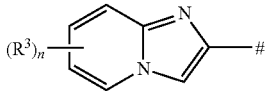 Q3a
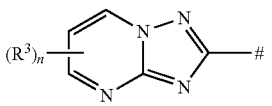 Q4a
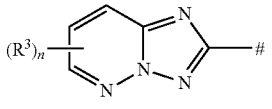 Q4b
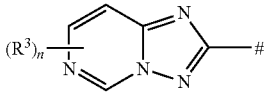 Q5a
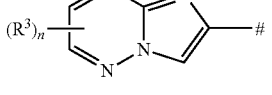 Q5b
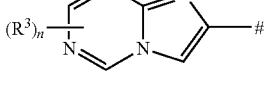 Q5c
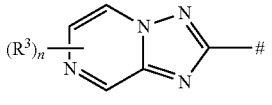 Q5d
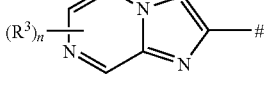 Q6a
Q6b Q7a
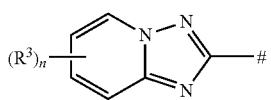

Q8a
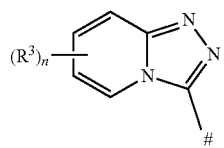

Q9a

Q9b
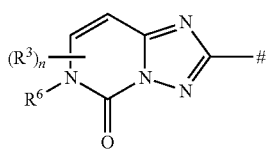

Q10a
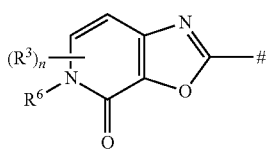

Q10b
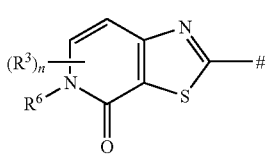

wherein, # denotes the point of attachment to the ring D, $R^6$ is selected from the group consisting of hydrogen, $C_1$-$C_6$-alkyl and cyclic $C_{3-10}$-alkyl; wherein each group of $R^6$ is optionally substituted by one or more halogen and "n" is an integer ranging from 0 to 4.

In one embodiment, the present invention provides a compound of formula (I), wherein at least one nitrogen is present in the fused ring system DE.

In another embodiment, the fused ring system DE is selected from the group consisting of DE-1 to DE-15:

DE-1
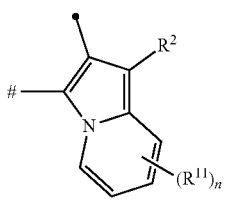

DE-2
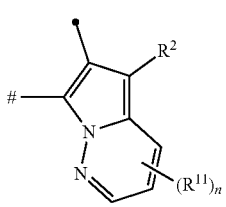

DE-3
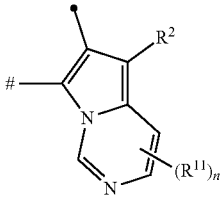

DE-4
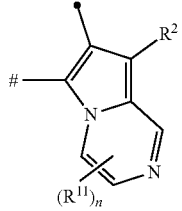

DE-5
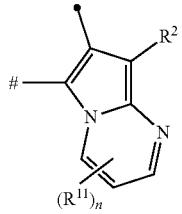

DE-6
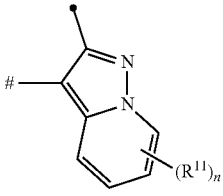

DE-7
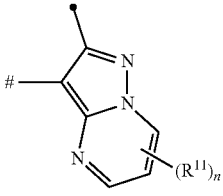

DE-8
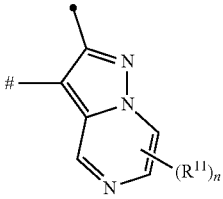

DE-9
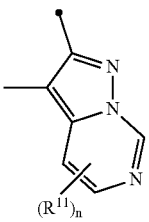

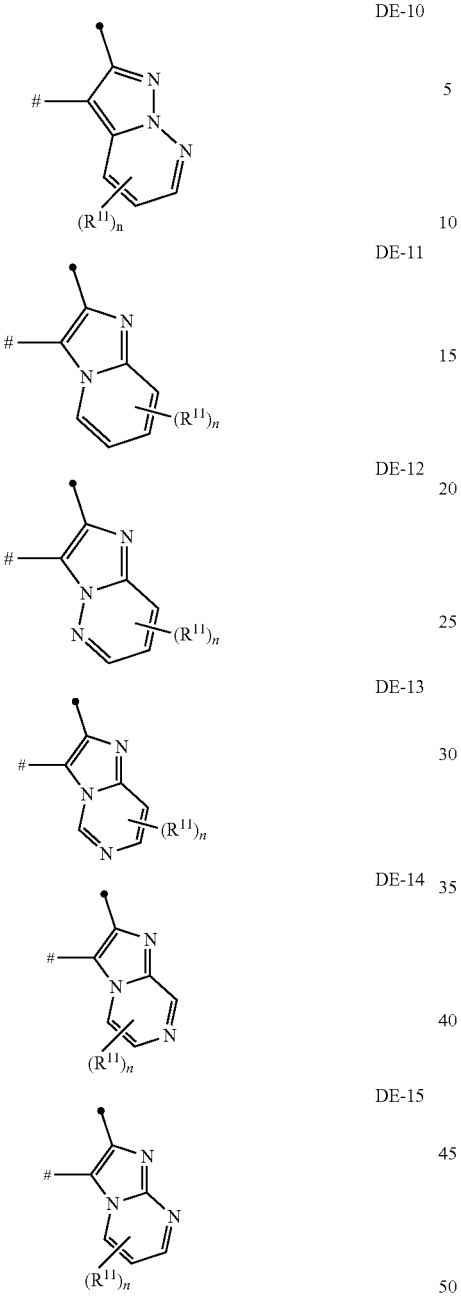
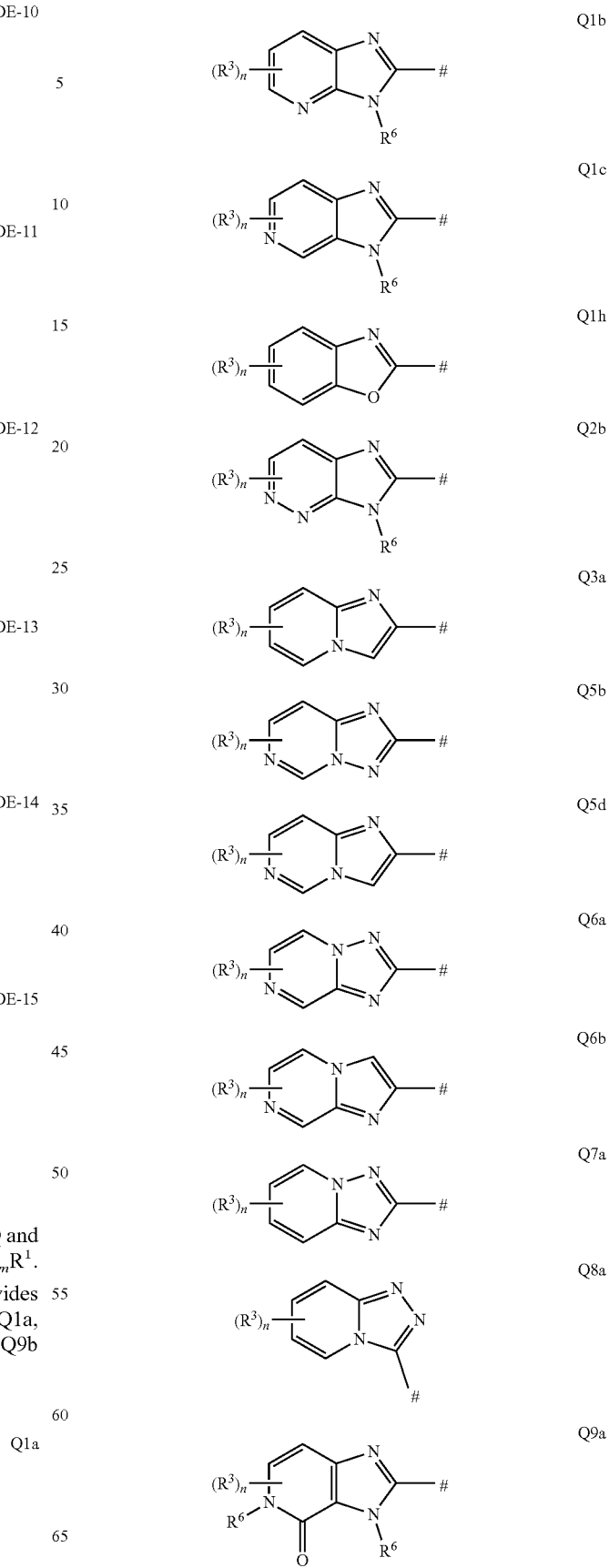
wherein, # denotes the point of attachment to the ring Q and ● denotes the point of attachment to the group —S(Y)$_m$R$^1$.
In a preferred embodiment, the present invention provides a compound of formula (I) wherein, Q is selected from Q1a, Q1b, Q1c, Q1h, Q2b, Q3a, Q5b, Q5d, Q6a Q6b, Q9a, Q9b Q7a or Q8a;

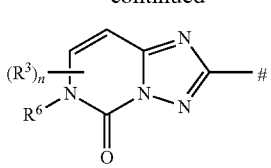

wherein, # denotes the point of attachment to the ring D;
R³ is selected from the group consisting of halogen, cyano, $C_1$-$C_6$-alkyl, $C_1$-$C_6$-haloalkyl, $C_3$-$C_8$-cycloalkyl and $S(Y)_{0-2}R^7$;
R⁶ is selected from the group consisting of hydrogen, $C_1$-$C_6$-alkyl and $C_3$-$C_{10}$-cycloalkyl;
R⁷ is selected from the group consisting of $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl;
fused rings DE are selected from the group consisting of

DE-1

DE-7

DE-11 wherein, # denotes the point of attachment to the ring Q and ● denotes the point of attachment to the group —$S(Y)_mR^1$;
R² is selected from the group consisting of halogen, cyano, $C_1$-$C_6$-alkyl, $C_1$-$C_6$-haloalkyl, $C_3$-$C_8$-cycloalkyl, $C_6$-$C_8$-aryl, $C_7$-$C_9$-aralkyl and $C_3$-$C_6$-heterocyclyl; wherein each aliphatic group may be optionally substituted with one or more groups of $R^{2a}$ and cyclic groups of R² may be optionally substituted with one or more groups of $R^{2b}$;
"m" is an integer ranging from 0 to 2;
"n" is an integer ranging from 0 to 4;
R¹¹ is selected from the group consisting of halogen, cyano, $C_1$-$C_6$-alkyl, $C_1$-$C_6$-haloalkyl, $C_3$-$C_8$-cycloalkyl, OR⁴, NR⁵R⁶, $C_6$-$C_{10}$-aryl, $C_7$-$C_{14}$-aralkyl and $C_3$-$C_{10}$-heterocyclyl; wherein each aliphatic group may be optionally substituted with one or more groups of $R^{11a}$ and cyclic groups of R¹¹ may be optionally substituted with one or more groups of $R^{11b}$.

In another preferred embodiment, the compound of formula (I) is selected from 2-(1-(3,5-dichlorophenyl)-2-(ethylsulfonyl)indolizin-3-yl)-3-methyl-6-(trifluoromethyl)-3H-imidazo[4,5-b]pyridine; 2-(2-(ethylsulfonyl)imidazo[1,2-a]pyridin-3-yl)-3-methyl-6-(trifluoromethyl)-3H-imidazo[4,5-b]pyridine; 6-(1-bromo-2-(ethylsulfonyl)indolizin-3-yl)-7-methyl-3-(trifluoromethyl)-7H-imidazo[4,5-c]pyridazine; 2-(2-(ethylsulfonyl)imidazo[1,2-a]pyridin-3-yl)-5-(trifluoromethyl)benzo[d]oxazole; 2-(2-(ethylsulfonyl)-7-(trifluoromethyl)indolizin-3-yl)-3-methyl-6-(trifluoromethyl)-3H-imidazo[4,5-b]pyridine; 2-(8-(3,5-dichlorophenyl)-2-(ethylsulfonyl)indolizin-3-yl)-3-methyl-6-(trifluoromethyl)-3H-imidazo[4,5-b]pyridine; 2-(1-(3,5-dichlorophenyl)-2-(ethylsulfonyl)-7-(trifluoromethyl)indolizin-3-yl)-3-methyl-6-(trifluoromethyl)-3H-imidazo[4,5-b]pyridine; 2-(6-(3,5-dichlorophenyl)-2-(ethylsulfonyl)indolizin-3-yl)-3-methyl-6-(trifluoromethyl)-3H-imidazo[4,5-b]pyridine; 2-(2-(ethylthio)-5,7-dimethylpyrazolo[1,5-a]pyrimidin-3-yl)-3-methyl-6-(trifluoromethyl)-3H-imidazo[4,5-b]pyridine; 2-(2-(ethylsulfonyl)-5,7-dimethylpyrazolo[1,5-a]pyrimidin-3-yl)-3-methyl-6-(trifluoromethyl)-3H-imidazo[4,5-b]pyridine; 2-(2-(ethylthio)-5,7-dimethylpyrazolo[1,5-a]pyrimidin-3-yl)-3-methyl-6-(trifluoromethyl)-3H-imidazo[4,5-c]pyridine; 2-(2-(ethylsulfonyl)-5,7-dimethylpyrazolo[1,5-a]pyrimidin-3-yl)-3-methyl-6-(trifluoromethyl)-3H-imidazo[4,5-c]pyridine; 2-(2-(ethylthio)-5,7-dimethylpyrazolo[1,5-a]pyrimidin-3-yl)-5-((trifluoromethyl)thio)benzo[d]oxazole; 2-(2-(ethylthio)pyrazolo[1,5-a]pyrimidin-3-yl)-3-methyl-6-(trifluoromethyl)-3H-imidazo[4,5-b]pyridine; 2-(2-(ethylsulfonyl)-5,7-dimethylpyrazolo[1,5-a]pyrimidin-3-yl)-5-((trifluoromethyl)sulfonyl)benzo[d]oxazole; 2-(2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)pyrazolo[1,5-a]pyrimidin-3-yl)-5-((trifluoromethyl)thio)benzo[d]oxazole; 2-(2-(ethylsulfonyl)pyrazolo[1,5-a]pyrimidin-3-yl)-5-((trifluoromethyl)sulfonyl)benzo[d]oxazole; 2-(2-(ethylthio)-7-(4-fluorophenyl)pyrazolo[1,5-a]pyrimidin-3-yl)-3-methyl-6-(trifluoromethyl)-3H-imidazo[4,5-b]pyridine; 2-(2-(ethylthio)-7-(4-fluorophenyl)pyrazolo[1,5-a]pyrimidin-3-yl)-3-methyl-6-(trifluoromethyl)-3H-imidazo[4,5-c]pyridine; 2-(2-(ethylsulfonyl)-7-(4-fluorophenyl)pyrazolo[1,5-a]pyrimidin-3-yl)-3-methyl-6-(trifluoromethyl)-3H-imidazo[4,5-c]pyridine; 2-(2-(ethylthio)pyrazolo[1,5-a]pyrimidin-3-yl)-3-methyl-6-(trifluoromethyl)-3H-imidazo[4,5-c]pyridine; 2-(2-(ethylsulfonyl)pyrazolo[1,5-a]pyrimidin-3-yl)-3-methyl-6-(trifluoromethyl)-3H-imidazo[4,5-c]pyridine; 2-(7-(3,5-dichlorophenyl)-2-(ethylthio)pyrazolo[1,5-a]pyrimidin-3-yl)-3-methyl-6-(trifluoromethyl)-3H-imidazo[4,5-c]pyridine; 2-(2-(ethylsulfonyl)-7-(4-fluorophenyl)pyrazolo[1,5-a]pyrimidin-3-yl)-3-methyl-6-(trifluoromethyl)-3H-imidazo[4,5-b]pyridine; 2-(7-(3,5-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)-7-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylthio)-7-(4-(trifluoromethoxy)phenyl)pyrazolo[1,5-a]pyrimidin-3-yl)-3-methyl-6-(trifluoromethyl)-3H-imidazo[4,5-c]pyridine; 2-(2-(ethylsulfonyl)-7-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-7-(4-(trifluoromethoxy)phenyl)pyrazolo[1,5-a]pyrimidin-3-yl)-3-methyl-6-(trifluoromethyl)-3H-imidazo[4,5-c]pyridine; 2-(2-(ethylthio)-7-(4-(trifluoromethoxy)phenyl)pyrazolo[1,5-a]pyrimidin-3-yl)-5-((trifluoromethyl)thio)benzo[d]oxazole; 2-(2-(ethylsulfonyl)-7-(4-(trifluoromethoxy)phenyl)pyrazolo[1,5-a]pyrimidin-3-yl)-5-((trifluoromethyl)

sulfonyl)benzo[d]oxazole; 2-(2-(ethylthio)-7-(4-fluorophenyl)pyrazolo[1,5-a]pyrimidin-3-yl)-5-((trifluoromethyl)thio)benzo[d]oxazole; 2-(2-(ethylsulfonyl)-7-(4-fluorophenyl)pyrazolo[1,5-a]pyrimidin-3-yl)-5-((trifluoromethyl)sulfonyl)benzo[d]oxazole; 2-(7-(4-chlorophenyl)-2-(ethylthio)pyrazolo[1,5-a]pyrimidin-3-yl)-3-methyl-6-(trifluoromethyl)-3H-imidazo[4,5-c]pyridine; 2-(7-(4-chlorophenyl)-2-(ethylthio)pyrazolo[1,5-a]pyrimidin-3-yl)-3-methyl-6-(trifluoromethyl)-3H-imidazo[4,5-b]pyridine; 2-(7-(4-chlorophenyl)-2-(ethylsulfonyl)pyrazolo[1,5-a]pyrimidin-3-yl)-3-methyl-6-(trifluoromethyl)-3H-imidazo[4,5-c]pyridine; 2-(7-(4-chlorophenyl)-2-(ethylthio)pyrazolo[1,5-a]pyrimidin-3-yl)-5-((trifluoromethyl)thio)benzo[d]oxazole; 2-(7-(4-chlorophenyl)-2-(ethylsulfonyl)pyrazolo[1,5-a]pyrimidin-3-yl)-3-methyl-6-(trifluoromethyl)-3H-imidazo[4,5-b]pyridine; 2-(7-(4-chlorophenyl)-2-(ethylsulfonyl)pyrazolo[1,5-a]pyrimidin-3-yl)-5-((trifluoromethyl)sulfonyl)benzo[d]oxazole; 2-(7-(3,5-dichlorophenyl)-2-(ethylsulfonyl)pyrazolo[1,5-a]pyrimidin-3-yl)-3-methyl-6-(trifluoromethyl)-3H-imidazo[4,5-c]pyridine; 2-(7-(3,5-dichlorophenyl)-2-(ethylthio)pyrazolo[1,5-a]pyrimidin-3-yl)-5-((trifluoromethyl)thio)benzo[d]oxazole; 2-(7-(3,5-dichlorophenyl)-2-(ethylsulfonyl)pyrazolo[1,5-a]pyrimidin-3-yl)-5-((trifluoromethyl)sulfonyl)benzo[d]oxazole; 2-(2-(ethylthio)-5-phenylpyrazolo[1,5-a]pyrimidin-3-yl)-3-methyl-6-(trifluoromethyl)-3H-imidazo[4,5-c]pyridine; 2-(2-(ethylthio)-5-phenylpyrazolo[1,5-a]pyrimidin-3-yl)-3-methyl-6-(trifluoromethyl)-3H-imidazo[4,5-c]pyridine; 2-(2-(ethylsulfonyl)-5-phenylpyrazolo[1,5-a]pyrimidin-3-yl)-3-methyl-6-(trifluoromethyl)-3H-imidazo[4,5-b]pyridine; 2-(2-(ethylsulfonyl)-5-phenylpyrazolo[1,5-a]pyrimidin-3-yl)-3-methyl-6-(trifluoromethyl)-3H-imidazo[4,5-c]pyridine; 2-(6-chloro-2-(ethylthio)pyrazolo[1,5-a]pyrimidin-3-yl)-3-methyl-6-(trifluoromethyl)-3H-imidazo[4,5-b]pyridine; 2-(2-(ethylthio)-6-phenylpyrazolo[1,5-a]pyrimidin-3-yl)-3-methyl-6-(trifluoromethyl)-3H-imidazo[4,5-b]pyridine; 2-(6-chloro-2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)-5-(4-(trifluoromethoxy)phenyl)pyrazolo[1,5-a]pyrimidin-3-yl)-3-methyl-6-(trifluoromethyl)-3H-imidazo[4,5-c]pyridine; 2-(6-chloro-2-(ethylthio)pyrazolo[1,5-a]pyrimidin-3-yl)-3-methyl-6-(trifluoromethyl)-3H-imidazo[4,5-c]pyridine; 2-(6-chloro-2-(ethylsulfonyl)pyrazolo[1,5-a]pyrimidin-3-yl)-3-methyl-6-(trifluoromethyl)-3H-imidazo[4,5-c]pyridine; 2-(2-(ethylsulfonyl)-6-phenylpyrazolo[1,5-a]pyrimidin-3-yl)-3-methyl-6-(trifluoromethyl)-3H-imidazo[4,5-b]pyridine; 2-(2-(ethylthio)-5-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-5-(4-(trifluoromethoxy)phenyl)pyrazolo[1,5-a]pyrimidin-3-yl)-3-methyl-6-(trifluoromethyl)-3H-imidazo[4,5-c]pyridine; 2-(2-(ethylthio)-5-(4-fluorophenyl)pyrazolo[1,5-a]pyrimidin-3-yl)-3-methyl-6-(trifluoromethyl)-3H-imidazo[4,5-b]pyridine; 2-(6-(4-chlorophenyl)-2-(ethylthio)pyrazolo[1,5-a]pyrimidin-3-yl)-3-methyl-6-(trifluoromethyl)-3H-imidazo[4,5-b]pyridine; 2-(2-(ethylsulfonyl)-5-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylthio)-5-(4-fluorophenyl)pyrazolo[1,5-a]pyrimidin-3-yl)-3-methyl-6-(trifluoromethyl)-3H-imidazo[4,5-c]pyridine; 2-(2-(ethylsulfonyl)-5-(4-fluorophenyl)pyrazolo[1,5-a]pyrimidin-3-yl)-3-methyl-6-(trifluoromethyl)-3H-imidazo[4,5-c]pyridine; 2-(2-(ethylsulfonyl)-5-(4-fluorophenyl)pyrazolo[1,5-a]pyrimidin-3-yl)-3-methyl-6-(trifluoromethyl)-3H-imidazo[4,5-b]pyridine; 2-(6-(4-chlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)-6-phenylpyrazolo[1,5-a]pyrimidin-3-yl)-3-methyl-6-(trifluoromethyl)-3H-imidazo[4,5-c]pyridine; 2-(5-(3,5-dichlorophenyl)-2-(ethylthio)pyrazolo[1,5-a]pyrimidin-3-yl)-3-methyl-6-(trifluoromethyl)-3H-imidazo[4,5-b]pyridine; 2-(2-(ethylsulfonyl)-6-phenylpyrazolo[1,5-a]pyrimidin-3-yl)-3-methyl-6-(trifluoromethyl)-3H-imidazo[4,5-c]pyridine; 2-(5-(3,5-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(5-(3,5-dichlorophenyl)-2-(ethylthio)pyrazolo[1,5-a]pyrimidin-3-yl)-3-methyl-6-(trifluoromethyl)-3H-imidazo[4,5-c]pyridine; 2-(5-(3,5-dichlorophenyl)-2-(ethylsulfonyl)pyrazolo[1,5-a]pyrimidin-3-yl)-3-methyl-6-(trifluoromethyl)-3H-imidazo[4,5-c]pyridine; 2-(6-bromo-2-(ethylthio)pyrazolo[1,5-a]pyrimidin-3-yl)-3-methyl-6-(trifluoromethyl)-3H-imidazo[4,5-b]pyridine; 2-(6-bromo-2-(ethylsulfonyl)pyrazolo[1,5-a]pyrimidin-3-yl)-3-methyl-6-(trifluoromethyl)-3H-imidazo[4,5-b]pyridine; 2-(6-(3,5-dichlorophenyl)-2-(ethylthio)pyrazolo[1,5-a]pyrimidin-3-yl)-3-methyl-6-(trifluoromethyl)-3H-imidazo[4,5-b]pyridine; 2-(6-(4-chlorophenyl)-2-(ethylthio)pyrazolo[1,5-a]pyrimidin-3-yl)-3-methyl-6-(trifluoromethyl)-3H-imidazo[4,5-c]pyridine; 2-(6-(4-chlorophenyl)-2-(ethylsulfonyl)pyrazolo[1,5-a]pyrimidin-3-yl)-3-methyl-6-(trifluoromethyl)-3H-imidazo[4,5-c]pyridine; 2-(2-(ethylthio)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 2-(6-(3,5-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 2-(2-(ethylsulfonyl)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(6-(3,5-dichlorophenyl)-2-(ethylthio)pyrazolo[1,5-a]pyrimidin-3-yl)-3-methyl-6-(trifluoromethyl)-3H-imidazo[4,5-c]pyridine; 2-(6-(3,5-dichlorophenyl)-2-(ethylsulfonyl)pyrazolo[1,5-a]pyrimidin-3-yl)-3-methyl-6-(trifluoromethyl)-3H-imidazo[4,5-c]pyridine; 2-(2-(ethylthio)-6-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-6-(4-(trifluoromethoxy)phenyl)pyrazolo[1,5-a]pyrimidin-3-yl)-3-methyl-6-(trifluoromethyl)-3H-imidazo[4,5-b]pyridine; 2-(5-(4-chlorophenyl)-2-(ethylthio)pyrazolo[1,5-a]pyrimidin-3-yl)-3-methyl-6-(trifluoromethyl)-3H-imidazo[4,5-b]pyridine; 2-(5-(4-chlorophenyl)-2-(ethylthio)pyrazolo[1,5-a]pyrimidin-3-yl)-3-methyl-6-(trifluoromethyl)-3H-imidazo[4,5-c]pyridine; 2-(2-(ethylthio)-6-(4-(trifluoromethoxy)phenyl)pyrazolo[1,5-a]pyrimidin-3-yl)-3-methyl-6-(trifluoromethyl)-3H-imidazo[4,5-c]pyridine; 2-(2-(ethylthio)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(5-(4-chlorophenyl)-2-(ethylsulfonyl)pyrazolo[1,5-a]pyrimidin-3-yl)-3-methyl-6-(trifluoromethyl)-3H-imidazo[4,5-b]pyridine; 2-(5-(4-chlorophenyl)-2-(ethylsulfonyl)pyrazolo[1,5-a]pyrimidin-3-yl)-3-methyl-6-(trifluoromethyl)-3H-imidazo[4,5-c]pyridine; 2-(2-(ethylsulfonyl)-7-(4-(1,1,2,2- tetrafluoroethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 3-(7-(3,5-dichlorophenyl)-2-(ethylthio)pyrazolo[1,5-a]pyrimidin-3-yl)-7-(trifluoromethyl)-[1,2,4]triazolo[4,3-a]pyridine; 2-(2-(ethylthio)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 3-(7-(3,5-dichlorophenyl)-2-(ethylsulfonyl)pyrazolo[1,5-a]pyrimidin-3-yl)-7-(trifluoromethyl)-[1,2,4]triazolo[4,3-a]pyridine; 2-(2-(ethylthio)-6-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-6-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(7-(3-chlorophenyl)-2-(ethylthio)pyrazolo[1,5-a]pyrimidin-3-yl)-3-methyl-6-(trifluoromethyl)-3H-imidazo[4,5-b]pyridine; 2-(7-(3,5-difluorophenyl)-2-(ethylthio)pyrazolo[1,5-a]pyrimidin-3-yl)-3-methyl-6-(trifluoromethyl)-3H-imidazo[4,5-b]pyridine; 2-(7-(3-chlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylsulfonyl)-6-(4-(trifluoromethoxy)phenyl)pyrazolo[1,5-a]pyrimidin-3-yl)-3-methyl-6-(trifluoromethyl)-3H-imidazo[4,5-c]pyridine; 2-(7-(3,5-difluorophenyl)-2-(ethylsulfonyl)pyrazolo[1,5-a]pyrimidin-3-yl)-3-methyl-6-(trifluoromethyl)-3H-imidazo[4,5-b]pyridine; 2-(7-(3-chloro-5-fluorophenyl)-2-(ethylthio)pyrazolo[1,5-a]pyrimidin-3-yl)-3-methyl-6-(trifluoromethyl)-3H-imidazo[4,5-b]pyridine; 2-(7-(3-chloro-5-fluorophenyl)-2-(ethylsulfonyl)pyrazolo[1,5-a]pyrimidin-3-yl)-3-methyl-6-(trifluoromethyl)-3H-imidazo[4,5-b]pyridine; 2-(7-(3,4-dichlorophenyl)-2-(ethylsulfonyl)pyrazolo[1,5-a]pyrimidin-3-yl)-3-methyl-6-(trifluoromethyl)-3H-imidazo[4,5-b]pyridine; 7-(3,5-dichlorophenyl)-2-(ethylthio)-3-(1-methyl-5-(trifluoromethyl)-1H-benzo[d]imidazol-2-yl)pyrazolo[1,5-a]pyrimidine; 2-(ethylthio)-3-(1-methyl-5-(trifluoromethyl)-1H-benzo[d]imidazol-2-yl)pyrazolo[1,5-a]pyrimidine; 7-(3,5-dichlorophenyl)-2-(ethylsulfonyl)-3-(1-methyl-5-(trifluoromethyl)-1H-benzo[d]imidazol-2-yl)pyrazolo[1,5-a]pyrimidine; 2-(ethylsulfonyl)-3-(1-methyl-5-(trifluoromethyl)-1H-benzo[d]imidazol-2-yl)pyrazolo[1,5-a]pyrimidine; 2-(2-(ethylsulfonyl)-6-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 3-(7-(3,5-dichlorophenyl)-2-(ethylthio)pyrazolo[1,5-a]pyrimidin-3-yl)-6-(trifluoromethyl)-[1,2,4]triazolo[4,3-a]pyridine; 3-(7-(3,5-dichlorophenyl)-2-(ethylsulfonyl)pyrazolo[1,5-a]pyrimidin-3-yl)-6-(trifluoromethyl)-[1,2,4]triazolo[4,3-a]pyridine; 2-(7-(2,3-dichlorophenyl)-2-(ethylthio)pyrazolo[1,5-a]pyrimidin-3-yl)-3-methyl-6-(trifluoromethyl)-3H-imidazo[4,5-b]pyridine; 2-(2-(ethylthio)-7-phenylpyrazolo[1,5-a]pyrimidin-3-yl)-3-methyl-6-(trifluoromethyl)-3H-imidazo[4,5-b]pyridine; 2-(7-(2,3-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylsulfonyl)-7-phenylpyrazolo[1,5-a]pyrimidin-3-yl)-3-methyl-6-(trifluoromethyl)-3H-imidazo[4,5-b]pyridine; 2-(7-(4-chloro-3-fluorophenyl)-2-(ethylthio)pyrazolo[1,5-a]pyrimidin-3-yl)-3-methyl-6-(trifluoromethyl)-3H-imidazo[4,5-b]pyridine; 2-(7-(3,5-dichlorophenyl)-2-(ethylthio)pyrazolo[1,5-a]pyrimidin-3-yl)-3-methyl-6-(trifluoromethyl)-3H-imidazo[4,5-b]pyridine; 2-(7-(4-chloro-3-fluorophenyl)-2-(ethylsulfonyl)pyrazolo[1,5-a]pyrimidin-3-yl)-3-methyl-6-(trifluoromethyl)-3H-imidazo[4,5-b]pyridine; 2-(7-(4-chloro-3-fluorophenyl)-2-(ethylthio)pyrazolo[1,5-a]pyrimidin-3-yl)-3-methyl-6-(trifluoromethyl)-3H-imidazo[4,5-c]pyridine; 2-(7-(2,4-dichlorophenyl)-2-(ethylthio)pyrazolo[1,5-a]pyrimidin-3-yl)-3-methyl-6-(trifluoromethyl)-3H-imidazo[4,5-b]pyridine; 2-(7-(2,4-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(7-(2,4-dichlorophenyl)-2-(ethylthio)pyrazolo[1,5-a]pyrimidin-3-yl)-3-methyl-6-(trifluoromethyl)-3H-imidazo[4,5-c]pyridine; 2-(7-(3-chloro-5-fluorophenyl)-2-(ethylthio)pyrazolo[1,5-a]pyrimidin-3-yl)-3-methyl-6-(trifluoromethyl)-3H-imidazo[4,5-c]pyridine; 2-(7-(3-chloro-5-fluorophenyl)-2-(ethylsulfonyl)pyrazolo[1,5-a]pyrimidin-3-yl)-3-methyl-6-(trifluoromethyl)-3H-imidazo[4,5-c]pyridine; 2-(7-(3,5-bis(trifluoromethyl)phenyl)-2-(ethylthio)pyrazolo[1,5-a]pyrimidin-3-yl)-3-methyl-6-(trifluoromethyl)-3H-imidazo[4,5-b]pyridine; 2-(2-(ethylthio)-7-(3-(trifluoromethyl)phenyl)pyrazolo[1,5-a]pyrimidin-3-yl)-3-methyl-6-(trifluoromethyl)-3H-imidazo[4,5-b]pyridine; 2-(2-(ethylthio)-7-(3-fluorophenyl)pyrazolo[1,5-a]pyrimidin-3-yl)-3-methyl-6-(trifluoromethyl)-3H-imidazo[4,5-b]pyridine; 2-(7-(3,5-bis(trifluoromethyl)phenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylsulfonyl)-7-(3-(trifluoromethyl)phenyl)pyrazolo[1,5-a]pyrimidin-3-yl)-3-methyl-6-(trifluoromethyl)-3H-imidazo[4,5-b]pyridine; 2-(2-(ethylsulfonyl)-7-(3-fluorophenyl)pyrazolo[1,5-a]pyrimidin-3-yl)-3-methyl-6-(trifluoromethyl)-3H-imidazo[4,5-b]pyridine; 2-(2-(ethylthio)-7-methylpyrazolo[1,5-a]pyrimidin-3-yl)-3-methyl-6-(trifluoromethyl)-3H-imidazo[4,5-b]pyridine; 2-(2-(ethylthio)-7-(3-fluorophenyl)pyrazolo[1,5-a]pyrimidin-3-yl)-3-methyl-6-(trifluoromethyl)-3H-imidazo[4,5-c]pyridine; 2-(2-(ethylsulfonyl)-7-methylpyrazolo[1,5-a]pyrimidin-3-yl)-3-methyl-6-(trifluoromethyl)-3H-imidazo[4,5-b]pyridine; 2-(2-(ethylthio)-7-(3-(trifluoromethyl)phenyl)pyrazolo[1,5-a]pyrimidin-3-yl)-3-methyl-6-(trifluoromethyl)-3H-imidazo[4,5-c]pyridine; (7-(3,5-dichlorophenyl)-3-(3-methyl-6-(trifluoromethyl)-3H-imidazo[4,5-b]pyridin-2-yl)pyrazolo[1,5-a]pyrimidin-2-yl)(ethyl)(imino)-□6-sulfanone; 2-(2-(ethylsulfonyl)-7-(3-(trifluoromethyl)phenyl)pyrazolo[1,5-a]pyrimidin-3-yl)-3-methyl-6-(trifluoromethyl)-3H-imidazo[4,5-c]pyridine; 2-(2-(ethylsulfonyl)-7-(3-fluorophenyl)pyrazolo[1,5-a]pyrimidin-3-yl)-3-methyl-6-(trifluoromethyl)-3H-imidazo[4,5-c]pyridine; 2-(2-(ethylthio)-7-methylpyrazolo[1,5-a]pyrimidin-3-yl)-3-methyl-6-(trifluoromethyl)-3H-imidazo[4,5-c]pyridine; 2-(7-(3-chloro-4-fluorophenyl)-2-(ethylthio)pyrazolo[1,5-a]pyrimidin-3-yl)-3-methyl-6-(trifluoromethyl)-3H-imidazo[4,5-b]pyridine; 2-(2-(ethylthio)-5,7-bis(trifluoromethyl)pyrazolo[1,5-a]pyrimidin-3-yl)-3-methyl-6-(trifluoromethyl)-3H-imidazo[4,5-b]pyridine; 2-(2-(ethylsulfonyl)-5,7-bis(trifluoromethyl)pyrazolo[1,5-a]pyrimidin-3-yl)-3-methyl-6-(trifluoromethyl)-3H-imidazo[4,5-b]pyridine; 2-(ethylthio)-3-(3-methyl-6-(trifluoromethyl)-3H-imidazo[4,5-b]pyridin-2-yl)pyrazolo[1,5-a]pyrimidin-7(4H)-one; 2-(7-bromo-2-(ethylthio)pyrazolo[1,5-a]pyrimidin-3-yl)-3-methyl-6-(trifluoromethyl)-3H-imidazo[4,5-b]pyridine; 2-(ethylsulfonyl)-N-methyl-3-(7-(trifluoromethyl)-[1,2,4]triazolo[1,5-c]pyrimidin-2-yl)pyrazolo[1,5-a]pyrimidin-7-amine; 6-(8-(4-chloro-3-fluorophenyl)-2-(ethylsulfonyl)indolizin-3-yl)-7-methyl-3-(trifluoromethyl)-7H-imidazo[4,5-c]pyridazine; 2-(2-(ethylsulfonyl)-7-(5-methyl-3-(trifluoromethyl)-1H-pyrazol-1-yl)pyrazolo[1,5-a]

pyrimidin-3-yl)-3-methyl-6-(trifluoromethyl)-3H-imidazo[4,5-b]pyridine; 2-(ethylthio)-N-methyl-3-(3-methyl-6-(trifluoromethyl)-3H-imidazo[4,5-b]pyridin-2-yl)pyrazolo[1,5-a]pyrimidin-7-amine; 2-(2-(ethylsulfonyl)-7-(3-fluorophenoxy)pyrazolo[1,5-a]pyrimidin-3-yl)-3-methyl-6-(trifluoromethyl)-3H-imidazo[4,5-b]pyridine; 6-(8-(4-chloro-3-fluorophenyl)-2-(ethylsulfonyl)imidazo[1,2-a]pyridin-3-yl)-7-methyl-3-(trifluoromethyl)-7H-imidazo[4,5-c]pyridazine; 2-(6-(3,5-dichlorophenyl)-2-(ethylsulfonyl)pyrazolo[1,5-a]pyrimidin-3-yl)-6-(trifluoromethyl)imidazo[1,2-a]pyrazine; 4-(2-(ethylsulfonyl)-3-(7-methyl-3-(trifluoromethyl)-7H-imidazo[4,5-c]pyridazin-6-yl)indolizin-8-yl)-2-fluorobenzonitrile; 2-(8-(cyclopropylmethyl)-2-(ethylsulfonyl)imidazo[1,2-a]pyridin-3-yl)-3-methyl-6-(trifluoromethyl)-3H-imidazo[4,5-b]pyridine; 2-(7-(4-chloro-1H-pyrazol-1-yl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylsulfonyl)-7-(5-methyl-1H-1,2,4-triazol-1-yl)pyrazolo[1,5-a]pyrimidin-3-yl)-3-methyl-6-(trifluoromethyl)-3H-imidazo[4,5-b]pyridine; 2-(2-(ethylsulfonyl)-7-(1-methyl-1H-pyrazol-5-yl)pyrazolo[1,5-a]pyrimidin-3-yl)-3-methyl-6-(trifluoromethyl)-3H-imidazo[4,5-b]pyridine; 2-(2-(ethylsulfonyl)-7-(1-methyl-3-(trifluoromethyl)-1H-pyrazol-5-yl)pyrazolo[1,5-a]pyrimidin-3-yl)-3-methyl-6-(trifluoromethyl)-3H-imidazo[4,5-b]pyridine; 2-(7-cyclopropyl-2-(ethylsulfonyl)pyrazolo[1,5-a]pyrimidin-3-yl)-6-(trifluoromethyl)-[1,2,4]triazolo[1,5-a]pyrazine; 2-(2-(ethylsulfonyl)-7-(1-methyl-3-(trifluoromethyl)-1H-pyrazol-5-yl)pyrazolo[1,5-a]pyrimidin-3-yl)-7-(trifluoromethyl)imidazo[1,2-c]pyrimidine; 4-(2-(ethylsulfonyl)-3-(7-(trifluoromethyl)imidazo[1,2-a]pyridin-2-yl)pyrazolo[1,5-a]pyrimidin-7-yl)morpholine; 2-(7-(4-chloro-3-fluorophenyl)-2-(ethylsulfonyl)pyrazolo[1,5-a]pyrimidin-3-yl)-7-(trifluoromethyl)-[1,2,4]triazolo[1,5-c]pyrimidine; 2-(2-(ethylsulfonyl)-7-(1H-1,2,4-triazol-1-yl)pyrazolo[1,5-a]pyrimidin-3-yl)-7-(trifluoromethyl)-[1,2,4]triazolo[1,5-c]pyrimidine; 2-(2-(ethylsulfonyl)-5,7-bis(trifluoromethyl)pyrazolo[1,5-a]pyrimidin-3-yl)-3-methyl-6-(trifluoromethyl)-3H-imidazo[4,5-b]pyridine; 6-(1-bromo-2-(ethylsulfonyl)-8-methylindolizin-3-yl)-7-methyl-3-(trifluoromethyl)-7H-imidazo[4,5-c]pyridazine; 6-(8-bromo-2-(ethylsulfonyl)indolizin-3-yl)-3-(difluoromethyl)-7-methyl-7H-imidazo[4,5-c]pyridazine; 2-(2-(ethylsulfonyl)-7-methoxypyrazolo[1,5-a]pyrimidin-3-yl)-3-methyl-6-(trifluoromethyl)-3H-imidazo[4,5-b]pyridine; 2-(2-(ethylsulfonyl)-7-(methylthio)pyrazolo[1,5-a]pyrimidin-3-yl)-3-methyl-6-(trifluoromethyl)-3H-imidazo[4,5-b]pyridine; 2-(ethylsulfonyl)-3-(3-methyl-6-(trifluoromethyl)-3H-imidazo[4,5-b]pyridin-2-yl)pyrazolo[1,5-a]pyrimidine-7(4H)-thione; 2-(2-(ethylsulfonyl)-7-(1,1,2,2-tetrafluoroethoxy)pyrazolo[1,5-a]pyrimidin-3-yl)-3-methyl-6-(trifluoromethyl)-3H-imidazo[4,5-b]pyridine; 2-(7-ethoxy-2-(ethylsulfonyl)pyrazolo[1,5-a]pyrimidin-3-yl)-6-(trifluoromethyl)imidazo[1,2-a]pyrazine; diethyl((2-(ethylsulfonyl)-3-(6-(trifluoromethyl)imidazo[1,2-a]pyrazin-2-yl)pyrazolo[1,5-a]pyrimidin-7-yl)imino)-16-sulfanone; 2-(ethylsulfonyl)-N,N-dimethyl-3-(3-methyl-6-(trifluoromethyl)-3H-imidazo[4,5-b]pyridin-2-yl)imidazo[1,2-a]pyridin-8-amine; 6-(2-(ethylsulfonyl)-7-(5-(trifluoromethyl)pyridin-2-yl)pyrazolo[1,5-a]pyrimidin-3-yl)-7-methyl-3-(trifluoromethyl)-7H-imidazo[4,5-c]pyridazine; 2-(7-(4-chloro-3-fluorophenyl)-2-(ethylsulfonyl)pyrazolo[1,5-a]pyrimidin-3-yl)-3,5-dimethyl-6-(trifluoromethyl)-3,5-dihydro-4H-imidazo[4,5-c]pyridin-4-one; 2-(2-(ethylsulfonyl)-7-(3-(trifluoromethyl)-1H-1,2,4-triazol-1-yl)pyrazolo[1,5-a]pyrimidin-3-yl)-3,5-dimethyl-6-(trifluoromethyl)-3,5-dihydro-4H-imidazo[4,5-c]pyridin-4-one; 2-(7-(3-chloro-5-fluorophenyl)-2-(ethylsulfonyl)pyrazolo[1,5-a]pyrimidin-3-yl)-6-(trifluoromethyl)-[1,2,4]triazolo[1,5-a]pyrazine; 2-(7-(3,5-dichlorophenyl)-2-(ethylsulfonyl)pyrazolo[1,5-a]pyrimidin-3-yl)-7-(trifluoromethyl)imidazo[1,2-c]pyrimidine; 2-(7-(4-chloro-3-fluorophenyl)-2-(ethylsulfonyl)pyrazolo[1,5-a]pyrimidin-3-yl)-6-methyl-7-(trifluoromethyl)-[1,2,4]triazolo[1,5-c]pyrimidin-5(6H)-one; 2-(7-(5-chloropyridin-2-yl)-2-(ethylsulfonyl)pyrazolo[1,5-a]pyrimidin-3-yl)-6-(trifluoromethyl)-[1,2,4]triazolo[1,5-a]pyridine; 2-(2-(ethylsulfonyl)-7-(5-methyl-3-(trifluoromethyl)-1H-pyrazol-1-yl)pyrazolo[1,5-a]pyrimidin-3-yl)-6-methyl-7-(trifluoromethyl)-[1,2,4]triazolo[1,5-c]pyrimidin-5(6H)-one; 2-(2-(ethylsulfonyl)-7-(3-(trifluoromethyl)-1H-1,2,4-triazol-1-yl)pyrazolo[1,5-a]pyrimidin-3-yl)-7-(trifluoromethyl)-[1,2,4]triazolo[1,5-c]pyrimidine; ethyl(3-(3-methyl-6-(trifluoromethyl)-3H-imidazo[4,5-c]pyridin-2-yl)pyrazolo[1,5-a]pyrimidin-2-yl)(methylimino)-16-sulfanone.

The compounds of the present invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the present invention may be present as a mixture of stereoisomers, individual stereoisomers or as an optically active form.

An anion part of the salt in case the compound of formula (I) is a cationic or capable of forming a cation can be inorganic or organic. Alternatively, a cation part of the salt in case the compound of formula (I) is an anionic or capable of forming anion can be inorganic or organic. Examples of inorganic anion part of the salt include but are not limited to chloride, bromide, iodide, fluoride, sulfate, phosphate, nitrate, nitrite, hydrogen carbonates and hydrogen sulfate. Examples of organic anion part of the salt include but are not limited to formate, alkanoates, carbonates, acetates, trifluoroacetate, trichloroacetate, propionate, glycolate, thiocyanate, lactate, succinate, malate, citrates, benzoates, cinnamates, oxalates, alkylsulphates, alkylsulphonates, arylsulphonates, aryldisulphonates, alkylphosphonates, arylphosphonates, aryldiphosphonates, p-toluenesulphonate, and salicylate. Examples of inorganic cation part of the salt include but are not limited to alkali and alkaline earth metals. Examples of organic cation part of the salt include but are not limited to pyridine, methyl amine, imidazole, benzimidazole, hitidine, phosphazene, tetramethyl ammonium, tetrabutyl ammonium, choline and trimethylamine.

Metal ions in metal complexes of the compound of formula (I) are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period and the first to eighth transition groups. Here, the metals can be present in the various valencies that they can assume.

In one embodiment, the present invention provides a compound of formula (I), agriculturally acceptable salts, metal complexes, constitutional isomers, stereo-isomers, diastereoisomers, enantiomers, chiral isomers, atropisomers, conformers, rotamers, tautomers, optical isomers, polymorphs, geometric isomers, or N-oxides thereof and its composition with the excipient, inert carrier or any other essential ingredient such as surfactants, additives, solid diluents and liquid diluents.

The compounds of formula (I), (including all stereoisomers, N-oxides, and salts thereof), typically exist in more than one form, and formula (I) thus includes all crystalline and non-crystalline forms of the compounds that formula (I) represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by formula (I) can exhibit beneficial effects (e.g., suitability for preparation of useful formulations, improved biological performance) relative to another polymorph or a mixture of polymorphs of the same compound represented by formula (I). Preparation and isolation of a particular polymorph of a compound represented by formula (I) can be achieved by methods known to those skilled in the art including, for example, crystallization using selected solvents and temperatures.

In an embodiment, the present invention provides a process for preparing the compound of formula (I) or agriculturally acceptable salts.

The compound of formula (I) can be prepared according to schemes: 1-23/examples described herein.

The process for preparing compound of formula (I), more specifically compound of formula (Ia) or compound of formula (Ib) wherein Q is Q1 or Q2 comprises the reaction of compound of formula (2), with compound of formula (3) or (4), wherein M is O, S, NR' to obtain compound of formula (Ia) and (Ib). The process is summarized in scheme 1:

Scheme: 1

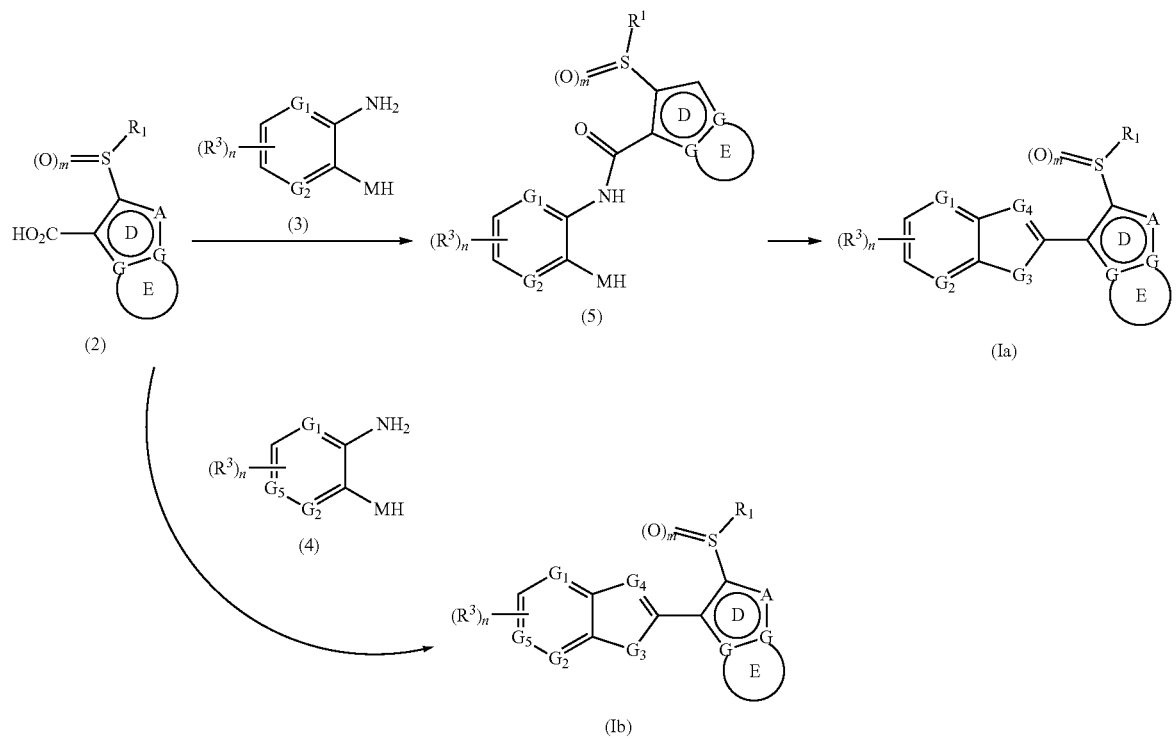

wherein, $R^1$, $R^3$, A, G, $G_1$, $G_2$, $G_3$, $G_4$, $G_5$, E, m and n have the meanings as described above.

The compound of formula (3) and formula (4) are either commercially available or can be prepared by using the methods known or analogously described in US200369257, WO200665703, WO2009131237, WO2010125985, WO2011043404, WO2011040629, WO2012086848, WO2013018928 and WO2015000715.

In scheme 1, carboxylic acid group present in the compound of formula (2) can be converted to a more reactive functional group, such as an acyl halide, mixed anhydride, acyl azide, N-acylbenzotriazoles, active esters, or via an in situ activation by peptide coupling reagents such as bis(2-oxo-3-oxazolidinyl)phosphinic chloride (BOP-Cl); dicyclohexyl carbodiimide (DCC) or 1-ethyl-3-(3-dimethylaminopropyl)carbodiimide (EDC), followed by amide bond formation with compound of formula (3) in solvents such as dichloromethane, dichloroethane, N,N-dimethylacetamide, tetrahydrofuran, acetonitrile or a mixture thereof to obtain compound of formula (5). Organic non-nucleophilic bases such as triethyl amine, ethyldiisopropyl amine, pyridine, N-methyl pyrrolidine, 1,8-diazabicyclo[5.4.0]undec-7-ene may be used. The reaction can be carried out at a temperature ranging from about 0° C. and about 150° C.

The compound of formula (5) can be converted to a compound of formula (Ia) by dehydration, following conventional or under microwave conditions, in the presence of an acid catalyst, for example methane sulfonic acid, or para-toluene sulfonic acid, in an inert solvent such as N-methyl pyrolidine at temperature ranging from about 25° C. and about 185° C. Such processes have been described previously in WO2009131237, WO2010125985, WO2011043404, WO2011040629, WO2012086848, WO2013018928, WO2015000715 and WO2015121136.

Alternatively, the compound of formula (5) can be converted to a compound of formula (Ia) wherein M is oxygen under Mitsunobu conditions well known to those skilled in the art using di-isopropyl azodicarboxylate, triphenyl phosphine in an inert solvent such as diethyl ether, tetrahydrofuran at a temperature ranging from about 25° C. and about 50° C. This process is described previously in WO2009131237.

Application of methods of scheme 1 in the reaction of compound of formula (2) with compound of formula (4), can lead to compound of formula (Ib).

A process for the synthesis of compound of formula (I) represented by compound of formula (Ic and Id) is depicted in scheme 2. The compound of formula (Ic) or (Id) can be prepared by reacting compound of formula (6) with compound of formula (3) or (4) to obtain compound of formula (7) or (8). Further, the compound of formula (7) and (8) (wherein X is a halogen, for example fluorine, chlorine or bromine) can be reacted with a compound of formula (9) or with a compound of formula (10), wherein $M_1$ is for example sodium or potassium, optionally in the presence of a suitable base, such as alkali metal carbonates, for example sodium carbonate or potassium carbonate, or alkali metal hydrides such as sodium hydride, or alkali metal hydroxides such as sodium hydroxide and potassium hydroxide, in an inert solvent at temperatures ranging from about 25° C. and about 110° C. to obtain compound of formula (Ic) or (Id).

Scheme: 2

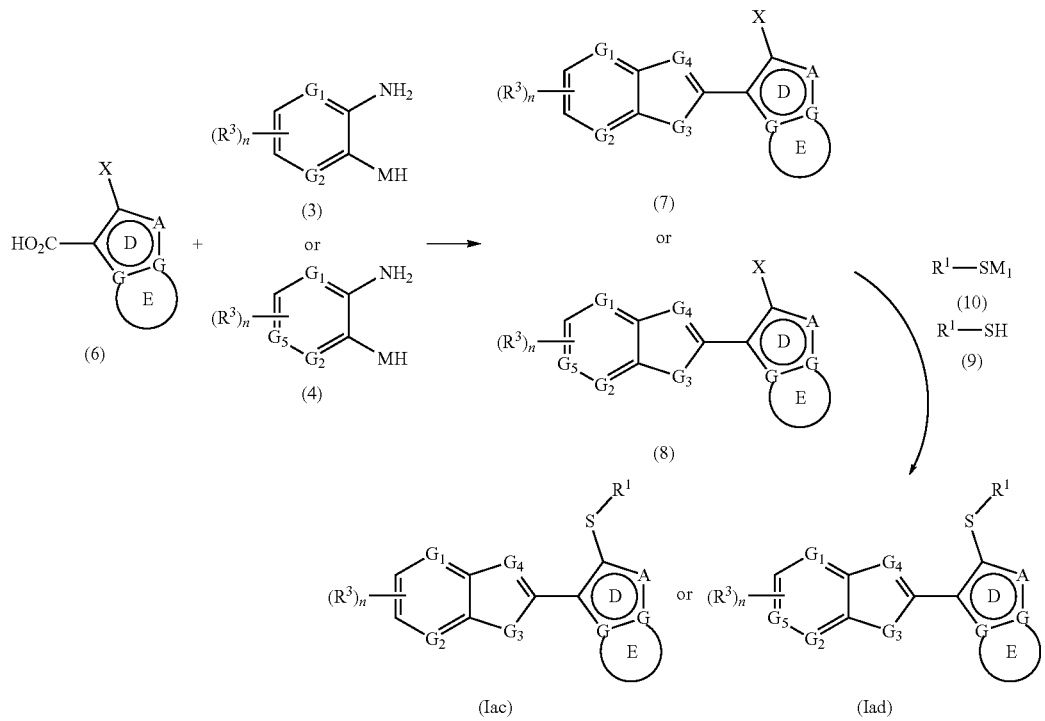

wherein, $R^1$, $R^3$, A, G, $G_1$, $G_2$, $G_3$, $G_4$, $G_5$, E, m and n have the meanings as described above.

Alternatively, the above reaction can also be carried out in the presence of a palladium catalyst, such as tris(dibenzylideneacetone)dipalladium(0), in the presence of a ligand such as xantphos, in an inert solvent, for example toluene, xylene at temperatures ranging from about 100° C. and about 150° C., as described in *Tetrahedron*, 2005, 61, 5253. The compound of formula (I) wherein Y=O, m=1 (sulfoxide) and/or m=2 (sulfone), can be obtained by oxidation of the corresponding sulfide compound of formula (Ic) and (Id) while applying appropriate oxidizing agents and conditions well known to those skilled in the art. Oxidizing agents such as m-chloroperoxybenzoic acid (mCPBA), hydrogen peroxide/glacial acetic acid, hydrogen peroxide/trifluoroacetic acid, hydrogen peroxide/potassium permanganate, hydrogen peroxide/p-toulenesulfonylimidazole, urea hydrogen peroxide/trifluoroacetic acid, oxone, sodium periodate, sodium hypochlorite and other organic peracids and the like can be used for this. Examples of the solvent used in this reaction include aliphatic halogenated hydrocarbons such as dichloromethane and chloroform; alcohols such as methanol and ethanol and the mixtures thereof.

The compound of formula (I) wherein m=1 or 2 and Y=NR$^Y$ and/or Y=O, can be obtained by sulfoximination/sulfilimination of the corresponding sulfide compound of formula (Ic) and (Id) by using the analogous procedure as described in *Chem. Commun.,* 2017, 53, 2064-2067; *Tetrahedron Lett.* 2005, 46, 8007-8008 and WO2015071180A1.

The compound of formula (2) is selected from the group consisting of formula (2a), (2b) and (2c);

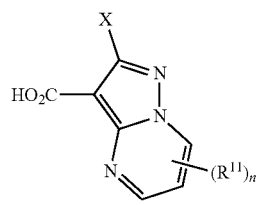
(2a)

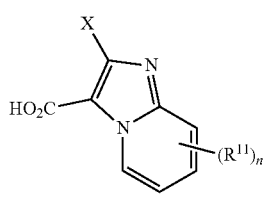
(2b)

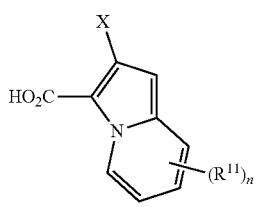
(2c)

X = Halogen, —S(O)$_m$R$_1$
n = 0-2 wherein, R$^1$ and R$^{11}$ have the same meanings as described above.

The synthesis of compounds of formula (2a), (2b) and (2c) is described in the scheme 3 to scheme 9.

Scheme: 3

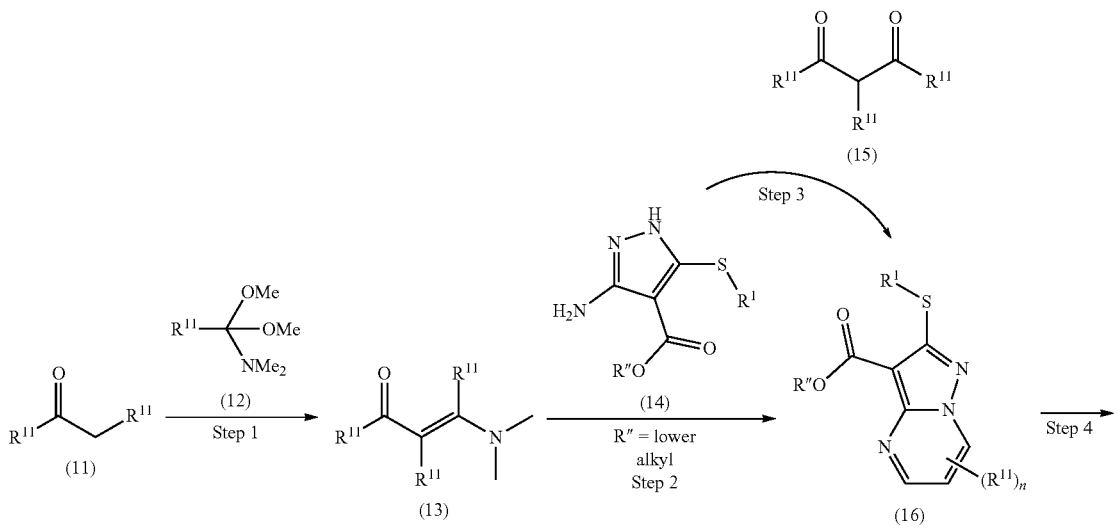

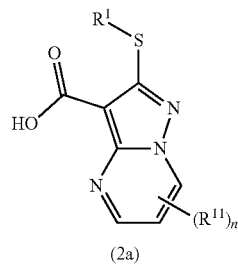
(2a)

wherein, $R^1$, $R^{11}$ and n have the meanings as described above.

The reaction of compound of formula (11) with compound of formula (12) can be carried out in an appropriate solvent at temperatures ranging from 50-200° C. to obtain dielectrophilic compound of formula (13). Examples of the solvents include but are not limited to N,N-dimethylformamide, dimethylacetamide, 1,4-dioxane, 1,2-dichloromethane, toluene, xylene and the like.

In the pyrimidine formation, step-2; pyrazole derivative compound of formula (14) can undergo cyclocondensation reaction when treated with dielectrophilic compound of formula (13) or 1,3-diketone compound of formula (15) (e.g., a 1,3-dialdehyde or a 3-(dialkylamino)-prop-2-enal) in the presence or absence of a base to obtain bicyclic compound of formula (16). The preparation of a compound of formula (14) has been described in the literature (*Acta Chimica Sinica* 2003, 63, 855; *Organic & Biomolecular Chemistry* 2010, 8, 3394). Examples of the bases include but are not limited to piperidine, morpholine, N-methylpiperazine, diethyl amine, triethylamine and the like. Examples of the solvent include but are not limited to methanol, ethanol, isopropanol, ethyleneglycol and the like. The reaction can be carried out at temperatures ranging from about 50° C. and about 150° C.

When one or both of the electrophilic centers present in compounds of formula (13) and (15) are protected/masked (e.g aldehyde masked as a ketal) the condensation can be effected in a solvent in the presence of an acid. Examples of acid include acetic acid, sulfonic acid (e.g PTSA), sulfuric acid, hydrochloric acid which liberate the reactive functional group. Examples of the solvent include but are not limited to methanol, ethanol, isopropanol, ethyleneglycol and the like. The reaction can be carried out at temperatures ranging from about 0° C. and about 150° C. The hydrolysis of a compound of formula (16) can be achieved by using a base such as sodium hydroxide, potassium hydroxide, lithium hydroxide, bis(tributyltin) oxide and the like; in solvents such as tetrahydrofuran, water, methanol, ethanol or a mixture(s) thereof, to obtain a compound of formula (2a). The reaction can be carried out at temperatures ranging from about 50° C. and about 150° C.

Alternatively, the compound of formula (2a) can also be prepared by following scheme4:

Scheme: 4

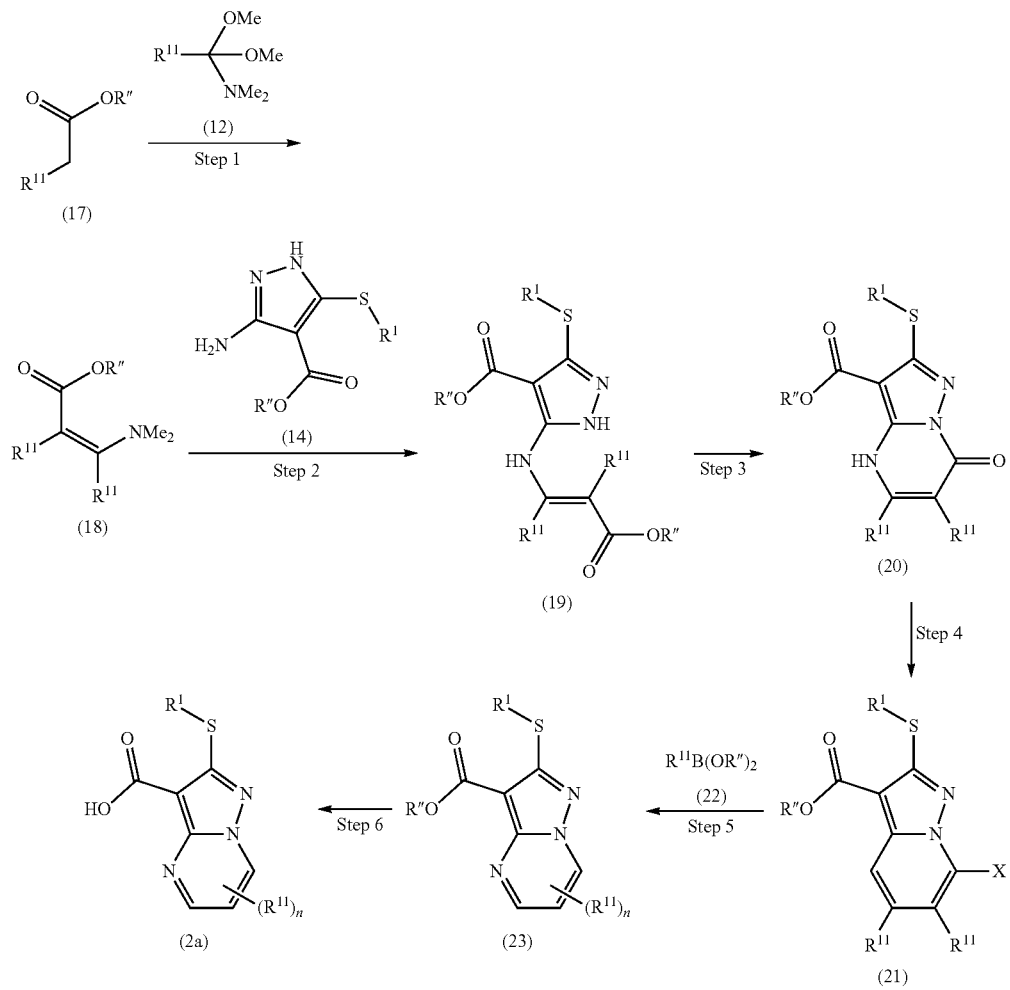

R″ = lower alkyl
(R‴ = H; or R‴ = pinacolate)

wherein, X is halogen, $R^1$ and $R^{11}$ have the meanings as described above.

The compound of the formula (19) can be obtained starting from compound of formula (18) in the same manner as described in step 1 of scheme3. The reaction of compound of formula (18) can be carried out in the same manner as described in step 2 of scheme 3. Besides, the compound of formula (20) can be obtained without conducting step 3, when step 2 is conducted in the presence of acetic acid.

The conversion of compound of formula (20) to compound of formula (21) can be carried out in a solvent in the presence of a halogenating agent and in the presence or absence of a base. Examples of the solvent include but are not limited to acetonitrile, chloroform, tetrahydrofuran, 1,4-dioxane, toluene, N,N-dimethylformamide and the like. Examples of halogenating agents include but are not limited to phosphorus oxychloride, thionyl chloride, phosphorus pentachloride, oxalyl chloride and the like-. Examples of base include but are not limited to N,N-dimethylaniline, diisopropylethylamine, N-methylmorpholine and the like. The reaction can be carried out at temperatures ranging from 50-200° C.

The compound of formula (21) can be conveniently coupled under standard Suzuki cross coupling conditions with boronic acids or a boronic ester compound of formula (22) to obtain the compound of formula (23). The Suzuki cross coupling reaction can be catalyzed by a palladium based catalyst, including but not limited to 1,1'-bis(diphenylphosphino)ferrocene]dichloropalladium(II) or tetrakis(triphenylphosphine) palladium(0), in a suitable solvent for example, tetrahydrofuran (THF), N,N'-dimethylformamide (DMF), 1,2-dimethoxyethane, 1,4-dioxane or a solvent system such as a mixture of tetrahydrofuran (THF)/water, 1,2-dimethoxyethane/water, 1,4-dioxane/water, or the like. The reaction is usually carried out in the presence of a base, for example potassium carbonate, cesium carbonate or potassium phosphate. The reaction temperature can preferentially range from ambient temperature (20° C.) to the boiling point of the reaction mixture as precedented in the literature, see for example *Chem. Soc. Rev.* 2014, 43, 412-443 or in WO2014070978. The hydrolysis of a compound of formula (23) can be achieved by using a base such as sodium hydroxide, potassium hydroxide, lithium hydroxide, Bis(tributyltin) oxide and the like; in solvents such as tetrahydrofuran, water, methanol, ethanol, toluene or a mixture(s) thereof, to obtain a compound of formula (2a). The reaction can be carried out at temperatures ranging from about 50° C. and 150° C.

The compound of formula (2aa) can be prepared according to the following scheme 5:

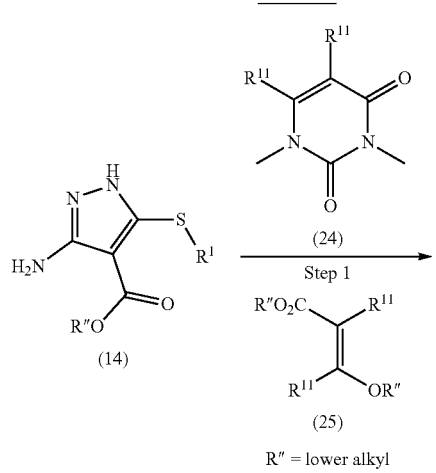

Scheme: 5

R" = lower alkyl

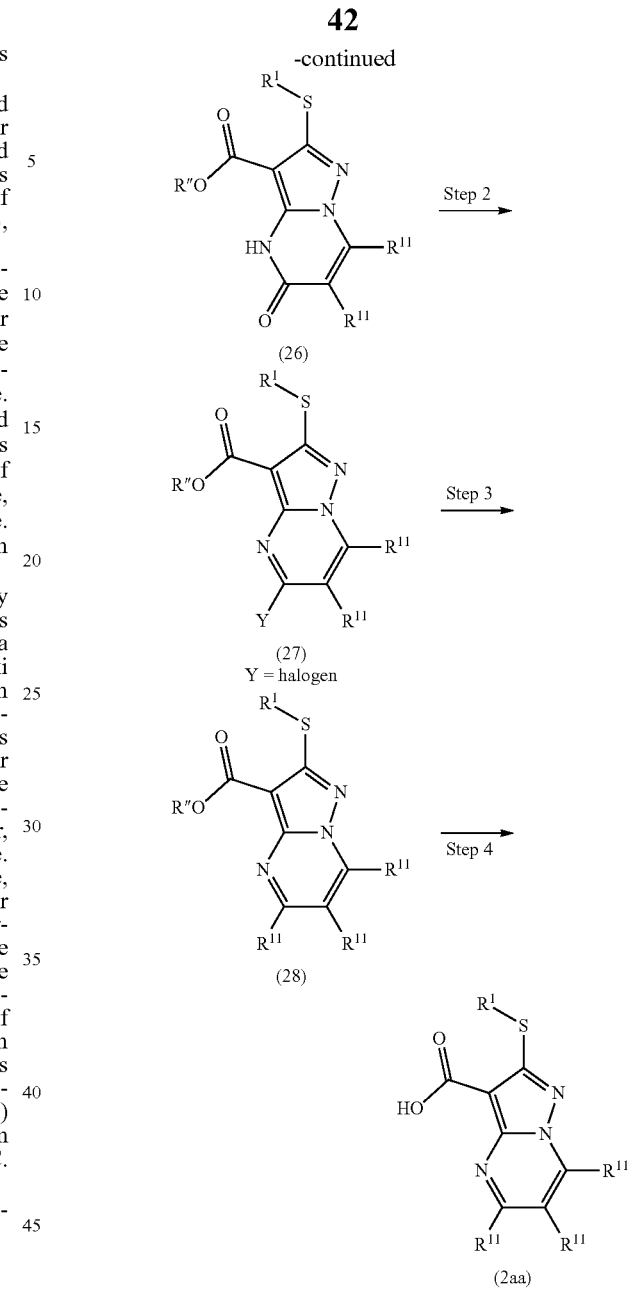

wherein, $R^1$ and $R^{11}$ have the meanings as described above.

Pyrazole derivative compound of formula (14) can undergo cyclocondensation with 1,3-dimethyluracil compound of formula (24) or alkoxyacrylate derivatives of formula (25) in the presence of a base to obtain pyrimidin-5-one derivatives of formula (26). Examples of the bases include sodium ethoxide, sodium methoxide, potassium tert-butoxide, potassium carbonate, sodium carbonate, cesium carbonate, potassium phosphate and the like. Examples of the solvent include methanol, ethanol, isopropanol, ethyleneglycol, N,N-dimethylacetamide, N,N-dimethylformamide and the like. The reaction can be carried out at temperatures ranging from about 50° C. and about 150° C. Such a reaction is well known in the literature, and also alternative reactions are well described in literature, for example *J. Org. Chem* 2007, 72, 1046; WO2018081417. Halogenation of compound of formula (26) with phosphorous oxychloride or phosphorous oxybromide can obtain compound of formula (28) as described in WO201108689, for example. The compound of formula (27) can be conveniently coupled under standard Suzuki cross coupling conditions to obtain the compound of formula (28) as described in step 5 of scheme 4. Subsequent alkaline hydrolysis of compound of formula (28) as described in step 6 of scheme 4 can obtain compound of formula (2aa).

A process for the synthesis of compound of formula (2ab) is depicted in scheme 6:

limited to dimethyl sulfoxide N,N-dimethylacetamide, N,N-dimethylformamide and the mixture thereof. The reaction can be carried out at temperatures ranging from about 50° C. and about 150° C. The compound of formula (31) can be further conveniently coupled under standard Suzuki cross coupling conditions to obtain the compound of formula (32) as described in step 5 of scheme 4. Subsequent alkaline hydrolysis of compound of formula (32) as described in step 6 of scheme 4 can obtain compound of formula (2ab).

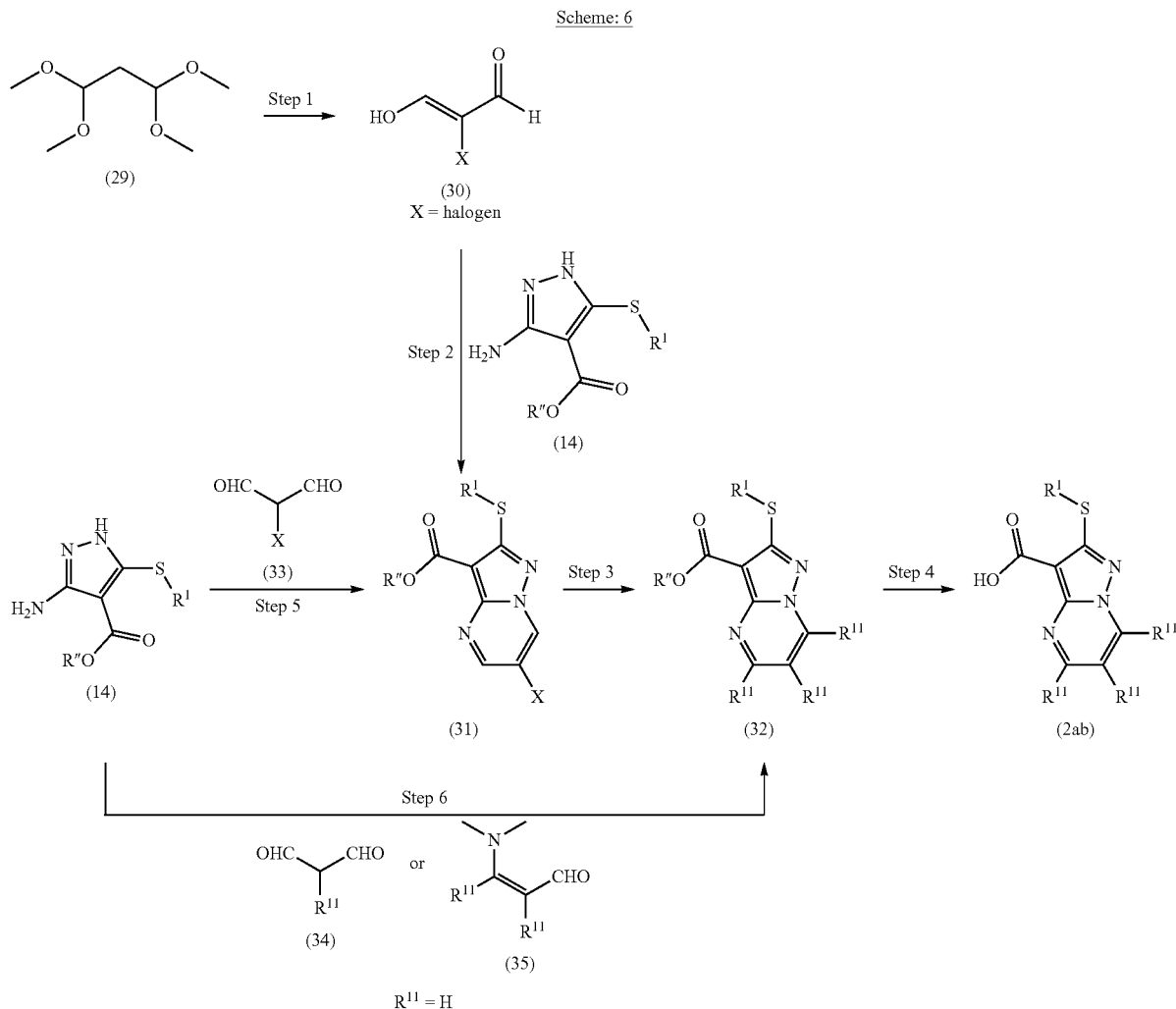

wherein, $R^1$ and $R^{11}$ have the meanings as described above.

Bisacetal protected malonaldehyde compound of formula (29) can be activated by halogenation with a halogenating agent, such as bromine, iodine, or chlorine, or N-Bromosuccinimide, N-Iodosuccinimide or N-Chlorosuccinimide under the acidic conditions, which may be generated by utilizing an acid independently selected from hydrochloric acid, sulfuric acid, methanesulfonic acid, trifluoroacetic acid, tetrafluoroboric acid or p-toluenesulfonic acid in a suitable solvent, e.g., water, to obtain a halogenated aldehyde, such as chloro-, iodo- or bromomalonaldehyde of formula (30). Following step 2, compound of formula (30) can be reacted with pyrazole derivative of formula (14) under suitable condensation conditions to obtain compound of formula (31). Examples of the solvent include but are not Alternatively, the compound of formula (31) can also be prepared by cyclization of pyrazole derivative of formula (14) with commercially available 2-halo-malonaldehydes of formula (33) under acid catalyzed conditions. Examples of acid include but not limited to acetic acid, sulfonic acid (e.g PTSA), sulfuric acid, hydrochloric acid. Examples of the solvent include but not limited to methanol, ethanol, isopropanol, ethyleneglycol and the like. The reaction can be carried out at temperatures ranging from about 0° C. and about 150° C. Pyrazolo[1,5-a]pyrimidine derivative of formula (32) can also be prepared following cyclocondensation of pyrazole derivative of formula (14) with either a commercially available malonaldehyde (34) or its equivalent (35). Derivative (35) may be prepared by methods described in *J. Het. Chem.* 1974, 44, 51.

A process for the synthesis of compound of formula (2b) is depicted in scheme 7:

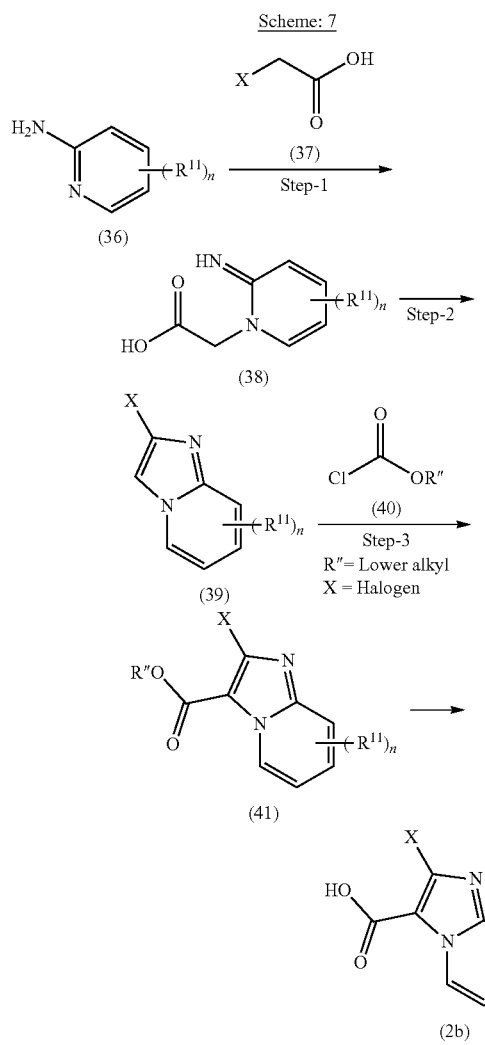

wherein, $R^{11}$ and n have the meanings as described above.

Compound of formula (38) can be prepared in a two-step procedure from 2-aminopyridine derivatives of formula (36) in which the first step involves the condensation reaction of 2-aminopyridine derivatives of formula (36) with haloacetic acid (37) under basic conditions, in a suitable solvent. Examples of suitable bases include but are not limited to, tertiary amines such as trimethylamine and diisopropylethyl amine. Examples of the suitable solvent include but are not limited to, water, methanol, ethanol, isopropanol, and the mixtures thereof. The reaction can be carried out at temperatures ranging from about 50° C. and about 150° C.

Intramolecular cyclization of compound of formula (38) in the presence of phosphorus oxychloride or phosphorus oxybromide at elevated temperature in a suitable solvent (e.g., toluene) can provide 2-haloimidazol[1,2-a]pyridine analogues of formula (39). Alkoxycarbonylation of compound of formula (38) using alkyl chlorocarbonate of formula (40) as one carbon source can be carried out using organometallic reagents such as n-butyl lithium and the like in ethereal solvents such as tetrahydrofuran, diethyl ether, methyl tert-butyl ether and the like to obtain compound of formula (41). The reaction can be carried out at temperatures ranging from about −78° C. and about 25° C. (WO2011163355). Subsequent alkaline hydrolysis of compound of formula (41) as described in step 6 of scheme 4 can obtain compound of formula (2b).

A process for the synthesis of compound of formula (2c) is depicted in scheme 8:

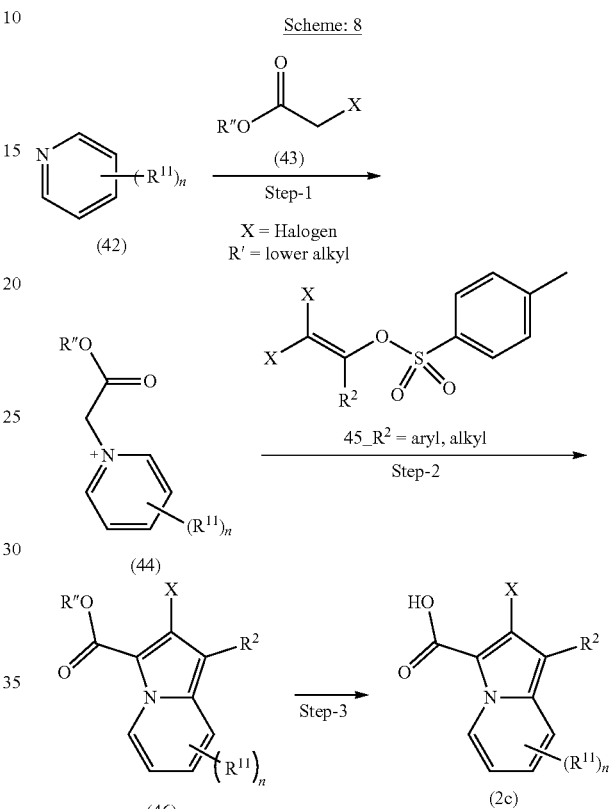

wherein, $R^2$, $R^{11}$ and n have the meanings as described above.

The compound of formula (44) can be prepared by allowing substituted pyridine compound of formula (42) to react with alkyl 2-haloacetate of formula (43) in an inert solvent include but are not limited to, ethyl acetate, acetone, diethyl ether, tetrahydrofuran, 1,4-dioxane, 1,2-dimethoxyethane, dichloroform, chloroform, N,N-dimethylformamide, toluene, xylene, methanol, ethanol, a mixture thereof and the like. Base such as, trimethylamine, pyridine, N,N-diisopropyl ethylamine, 2,6-lutidine can be used in the reaction. The reaction can be carried out at temperatures ranging from 0° C. to reflux temperature, and the reaction time is usually ranging from 30 minutes to 48 hours and is varying based on starting material, solvent used and the reaction temperature or the like.

Indolizine derivatives of formula (46) can be prepared by allowing compound of formula (44) to react with halo alkenyl tosylates of formula (45). The preparation of a compound of formula (45) has been described in the literature (*Tetrahedron* 2018, 74, 5295; *Organic Letters* 2010, 12, 5518). As an inert solvent, ethyl acetate, acetone, diethyl ether, tetrahydrofuran, 1,4-dioxane, 1,2-dimethoxyethane, dichloroform, chloroform, N,N-dimethylformamide, toluene, xylene, methanol, ethanol, a mixture thereof can be used in the reaction. As a base, potassium carbonate, sodium carbonate, cesium carbonate, sodium hydroxide, potassium fluoride, lithium hydroxide, trimethylamine, pyridine, N,N-diisopropyl ethylamine, 2,6-lutidine can be used in the reaction. The reaction can be carried out at temperatures ranging from 0° C. to reflux temperature. The reaction time is usually from 1 hour to 48 hours and is varying based on starting material, solvent used and the reaction temperature or the like. Such a reaction is known in the literature, and is well described, for example *Tetrahedron* 2004, 60, 5487.

Subsequent alkaline hydrolysis of compound of formula (46) as described in step 6 of scheme 4 can obtain compound of formula (2c).

A process for the synthesis of compound of formula (2ca) is depicted in scheme 9:

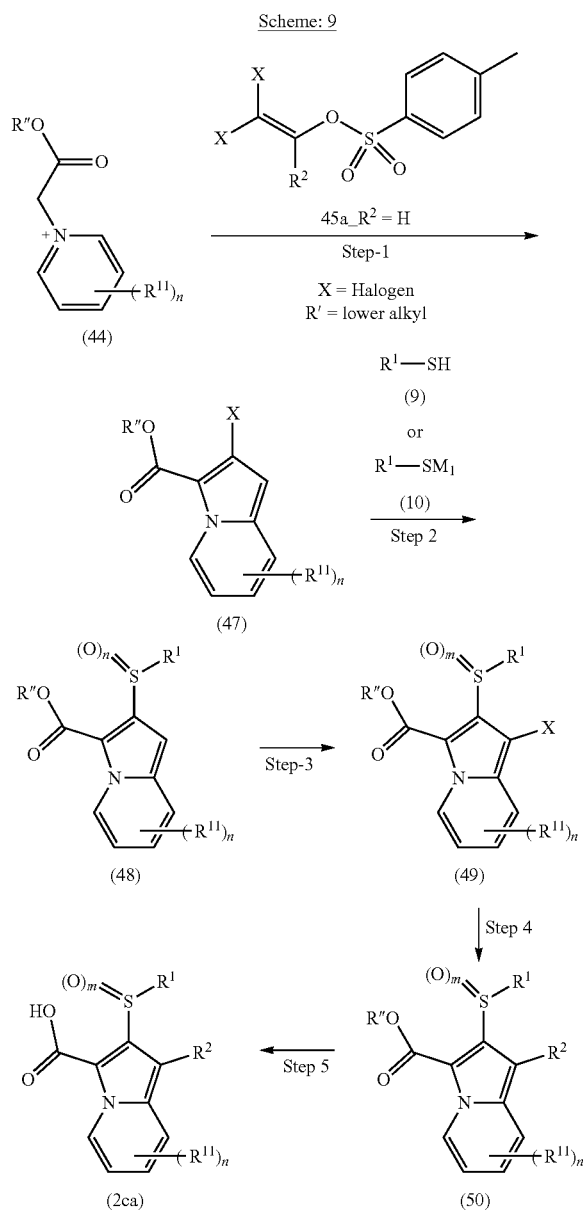

wherein, $R^1$, $R^2$, $R^{11}$ and n have the meanings described above.

Indolizine derivatives of formula (47) can be prepared by allowing compound of formula (44) to react with halo alkenyl tosylates of formula (45a) following step 2 as described in scheme 8. Compound of formula (47) can be reacted with compound of formula (9) or with a compound of formula (10) followed by oxidation to obtain compound of formula (48). Compound of formula (49) can be prepared from compound of formula (48) by halogenation with a halogenating agent, such as N-bromosuccinimide, N-chlorosuccinimide, N-iodosuccinimide. The reaction can be carried out in an inert solvent selected from dichloromethane, 2-dichloromethane, chloroform, carbon tetrachloride, acetic acid, acetonitrile, methanol, N,N-dimethyl formamide, and the like or a mixture thereof. The reaction can be carried out at temperatures ranging from 0° C. to reflux temperature. The reaction time is usually from 30 minutes to 48 hours and is varying based on starting material, solvent used and the reaction temperature.

The compound of formula (49) can be conveniently coupled under standard Suzuki cross coupling conditions to obtain the compound of formula (50) as described in step 5 of scheme 4. Subsequent alkaline hydrolysis of compound of formula (50) as described in step 6 of scheme 4 can obtain compound of formula (2ca).

The subgroup of compound of formula (I), wherein Q is $Q_3$ and $G_5$ is $CR^3$; R=H can be represented by compound of formula (52) and can be prepared by reacting compound of formula (6b) with compound of formula (51) to obtain compound of formula (52), wherein $G_5$ is $CR^3$, $R^3$=H,

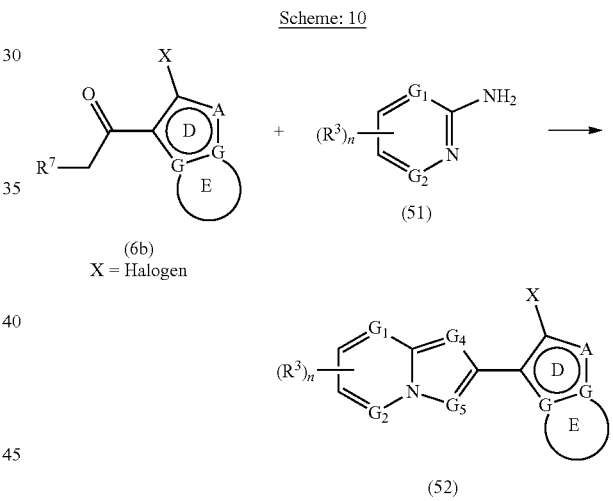

wherein, $R^3$, $R^7$, A, G, $G_1$, $G_2$, $G_4$, $G_5$, E and n have the meanings as described above.

Cyclization to obtain compound of formula (52) can be effected in the presence of a Lewis acid, such as Indium (III) triflate or Zinc (II) iodide, in solvents such as 1,2-dichlorobenzene, chlorobenzene, in the presence of catalytic copper (II) salts, such as copper (II) acetate, under an oxygen or air atmosphere. The reaction can be carried out at temperatures ranging from about 100° C. and about 180° C. Such reaction is precedented in the literature; see for example (*Adv. Synth. Catalysis,* 2013, 355, 1741; *J. Org. Chem,* 2013, 78, 12494). The synthesis of compound of formula (51) has been described in WO2015000715.

The compound of formula (52) can be reacted with a compound of formula (9) or with a compound of formula (10) to obtain compound of formula (53).

The compound of formula (53A) can be prepared according to the synthesis process as described in *Chem. Commun.,* 2017, 53, 2064-2067; *Tetrahedron Lett.* 2005, 46, 8007-8008 and WO2015071180A1.

Scheme: 11

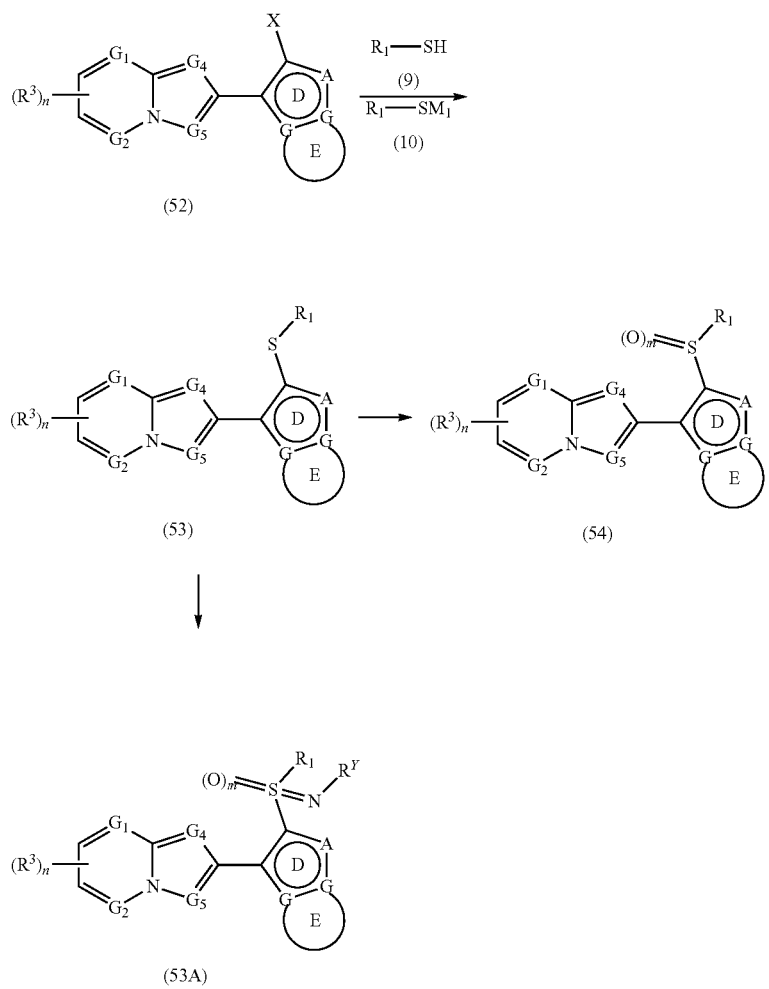

wherein, $R^1$, $R^3$, A, G, $G_1$, $G_2$, $G_4$, $G_5$, E, m and n have the meanings as described above.

The compound represented by formula (54) wherein m=1 (sulfoxide) and/or m=2 (sulfone), can be obtained by oxidation of the corresponding sulfide compound of formula (53) while applying appropriate oxidizing agents and conditions well known to those skilled in the art. Oxidizing agents such as m-chloroperoxybenzoic acid (mCPBA), hydrogen peroxide/glacial acetic acid, hydrogen peroxide/trifluoroacetic acid, hydrogen peroxide/potassium permanganate, hydrogen peroxide/p-toulenesulfonylimidazole, urea hydrogen peroxide/trifluoroacetic acid, oxone, sodium periodate, sodium hypochlorite and other organic peracids and the like can be used for oxidation. Examples of the solvent used in this reaction include aliphatic halogenated hydrocarbons such as dichloromethane and chloroform; alcohols such as methanol and ethanol and the mixtures thereof.

Halogenation of compound of formula (54) wherein $G_5=CR^3$; $R^3=H$, with a halogenating agent such as N-chlorosuccinamide, N-bromorosuccinamide, N-iodorosuccinamide, in a polar aprotic solvent such as acetonitrile or N,N-dimethylformamide, at ambient temperature can lead to compounds of formula ($Ic_1$),

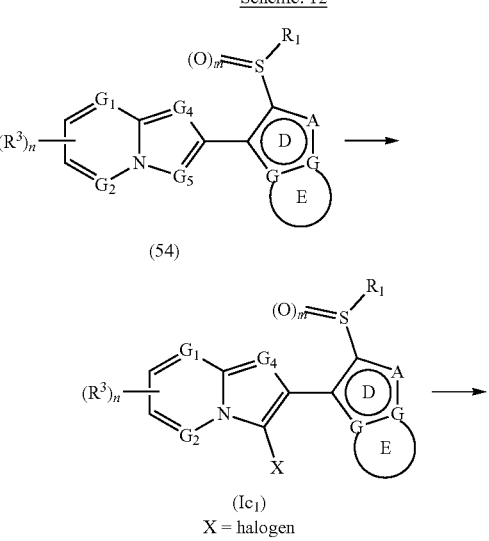

Scheme: 12

-continued

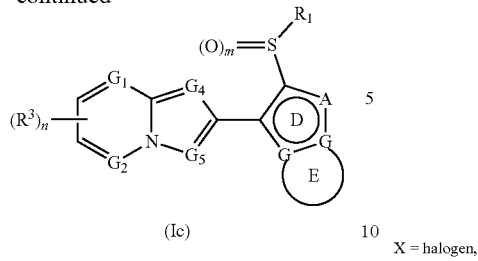

(Ic)

wherein, $R^1$, $R^3$, A, G, $G_1$, $G_2$, $G_4$, $G_5$, E, m and n have the meanings as described above.

The compounds of formula ($Ic_1$) can be reacted with compounds $R^3$—B(OR''')2 (R'''=H or R'''=pinacolate); in the presence of a palladium catalyst to give compounds of formula (Ic), wherein $G_5$=$CR^3$; $R^3$=alkyl, cycloalkyl, aryl, hetroaryl. Such Suzuki reactions are well precedented in the literature, see for example WO2012133607.

The process for the synthesis of compound of formula (6b), is depicted in scheme 12a:

Scheme: 12a

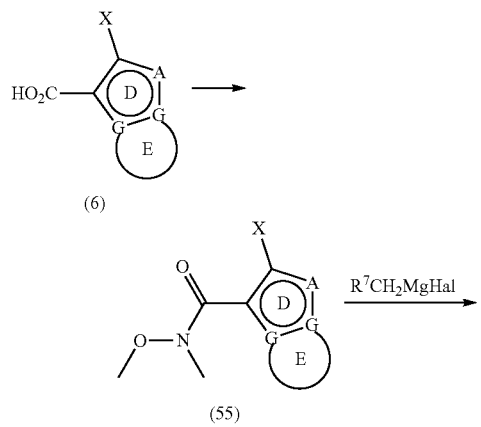

-continued (6b)

X = halogen, wherein, G, E and A have the meanings as described above.

Carboxylic acid of formula (6) can be converted to Weinreb amide of formula (55) upon reaction with N,O-Dimethylhydroxylamine by methods known to those skilled in art in analogy to procedures described in WO201175643 and EP2671582. Subsequent treatment of Weinreb amide of formula (55) with Grignard reagents of formula ($R^7CH_2MgHal$) according to the method described in *Tetrahedron Letters* 1981, 22, 3815 can obtain compound of formula (6b).

The process for the synthesis of compound of formula (1d) is depicted in scheme 13, wherein Q is $Q_4$ and $G_5$ is nitrogen, $G_4$ is $CR^3$ then compound of formula (1d) can be prepared by reacting compound of formula (56) with a compound of formula (57), optionally in the presence of a suitable base in an inert solvent. Alternatively, when $G_4$ is nitrogen, compound of formula (Id) can be prepared by reacting a compound of formula (58), in which $X^-$ is a halide ion or mesityl sulfonate with a compound of formula (59), optionally in the presence of a suitable base in an inert solvent.

Scheme: 13

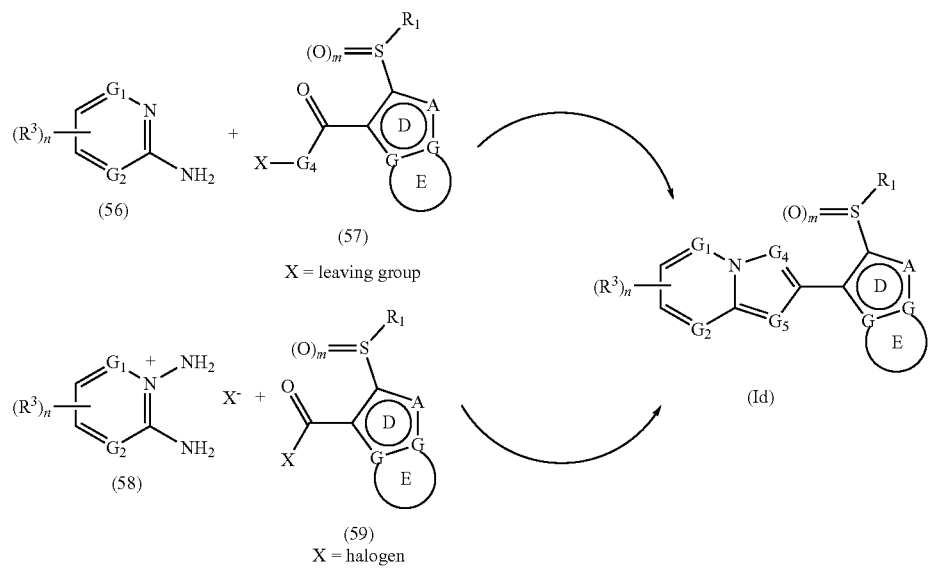

wherein, $R^1$, $R^3$, A, G, $G_1$, $G_2$, $G_4$, $G_5$, E, m and n have the meanings as described above.

The synthesis of compound of formula (56) has been described in the literature WO2015000715. Synthesis of compound of formula (57) can be achieved, for example, in analogy to EP1371638. Compound of formula (58) can be prepared via N-amination by reacting compound of formula (56) with O-mesitylenesulfonylhydroxylamine (MSH) as amination reagent or one of its equivalents, as described for example in *J. Heterocyclic Chem.* 1975, 12, 107 and *Synthesis* 1977, 1, 17.

The subgroup of compounds of formula (I), wherein Q is $Q_5$ and $G_5$ is $CR^3$, can be represented by the compounds of formula (Ie). The compound of formula (Ie) can be synthesized by reacting compound of formula (60) with a compound of formula (6b) analogously to the preparation of compound of formula (Ic).

Scheme: 14

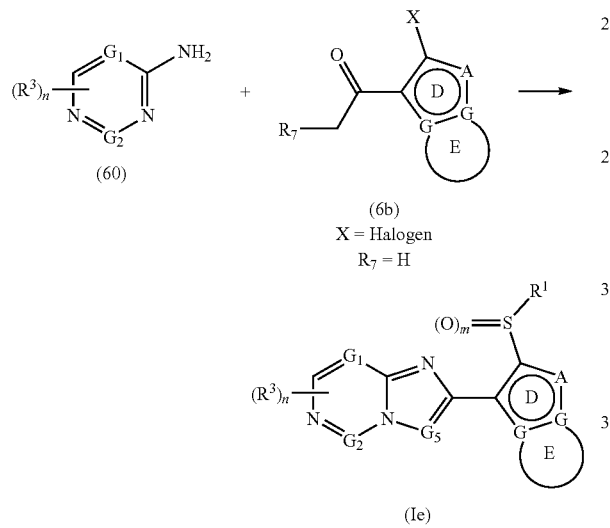

wherein, $R^1$, $R^3$, A, G, $G_1$, $G_2$, $G_5$, E, m and n have the meanings as described above.

Those skilled in the art will recognize that compound of formula (If) wherein Q is $Q_6$ and G5 is $CR^3$ can be similarly prepared by reaction of compound of formula (61) with compound of formula (57a) or (6a).

Scheme: 16

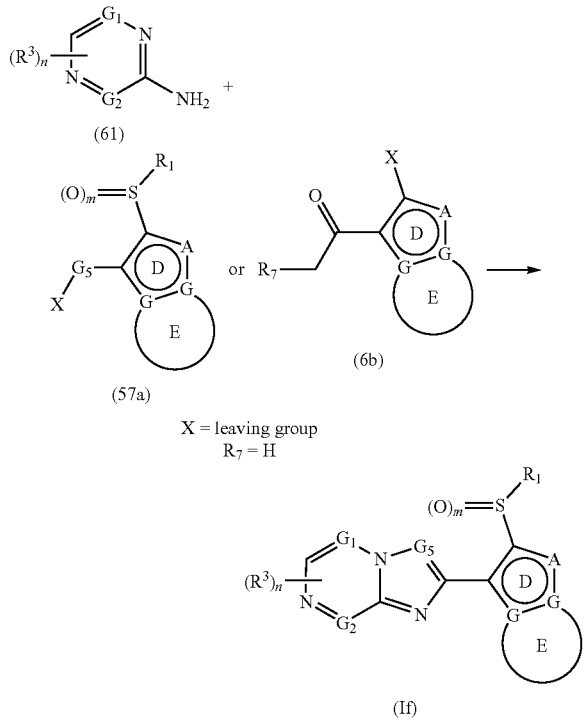

wherein, $R^1$, $R^3$, A, G, $G_1$, $G_2$, $G_5$, E, m and n have the meanings as described above.

The subgroup of compound of formula (I), wherein Q is $Q_3$ and $G_5$ is nitrogen, can be represented by the compound of formula (Ig) can be prepared by reacting a compound of formula (62) with compound of formula (59), optionally in the presence of a suitable base in an inert solvent.

Scheme: 16

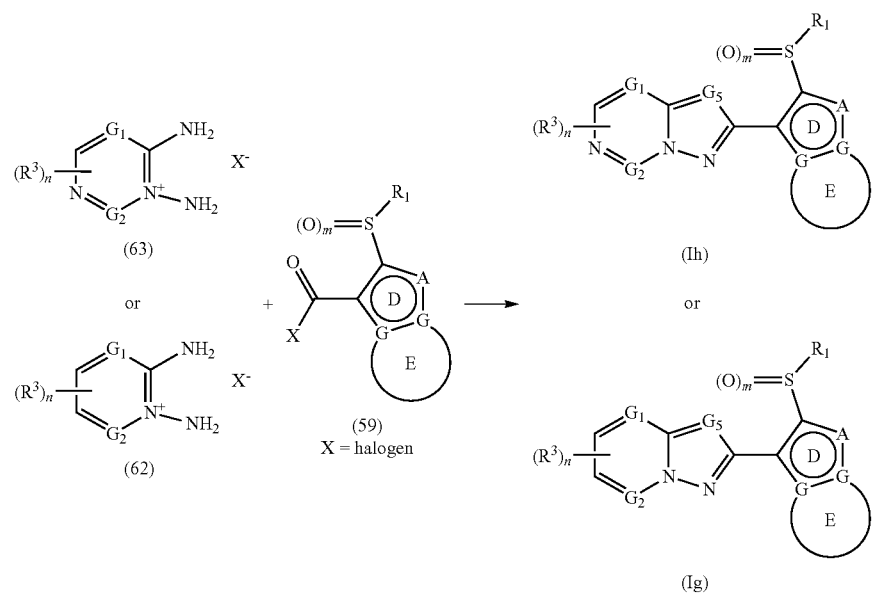

wherein, $R^1$, $R^3$, A, G, $G_1$, $G_2$, $G_5$, E, m and n have the meanings as described above.

The compound of formula (62) can be prepared via N-amination by reacting a compound of formula (51) with O-mesitylenesulfonylhydroxylamine (MSH) as amination reagent or one of its equivalent, as described for example in *J. Heterocyclic Chem.* 1975, 12, 107 and *Synthesis* 1977, 1, 17. The subgroup of compound of formula (I), wherein Q is $Q_5$ and $G_5$ is nitrogen, can be represented by the compound of formula (Ih) can be prepared by reacting a compound of formula (63) with compound of formula (59), optionally in the presence of a suitable base in an inert solvent.

The compound of formula (63) can be prepared via N-amination by reacting a compound of formula (60) with O-mesitylenesulfonylhydroxylamine (MSH) as amination reagent; the process is described in *J. Heterocyclic Chem.* 1975, 12, 107 and *Synthesis* 1977, 1, 17. Synthesis of compound of formula (60) has been described in the literature WO2007113558.

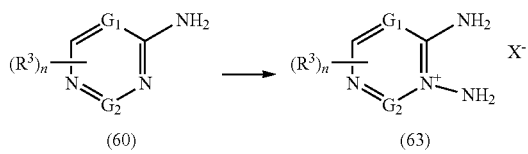

wherein, $R^3$, $G_1$ and $G_2$ have the meanings as described above.

In a further embodiment, Q is $Q_7$ involves the reaction of compound of formula (64) with compound of formula (65) to obtain compound of formula (Ii) wherein $G_5$ is $CR^3$ or N. The process is summarized in scheme 17 for compound of formula (Ii):

such as potassium or sodium tert-butoxides, or lithium diisopropylamide. The reaction can be carried out in solvents, preferably such that are inert under the prevailing reaction conditions for example ethereal solvents like diethyl ether, tetrahydrofuran, 1,4-dioxane, diisopropyl ether, 1,2-dimethoxy ethane, tert-butylmethyl ether; nitriles such as acetonitrile or propionitrile; aromatic hydrocarbons such as toluene, xylene; aprotic polar solvents such as N,N-dimethylformamide, N-methylpyrrolidine or dimethyl sulfoxide. The reaction can be carried out at temperatures ranging from about 0° C. and about 150° C. Such reaction is precedented in the literature; see for example *J. Am. Chem. Soc.* 2009, 131, 15080.

Intramolecular oxidative cyclization of N-substituted amidines of formula (66) in the presence or absence of a suitable base can be carried out analogously to that described in *J. Org. Chem* 2015, 80, 7219; *J. Org. Chem* 2014, 79, 4687. Examples of oxidants includes sodium hypochlorite, Lead(IV) acetate, manganese dioxide, Iodine, hypervalent iodine(III) reagents such as phenyliodine(III) diacetate (PIDA) and phenyliodine(III) bis(trifluoroacetate) (PIFA). The reaction can be carried out in solvents, preferably which are inert under the prevailing reaction conditions for example nitriles such as acetonitrile or propionitrile; aromatic hydrocarbons such as toluene or xylene; aprotic polar solvents such as N,N-dimethylformamide, N-methylpyrrolidine or dimethyl sulfoxide or ethyl acetate; halogenated hydrocarbons such as dichloromethane or dichloroethane; alcoholic solvents such as hexafluoroisopropanol, methanol, ethanol, trifluoroethanol, isopropanol. Suitable bases include potassium carbonate, sodium, carbonate and cesium carbonate. The reaction can be carried out at temperatures ranging from about 25° C. and about 180° C.

Alternatively, the compound of formula (1i) can be synthesized following step 3 in a single step involving transition-metal-catalyzed oxidative coupling of compound of formula (65) with compound of formula (64) analogously to that described in WO201341472 and *J. Am. Chem. Soc.* 2009, 131, 15080. Transition metal catalyst include zinc or copper salts such as copper(I) bromide, copper(I) chloride, copper(I) iodide, copper(II) acetate, zinc chloride, zinc(II) bromide, zinc iodide. Suitable bases include for example 1,10-phenanthroline, cesium carbonate, sodium carbonate, potassium carbonate. The reaction can be carried out in solvents, preferably which are inert under the prevailing reaction conditions for example aromatic hydrocarbons such

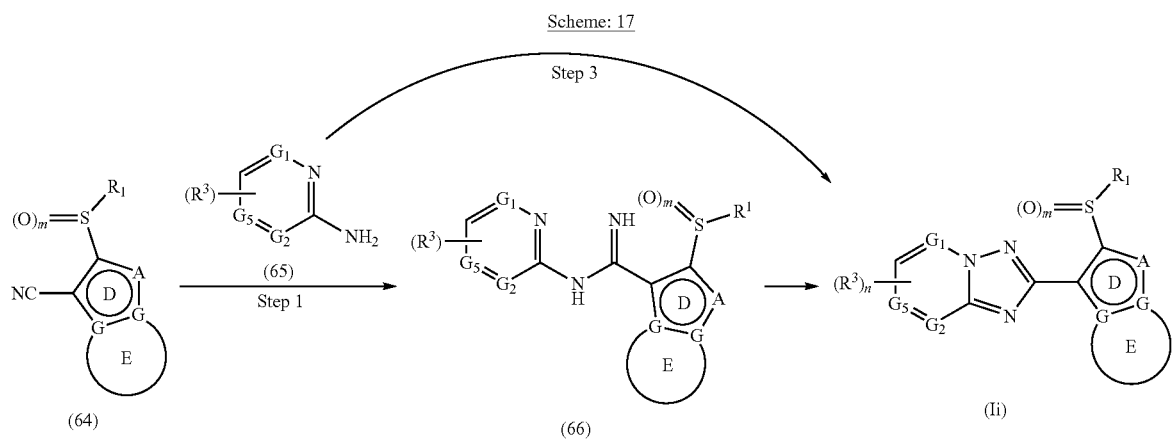

Scheme: 17 wherein, $R^1$, $R^3$, G, A, $G_1$, $G_2$, $G_5$, $G_6$, E, m and n have the meanings as described above.

The compound of formula (65) are either commercially available or can be prepared by methods known per se or analogously as described in WO2017113558 and WO2011090122.

In scheme 17, N-substituted amidines of formula (66) can be prepared by reacting the compound of formula (64) with the compound of formula (65) in the presence of suitable base. Examples of suitable bases are alkali metal hydrides such as sodium hydride, alkali metal salts of hexamethyldisilazane such as sodium hexamethyldisilazane, alcoholates as 1,2-dichlorobenzene, toluene or xylene. The reaction can be carried out at temperatures ranging from 50° C. to 150° C.

The compound of formula (64) are selected from the group consisting of formula (64a), (64b) and (64c)

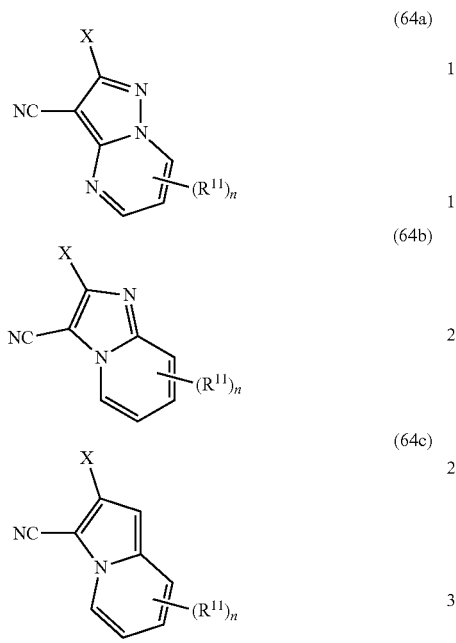

X = Halogen, —S(O)$_n$R$_1$
n = 0-2 wherein, R$^{11}$ and n have the meanings as described above.

The synthesis of compounds of formula (64a), (64b) and (64c) is described in the scheme 18 and scheme 19,

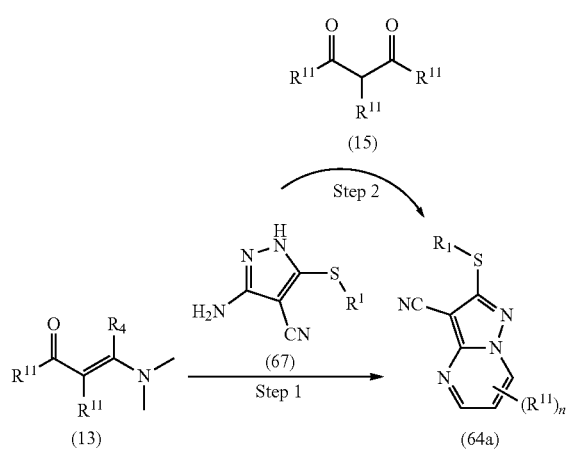

wherein, R$^1$, R$^{11}$ and m have the meanings as described above.

In the pyrimidine formation step, pyrazole derivative of formula (67) can undergo cyclocondensation reaction when treated with dielectrophilic compound of formula (13) or 1,3-diketone of formula (15) (e.g., a 1,3-dialdehyde or a 3-(dialkylamino)-prop-2-enal) following the similar procedure as described in scheme 3 to obtain compound of formula (64a). The preparation of a compound of formula (67) has been described in the literature (*Journal of Heterocyclic Chemistry* 2016, 53, 1231).

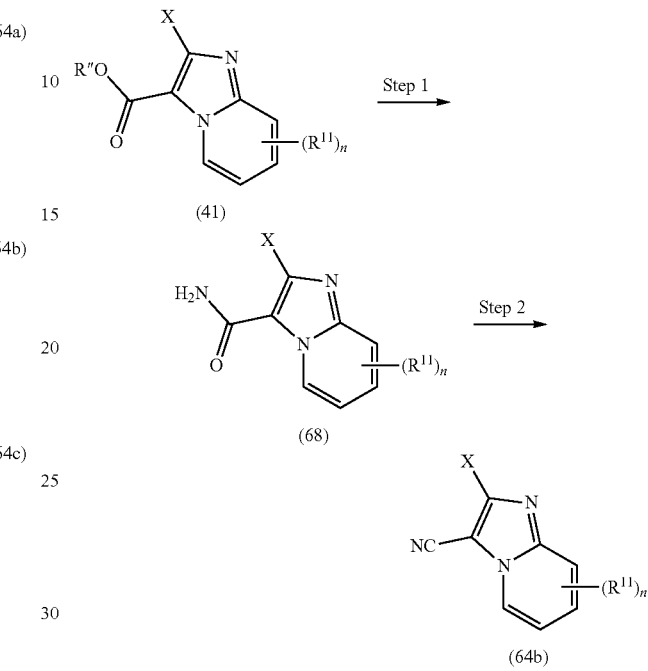

wherein, R$^{11}$ and n have the meanings described above.

The compound of formula (68) can be prepared from compound of formula (41) in analogy to the method described in WO201065760 and WO2016133838 using an ammonia source. Ammonium hydroxide or methanolic ammonia solution is usually used as a source of ammonia. The synthesis of compound of formula (41) has been described in scheme7. The reaction can be carried out under the prevailing reaction conditions employing ethereal solvents such as 1,4-dioxane or tetrahydrofuran or alcoholic solvents such as methanol, ethanol and the like at temperatures ranging from about 25° C. and about 100° C. Compound of formula (64b) can be prepared in analogy to the method described in WO201065760 and EP2740730 by the reaction of compound of formula (68) with dehydrating reagents such as but not limited to phosphoryl chloride or trifluoroacetic anhydride. The reaction can be carried out under the prevailing reaction conditions employing ethereal solvents such as 1,4-dioxane or tetrahydrofuran at temperatures ranging from about 25° C. and about 120° C.

The compound of formula (64c) can be prepared starting from compound of formula (46) following the similar reaction sequence and conditions as described for the preparation of compound of formula (64b) as described in scheme 19. The general synthesis of compound of formula (46) has been described in scheme8.

In one embodiment, Q is Q$_8$ involves the reaction of the compound of formula (2) or formula (59) or formula (69) with compound of formula (70) to obtain compound of formula (1j) wherein G$_4$ and G$_5$ is N. Scheme 20 describes a method of preparing compound of formula (Ij).

Scheme: 20

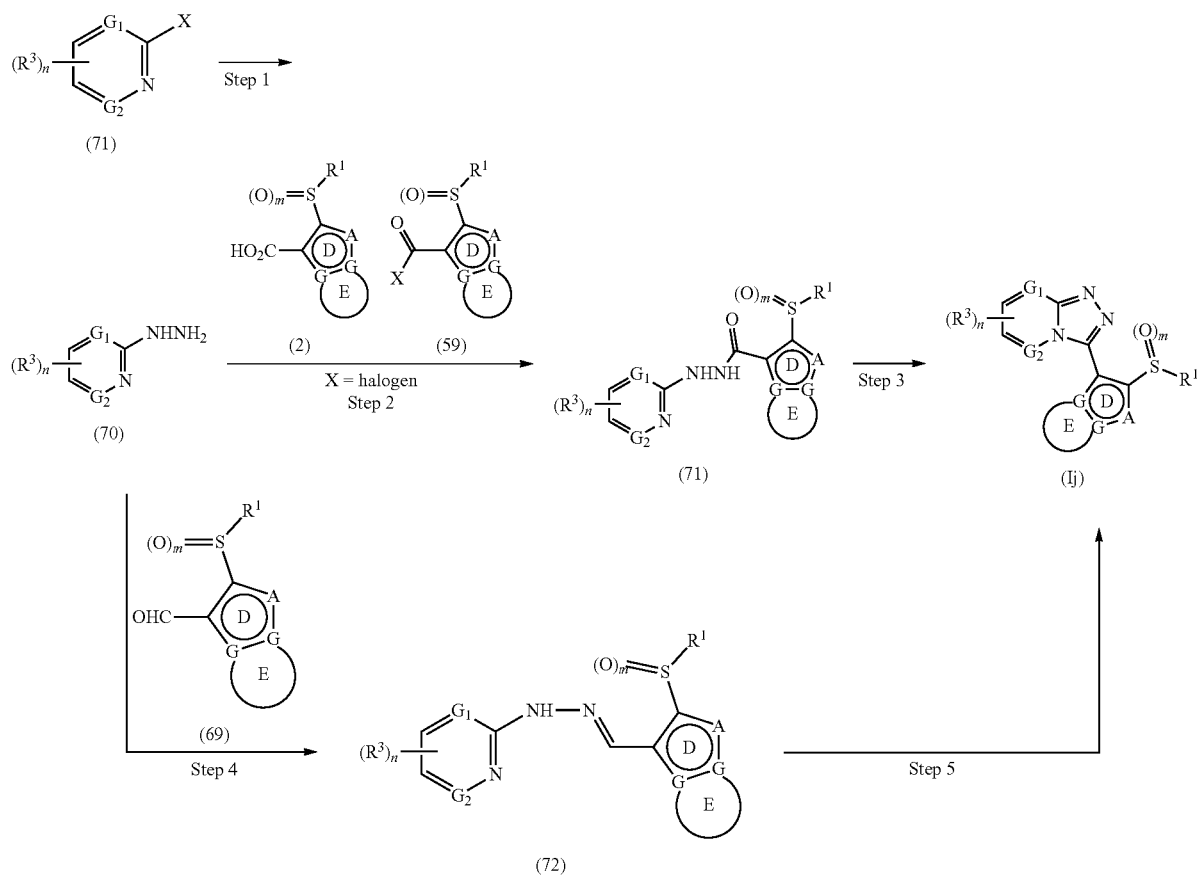

wherein, $R^1$, $R^3$, A, Z, G, $G_1$, $G_2$, E, m and n have the meanings as described above.

A halo derivative of compound of formula (71) can be obtained commercially or can be prepared by methods known in the literature or by other methods known to one skilled in the art. The reaction of a compound of formula (71) with hydrazine can be carried out using reaction conditions known to one skilled in the art (for example, Larock, R. C. "Comprehensive Organic Transformations: A Guide to functional Group Preparations, 2nd Ed.", 1999, Wiley-VCH). An intermediate compound of formula (70) in step 2 can react with an acid of compound of formula (2) using an appropriate set of amide coupling reagents such as N-methylmorpholine/isobutyl chloroformate, 1-ethyl-3-(3-dimethylaminopropyl)carbodiimide/hydroxybenzotriazole or other reagents described in "The Practice of Peptide Synthesis, 2nd Ed., Spring-Verlag, Bodanszy, Miklos (1993) can provide intermediate hydrazides of formula (71). Besides, acyl hydrazides of formula (71) can also be prepared following the reaction of a compound of formula (70) and an acid chloride of formula (59) in the presence of an appropriate base such as N,N-diisopropylethylamine or triethyl amine. Formation of triazolo compound of formula (Ij) can be achieved following cyclodehydration of compound of formula (71) using phosphorus oxychloride/phosphorus pentachloride, Lawesson's reagent, acetic acid or polyphosphoric acid at an elevated temperature, either under conventional procedure or under microwave irradiation. Alternatively, the transformation can also be achieved following the reaction of compound of formula (71) with triphenylphosphine dichloride or P(alkyl)$_3$/carbon tetrachloride in the presence of base such as triethyl amine or N,N-diisopropylethylamine, or other methods known to one skilled in the art. As an alternate approach hydrazones of formula (72) can be prepared following step 4 by carrying out reaction of compound of formula (70) with aldehyde compound of formula (69) by other methods known to one skilled in the art or by methods known in the literature (for example, Larock, R. C. "Comprehensive Organic Transformations: A Guide to functional Group Preparations, 2nd Ed.", 1999, Wiley-VCH). Further, following step 5 compound of formula (Ij) can also be prepared by oxidative cyclization of hydrazones of formula (72) using oxidants such as diacetoxy iodobenzene, N-bromosuccinimide, chloramine T, ceric ammonium nitrate, trichlorocyanuric acid, and copper(II) chloride.

The compound of formula (69) are selected from the group consisting of formula (69a), (69b) and (69c)

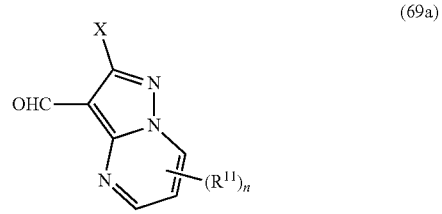

(69a)

-continued

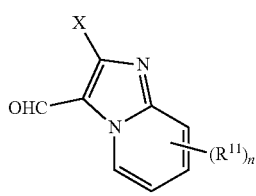
(69b)

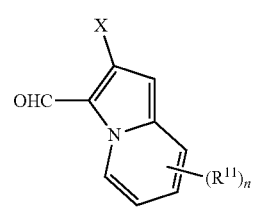
(69c)

n = 0-2; X = Halogen, —S(O)ₙR₁ wherein, $R^1$, $R^{11}$ and n have the meanings as described above.

The compound of formula (69a-c) can be prepared by partial reduction of compounds of formula (23), (41) and (46) by methods known in the literature (for example, Larock, R. C. "Comprehensive Organic Transformations: A Guide to functional Group Preparations, 2nd edition", 1999, Wiley-VCH).

The process for preparing compound of formula (I) wherein Q is $Q_9$ involves the reaction of compound of formula (6b) with compound of formula (73) to obtain compound of formula (74), wherein $G_3$ is $CR^3$; $R^3$=H. Subsequently compound of formula (1k) can be obtained from compound of formula (74), following the set of general reactions as described for the synthesis of compound (1c) in scheme 1. The synthesis of compound of formula (73) has been described in WO2018206479.

Scheme: 21

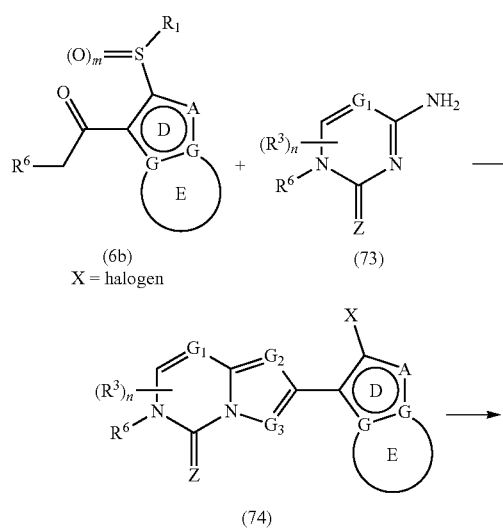

-continued

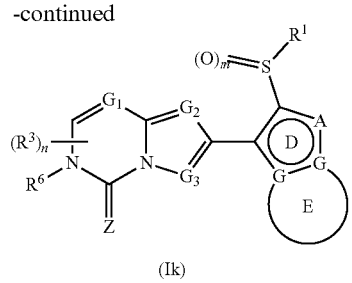
(Ik)

wherein, $R^1$, $R^3$, $R^6$, A, G, $G_1$, $G_2$, $G_3$, Z, E, m and n have the meanings as described above.

The process for preparing compound of formula (I) wherein Q is $Q_{10}$ involves the reaction of compound of formula (2) with compound of formula (75) to obtain compound of formula (76), wherein $G_3$=$NR^6$. Subsequently compound of formula (IL) can be obtained from compound of formula (76), following the set of general reactions as described in scheme 1. The synthesis of compound of formula (75) has been described in WO2017084879.

Scheme: 22

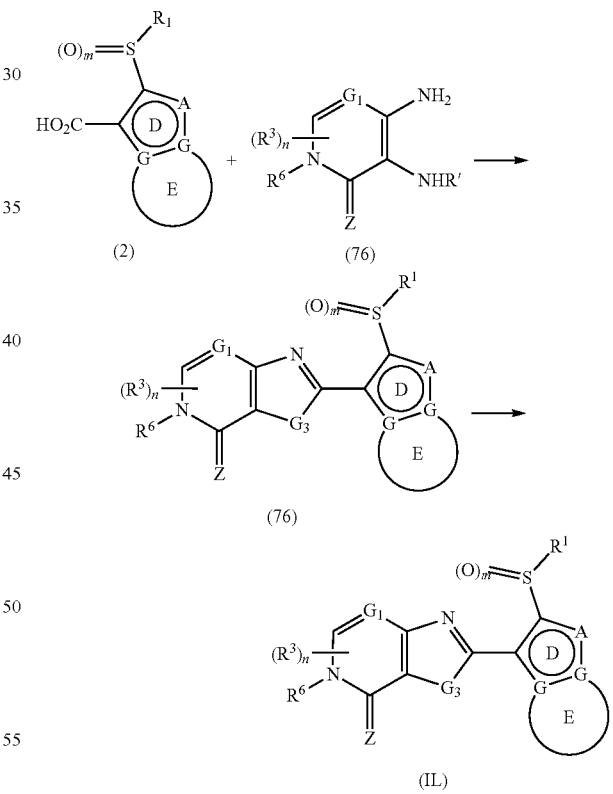

wherein, X is halogen, $R^1$, $R^3$, $R^6$, R', A, Z, $G_1$, $G_3$, E, m and n have the meanings as described above.

The process for preparing compound of formula (I) represented by compound of formula (IB) is by sulfilimination/sulfoximination of compound of formula (IA) wherein n=0 as described in *Chem. Commun.*, 2017, 53, 2064-2067; *Tetrahedron Lett.* 2005, 46, 8007-8008 and WO2015071180A1

Scheme: 23

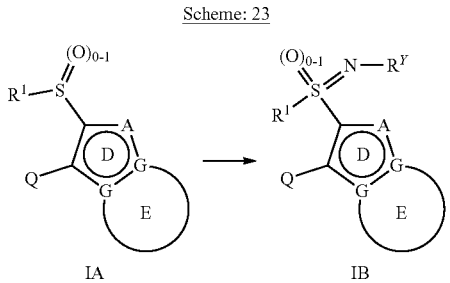

wherein, Q, $R^1$, $R^Y$, A, G, E, and n have the meanings as described above.

In one embodiment, the present invention provides a composition for controlling or preventing invertebrate pests. The composition comprises a biologically effective amount of the compound of formula (I) and at least one additional component selected from the group consisting of surfactants and auxiliaries.

In yet another embodiment, the present invention provides a compound of formula (I) or its N-oxides and salts into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T and F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers or binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers and Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar based surfactants are sorbitans, ethoxylated sorbitans, sucrose and glucose esters or alkylpolyglucosides. Examples of polymeric surfactants are homeor copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T and F Informa UK, 2006, chapter 5.

Suitable thickeners are polysaccharides (e.g. xanthan gum, carboxymethylcellulose), anorganic clays (organically modified or unmodified), polycarboxylates, and silicates. Suitable bactericides are bronopol and isothiazolinone derivatives such as alkylisothiazolinones and benzisothiazolinones. Suitable anti-freezing agents are ethylene glycol, propylene glycol, urea and glycerin. Suitable anti-foaming agents are silicones, long chain alcohols, and salts of fatty acids. Suitable colorants (e.g. in red, blue, or green) are pigments of low water solubility and watersoluble dyes. Examples are inorganic colorants (e.g. iron oxide, titan oxide, iron hexacyanoferrate) and organic colorants (e.g. alizarin-, azo and phthalocyanine colorants). Suitable tackifiers or binders are polyvinylpyrrolidone, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I or an N-oxide or salt thereof and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)

5-25 wt % of a compound I or an N-oxide or salt thereof and 1-10 wt % dispersant (e. g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I or an N-oxide or salt thereof and 5-10 wt % emulsifiers (e.g. calcium dodecylbenzenesulfonate and castor oil ethoxylate) are dissolved in up to 100 wt % water insoluble organic solvent (e.g. aromatic hydrocarbon). Dilution with water gives an emulsion.

iv) Emulsions (EW, EO, ES)

5-40 wt % of a compound I or an N-oxide or salt thereof and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I or an N-oxide or salt thereof are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I or an N-oxide or salt thereof are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I or an N-oxide or salt thereof are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I or an N-oxide or salt thereof are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance, iv) Microemulsion (ME) 5-20 wt % of a compound I or an N-oxide or salt thereof are added to 5-30 wt % organic solvent blend (e.g. fatty acid dimethylamide and cyclohexanone), 10-25 wt % surfactant blend (e.g. alkohol ethoxylate and arylphenol ethoxylate), and water up to 100%. This mixture is stirred for 1 h to produce spontaneously a thermodynamically stable microemulsion.

iv) Microcapsules (CS)

An oil phase comprising 5-50 wt % of a compound I or an N-oxide or salt thereof, 0-40 wt % water insoluble organic solvent (e.g. aromatic hydrocarbon), 2-15 wt % acrylic monomers (e.g. methylmethacrylate, methacrylic acid and a di or triacrylate) are dispersed into an aqueous solution of a protective colloid (e.g. polyvinyl alcohol). Radical polymerization initiated by a radical initiator results in the formation of poly(methyl acrylate) microcapsules. Alternatively, an oil phase comprising 5-50 wt % of a compound I according to the present invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition, ix) Dustable powders (DP, DS) 1-10 wt % of a compound I or an N-oxide or salt thereof are ground finely and mixed intimately with up to 100 wt % solid carrier, e.g. finely divided kaolin.

x) Granules (GR, FG) 0.5-30 wt % of a compound I or an N-oxide or salt thereof is ground finely and associated with up to 100 wt % solid carrier (e.g. silicate). Granulation is achieved by extrusion, spray-drying or the fluidized bed.

xi) Ultra-low volume liquids (UL) 1-50 wt % of a compound I or an N-oxide or salt thereof are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

In one another embodiment of present invention provides a agrochemical compositions compound of formula (I), which comprise active substance between 0.01 and 95% by weight, preferably between 0.1 and 90%, and more preferably between 1 and 70%, in particular between 10 and 60 by weight of active substance. The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying or treating compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e. g. by dusting, coating or drenching seed, amounts of active substance of from 0.1 to 1000 g, preferably from 1 to 500 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix).

These agents can be admixed with the compositions according to the present invention in a weight ratio of 1:100 to 100:1, preferably 1:10 to 10:1.

The user can apply the composition according to the present invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the present invention is thus obtained. Usually, 20 to 6000 liters, preferably 35 to 1000 litres, more preferably 50 to 500 liters, of the ready-to-use spray liquor are applied per hectare of agricultural useful area.

According to one embodiment, individual components of the composition according to the present invention such as parts of a kit or parts of a binary or ternary mixture may be mixed by the user himself in a spray tank and further auxiliaries may be added, if appropriate.

The compounds and compositions of the present invention are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits.

The compounds of the present invention are characterized by favorable metabolic and/or soil residual patterns and exhibit activity controlling a spectrum of agronomic and non-agronomic invertebrate pests. The compounds of the present invention are preventively and/or curatively valuable active ingredients in the field of pest control, even at low rates of application, which can be used against insecticide resistant pests such as insects and mites, and are well tolerated by warm-blooded species, fish and plants.

In the context of the present invention "invertebrate pest control" means inhibition of invertebrate pest development (including mortality) that causes significant reduction in feeding or other injury or damage caused by the pest; (related expressions are defined analogously.) As referred to in the present invention, the term "invertebrate pest" includes arthropods, gastropods and nematodes of economic importance as pests. The term "arthropod" includes insects, mites, spiders, scorpions, centipedes, millipedes, pill bugs and symphylans.

The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests.

The compounds of the present invention display activity against economically important agronomic pests in forest, greenhouse, nursery, ornamentals, turfgrass, food and fiber, public and animal health, domestic and commercial structure, household, and stored product pests. These include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hubner), black cutworm (*Agrotis ipsilon* Hufnagel), cabbage looper (*Trichoplusia ni* Hubner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hubner), navel orangeworm (*Amyelois transitella* Walker), corn root webworm (*Crambus caliginosellus* Clemens), sod webworm (*Herpetogramma licarsisalis* Walker)); leafrohers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella gemnanica* Linnaeus), brown-banded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition it includes: adults and larvae of the order Dermaptera including earwigs from the family Forficulidae (e.g., European earwig (*Forficula auricularia* Linnaeus), black earwig (*Chelisoches mono* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whitefiies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, M. differentialis Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinellafrit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chiysomya* spp., *Phonnia* spp.), and other muscoid fly pests, horse flies (e.g., *Tabanus* spp.), botflies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Fôrster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga including the head louse (*Pediculus humanus* capitis De Geer), body louse (*Pediculus humanus humanus* Linnaeus), chicken body louse (*Menacanthus stramineus* Nitszch), dog biting louse (*Trichodectes cams* De Geer), fluff louse (*Goniocotes gallinae* De Geer), sheep body louse (*Bovicola ovis* Schrank), short-nosed cattle louse (*Haematopinus eurystemus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephatides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch and Mulaik) and the black widow spider (*Latrodectus mactans* Fabricius), and centipedes in the order Scutigeromorpha such as the house centipede (*Scutigera coleoptrata* Linnaeus). Activity also includes members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala peifoliata* in horses, *Fasciola hepatica* Linnaeus in ruminants, etc.).

The compounds of the present invention show particularly high activity against pests in the order of Lepidoptera (e.g., *Alabama argillacea* Hubner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoveipa armigera* Hubner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis and Schiffernnüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hubner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tula absoluta* Meyrick (tomato leafminer)).

Compounds of the present invention also have commercially significant activity on members from the order Homoptera including: *Acyrthisiplionpisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (tarnip aphid), *Metopolophium dirrhodum* Walker (cereal aphid), *Macrosipum euphorbiae* Thomas (pqtato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii*, Boyer de Fonscolombe (black citrus aphid), and *Toxoptera citiicida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows and Perring (silverleaf whitefly), *Dialeurodes citri* Ashmead (citrus whitefly) and *Trialeurodes vaporariorum* Westwood (greenhouse whitefly); *Empoasca fabae* Harris, (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stal (rice leafhopper), *Nilaparvata lugens* Stal (brown planthopper), *Peregrinus maidis* Ashmead (corn planthopper), *Sogatella furcifera* Horvath (white-backed planthopper), *Sogatodes orizicola* Muir (rice delphacid), *Typhloeyba pomaria* McAfee white apple leafhopper, *Erythroneoura* spp. (grape leafhoppers); *Magicidada septendecim* Linnaeus (periodical cicada); *Iceryapurchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

These compounds also have activity on members from the order Hemiptera including: *Acrostemum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-S chaffer (cotton stainer), *Euchistus servus* Say (brown stink bug), *Euchistus variolrius* Palisot deBeauvois (one-spotted stink bug), *Graptósthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* DaEas (large milkweed bug), *Pseudatomoscelis seriatus* Reuter (cotton fleahopper).

Other insect which are controlled by compounds of formula (I) of the present invention include: Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes*, *Athous* or *Limonius*).

Particularly, the compounds of formula (I), their N-oxides, their isomers, their polymorphs and their salts are especially suitable for efficiently combating the following pests: Insects from the order of the lepidopterans (Lepidoptera), for example *Agrotis ypsilon*, *Agrotis segetum*, *Alabama argillacea*, *Anticarsia gemmatalis*, *Argyresthia conjugella*, *Autographa gamma*, *Bupalus piniarius*, *Cacoecia murinana*, *Capua reticulana*, *Cheimatobia brumata*, *Chilo infuscatellus*, *Choristoneura fumiferana*, *Choristoneura occidentalis*, *Cirphis unipuncta*, *Cydia pomonella*, *Dendrolimus pini*, *Diaphania nitidalis*, *Diatraea grandiosella*, *Earias insulana*, *Earias vittela*, *Elasmopalpus lignosellus*, *Eupoecilia ambiguella*, *Evetria bouliana*, *Feltia subterranea*, *Galleria mellonella*, *Grapholita funebrana*, *Grapholita molesta*, *Helicoverpa armigera*, *Helicoverpa virescens*, *Helicoverpa zea*, *Hellula undalis*, *Hibernia defoliaria*, *Hyphantria cunea*, *Hyponomeuta malinellus*, *Keiferia lycopersicella*, *Lambdina fiscellaria*, *Laphygma exigua*, *Leucoptera coffeella*, *Leucoptera scitella*, *Lithocolletis blancardella*, *Lobesia botrana*, *Loxostege sticticalis*, *Leucinodes orbonalis*, *Lymantria dispar*, *Lymantria monacha*, *Lyonetia clerkella*, *Malacosoma neustria*, *Mamestra brassicae*, *Orgyia pseudotsugata*, *Ostrinia nubilalis*, *Panolis flammea*, *Pectinophora gossypiella*, *Peridroma saucia*, *Phalera bucephala*, *Phthorimaea operculella*, *Phyllocnistis citrella*, *Pieris brassicae*, *Plathypena scabra*, *Plutella xylostella*, *Pseudoplusia includens*, *Rhyacionia frustrana*, *Scirpophaga incertulas*, *Scrobipalpula absoluta*, *Sitotroga cerealella*, *Sparganothis pilleriana*, *Spodoptera frugiperda*, *Spodoptera littoralis*, *Spodoptera litura*, *Spodoptera exigua*, *Thaumatopoea pityocampa*, *Tortrix viridana*, *Trichoplusia ni* and *Zeiraphera canadensis*; and Beetles (Coleoptera), for example *Agrilus sinuatus*, *Agriotes lineatus*, *Agriotes obscurus*, *Amphimallus solstitialis*, *Anisandrus dispar*, *Anthonomus grandis*, *Anthonomus pomorum*, *Aphthona euphoridae*, *Athous haemorrhoidalis*, *Atomaria linearis*, *Blastophagus piniperda*, *Blitophaga undata*, *Bruchus rufimanus*, *Bruchus pisorum*, *Bruchus lentis*, *Byctiscus betulae*, *Cassida nebulosa*, *Cerotoma trifurcata*, *Cetonia aurata*, *Ceuthorrhynchus assimilis*, *Ceuthorrhynchus napi*, *Chaetocnema tibialis*, *Conoderus vespertinus*, *Crioceris asparagi*, *Ctenicera* ssp., *Diabrotica longicornis*, *Diabrotica semipunctata*, *Diabrotica undecimpunctata Diabrotica speciosa*, *Diabrotica virgifera*, *Epilachna varivestis*, *Epitrix hirtipennis*, *Eutinobothrus brasiliensis*, *Hylobius abietis*, *Hypera brunneipennis*, *Hypera postica*, *Ips typographus*, *Lema bilineata*, *Lema melanopus*, *Leptinotarsa decemlineata*, *Limonius californicus*, *Lissorhoptrus oryzophilus*, *Melanotus communis*, *Meligethes aeneus*, *Melolontha hippocastani*, *Melolontha melolontha*, *Oulema oryzae*, *Otiorrhynchus sulcatus*, *Otiorrhynchus ovatus*, *Phaedon cochleariae*, *Phyllobius pyri*, *Phyllotreta chrysocephala*, *Phyllophaga* sp., *Phyllopertha horticola*, *Phyllotreta nemorum*, *Phyllotreta striolata*, *Popillia japonica*, *Sitona lineatus* and *Sitophilus granaria*; flies, mosquitoes (Diptera), e.g. *Aedes aegypti*, *Aedes albopictus*, *Aedes vexans*, *Anastrepha ludens*, *Anopheles maculipennis*, *Anopheles crucians*, *Anopheles albimanus*, *Anopheles gambiae*, *Anopheles freeborni*, *Anopheles leucosphyrus*, *Anopheles minimus*, *Anopheles quadrimaculatus*, *Calliphora vicina*, *Ceratitis capitata*, *Chrysomya bezziana*, *Chrysomya hominivorax*, *Chrysomya macellaria*, *Chrysops discalis*,

*Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa*; termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus*; cockroaches (Blattaria Blattodea), e.g. *Blattella germanica, Blattella asahinae, Periplaneta americana, Periplaneta japonica, Periplaneta brunnea, Periplaneta fulligginosa, Periplaneta australasiae,* and *Blatta orientalis*; ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonic, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile*; crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina*; Araneida, e.g. *Latrodectus mactans,* and *Loxosceles reclusa*; fleas (Siphonaptera), e.g. *Ctenocephalides felis, Ctenocephalides canis, Xenopsylla cheopis, Pulex irritans, Tunga penetrans,* and *Nosopsyllus fasciatus*, silverfish, firebrat (Thysanura), e.g. *Lepisma saccharina* and *Thermobia domestica*, centipedes (Chilopoda), e.g. *Scutigera oleoptrata*, millipedes (Diplopoda), e.g. *Narceus* spp., Earwigs (Dermaptera), e.g. *Forficula auricularia*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon allinae, Menacanthus stramineus* and *Solenopotes capillatus*. Collembola (springtails), e.g. *Onychiurus* ssp.

The compounds of formula (I) of the present invention are also suitable for controlling Nematodes: plant parasitic nematodes such as root knot nematodes, *Meloidogyne hapla, Meloidogyne incognita, Meloidogyne javanica,* and other *Meloidogyne* species; cyst forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of formula (I) and their salts are also useful for controlling arachnids (Arachnoidea), such as acarian (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis*.

In one embodiment of the present invention, the present invention provides the compound of formula (I) is useful for controlling insects selected form sucking or piercing insects such as insects from the genera Thysanoptera, Diptera and Hemiptera, in particular the following species:

Thysanoptera: *Frankliniella furca, Frankliniella occidentalis, Frankliniella tritici, Scirtothrips citri, Thrips oryzae, Thrips palmi* and *Thrips tabaci,*

Diptera: *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria,*

*Chrysops discalis, Chrysops silacea, Chrysops atlanticus, Cochliomyia hominivorax, Contarinia sorghicola Cordylobia anthropophaga, Culicoides furens, Culex pipiens, Culex quinquefasciatus, Culex nigripalpus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates spp., Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga spp., Simulium vittatum, Stomoxys calcitrans, Tabanus bovinus, Tabanus atratus, Tabanus lineola,* and *Tabanus similis, Tipula oleracea,* and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulocorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mail, Psylla pini, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii.*

In one embodiment, the present invention provides a composition comprising a biologically effective amount of the compound of formula (I) and at least one additional biological active compatible compound selected from fungicides, insecticides, nematicides, acaricides, biopesticides, herbicides, plant growth regulators, antibiotics, fertilizers and nutrients. The compounds used in the composition and in combination with the compound of formula (I) are also termed as active compatible compounds.

The known and reported fungicides, insecticides, nematicides, acaricides, biopesticides, herbicides, plant growth regulators, antibiotics and nutrients can be combined with at least one compound of the formula (I) of the present disclosure. For example, fungicides, insecticides, nematicides, acaricides, biopesticides, herbicides, plant growth regulators, antibiotics, fertilizers and nutrients disclosed and reported in WO2016156129 and/or WO2017153200 can be combined with at least one compound of formula (I) of the present disclosure.

The fungicides, insecticides, nematicides, acaricides, biopesticides, herbicides, plant growth regulators, antibiotics, fertilizers and nutrients reported in WO2016156129 and or WO2017153200 are incorporated herein by way of reference as non-limiting examples to be combined with at least one compound of the formula (I) of the present disclosure.

Particularly, the compounds of the present invention can be mixed with at least one additional biological active compatible compound (mixing partner) which includes but is not limited to insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility.

Examples of such biologically active compounds or agents/mixing partners with which compound of formula (I) of the present invention can be combined/formulated are disclosed in the WO2019072906A1 (page 27 to 37).

In one embodiment, the biological agents for mixing with compounds of the present invention include *Bacillus thuringiensis, Bacillus thuringiensis* delta endotoxin as well as naturally occurring and genetically modified viral insecticides including members of the family Baculoviridae as well as entomophagous fungi.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compounds or agents having a similar spectrum of control but a different mode of action. Contacting a plant genetically modified to express a plant protection compound (e.g., protein) or the locus of the plant with a biologically effective amount of a compound of the invention can also provide a broader spectrum of plant protection and be advantageous for resistance management.

In one embodiment of the present invention, the biologically effective amount of the compound of formula (I) in the compositions ranges from 0.1% to 99% by weight with respect to the total weight of the composition, preferably from 5% to 50% by weight with respect to the total weight of the composition.

The present invention furthermore provides a method of combating invertebrate pests, said method comprising contacting the invertebrate pests, their habitat, breeding ground, food supply, plant, seed, soil, area, material or environment in which the invertebrate pests are growing or may grow, or the materials, plants, seeds, soils, surfaces or spaces to be protected from pest attack or infestation with a biologically effective amount of the compound or the composition of the present invention.

Invertebrate pests are controlled and protection of agronomic, horticultural and specialty crops, animal and human health is achieved by applying one or more of the compounds of the present invention, in an effective amount, to the environment of the pests including the agronomic and/or nonagronomic locus of infestation, to the area to be protected, or directly on the pests to be controlled. Thus, the present invention further comprises a method for the control of foliar- and soil-inhabiting invertebrates and protection of agronomic and/or nonagronomic crops, comprising contacting the invertebrates or their environment with a biologically effective amount of one or more of the compounds of the present invention, or with a composition comprising at least one such compound or a composition comprising at least one such compound and an effective amount of at least one additional biologically active compound or agent. A preferred method of contact is by spraying. Alternatively, a granular composition comprising a compound of the present invention can be applied to the plant foliage or the soil. Compounds of the present invention are effective in delivery through plant uptake by contacting the plant with a composition comprising a compound of the present invention applied as a soil drench of a liquid formulation, a granular formulation to the soil, a nursery box treatment or a dip of transplants. Other methods of contact include application of a compound or a composition of the present invention by direct and residual sprays, aerial sprays, seed coats, microencapsulations, systemic uptake, baits, eartags, boluses, foggers, fumigants, aerosols, dusts and many others.

The compounds of the present invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact. The compounds of the present invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butpxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The animal pest, i.e. the insects, arachnids and nematodes, the plant, soil or water in which the plant is growing can be contacted with compounds of formula (I), their N-oxides and salts or composition(s) containing them by any application method known in the art. As such, "contacting" includes both direct contact (applying the compounds/compositions directly on the animal pest or plant typically to the foliage, stem or roots of the plant) and indirect contact (applying the compounds/compositions to the locus of the animal pest or plant).

The compounds of the present invention or the pesticidal compositions comprising them may be used to protect growing plants and crops from attack or infestation by animal pests, especially insects, acaridae or arachnids by contacting the plant/crop with a pesticidally effective amount of at least one compound of the present invention. The term "crop" refers both to growing and harvested crops.

In one embodiment, the present invention provides a method for protecting crops from attack or infestation by invertebrate pests, which comprises contacting the crop with a biologically effective amount of the compound or the composition of the present invention, isomer, polymorph, N-oxide or salt thereof.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

In one embodiment, the present invention provides to a method for the protection of seeds from soil insects and of the seedlings roots and shoots from soil and foliar insects comprising contacting the seeds before sowing and/or after pre-germination with the compound or the composition of the present invention, N-oxide or salt thereof.

Furthermore, the present invention provides a method for treating or protecting animals against infestation or infection by parasites which comprises orally, topically or parenterally administering or applying to the animals a biologically effective amount of compound or composition of the present invention, isomer, polymorph, N-oxide or veterinary acceptable salt thereof.

For use in treating crop plants, the rate of application (applying effective dosages) of the compound of the present invention may be in the range of 1 gai to 5000 gai per hectare in agricultural or horticultural crops, preferably from 25 g to 600 g per hectare, more preferably from 50 g to 500 g per hectare.

The compounds and the compositions of the present invention are particularly useful in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

Particularly, the compound or the composition of the present invention are useful in protecting agricultural crops such as cereals, corn, rice, soybean and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and other vegetables, and ornamentals.

The compounds of the present invention are effective through both contact (via soil, glass, wall, bed net, carpet, plant parts or animal parts), and ingestion (bait or plant part).

The compounds of the present invention may also be applied against non-crop invertebrate pests, such as ants, termites, wasps, flies, mosquitos, crickets, or cockroaches.

For use against said non-crop pests, compounds of the present invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish or blood meal, insect parts, egg yolk), from fats and oils of animal and/or plant origin, or mono-, oligoor polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used. For use in spray compositions, the content of active ingredient is from 0.001 to 80 weights %, preferably from 0.01 to 50 weight % and most preferably from 0.01 to 15 weight %.

The compounds of the present invention and their respective compositions can also be used in mosquito and fumigating coils, smoke cartridges, vaporizer plates or long-term vaporizers and also in moth papers, moth pads or other heat-independent vaporizer systems.

The methods to control infectious diseases transmitted by insects (e.g. malaria, dengue and yellow fever, lymphatic filariasis, and leishmaniasis) with compounds of formula (I) and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of the present invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc.

In case of application against ants doing harm to crops or human beings, a compound of the present invention is applied to the crops or the surrounding soil, or is directly applied to the nest of ants or the like.

Seed Treatment

The present invention further provides a treated seed comprising the compounds of the present invention, particularly in an amount ranging from about 0.0001% to about 1% by weight of the seed before treatment.

The compounds of the present invention are also suitable for the treatment of seeds in order to protect the seed from insect pest, in particular from soil-living insect and mite pests and the resulting plant's roots and shoots against soil pests and foliar insects.

The compounds of the present invention are particularly useful for the protection of the seed from soil pests and the resulting plant's roots (white grub, termites, wireworms) and shoots against soil pests and foliar insects. The protection of the resulting plant's roots and shoots is preferred. More preferred is the protection of resulting plant's shoots from piercing and sucking insects, wherein the protection from aphids, jassids, thrips and white fly is most preferred.

The present invention therefore comprises a method for the protection of seeds from insects, in particular from soil insects and of the seedling roots and shoots from insects, in particular from soil and foliar insects, said method comprising contacting the seeds before sowing and/or after pregermination with a compound of the present invention thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound. The seeds can be coated with seed coating compositions containing the compounds of the present invention. For example, seed coating compositions reported in EP3165092, EP3158864, WO2016198644, WO2016039623, WO2015192923, CA2940002, US2006150489, US2004237395, WO2011028115, EP2229808, WO2007067042, EP1795071, EP1273219, WO200178507, EP1247436, NL1012918 and CA2083415.

The term "coated with and/or containing" generally signifies that the active ingredient is for the most part on the surface of the propagation product at the time of application, although a greater or lesser part of the ingredient may penetrate into the propagation product, depending on the method of application. When the propagation product is (re)planted, it may absorb the active ingredient along with moisture.

Suitable seed is seeds of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the compounds of the present invention may be used for treating seed from plants, which tolerate the action of herbicides or fungicides or insecticides owing to breeding, including genetic engineering methods.

For example, the compound of the present invention can be employed in treatment of seeds from plants, which are resistant to herbicides from the group consisting of the sulfonylureas, imidazolinones, glufosinate-ammonium or glyphosate-isopropylammonium and analogous active substances (see for example, EP242236, EP242246) (WO92/00377) (EP257993, U.S. Pat. No. 5,013,659) or in transgenic crop plants, for example cotton, with the capability of producing *Bacillus thuringiensis* toxins (Bt toxins) which make the plants resistant to certain pests (EP142924, EP193259), Furthermore, the compound of the present invention can be used for the treatment of seeds from plants, which have modified characteristics in comparison with existing plants, which can be generated for example by traditional breeding methods and/or the generation of mutants, or by recombinant procedures). For example, a number of cases have been described of recombinant modifications of crop plants for the purpose of modifying the starch synthesized in the plants (e.g. WO92/11376, WO92/14827, WO91/19806) or of transgenic crop plants having a modified fatty acid composition (WO91/13972).

The seed treatment application of the compound of the present invention is carried out by spraying or by dusting the seeds before sowing of the plants and before emergence of the plants.

Compositions which are especially useful for seed treatment are e.g.:

A. Soluble concentrates (SL, LS)
B. Emulsions (EW, EO, ES)
C. Suspensions (SC, OD, FS)
D. Water-dispersible granules and water-soluble granules (WG, SG)
E. Water-dispersible powders and water-soluble powders (WP, SP, WS)
F. Gel-Formulations (GF)
G. Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a one embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed treatment formulations may additionally comprise binders and optionally colorants.

Binders can be added to improve the adhesion of the active materials on the seeds after treatment. Suitable binders are homo and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo and copolymers, polyethyleneamines, polyethyleneamides and polyethylenepyrimidines, polysaccharides like celluloses, tylose and starch, polyolefin homo and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 1 12, C.I. Solvent Red 1, pigment blue 15:4, pigment blue 15:3, pigment blue 15:2, pigment blue 15:1, pigment blue 80, pigment yellow 1, pigment yellow 13, pigment red 1 12, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®)

In the treatment of seed, the application rates of the compounds of the present invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed. The present invention therefore also provides to seeds comprising a compound of formula (I), or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The present invention also provides an agricultural and/or veterinary composition comprising at least one compound of the present invention.

The present invention still further relates to a use of the compound, N-oxide or veterinarily acceptable salt thereof or the composition of the present invention in the preparation of a medicament for treating or protecting animals against infestation or infection by invertebrate pests or parasites.

The compounds of formula (I), their N-oxides and/or veterinarily acceptable salts thereof are in particular also suitable for being used for combating parasites in and on animals.

One object of the present invention is therefore to provide new methods to control parasites in and on animals. Another object of the present invention is to provide safer pesticides for animals. Another object of the present invention is to provide pesticides for animals that may be used in lower doses than existing pesticides. Another object of the present invention is to provide pesticides for animals, which provide a long residual control of parasites.

The present invention also relates to compositions containing a parasiticidally effective amount of at least one compound of formula (I), N-oxide or veterinarily acceptable salt thereof and an acceptable carrier, for combating parasites in and on animals.

The present invention also provides a method for treating, controlling, preventing and protecting animals against infestation and infection by parasites, which comprises orally, topically, or parenteral administering or applying to the animals a parasiticidally effective amount of a compound of the present invention or a composition comprising it.

The present invention also provides a process for the preparation of a composition for treating, controlling, preventing or protecting animals against infestation or infection by parasites which comprises a parasiticidally effective amount of a compound of the present invention or a composition comprising it.

Activity of compounds against agricultural pests does not suggest their suitability for control of endo and ectoparasites in and on animals which requires, for example, low, nonemetic dosages in the case of oral application, metabolic compatibility with the animal, low toxicity, and a safe handling.

Surprisingly it has now been found that compounds of the present invention are suitable for combating endo and ectoparasites in and on animals.

Compounds of the present invention and compositions comprising them are preferably used for controlling and preventing infestations and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh and salt-water fish such as trout, carp and eels.

Compounds of the present invention and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention and compositions comprising them are suitable for systemic and/or non-systemic control of ecto and/or endoparasites. They can be active against all or some stages of development.

The compounds of the present invention are especially useful for combating ectoparasites.

The compounds of the present invention are especially useful for combating parasites of the following orders and species, respectively: fleas (Siphonaptera), e.g. *Ctenocephalides felis, Ctenocephalides cams, Xenopsylla cheopis, Pulex irritans, Tunga penetrans*, and *Nosopsyllus fasciatus*, cockroaches (Blattaria Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*, ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g.

*Ornithonyssus bacoti* and *Dermanyssus gallinae*, Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,* Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.

Roundworms Nematoda:

Wipeworms and Trichinosis (Trichosyringida), e.g. Trichinellidae (*Trichinella* spp.), (Trichuridae,) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,* Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,* Camallanida, e.g. *Dracunculus medinensis* (guinea worm) Spirurida, e.g. *Thelazia* spp. *Wuchereria* spp., *Brugia* spp., *Onchocerca* spp., *Dirofilari* spp. a, *Dipetalonema* spp., *Setaria* spp., *Elaeophora* spp., *Spirocerca lupi,* and *Habronema* spp, Thorny headed worms (Acanthocephala), e.g. *Acanthocephalus* spp., *Macracanthorhynchus hirudinaceus* and *Oncicola* spp, Planarians (Plathelminthes): Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., Alaria a lata, *Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula (I) and compositions containing them are particularly useful for the control of pests from the orders Diptera, Siphonaptera and Ixodida.

In one embodiment, the present invention provides use of the compounds of formula (I) and compositions containing them for combating mosquitoes.

In one embodiment, the present invention provides use of the compounds of formula (I) and compositions containing them for combating flies.

In one embodiment, the present invention provides use of the compounds of of formula (I) and compositions containing them for combating fleas.

The use of the compounds of the present invention and compositions containing them for combating ticks is still another embodiment of the present invention.

The compounds of the present invention are also especially useful for combating endoparasites (roundworms nematoda, thorny headed worms and planarians).

In one embodiment, the administration of the compounds of the present invention can be carried out both prophylactically and therapeutically.

In another embodiment, administration of the compounds of the present invention is carried out directly or in the form of suitable preparations, orally, topically/dermally or parenterally.

For oral administration to warm-blooded animals, compounds of the present invention may be formulated as animal feeds, animal feed premixes, animal feed concentrates, pills, solutions, pastes, suspensions, drenches, gels, tablets, boluses and capsules. In addition, the compounds of the present invention may be administered to the animals in their drinking water. For oral administration, the dosage form chosen should provide the animal with 0.01 mg/kg to 100 mg/kg of animal body weight per day of the compound of the present invention, preferably with 0.5 mg/kg to 100 mg/kg of animal body weight per day.

Alternatively, the compounds of the present invention may be administered to animals parenterally, for example, by intraruminal, intramuscular, intravenous or subcutaneous injection. The compounds of the present invention may be dispersed or dissolved in a physiologically acceptable carrier for subcutaneous injection. Alternatively, the compounds of the present invention may be formulated into an implant for subcutaneous administration. In addition the compound of the present invention may be transdermally administered to animals. For parenteral administration, the dosage form chosen should provide the animal with 0.01 mg/kg to 100 mg/kg of animal body weight per day of the compound of the present invention.

The compounds of the present invention may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compound of the present invention. In addition, the compounds of the present invention may be formulated as ear tags for animals, particularly quadrupeds such as cattle and sheep.

Suitable preparations are: Solutions such as oral solutions, concentrates for oral administration after dilution, solutions for use on the skin or in body cavities, pouring-on formulations, gels; Emulsions and suspensions for oral or dermal administration; semi-solid preparations; Formulations in which the active compound is processed in an ointment base or in an oil-in water or water-in-oil emulsion base; Solid preparations such as powders, premixes or concentrates, granules, pellets, tablets, boluses, capsules; aerosols and inhalants, and active compound-containing shaped articles.

The compositions suitable for injection are prepared by dissolving the active ingredient in a suitable solvent and optionally adding further ingredients such as acids, bases, buffer salts, preservatives, and solubilizers.

The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the used concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency result. The thickeners employed are the thickeners given above.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are for example, water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or noctylpyrrolidone, N-methylpyrrolidone, 2-pyrrolidone, 2,2-dimethyl-4-oxy-methylene-1,3-dioxolane or glycerol formal.

Suitable colorants are for example, all colorants permitted for use on animals and which can be dissolved or suspended.

Suitable absorption-promoting substances are for example, dimethyl sulfoxide, spreading oils such as isopropyl myristate, dipropylene glycol pelargonate, silicone oils and copolymers thereof with polyethers, fatty acid esters, triglycerides or fatty alcohols.

Suitable antioxidants are for example, sulfites or metabisulfites such as potassium metabisulfite, ascorbic acid, butylhydroxytoluene, butylhydroxyanisole or tocopherol.

Suitable light stabilizers are for example, novantisolic acid. Suitable adhesives are, for example, cellulose derivatives, starch derivatives, polyacrylates or natural polymers such as alginates, gelatin. Emulsions can be administered orally, dermally or as injections. Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable Hydrophobic Phases (Oils) are:

Liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_1$-$C_{12}$ or other specially selected natural fatty acids, partial glyceride mixtures of saturated or unsaturated fatty acids possibly also containing hydroxyl groups, mono and diglycerides of the Cs-do fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof. Suitable hydrophilic phases are: water, alcohols such as propylene glycol, glycerol, sorbitol and mixtures thereof.

Suitable emulsifiers are for example, non-ionic surfactants, e.g. polyethoxylated castor oil, polyethoxylated sorbitan monooleate, sorbitan monostearate, glycerol monostearate, polyoxyethyl stearate, alkylphenol polyglycol ether; ampholytic surfactants such as di-sodium N-lauryl-p-iminodipropionate or lecithin.

Suitable anionic surfactants are for example, sodium lauryl sulfate, fatty alcohol ether sulfates, mono/dialkyl polyglycol etherorthophosphoric acid ester monoethanolamine salt; suitable cation-active surfactants are cetyltrimethylammonium chloride.

Suitable further auxiliaries are for example, substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the present invention. A parasiticidally effective amount of the compositions will also vary according to the prevailing conditions such as desired parasiticidal effect and duration, target species, mode of application, and the like. The compositions which can be used in the present invention generally comprise from about 0.001 to 95% of the compound of the present invention.

Generally, it is favorable to apply the compounds of the present invention in total amounts of 0.5 mg/kg to 100 mg/kg per day, preferably 1 mg/kg to 50 mg/kg per day. Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight. Preparations are diluted before use contain the compounds acting against ectoparasites in concentrations of 0.5 to 90 percent by weight, preferably of 1 to 50 percent by weight. Furthermore, the preparations comprise the compounds of the present invention against endoparasites in concentrations of 10 ppm to 2 percent by weight, preferably of 0.05 to 0.9 percent by weight, very particularly preferably of 0.005 to 0.25 percent by weight.

In one embodiment, the compositions comprising the compounds of the present invention are applied dermally/topically.

In another embodiment, the topical application is conducted in the form of compound-containing shaped articles such as collars, medallions, ear tags, bands for fixing at body parts, and adhesive strips and foils.

Generally, it is favorable to apply solid formulations which release compounds of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of the present invention. A detailed list of plastics and elastomers as well as preparation procedures for the shaped articles is given e.g. in WO 2003/086075.

Positive Crop Response:

The compounds of the present invention not only control insect and mite pests effectively but also show positive crop response such as plant growth enhancement effects like enhanced root growth, enhanced tolerant to drought, high salt, high temperature, chill, frost or light radiation, improved flowering, enhanced nutrient utilization (such as improved nitrogen assimilation), enhanced quality plant product, more number of productive tillers, enhanced resistance to fungi, insects, pests and the like, which results in higher yields.

CHEMISTRY EXAMPLES

The following examples set forth the manner and process of making compounds of the present invention without being a limitation thereof and include the best mode contemplated by the inventors for carrying out the invention.

Example 1: Synthesis of 2-(1-(3,5-dichlorophenyl)-2-(ethylsulfonyl)indolizin-3-yl)-3-methyl-6-(trifluoromethyl)-3H-imidazo[4,5-b]pyridine (Compound No. 1)

a) Step-1: 1-(2-Ethoxy-2-oxoethyl)pyridin-1-ium

To a stirred solution of pyridine (10.2 mL, 126 mmol) in acetonitrile (10 mL), ethyl 2-bromoacetate (15.4 mL, 139 mmol) was added and the reaction mixture was heated at reflux for 18 h. After completion of the reaction, the reaction mixture was allowed to cool to 25° C. The precipitate thus obtained was filtered to obtain 1-(2-ethoxy-2-oxoethyl)pyridin-1-ium (20 g, 120 mmol, 95% yield). $^1$H-NMR (400 MHz, DMSO-d6) δ 9.09-9.11 (m, 2H), 8.70-8.74 (m, 1H), 8.25 (dd, J=7.9, 6.7 Hz, 2H), 5.73 (s, 2H), 4.22 (q, J=7.1 Hz, 2H), 1.21 (t, J=7.1 Hz, 3H); ESI MS (m/z) 166.20 (MH)$^+$.

b) Step-2: Ethyl 2-fluoroindolizine-3-carboxylate

To a stirred solution of 1-(2-ethoxy-2-oxoethyl)pyridin-1-ium (8 g, 48.1 mmol) in N,N-dimethyl formamide (80 mL), 2,2-difluorovinyl 4-methylbenzenesulfonate (7.9 g, 33.7 mmol), potassium carbonate (6.7 g, 48.1 mmol) and triethyl amine (6.7 mL, 48.1 mmol) were added. The reaction mixture was heated at 70° C. for 12 h. After completion of the reaction, the reaction mixture was cooled to 25° C. Water (150 mL) was added to the above reaction mixture and extracted twice with ethyl acetate (300 mL). The combined ethyl acetate layers were washed with brine (100 mL), dried over anhydrous sodium sulfate and concentrated under reduced pressure to obtain the crude product. The crude product was purified by flash column chromatography on silica gel using ethyl acetate in hexane as an eluent to obtain ethyl 2-fluoroindolizine-3-carboxylate (4.2 g, 20.3 mmol, 42% yield). $^1$H-NMR (400 MHz, DMSO-d6) δ 9.29 (dq, J=7.2, 1.0 Hz, 1H), 7.51-7.65 (m, 1H), 7.23-7.27 (m, 1H), 6.72-7.08 (m, 1H), 6.27-6.50 (m, 1H), 4.33 (q, J=7.1 Hz, 2H), 1.34 (t, J=7.1 Hz, 3H); ESI MS (m/z) 208.20 (MH)$^+$.

c) Step-3: 2-Fluoro-N-(2-(methylamino)-5-(trifluoromethyl)pyridin-3-yl)indolizine-3-carboxamide To a stirred solution of potassium tert-butoxide (1.2 g, 10.9 mmol) in N,N-dimethyl formamide (5 mL), a solution of ethyl 2-fluoroindolizine-3-carboxylate (0.9 g, 4.4 mmol) and N-2-methyl-5-(trifluoromethyl)pyridine-2,3-diamine (1 g, 5.2 mmol) in N,N-dimethyl formamide (5 mL) was added at 0° C. The reaction mixture was allowed to stir at 25° C. for 2 h. After completion of the reaction, tetrahydrofuran was removed under reduced pressure to obtain the crude product, which was taken up in water (25 mL) and extracted with ethyl acetate (75 mL). The ethyl acetate layer was washed with brine (50 mL) and water (50 mL), dried over anhydrous sodium sulphate and concentrated to obtain the crude product. The crude product was purified by column chromatography on silica gel using 40% ethyl acetate in hexane to give 2-fluoro-N-(2-(methylamino)-5-(trifluoromethyl)pyridin-3-yl)indolizine-3-carboxamide (550 mg, 1.6 mmol, 36% yield). $^1$H-NMR (400 MHz, DMSO-d6) δ 9.38 (dd, J=7.1, 0.7 Hz, 1H), 8.75 (d, J=4.6 Hz, 1H), 8.30 (t, J=1.1 Hz, 1H), 7.51-7.72 (m, 2H), 7.17-7.21 (m, 1H), 6.94-7.05 (m, 2H), 6.55 (s, 1H), 2.84-2.89 (d, J=4.6 Hz, 3H); ESI MS (m/z) 352.95 (MH)$^+$.

d) Step-4: 2-(2-Fluoroindolizin-3-yl)-3-methyl-6-(trifluoromethyl)-3H-imidazo[4,5-b]pyridine A mixture of 2-fluoro-N-(2-(methylamino)-5-(trifluoromethyl)pyridin-3-yl)indolizine-3-carboxamide (1.4 g, 4 mmol), p-toluenesulfonic acid monohydrate (2.3 g, 11.9 mmol) in N-methyl-2-pyrrolidone (15 mL) was irradiated in a microwave oven at 150° C. for 1 h under nitrogen atmosphere. After completion of the reaction, the reaction mixture was allowed to cool to 25° C. Water (100 mL) was added to the above reaction mixture followed by extraction with ethyl acetate (200 mL). The ethyl acetate layer was washed with water (50 mL), dried over anhydrous sodium sulfate and concentrated under reduced pressure to obtain the crude product. The crude product was purified by flash column chromatography on silica gel using 20% ethyl acetate in hexane as an eluent to obtain 2-(2-fluoroindolizin-3-yl)-3-methyl-6-(trifluoromethyl)-3H-imidazo[4,5-b]pyridine (830 mg, 2.5 mmol, 62% yield). $^1$H-NMR (400 MHz, DMSO-d6) δ 9.12 (dd, J=7.1, 0.7 Hz, 1H), 8.78-8.82 (m, 1H), 8.55 (d, J=1.5 Hz, 1H), 7.65-7.75 (m, 1H), 7.16-7.19 (m, 1H), 6.96 (td, J=7.0, 1.3 Hz, 1H), 6.68 (s, 1H), 3.92 (s, 3H); ESI MS (m/z) 335 (MH)$^+$.

e) Step-5: 2-(2-(Ethylsulfonyl)indolizin-3-yl)-3-methyl-6-(trifluoromethyl)-3H-imidazo[4,5-b]pyridine To a stirred solution of 2-(2-fluoroindolizin-3-yl)-3-methyl-6-(trifluoromethyl)-3H-imidazo[4,5-b]pyridine (830 mg, 2.5 mmol) in dry N,N-dimethylformamide (10 mL), sodium hydride (149 mg, 3.7 mmol) was added at 0° C. and the reaction mixture was allowed to stir for 30 min. Ethanethiol (0.4 mL, 5 mmol) was added to the above reaction mixture dropwise at 0° C. and the reaction mixture was heated at 60° C. for 1 h. After completion of the reaction, the reaction mixture was allowed to cool to 25° C. Water (50 mL) was added to the reaction mixture followed by extraction with ethyl acetate (150 mL). The ethyl acetate layer was washed with water (50 mL), dried over anhydrous sodium sulfate and concentrated under reduced pressure to obtain the crude product. The crude product was purified by flash column chromatography on silica gel ethyl acetate in hexane as an eluent to get 2-(2-(ethylthio)indolizin-3-yl)-3-methyl-6-(trifluoromethyl)-3H-imidazo[4,5-b]pyridine (730 mg, 1.94 mmol, 78% yield). $^1$H-NMR (400 MHz, DMSO-d6) δ 8.83 (q, J=0.9 Hz, 1H), 8.59-8.60 (m, 1H), 8.43 (dd, J=7.1, 0.7 Hz, 1H), 7.57 (dd, J=7.8, 1.2 Hz, 1H), 7.00 (ddd, J=9.0, 6.6, 1.0 Hz, 1H), 6.81 (s, 1H), 6.72 (td, J=6.9, 1.2 Hz, 1H), 3.89(s, 3H), 2.90-2.96 (q, J=7.1 Hz, 2H), 1.19 (t, J=7.3 Hz, 3H); ESI MS (m/z) 377.05 (MH)$^+$.

f) Step-6: 2-(2-(Ethylsulfonyl)indolizin-3-yl)-3-methyl-6-(trifluoromethyl)-3H-imidazo[4,5-b]pyridine To a solution of 2-(2-(ethylthio)indolizin-3-yl)-3-methyl-6-(trifluoromethyl)-3H-imidazo[4,5-b]pyridine (200 mg, 0.5 mmol) in dichloromethane (3 mL), m-chloroperbenzoic acid (306 mg, 1.1 mmol) was added portion wise at 0-5° C. The reaction mixture was stirred at 25° C. for 2 h. After completion of the reaction, the reaction mixture was diluted with aqueous sodium thiosulfate solution and extracted with dichloromethane (150 mL). The dichloromethane layer was washed with a saturated aqueous sodium bicarbonate solution, dried over anhydrous sodium sulfate and concentrated under reduced pressure to obtain the crude product. The crude product was purified by flash column chromatography on silica gel using 40% ethyl acetate in hexane as an eluent to obtain 2-(2-(ethylsulfonyl)indolizin-3-yl)-3-methyl-6-(trifluoromethyl)-3H-imidazo[4,5-b]pyridine (150 mg, 0.4 mmol, 69% yield). $^1$H-NMR (400 MHz, DMSO-d6) δ 8.91 (t, J=1.0 Hz, 1H), 8.70 (d, J=1.5 Hz, 1H), 8.14 (dd, J=7.1, 1.0 Hz, 1H), 7.71-7.91 (m, 1H), 7.11-7.16 (m, 2H), 6.88-6.91 (m, 1H), 3.7 (s, 3H), 3.39 (q, J=7.1 hz, 2H), 1.15 (t, J=7.1 Hz, 3H); ESI MS (m/z) 409 (MH)$^+$.

g) Step-7: 2-(1-Bromo-2-(ethylsulfonyl)indolizin-3-yl)-3-methyl-6-(trifluoromethyl)-3H-imidazo[4,5-b]pyridine To a stirred solution of 2-(2-(ethylsulfonyl)indolizin-3-yl)-3-methyl-6-(trifluoromethyl)-3H-imidazo[4,5-b]pyridine (185 mg, 0.45 mmol) in dichloromethane (2 mL), N-bromosuccinimide (89 mg, 0.5 mmol) was added at 0° C., and the reaction mixture was stirred at 25° C. for 30 min. After completion of the reaction, the reaction mixture was diluted with water (20 mL) and extracted thrice with dichloromethane (50 mL).

The combined dichloromethane layers were washed with brine (100 mL), dried over anhydrous sodium sulfate and concentrated under reduced pressure to obtain the crude product. The crude product was purified by flash column chromatography on silica gel using 30% ethyl acetate in hexane to get 2-(1-bromo-2-(ethylsulfonyl)indolizin-3-yl)-3-methyl-6-(trifluoromethyl)-3H-imidazo[4,5-b]pyridine (160 mg, 0.3 mmol, 72% yield). $^1$H-NMR (400 MHz, DMSO-d6) δ 8.90 (d, J=1.8 Hz, 1H), 8.69 (d, J=1.8 Hz, 1H), 8.11 (d, J=7.3 Hz, 1H), 7.68 (d, J=9.2 Hz, 1H), 7.24 (dd, J=9.2, 6.7 Hz, 1H), 6.90-6.94 (m, 1H), 3.70 (s, 3H), 3.36-3.46 (m, 2H), 1.12 (t, J=7.3 Hz, 3H); ESI MS (m/z) 486.85, 489.05 [(MH)$^+$ Br$^{79,81}$].

h) Step-8: 2-(1-(3,5-Dichlorophenyl)-2-(ethylsulfonyl)indolizin-3-yl)-3-methyl-6-(trifluoromethyl)-3H-imidazo[4,5-b]pyridine To a solution of 2-(1-bromo-2-(ethylsulfonyl)indolizin-3-yl)-3-methyl-6-(trifluoromethyl)-3H-imidazo[4,5-b]pyridine (110 mg, 0.2 mmol) and (3,5-dichlorophenyl)boronic acid (43.1 mg, 0.2 mmol) in a mixture of 1,4-dioxane (2 mL) and water (0.2 mL), sodium carbonate (71.8 mg, 0.7 mmol) and tetrakis(triphenylphosphine)palladium(0) (13 mg, 0.01 mmol) were added. The reaction mixture was thoroughly deoxygenated by subjecting to vacuum/nitrogen cycles three times and was heated in a microwave oven at 110° C. for 1.5 h. After completion of the reaction, the reaction mixture was cooled to 25° C. and filtered through a pad of celite. The filtrate was concentrated under reduced pressure and the crude product was purified by flash column chromatography on silica gel using ethyl acetate in hexane as an eluent to obtain 2-(1-(3,5-dichlorophenyl)-2-(ethylsulfonyl)indolizin-3-yl)-3-methyl-6-(trifluoromethyl)-3H-imidazo[4,5-b]pyridine (73 mg, 0.1 mmol, 58% yield). $^1$H-NMR (400 MHz, DMSO-d6) δ 8.92 (t, J=2.2 Hz, 1H), 8.71 (t, J=2.2 Hz, 1H), 8.15-8.17 (m, 1H), 7.68-7.74 (m, 3H), 7.52-7.55 (m, 1H), 7.16-7.20 (m, 1H), 6.93-6.99 (m, 1H), 3.79 (s, 3H), 3.05 (dtd, J=63.8, 14.5, 7.3 Hz, 2H), 0.89-1.1 (m, 3H); ESI-MS (m/z) 553.90, 554.90 [(MH)$^+$ Cl$^{35,37}$].

Example 2: Synthesis of 2-(2-(ethylsulfonyl)imidazo[1,2-a]pyridin-3-yl)-3-methyl-6-(trifluoromethyl)-3H-imidazo[4,5-b]pyridine (Compound No. 2)

a) Step-1: 2-(2-Iminopyridin-1(2H)-yl)acetic acid

To a stirred solution of 2-chloroacetic acid (4.0 g, 42.3 mmol) in water (10 mL), triethyl amine (6.8 mL, 48.7 mmol) was added dropwise at 25° C. After stirring for 10 min, pyridin-2-amine (4.8 g, 50.8 mmol) was added and the resulting brown solution was heated at 90° C. for 5 h. After cooling to 25° C., ethanol (20 mL) was added and the resulting suspension was stirred at 5° C. for 2 h. The precipitate was collected by filtration and washed with cold ethanol (30 mL) to obtain 2-(2-iminopyridin-1(2H)-yl) acetic acid (4.2 g, 28 mmol, 65% yield). $^1$H-NMR (400 MHz, DMSO-d6) δ 8.11 (s, 1H), 7.79-7.91 (m, 2H), 6.98 (d, J=7.8 Hz, 1H), 6.82 (s, 1H), 4.44 (s, 2H); ESI MS (m/z) 152.95 (MH)$^+$.

b) Step-2: 2-Chloroimidazo[1,2-a]pyridine

To a stirred solution of 2-(2-iminopyridin-1(2H)-yl)acetic acid (4.2 g, 27.6 mmol) in toluene (50 mL), phosphorus oxychloride (7.7 mL, 83 mmol) was added dropwise, and the resulting reaction mixture was heated at 100° C. for 16 h. After completion of the reaction, the reaction mixture was cooled to 25° C. Cold water (500 mL) was added and the solution was stirred for 15 min. The aqueous layer was neutralized with 10% sodium hydroxide aqueous solution and extracted twice with dichloromethane (250 mL). The combined dichloromethane layers were washed with water (100 mL), dried over anhydrous sodium sulfate and concentrated under reduced pressure to obtain the crude product. The crude product was purified by flash column chromatography on silica gel using ethyl acetate hexane as eluent to give 2-chloroimidazo[1,2-a]pyridine (3.2 g, 21 mmol, 76% yield). $^1$H-NMR (400 MHz, DMSO-d6) δ 8.50 (dt, J=6.8, 1.2 Hz, 1H), 8.05-8.08 (m, 1H), 7.54 (dq, J=9.1, 0.9 Hz, 1H), 7.33 (ddd, J=9.2, 6.8, 1.3 Hz, 1H), 6.99 (td, J=6.8, 1.2 Hz, 1H); ESI MS (m/z) 152.90 (MH)$^+$.

c) Step-3: Ethyl 2-chloroimidazo[1,2-a]pyridine-3-carboxylate

To a stirred solution of 2-chloroimidazo[1,2-a]pyridine (0.5 g, 3.3 mmol) in tetrahydrofuran (10 mL), n-butyl lithium (1.8 mL, 3.6 mmol) was added dropwise at −78° C. After stirring for 30 min, ethyl chlorocarbonate (0.36 g, 3.3 mmol) in tetrahydrofuran (10 mL) was added to the reaction mixture at the same temperature. The reaction mixture was allowed to stir for 1 h at −78° C. and subsequently at 25° C. for further 1 h. After completion of the reaction, the reaction was quenched by addition of saturated ammonium chloride solution (20 mL) and extracted twice with ethyl acetate (100 mL). The combined ethyl acetate layers were washed with water (100 mL), dried over anhydrous sodium sulfate and concentrated under reduced pressure to obtain crude product. The crude product was purified by flash chromatography on silica gel using 30% ethyl acetate in hexane as eluent to give ethyl 2-chloroimidazo[1,2-a]pyridine-3-carboxylate (0.5 g, 2.2 mmol, 68% yield). $^1$H-NMR (400 MHz, DMSO-d6) δ 9.24 (dt, J=6.9, 1.2 Hz, 1H), 7.77 (dt, J=9.0, 1.2 Hz, 1H), 7.66 (ddd, J=9.0, 6.9, 1.3 Hz, 1H), 7.31 (td, J=6.9, 1.3 Hz, 1H), 4.35 (q, J=7.1 Hz, 2H), 1.45 (t, J=6.8 Hz, 3H); ESI MS (m/z) 224.90 (MH)$^+$.

d) Step-4: 2-Chloro-N-(2-(methylamino)-5-(trifluoromethyl)pyridin-3-yl)imidazo[1,2-a]pyridine-3-carboxamide To a stirred solution of potassium tert-butoxide (0.5 g, 4.5 mmol) in tetrahydrofuran (10 mL), a solution of ethyl 2-chloroimidazo[1,2-a]pyridine-3-carboxylate (0.5 g, 2.2 mmol) and N-2-methyl-5-(trifluoromethyl)pyridine-2,3-diamine (0.4 g, 2.2 mmol) in tetrahydrofuran (10 mL) was added at 0° C. The reaction mixture was allowed to stir at 25° C. for 1 h. After completion of the reaction, tetrahydrofuran was removed under reduced pressure to obtain the crude product, which was taken up in water (20 mL) and extracted with dichloromethane (75 mL). The dichloromethane layer was washed with brine (50 mL) and water (50 mL), dried over anhydrous sodium sulphate and concentrated to obtain the crude product. The crude product was purified by column chromatography on silica gel using 40% ethyl acetate in hexane to give 2-chloro-N-(2-(methylamino)-5-(trifluoromethyl)pyridin-3-yl)imidazo[1,2-a]pyridine-3-carboxamide (0.45 g, 1.2 mmol, 55% yield). $^1$H-NMR (400 MHz, DMSO-d6) δ 9.16-9.22 (m, 2H), 8.34 (q, J=1.1 Hz, 1H), 7.59-7.76 (m, 3H), 7.24 (td, J=7.0, 1.4 Hz, 1H), 7.03 (q, J=4.6 Hz, 1H), 2.90 (d, J=4.6 Hz, 3H); ESI MS (m/z) 369.85 (MH)$^+$.

e) Step-5: 2-(2-Chloroimidazo[1,2-a]pyridin-3-yl)-3-methyl-6-(trifluoromethyl)-3H-imidazo[4,5-b]pyridine A mixture of 2-chloro-N-(2-(methylamino)-5-(trifluoromethyl)pyridin-3-yl)imidazo[1,2-a]pyridine-3-carboxamide (0.25 g, 0.68 mmol), p-toluenesulfonic acid monohydrate (0.39 g, 2.03 mmol) in N-methyl-2-pyrrolidone (10 mL) was irradiated in a microwave oven at 150° C. for 2 h under nitrogen atmosphere. After completion of the reaction, the reaction mixture was allowed to cool to 25° C. Water (50 mL) was added to the above reaction mixture followed by extraction with ethyl acetate (150 mL). The ethyl acetate layer was washed with water (50 mL), dried over anhydrous sodium sulfate and concentrated under reduced pressure to obtain the crude product. The crude product was purified by flash column chromatography on silica gel using 40% ethyl acetate in hexane as an eluent to obtain 2-(2-chloroimidazo[1,2-a]pyridin-3-yl)-3-methyl-6-(trifluoromethyl)-3H-imidazo[4,5-b]pyridine (0.2 g, 0.5 mmol, 76% yield). $^1$H-NMR (400 MHz, DMSO-d6) δ 8.89 (q, J=0.9 Hz, 1H), 8.68-8.73

(m, 2H), 7.79 (dt, J=9.0, 1.1 Hz, 1H), 7.60 (ddd, J=9.0, 7.0, 1.3 Hz, 1H), 7.20 (td, J=7.0, 1.2 Hz, 1H), 3.92 (s, 3H); ESI MS (m/z) 352.05 (MH)+.

f) Step-6: 2-(2-(Ethylthio)imidazo[1,2-a]pyridin-3-yl)-3-methyl-6-(trifluoromethyl)-3H-imidazo[4,5-b]pyridine To a stirred solution of 2-(2-chloroimidazo[1,2-a]pyridin-3-yl)-3-methyl-6-(trifluoromethyl)-3H-imidazo[4,5-b]pyridine (0.3 g, 0.9 mmol) in dry N,N-dimethylformamide (5 mL), sodium hydride (0.1 g, 1.7 mmol) was added at 0° C., and the reaction mixture was stirred for 30 min. Ethanethiol (0.1 mL, 1.3 mmol) was added to the above reaction mixture at 0° C., and the reaction mixture was heated at 60° C. for 2 h. After completion of the reaction, the reaction mixture was allowed to cool to 25° C. Cold water (150 mL) was added to the reaction mixture and the resulting precipitate was filtered off, washed with water (10 mL) and dried under vacuum to obtain crude product. The crude product was purified by flash column chromatography on silica gel using 40% ethyl acetate in hexane as an eluent to obtain 2-(2-(ethylthio)imidazo[1,2-a]pyridin-3-yl)-3-methyl-6-(trifluoromethyl)-3H-imidazo[4,5-b]pyridine (0.25 g, 0.7 mmol, 78% yield). $^1$H-NMR (400 MHz, DMSO-d6) δ 8.85 (t, J=1.0 Hz, 1H), 8.63-8.65 (m, 2H), 7.74 (dt, J=9.0, 1.1 Hz, 1H), 7.50 (ddd, J=9.0, 6.8, 1.2 Hz, 1H), 7.08 (td, J=6.8, 1.2 Hz, 1H), 3.90 (s, 3H), 3.25 (q, J=7.3 Hz, 2H), 1.23 (t, J=6.8 Hz, 3H); ESI MS (m/z) 378.10 (MH)+.

g) Step-7: 2-(2-(Ethylsulfonyl)imidazo[1,2-a]pyridin-3-yl)-3-methyl-6-(trifluoromethyl)-3H-imidazo[4,5-b]pyridine To a solution of 2-(2-(ethylthio)imidazo[1,2-a]pyridin-3-yl)-3-methyl-6-(trifluoromethyl)-3H-imidazo[4,5-b]pyridine (0.2 g, 0.5 mmol) in dichloromethane (5 mL), m-chloroperbenzoic acid (0.3 g, 1 mmol) was added portion wise at 0-5° C. The reaction mixture was stirred at 25° C. for 2 h. After completion of the reaction, the reaction mixture was diluted with aqueous sodium thiosulfate solution and extracted with dichloromethane (15 mL). The dichloromethane extract was washed with a saturated aqueous sodium bicarbonate solution, dried over anhydrous sodium sulfate and concentrated under reduced pressure to obtain the crude product. The crude product was purified by flash column chromatography on silica gel using 35% ethyl acetate in hexane as an eluent to obtain 2-(2-(ethylsulfonyl)imidazo[1,2-a]pyridin-3-yl)-3-methyl-6-(trifluoromethyl)-3H-imidazo[4,5-b]pyridine (0.1 g, 0.3 mmol, 67% yield). $^1$H-NMR (400 MHz, DMSO-d6) δ 8.93-8.93 (m, 1H), 8.73 (dd, J=2.1, 0.6 Hz, 1H), 8.47 (dt, J=7.0, 1.1 Hz, 1H), 7.94 (dt, J=9.2, 1.1 Hz, 1H), 7.68 (ddd, J=9.0, 6.8, 1.2 Hz, 1H), 7.22 (td, J=6.9, 1.1 Hz, 1H), 3.86 (s, 3H), 3.49-3.52 (q, J=6.8 Hz, 2H), 1.15-1.24 (t, J=7.6 Hz, 3H); ESI MS (m/z) 409.95 (MH)+.

Example 3: Synthesis of 2-(8-(3,5-dichlorophenyl)-2-(ethylsulfonyl)indolizin-3-yl)-3-methyl-6-(trifluoromethyl)-3H-imidazo[4,5-b]pyridine (Compound No. 6)

a) Step-1: 3-Bromo-1-(2-ethoxy-2-oxoethyl)pyridin-1-ium

To a stirred solution of 3-bromopyridine (12.4 mL, 127 mmol) in acetonitrile (200 mL), ethyl 2-bromoacetate (15.5 mL, 139 mmol) was added, and the reaction mixture was heated at reflux for 16 h. After completion of the reaction, the reaction mixture was allowed to cool to 25° C., and the precipitate thus obtained was filtered to obtain 3-bromo-1-(2-ethoxy-2-oxoethyl)pyridin-1-ium (30 g, 122 mmol, 97% yield). $^1$H-NMR (400 MHz, CHLOROFORM-D) δ 9.56 (m, 1H), 9.35 (s, 1H), 8.62 (d, J=8.3 Hz, 1H), 6.28 (s, 2H), 4.36 (q, J=7.1 Hz, 3H), 1.33-1.4 (t, J=7.2 Hz, 3H); ESI MS (m/z) 243.85, 245.85 [(MH)+ Br$^{79,81}$].

b) Step-2: Ethyl 6-bromo-2-fluoroindolizine-3-carboxylate and Ethyl 8-bromo-2-fluoroindolizine-3-carboxylate To a stirred solution of 3-bromo-1-(2-ethoxy-2-oxoethyl)pyridin-1-ium (3 g, 12.2 mmol) in N,N-dimethyl formamide (80 mL), 2,2-difluorovinyl 4-methylbenzenesulfonate (1 g, 4.3 mmol), potassium carbonate (0.85 g, 6.1 mmol) and triethyl amine (0.85 mL, 6.1 mmol) were added. The reaction mixture was heated at 70° C. for 16 h. After completion of the reaction, the reaction mixture was cooled to 25° C. Water (50 mL) was added to the above reaction mixture, which was extracted twice with ethyl acetate (200 mL). The combined ethyl acetate layers were washed with brine (100 mL), dried over anhydrous sodium sulfate and concentrated under reduced pressure to obtain the crude product. The crude product was purified by reverse phase preperative HPLC to obtain ethyl 6-bromo-2-fluoroindolizine-3-carboxylate (240 mg, 0.8 mmol, 14% yield) and ethyl 8-bromo-2-fluoroindolizine-3-carboxylate (160 mg, 0.56 mmol, 9%).

i. Ethyl 6-bromo-2-fluoroindolizine-3-carboxylate $^1$H-NMR (400 MHz, DMSO-d6) δ 9.37-9.47 (m, 1H), 7.63-7.71 (m, 1H), 7.35-7.41 (m, 1H), 6.58-6.69 (m, 1H), 4.35 (q, J=7.1 Hz, 2H), 1.35 (t, J=7.2 Hz, 3H); ESI MS (m/z) 286.05, 288.05 [(MH)+ Br$^{79,81}$].

ii. Ethyl 8-bromo-2-fluoroindolizine-3-carboxylate $^1$H-NMR (400 MHz, DMSO-d6) δ 9.28-9.40 (m, 1H), 7.58-7.64 (m, 1H), 6.97 (t, J=7.2 Hz, 1H), 6.57 (d, J=11.5 Hz, 1H), 4.33 (q, J=7.2 Hz, 2H), 1.3 (t, J=7.2 Hz, 3H); ESI MS (m/z) 286, 288 [(MH+ Br$^{79,81}$].

c) Step-3: 8-Bromo-2-fluoro-N-(2-(methylamino)-5-(trifluoromethyl)pyridin-3-yl)indolizine-3-carboxamide The reaction involving ethyl 6-bromo-2-fluoroindolizine-3-carboxylate (2.1 g, 7.3 mmol) and N-2-methyl-5-(trifluoromethyl)pyridine-2,3-diamine (1 g, 5.23 mmol) as appropriate reactants following the same synthetic procedure as described in step 3 of example 34 afforded 8-bromo-2-fluoro-N-(2-(methylamino)-5-(trifluoromethyl)pyridin-3-yl)indolizine-3-carboxamide (1.3 g, 3 mmol, 41% yield). $^1$H-NMR (400 MHz, CHLOROFORM-D) δ 9.62 (d, J=7.0 Hz, 1H), 8.37 (d, J=0.9 Hz, 1H), 7.72 (dd, J=6.7, 2.1 Hz, 1H), 7.46-7.52 (m, 1H), 7.33-7.38 (m, 1H), 6.75 (t, J=7.3 Hz, 1H), 6.49 (s, 1H), 5.13 (d, J=4.3 Hz, 1H), 3.05-3.08 (d, J=5.2 Hz, 3H); ESI MS (m/z) 430.75, 432.75 [(MH)+ Br$^{79,81}$].

d) Step-4: 2-(8-Bromo-2-fluoroindolizin-3-yl)-3-methyl-6-(trifluoromethyl)-3H-imidazo[4,5-b]pyridine Cyclization involving 8-bromo-2-fluoro-N-(2-(methylamino)-5-(trifluoromethyl)pyridin-3-yl)indolizine-3-carboxamide (2.2 g, 5.10 mmol) and following the same synthetic procedure as described in Step 4 of Example 34 afforded 2-(8-bromo-2-fluoroindolizin-3-yl)-3-methyl-6-

(trifluoromethyl)-3H-imidazo[4,5-b]pyridine (1.8 g, 4.4 mmol, 85% yield). ESI MS (m/z) 412.70, 414.70 [(MH)+ Br$^{79,81}$].

e) Step-5: 2-(8-Bromo-2-(ethylthio)indolizin-3-yl)-3-methyl-6-(trifluoromethyl)-3H-imidazo[4,5-b]pyridine 2-(8-Bromo-2-fluoroindolizin-3-yl)-3-methyl-6-(trifluoromethyl)-3H-imidazo[4,5-b]pyridine (100 mg, 0.2 mmol) as an appropriate starting material and following the same synthetic procedure as described in Step 5 of Example 34 afforded 2-(8-bromo-2-(ethylthio)indolizin-3-yl)-3-methyl-6-(trifluoromethyl)-3H-imidazo[4,5-b]pyridine (50 mg, 0.1 mmol, 45% yield). $^1$H-NMR (400 MHz, DMSO-d6) δ 8.83 (d, J=1.2 Hz, 1H), 8.61 (d, J=1.5 Hz, 1H), 8.41 (d, J=7.0 Hz, 1H), 7.33 (dd, J=7.3, 0.6 Hz, 1H), 6.83 (d, J=0.6 Hz, 1H), 6.66 (t, J=7.2 Hz, 1H), 3.82 (s, 3H), 2.98 (q, J=7.3 Hz, 2H), 1.18 (q, J=7.1 Hz, 3H); ESI MS (m/z) 454.95, 456.95 [(MH)+ Br$^{79,81}$].

f) Step-6: 2-(8-Bromo-2-(ethylsulfonyl)indolizin-3-yl)-3-methyl-6-(trifluoromethyl)-3H-imidazo[4,5-b]pyridine Oxidation of 2-(8-bromo-2-(ethylthio)indolizin-3-yl)-3-methyl-6-(trifluoromethyl)-3H-imidazo[4,5-b]pyridine (840 mg, 1.84 mmol) by following the same synthetic procedure as described in Step 6 of Example 34 afforded 2-(8-bromo-2-(ethylsulfonyl)indolizin-3-yl)-3-methyl-6-(trifluoromethyl)-3H-imidazo[4,5-b]pyridine pyridine (800 mg, 1.6 mmol, 89% yield). $^1$H-NMR (400 MHz, DMSO-d6) δ 8.89-8.93 (m, 1H), 8.55-8.72 (m, 1H), 8.12-8.23 (m, 1H), 7.50-7.57 (m, 1H), 7.11-7.26 (m, 1H), 6.75-6.85 (m, 1H), 3.72 (s, 3H), 3.39-3.51 (q, J=6.8 Hz, 2H), 1.15 (t, J=7.1 Hz, 3H); ESI MS (m/z) 487.05, 489.05 [(MH)+ Br$^{79,81}$].

g) Step-7: 2-(8-(3,5-Dichlorophenyl)-2-(ethylsulfonyl)indolizin-3-yl)-3-methyl-6-(trifluoromethyl)-3H-imidazo[4,5-b]pyridine Suzuki coupling involving 2-(8-bromo-2-(ethylsulfonyl)indolizin-3-yl)-3-methyl-6-(trifluoromethyl)-3H-imidazo[4,5-b]pyridine (150 mg, 0.31 mmol) and (3,5-dichlorophenyl)boronic acid (58.7 mg, 0.31 mmol) while following the same synthetic procedure as described in Step 7 of Example 34 afforded 2-(8-(3,5-dichlorophenyl)-2-(ethylsulfonyl)indolizin-3-yl)-3-methyl-6-(trifluoromethyl)-3H-imidazo[4,5-b]pyridine (65 mg, 0.1 mmol, 38% yield). $^1$H-NMR (400 MHz, DMSO-d6) δ 8.93 (s, 1H), 8.73 (s, 1H), 8.22 (d, J=7.1 Hz, 1H), 7.81 (s, 3H), 7.27 (d, J=6.8 Hz, 1H), 6.99-7.13 (m, 2H), 3.73 (s, 3H), 3.40 (q, J=7.2 Hz, 2H), 1.11 (t, J=7.3 Hz, 3H); ESI-MS (m/z) 553.15, 555.15 [(MH)+ Cl$^{35,37}$].

Example 4: Synthesis of 2-(6-(3,5-dichlorophenyl)-2-(ethylsulfonyl)indolizin-3-yl)-3-methyl-6-(trifluoromethyl)-3H-imidazo[4,5-b]pyridine (Compound No. 8)

The title compound was prepared starting from ethyl 8-bromo-2-fluoroindolizine-3-carboxylate as obtained in step 2 of example 42 and following the same sequence of steps 3-7 as described for the synthesis of 2-(8-(3,5-dichlorophenyl)-2-(ethylsulfonyl)indolizin-3-yl)-3-methyl-6-(trifluoromethyl)-3H-imidazo[4,5-b]pyridine afforded 2-(6-(3,5-dichlorophenyl)-2-(ethylsulfonyl)indolizin-3-yl)-3-methyl-6-(trifluoromethyl)-3H-imidazo[4,5-b]pyridine.

$^1$H-NMR (400 MHz, DMSO-d6) δ 8.92-8.93 (m, 1H), 8.71-8.71 (m, 1H), 8.55 (d, J=0.7 Hz, 1H), 7.90-7.94 (m, 1H), 7.73-7.77 (m, 2H), 7.62 (m, 1H), 7.53 (dd, J=9.4, 1.6 Hz, 1H), 7.01-7.28 (m, 1H), 3.75 (s, 3H), 3.33-3.42 (m, 2H), 1.15 (t, J=6.2 Hz, 3H); ESI MS (m/z) 553.00, 555.00 [(MH)+ Cl$^{35,37}$].

Example 5: Synthesis of 2-(2-(ethylthio)-5,7-dimethylpyrazolo[1,5-a]pyrimidin-3-yl)-3-methyl-6-(trifluoromethyl)-3H-imidazo[4,5-b]pyridine (Compound No. 9)

a) Step-1: Ethyl 2-(ethylthio)-5,7-dimethylpyrazolo[1,5-a]pyrimidine-3-carboxylate To a stirred solution of ethyl 5-amino-3-(ethylthio)-1H-pyrazole-4-carboxylate (2 g, 9.3 mmol) [prepared according to the procedure as described in *Acta Chimica Sinica* 2003, 63, 855; *Organic & Biomolecular Chemistry*, 2010, 8, 3394] and 2,4-pentanedione (1.15 mL, 11.15 mmol) in acetic acid (20 mL), two drops of concentrated sulfuric acid were added. The resulting mixture was heated at 50° C. for 15 min. After completion of the reaction, the reaction mixture was cooled to 25° C. Water (5 mL) was added to the above reaction mixture, and the reaction mixture was extracted thrice with ethyl acetate (10 mL). The combined ethyl acetate layers were dried over sodium sulphate and concentrated under reduced pressure to obtain the crude product. The crude product was purified by column chromatography on silica gel using 20% ethyl acetate in hexane as an eluent to obtain ethyl 2-(ethylthio)-5,7-dimethylpyrazolo[1,5-a]pyrimidine-3-carboxylate (2.0 g, 7.20 mmol, 77% yield). $^1$H-NMR (400 MHz, DMSO-d6) δ 7.04 (d, J=0.7 Hz, 1H), 4.25 (q, J=7.1 Hz, 2H), 3.17 (q, J=7.3 Hz, 2H), 2.67-2.83 (m, 3H), 2.56 (d, J=23.7 Hz, 3H), 1.36-1.53 (m, 3H), 1.30 (q, J=6.9 Hz, 3H); ESI MS (m/z) 280.20 (MH)+.

b) Step-2: 2-(Ethylthio)-5,7-dimethylpyrazolo[1,5-a]pyrimidine-3-carboxylic acid To a stirred suspension of ethyl 2-(ethylthio)-5,7-dimethylpyrazolo[1,5-a]pyrimidine-3-carboxylate (2.3 g, 8.2 mmol) in a mixture of ethanol (37.5 mL) and water (37.5 mL), lithium hydroxide monohydrate (5.18 g, 123.0 mmol) was added. The reaction mixture was stirred at 60° C. for 17 h. After completion of the reaction, the reaction mixture was concentrated under reduced pressure to strip of ethanol. The residue was treated with 1N hydrochloric acid solution and the resulting precipitate of 2-(ethylthio)-5,7-dimethylpyrazolo[1,5-a]pyrimidine-3-carboxylic acid (88 mg, 0.35 mmol, 59% yield) was filtered off, washed with water (10 mL) and dried under vacuum. $^1$H-NMR (400 MHz, DMSO-d6) δ 12.16 (s, 1H), 7.02 (d, J=0.7 Hz, 1H), 3.15 (q, J=7.3 Hz, 2H), 2.67 (d, J=0.9 Hz, 3H), 2.53 (s, 3H), 1.37 (t, J=7.3 Hz, 3H); ESI MS (m/z) 252.15 (MH)+.

c) Step-3: 2-(Ethylthio)-5,7-dimethyl-N-(2-(methylamino)-5-(trifluoromethyl)pyridin-3-yl)pyrazolo[1,5-a]pyrimidine-3-carboxamide To a solution of 2-(ethylthio)-5,7-dimethylpyrazolo[1,5-a]pyrimidine-3-carboxylic acid (500 mg, 2 mmol) in anhydrous N,N-dimethylformamide (27 mL), 1-[bis(dimethylamino)methylene]-1H-1,2,3-triazolo[4,5-b]pyridinium 3-oxide hexafluorophosphate (HATU) (908 mg, 2.4 mmol) was added and the reaction mixture was stirred at 0-5° C. for 15 min. Subsequently N-2-methyl-5-(trifluoromethyl)pyridine-2,3-diamine (761 mg, 4 mmol) and N,N-diisopropylethylamine (1 mL, 6 mmol) was added to the above reaction mixture, and the reaction was heated at 100° C. for 16 h. After completion of the reaction, water (40 mL) was added to the reaction mixture, which was then extracted thrice with ethyl acetate (30 mL). The combined ethyl acetate layers were dried over sodium sulphate and concentrated under reduced pressure to get crude product. The crude product was purified by column chromatography on silica gel using 40% ethyl acetate in hexane as an eluent to obtain 2-(ethylthio)-5,7-dimethyl-N-(2-(methylamino)-5-(trifluoromethyl)pyridin-3-yl)pyrazolo[1,5-a]pyrimidine-3-carboxamide (510 mg, 1.20 mmol, 60% yield). $^1$H-NMR (400 MHz, DMSO-d6) δ 9.74 (s, 1H), 8.27 (d, J=1.3 Hz, 1H), 8.05-8.07 (m, 1H), 7.14-7.28 (m, 1H), 6.80 (d, J=4.9 Hz, 1H), 3.22 (q, J=7.3 Hz, 2H), 2.92 (d, J=4.6 Hz, 3H), 2.76 (d, J=0.5 Hz, 3H), 2.64 (s, 3H), 1.41 (t, J=7.3 Hz, 3H); ESI MS (m/z) 425.20 (MH)$^+$.

d) Step-4: 2-(2-(Ethylthio)-5,7-dimethylpyrazolo[1,5-a]pyrimidin-3-yl)-3-methyl-6-(trifluoromethyl)-3H-imidazo[4,5-b]pyridine A mixture of 2-(ethylthio)-5,7-dimethyl-N-(2-(methylamino)-5-(trifluoromethyl)pyridin-3-yl)pyrazolo[1,5-a]pyrimidine-3-carboxamide (380 mg, 0.90 mmol), p-toluenesulfonic acid monohydrate (511 mg, 2.7 mmol) in N-methyl-2-pyrrolidone (8 mL) was irradiated in a microwave oven at 150° C. for 1.5 h under nitrogen atmosphere. After completion of the reaction, the reaction mixture was allowed to cool to 25° C. Water (50 mL) was added to the above reaction mixture followed by extraction with ethyl acetate (50 mL). The ethyl acetate layer was washed with water (30 mL), dried over anhydrous sodium sulfate and concentrated under reduced pressure to obtain the crude product. The crude product was purified by flash column chromatography on silica gel using 40% ethyl acetate in hexane as an eluent to obtain 2-(2-(ethylthio)-5,7-dimethylpyrazolo[1,5-a]pyrimidin-3-yl)-3-methyl-6-(trifluoromethyl)-3H-imidazo[4,5-b]pyridine (194 mg, 0.5 mmol, 53% yield). $^1$H-NMR (400 MHz, CDCl$_3$) δ 8.64 (d, J=1.2 Hz, 1H), 8.31 (d, J=1.5 Hz, 1H), 6.65 (d, J=0.7 Hz, 1H), 4.02 (s, 3H), 3.29 (q, J=7.4 Hz, 2H), 2.79 (d, J=0.7 Hz, 3H), 2.57 (s, 3H), 1.46 (t, J=7.3 Hz, 3H); ESI MS (m/z) 407.10 (MH)$^+$.

Example 6: Synthesis of 2-(2-(ethylsulfonyl)-5,7-dimethylpyrazolo[1,5-a]pyrimidin-3-yl)-3-methyl-6-(trifluoromethyl)-3H-imidazo[4,5-b]pyridine (Compound No. 10)

To a solution of 2-(2-(ethylthio)-5,7-dimethylpyrazolo[1,5-a]pyrimidin-3-yl)-3-methyl-6-(trifluoromethyl)-3H-imidazo[4,5-b]pyridine (165 mg, 0.4 mmol) in dichloromethane (8 mL) m-chloroperbenzoic acid (255 mg, 0.8 mmol) was added portion wise at 0-5° C. The reaction mixture was stirred at 25° C. for 5 h. After completion of the reaction, the reaction mixture was diluted with aqueous sodium thiosulfate solution and extracted with dichloromethane (20 mL). The dichloromethane layer was washed with a saturated aqueous sodium bicarbonate solution, dried over anhydrous sodium sulfate and concentrated under reduced pressure to obtain the crude product. The crude product was purified by flash column chromatography on silica gel using 60% ethyl acetate in hexane as an eluent to obtain 2-(2-(ethylsulfonyl)-5,7-dimethylpyrazolo[1,5-a]pyrimidin-3-yl)-3-methyl-6-(trifluoromethyl)-3H-imidazo[4,5-b]pyridine (92 mg, 0.2 mmol, 52% yield). $^1$H-NMR (400 MHz, DMSO-d6) δ 8.84 (s, 1H), 8.61 (d, J=2.0 Hz, 1H), 7.36 (d, J=1.0 Hz, 1H), 3.78 (s, 3H), 3.73 (q, J=7.3 Hz, 2H), 2.83 (s, 3H), 2.57 (s, 3H), 1.25 (t, J=7.3 Hz, 3H); ESI MS (m/z) 439.25 (MH)$^+$.

Example 7: Synthesis of 2-(2-(ethylthio)-7-(4-fluorophenyl)pyrazolo[1,5-a]pyrimidin-3-yl)-3-methyl-6-(trifluoromethyl)-3H-imidazo[4,5-b]pyridine (Compound No. 19)

a) Step 1: Ethyl 2-(ethylthio)-7-(4-fluorophenyl)pyrazolo[1,5-a]pyrimidine-3-carboxylate To a stirred solution of ethyl 3-amino-5-(ethylthio)-1H-pyrazole-4-carboxylate (1.9 g, 9 mmol) in acetic acid (65.4 mL), (E)-3-(dimethylamino)-1-(4-fluorophenyl)prop-2-en-1-one (1.7 g, 9 mmol) was added and the resulting mixture was heated at 50° C. for 2 h. After completion of the reaction, acetic acid was removed under reduced pressure to obtain the crude product. The crude product was purified by column chromatography on silica gel using 30% ethyl acetate in hexane as an eluent to obtain ethyl 2-(ethylthio)-7-(4-fluorophenyl)pyrazolo[1,5-a]pyrimidine-3-carboxylate (2.2 g, 6.37 mmol, 71% yield). $^1$H-NMR (400 MHz, DMSO-d6) δ 8.77 (d, J=4.6 Hz, 1H), 8.20-8.25 (m, 2H), 7.44-7.49 (m, 2H), 7.42 (d, J=4.6 Hz, 1H), 4.30 (q, J=7.1 Hz, 2H), 3.09 (q, J=7.3 Hz, 2H), 1.33 (dt, J=15.6, 7.2 Hz, 6H); ESI MS (m/z) 346.30 (MH)$^+$.

b) Step 2: 2-(Ethylthio)-7-(4-fluorophenyl)pyrazolo[1,5-a]pyrimidine-3-carboxylic acid To a stirred suspension of ethyl 2-(ethylthio)-7-(4-fluorophenyl)pyrazolo[1,5-a]pyrimidine-3-carboxylate (2.2 g, 6.4 mmol) in a mixture of ethanol (30 mL) and water (30 mL), lithium hydroxide monohydrate (2.7 g, 63.7 mmol) was added. The reaction mixture was stirred at 60° C. for 2 h. After completion of the reaction, the reaction mixture was concentrated under reduced pressure to strip off ethanol. The residue was treated with 1N hydrochloric acid solution and the resulting precipitate of 2-(ethylthio)-7-(4-fluorophenyl)pyrazolo[1,5-a]pyrimidine-3-carboxylic acid (1.6 g, 5 mmol, 79% yield) was filtered off, washed with water (10 mL) and dried under vacuum. $^1$H-NMR (400 MHz, DMSO-d6) δ 8.44 (d, J=4.6 Hz, 1H), 8.28 (ddd, J=12.1, 5.3, 3.2 Hz, 2H), 7.43-7.49 (m, 2H), 7.19 (d, J=4.6 Hz, 1H), 3.00 (q, J=7.3 Hz, 2H), 1.32 (t, J=7.3 Hz, 3H); ESI MS (m/z) 317.90 (M)$^+$.

c) Step 3: 2-(Ethylthio)-7-(4-fluorophenyl)-N-(2-(methylamino)-5-(trifluoromethyl)pyridin-3-yl)pyrazolo[1,5-a]pyrimidine-3-carboxamide To a suspension of 2-(ethylthio)-7-(4-fluorophenyl)pyrazolo[1,5-a]pyrimidine-3-carboxylic acid (500 mg, 1.58 mmol) in anhydrous dichloromethane (15 mL), 2 drops of N,N-dimethylformamide were added, followed by addition of oxalyl chloride (0.2 mL, 2.4 mmol), and the resulting reaction mixture was stirred at 25° C. for 4 h. The reaction mixture was evaporated under reduced pressure at a bath temperature of 60° C. The resulting residue was dissolved in anhydrous dichloromethane (15 mL) and was added dropwise at 0° C. to a stirred solution of N-2-methyl-5-(trifluoromethyl)pyridine-2,3-diamine (304 mg, 1.6 mmol) and triethyl amine (0.9 mL, 6.6 mmol). The reaction mixture was stirred at 25° C. for 16 h. After completion of the reaction, water (40 mL) was added to the reaction mixture, which was then extracted thrice with ethyl acetate (20 mL). The combined ethyl acetate layers were dried over sodium sulphate and concentrated under reduced pressure to obtain crude product. The crude product was purified by column chromatography on silica gel using 40% ethyl acetate in hexane as an eluent to obtain 2-(ethylthio)-7-(4-fluorophenyl)-N-(2-(methylamino)-5-(trifluoromethyl)pyridin-3-yl)pyrazolo[1,5-a]pyrimidine-3-carboxamide (377 mg, 0.8 mmol, 49% yield). $^1$H-NMR (400 MHz, DMSO-d6) δ 9.51 (s, 1H), 8.85 (d, J=4.6 Hz, 1H), 8.28-8.34 (m, 3H), 7.90 (d, J=1.8 Hz, 1H), 7.49-7.53 (m, 3H), 6.92 (d, J=4.6 Hz, 1H), 3.14 (q, J=7.2 Hz, 2H), 2.89 (d, J=4.6 Hz, 3H), 1.33-1.39 (m, 3H); ESI MS (m/z) 490.95 (M)$^+$.

d) Step 4: 2-(2-(Ethylthio)-7-(4-fluorophenyl)pyrazolo[1,5-a]pyrimidin-3-yl)-3-methyl-6-(trifluoromethyl)-3H-imidazo[4,5-b]pyridine A mixture of 2-(ethylthio)-7-(4-fluorophenyl)-N-(2-(methylamino)-5-(trifluoromethyl)pyridin-3-yl)pyrazolo[1,5-a]pyrimidine-3-carboxamide (377 mg, 0.8 mmol), p-toluenesulfonic acid monohydrate (439 mg, 2.3 mmol) in N-methyl-2-pyrrolidone (8 mL) was irradiated in a microwave oven at 150° C. for 1.5 h under nitrogen atmosphere. After completion of the reaction, the reaction mixture was allowed to cool to 25° C. Water (50 mL) was added to the above reaction mixture followed by extraction of the same with ethyl acetate (150 mL). The ethyl acetate layer was washed with water (50 mL), dried over anhydrous sodium sulfate and concentrated under reduced pressure to obtain the crude product. The crude product was purified by flash column chromatography on silica gel using 40% ethyl acetate in hexane as an eluent to obtain 2-(2-(ethylthio)-7-(4-fluorophenyl)pyrazolo[1,5-a]pyrimidin-3-yl)-3-methyl-6-(trifluoromethyl)-3H-imidazo[4,5-b]pyridine (185 mg, 0.4 mmol, 51% yield). $^1$H-NMR (400 MHz, DMSO-d6) δ 8.77 (q, J=0.9 Hz, 1H), 8.75 (d, J=4.4 Hz, 1H), 8.54-8.54 (m, 1H), 8.29-8.33 (m, 2H), 7.49-7.53 (m, 2H), 7.43 (d, J=4.6 Hz, 1H), 3.97 (s, 3H), 3.17 (q, J=7.3 Hz, 2H), 1.36 (t, J=7.3 Hz, 3H); ESI MS (m/z) 473.00 (MH)$^+$.

Example 8: Synthesis of 2-(2-(ethylthio)pyrazolo[1,5-a]pyrimidin-3-yl)-3-methyl-6-(trifluoromethyl)-3H-imidazo[4,5-c]pyridine (Compound No. 22)

a) Step 1: Ethyl 2-(ethylthio)pyrazolo[1,5-a]pyrimidine-3-carboxylate

To a stirred solution of ethyl 5-amino-3-(ethylthio)-1H-pyrazole-4-carboxylate (1.3 g, 6 mmol) in acetic acid (38 mL), 3-(dimethylamino)acrolein (0.9 mL, 9.1 mmol) was added. The reaction mixture was allowed to stir at 25° C. for 24 h. After completion of the reaction, the reaction mixture was neutralized using saturated aqueous sodium bicarbonate and extracted thrice with ethyl acetate (20 mL). The combined ethyl acetate layers were dried over sodium sulphate and concentrated under reduced pressure to obtain the crude product. The crude product was purified by column chromatography on silica gel using 30% ethyl acetate in hexane as an eluent to obtain ethyl 2-(ethylthio)pyrazolo[1,5-a]pyrimidine-3-carboxylate (0.9 g, 3.5 mmol, 57% yield). $^1$H-NMR (400 MHz, DMSO-d6) δ 9.18 (dd, J=6.9, 1.7 Hz, 1H), 8.74 (q, J=1.9 Hz, 1H), 7.20 (dd, J=7.0, 4.3 Hz, 1H), 4.27 (q, J=7.1 Hz, 2H), 3.16 (q, J=7.3 Hz, 2H), 1.37 (t, J=7.3 Hz, 3H), 1.25-1.31 (m, 3H); ESI MS (m/z) 252.10 (MH)$^+$.

b) Step 2: 2-(Ethylthio)pyrazolo[1,5-a]pyrimidine-3-carboxylic acid

To a stirred suspension of ethyl 2-(ethylthio)pyrazolo[1,5-a]pyrimidine-3-carboxylate (0.9 g, 3.5 mmol) in a mixture of ethanol (50 mL) and water (50 mL), lithium hydroxide monohydrate (1.45 g, 34.6 mmol) was added. The reaction mixture was stirred at 60° C. for 2 h. After completion of the reaction, the reaction mixture was concentrated under reduced pressure to strip of ethanol. The residue was treated with 1N hydrochloric acid solution and the resulting precipitate of 2-(ethylthio)pyrazolo[1,5-a]pyrimidine-3-carboxylic acid (0.6 g, 2.8 mmol, 81% yield) was filtered off, washed with water (10 mL) and dried under vacuum. $^1$H-NMR (400 MHz, DMSO-d6) δ 12.38 (s, 1H), 9.16 (dd, J=7.0, 1.8 Hz, 1H), 8.69 (q, J=2.0 Hz, 1H), 7.16 (dd, J=6.7, 4.3 Hz, 1H), 3.14 (q, J=7.3 Hz, 2H), 1.36 (t, J=7.5 Hz, 3H); ESI MS (m/z) 223.85 (M)$^+$.

c) Step 3: 2-(Ethylthio)-N-(5-(methylamino)-2-(trifluoromethyl)pyridin-4-yl)pyrazolo[1,5-a]pyrimidine-3-carboxamide To a suspension of 2-(ethylthio)pyrazolo[1,5-a]pyrimidine-3-carboxylic acid (325 mg, 1.5 mmol) in anhydrous dichloromethane (14 mL), 2 drops of N,N-dimethylformamide were added, followed by the addition of oxalyl chloride (0.2 mL, 2.2 mmol), and the resulting mixture was stirred at 25° C. for 4 h. The reaction mixture was evaporated under reduced pressure at a bath temperature of 60° C. The resulting residue was dissolved in anhydrous dichloromethane (14 mL) and added dropwise at 0° C. to a stirred solution of N-3-methyl-6-(trifluoromethyl) pyridine-3,4-diamine (278 mg, 1.5 mmol) and triethyl amine (0.85 mL, 6.1 mmol). The reaction mixture was stirred at 25° C. for 16 h. After completion of the reaction, water (40 mL) was added to the reaction mixture, which was then extracted thrice with ethyl acetate (20 mL). The combined ethyl acetate layers were dried over sodium sulphate and concentrated under reduced pressure to obtain crude product. The crude product was purified by column chromatography on silica gel using 40% ethyl acetate in hexane as an eluent to obtain 2-(ethylthio)-N-(5-(methylamino)-2-(trifluoromethyl)pyridin-4-yl)pyrazolo[1,5-a]pyrimidine-3-carboxamide (392 mg, 1 mmol, 68% yield). $^1$H-NMR (400 MHz, CDCl$_3$) δ 8.45 (d, J=6.8 Hz, 1H), 8.26 (d, J=3.9 Hz, 1H), 8.11 (d, J=6.1 Hz, 1H), 6.95 (s, 1H), 6.72 (dd, J=6.8, 4.2 Hz, 1H), 5.18-4.61 (2H), 3.35 (s, 3H), 3.21 (q, J=7.3 Hz, 2H), 1.41-1.44 (m, 3H); ESI MS (m/z) 397.05 (MH)$^+$.

d) Step 4: 2-(2-(Ethylthio)pyrazolo[1,5-a]pyrimidin-3-yl)-3-methyl-6-(trifluoromethyl)-3H-imidazo[4,5-c]pyridine A mixture of 2-(ethylthio)-N-(5-(methylamino)-2-(trifluoromethyl)pyridin-4-yl)pyrazolo[1,5-a]pyrimidine-3-carboxamide (392 mg, 1 mmol), p-toluenesulfonic acid monohydrate (564 mg, 3 mmol) in N-methyl-2-pyrrolidone (9 mL) was irradiated in a microwave oven at 150° C. for 1.5 h under nitrogen atmosphere. After completion of the reaction, the reaction mixture was allowed to cool to 25° C. Water (50 mL) was added to the above reaction mixture followed by extraction with ethyl acetate (150 mL). The ethyl acetate layer was washed with water (30 mL), dried over anhydrous sodium sulfate and concentrated under reduced pressure to obtain the crude product. The crude product was purified by flash column chromatography on silica gel using 40% ethyl acetate in hexane as an eluent to obtain 2-(2-(ethylthio)pyrazolo[1,5-a]pyrimidin-3-yl)-3-methyl-6-(trifluoromethyl)-3H-imidazo[4,5-c]pyridine (256 mg, 0.7 mmol, 68% yield). $^1$H-NMR (400 MHz, DMSO-d6) δ 9.27 (dd, J=6.8, 1.7 Hz, 1H), 9.14 (s, 1H), 8.70 (dd, J=4.3, 1.6 Hz, 1H), 8.19 (d, J=0.7 Hz, 1H), 7.21 (dd, J=6.8, 4.2 Hz, 1H), 4.01 (s, 3H), 3.22 (q, J=7.3 Hz, 2H), 1.32-1.38 (m, 3H); ESI MS (m/z) 378.90 (MH)+.

Example 9: Synthesis of 2-(2-(ethylsulfonyl)pyrazolo[1,5-a]pyrimidin-3-yl)-3-methyl-6-(trifluoromethyl)-3H-imidazo[4,5-c]pyridine (Compound No. 23)

To a solution of 2-(2-(ethylthio)pyrazolo[1,5-a]pyrimidin-3-yl)-3-methyl-6-(trifluoromethyl)-3H-imidazo[4,5-c]pyridine (187 mg, 0.5 mmol) in dichloromethane (9 mL), m-chloroperbenzoic acid (262 mg, 1 mmol) was added portion wise at 0-5° C. The reaction mixture was stirred at 25° C. for 5 h. After completion of the reaction, the reaction mixture was diluted with aqueous sodium thiosulfate solution and extracted with dichloromethane (20 mL). The dichloromethane extract was washed with a saturated aqueous sodium bicarbonate solution, dried over anhydrous sodium sulfate and concentrated under reduced pressure to obtain the crude product. The crude product was purified by flash column chromatography on silica gel using 60% ethyl acetate in hexane as an eluent to obtain 2-(2-(ethylsulfonyl)pyrazolo[1,5-a]pyrimidin-3-yl)-3-methyl-6-(trifluoromethyl)-3H-imidazo[4,5-c]pyridine (105 mg, 0.3 mmol, 52% yield). $^1$H-NMR (400 MHz, DMSO-d6) δ 9.50 (dd, J=7.1, 1.7 Hz, 1H), 9.22 (s, 1H), 8.87 (q, J=2.0 Hz, 1H), 8.25 (d, J=0.7 Hz, 1H), 7.51 (dd, J=7.2, 4.0 Hz, 1H), 3.90 (s, 3H), 3.74 (q, J=7.4 Hz, 2H), 1.24 (t, J=7.5 Hz, 3H) ESI MS (m/z) 411.05 (MH)+.

Example 10: Synthesis of 2-(2-(ethylsulfonyl)-7-(4-fluorophenyl)pyrazolo[1,5-a]pyrimidin-3-yl)-3-methyl-6-(trifluoromethyl)-3H-imidazo[4,5-b]pyridine (Compound No. 25)

To a solution of 2-(2-(ethylthio)-7-(4-fluorophenyl)pyrazolo[1,5-a]pyrimidin-3-yl)-3-methyl-6-(trifluoromethyl)-3H-imidazo[4,5-b]pyridine (185 mg, 0.4 mmol) in dichloromethane (6 mL), m-chloroperbenzoic acid (208 mg, 0.8 mmol) was added portion wise at 0-5° C. The reaction mixture was stirred at 25° C. for 5 h. After completion of the reaction, the reaction mixture was diluted with aqueous sodium thiosulfate solution and extracted with dichloromethane (15 mL). The dichloromethane layer was washed with a saturated aqueous sodium bicarbonate solution, dried over anhydrous sodium sulfate and concentrated under reduced pressure to obtain the crude product. The crude product was purified by flash column chromatography on silica gel using 60% ethyl acetate in hexane as an eluent to obtain 2-(2-(ethylsulfonyl)-7-(4-fluorophenyl)pyrazolo[1,5-a]pyrimidin-3-yl)-3-methyl-6-(trifluoromethyl)-3H-imidazo[4,5-b]pyridine (120 mg, 0.2 mmol, 61% yield). $^1$H-NMR (400 MHz, DMSO-d6) δ 8.90 (d, J=4.6 Hz, 1H), 8.85 (d, J=1.5 Hz, 1H), 8.63 (d, J=1.5 Hz, 1H), 8.25-8.28 (m, 2H), 7.69 (d, J=4.6 Hz, 1H), 7.53-7.59 (m, 2H), 3.81 (s, 3H), 3.73 (q, J=7.4 Hz, 2H), 1.26 (t, J=7.3 Hz, 3H); ESI MS (m/z) 505.10 (MH)+.

Example 11: Synthesis of 2-(7-(3-chloro-5-fluorophenyl)-2-(ethylthio)pyrazolo[1,5-a]pyrimidin-3-yl)-3-methyl-6-(trifluoromethyl)-3H-imidazo[4,5-b]pyridine (Compound No. 102)

a) Step-1: 2-cyano-N-(2-(methylamino)-5-(trifluoromethyl)pyridin-3-yl)acetamide

To a stirred solution of 2-cyanoacetic acid (7 g, 82 mmol), N2-methyl-5-(trifluoromethyl)pyridine-2,3-diamine (12.58 g, 65.8 mmol) and hydroxybenzotriazole (HOBt) (15.12 g, 99 mmol) in dimethylformamide (350 mL), 1-Ethyl-3-(3-dimethylaminopropyl)carbodiimide hydrochloride (EDC-HCl) (18.93 g, 99.0 mmol) and N,N-diisopropylethylamine (35.9 mL, 206 mmol) were added. The resulting mixture was stirred at 25° C. for 24 h under nitrogen atmosphere. After completion of the reaction, water (100 mL) was added to the above reaction mixture and the reaction mixture was extracted thrice with ethyl acetate (100 mL). The combined ethyl acetate layers were dried over anhydrous sodium sulphate and concentrated under reduced pressure to obtain the crude product. The crude product was purified by column chromatography on silica gel using 30% ethyl acetate in hexane as an eluent to obtain 2-cyano-N-(2-(methylamino)-5-(trifluoromethyl)pyridin-3-yl)acetamide (11.8 g, 45.7 mmol, 55.5% yield). $^1$H-NMR (400 MHz, DMSO-d6) δ 9.61 (s, 1H), 8.26 (d, J=1.0 Hz, 1H), 7.64 (d, J=2.4 Hz, 1H), 6.94 (d, J=4.4 Hz, 1H), 3.83 (d, J=17.6 Hz, 2H), 2.87 (d, J=4.6 Hz, 3H); ESI MS (m/z)258 (M)+.

b) Step-2: 2-(3-Methyl-6-(trifluoromethyl)-3H-imidazo[4,5-b]pyridin-2-yl)acetonitrile A solution of 2-cyano-N-(2-(methylamino)-5-(trifluoromethyl)pyridin-3-yl)acetamide (11.8 g, 45.7 mmol) in acetic acid (120 mL) were heated at 100° C. for 2 h. After completion of the reaction, the reaction mixture was allowed to cool to 25° C. The reaction mixture was concentrated under reduced pressure to strip of acetic acid. Water (100 mL) was added to the above concentrated reaction mixture and the reaction mixture were extracted thrice with ethyl acetate (75 mL). The ethyl acetate layer was washed with water (100 mL), dried over anhydrous sodium sulfate and concentrated under reduced pressure to obtain the crude product. The crude product was purified by flash column chromatography on silica gel using 15% ethyl acetate in hexane as an eluent to obtain 2-(3-methyl-6-(trifluoromethyl)-3H-imidazo[4,5-b]pyridin-2-yl)acetonitrile (9.0 g, 37.5 mmol, 82% yield). $^1$H-NMR (400 MHz, DMSO-d6) δ 8.76 (t, J=1.0 Hz, 1H), 8.55-8.56 (m, 1H), 4.69 (s, 2H), 3.82 (s, 3H); ESI MS (m/z) 240.95 (MH)+.

c) Step-3: 3,3-Bis(ethylthio)-2-(3-methyl-6-(trifluoromethyl)-3H-imidazo[4,5-b]pyridin-2-yl)acrylonitrile To a stirred solution of 2-(3-methyl-6-(trifluoromethyl)-3H-imidazo[4,5-b]pyridin-2-yl)acetonitrile (8.8 g, 36.6 mmol) in acetonitrile (80 mL), potassium hydroxide (4.84 g, 73.3 mmol) was added at 25° C. The resulting reaction mixture was stirred for 1 h at 25° C. The reaction mixture was further cooled to −5° C. and added dropwise addition of carbon disulfide (2.2 mL, 36.6 mmol) over 10 min. The reaction mixture was stirred for 1 h at −5° C. Further in the reaction mixture, the ethyl iodide (5.92 mL, 73.3 mmol) was added at 0° C. dropwise over 15 min. The reaction mixture again stirred for 2 h at 0° C. and left at 25° C. for 16 h. The reaction mixture was concentrated under reduced pressure. The crude product was purified by flash column chromatography on silica gel using 10% ethyl acetate in hexane as an eluent to obtain 3,3-bis(ethylthio)-2-(3-methyl-6-(trifluoromethyl)-3H-imidazo[4,5-b]pyridin-2-yl)acrylonitrile (12.4 g, 33.3 mmol, 91% yield). $^1$H-NMR (400 MHz, DMSO-d6) δ 8.84 (q, J=1.0 Hz, 1H), 8.62 (q, J=0.9 Hz, 1H), 3.87 (s, 3H), 3.25 (q, J=7.3 Hz, 2H), 2.84 (q, J=7.4 Hz, 2H), 1.37 (t, J=7.2 Hz, 3H), 1.14 (t, J=7.3 Hz, 3H); ESI MS (m/z)373.00 (MH)+.

d) Step-4: 3-(Ethylthio)-4-(3-methyl-6-(trifluoromethyl)-3H-imidazo[4,5-b]pyridin-2-yl)-1H-pyrazol-5-amine To a stirred solution of 3,3-bis(ethylthio)-2-(3-methyl-6-(trifluoromethyl)-3H-imidazo[4,5-b]pyridin-2-yl)acrylonitrile (1 g, 2.69 mmol) in a mixture of acetonitrile (1 mL) and ethanol (2 mL), hydrazine monohydrate (0.17 mL, 2.69 mmol (79% w/v)) was added drop wise at 0° C. The reaction mixture was stirred at 0° C. for 1 h. The reaction mixture was diluted with ice cold water (20 mL) and the solid was precipitated. The precipitated solid was filtered, washed with water and dried under vacuum to obtain the crude product. The crude product was purified by column chromatography on silica gel using 100% ethyl acetate as an eluent to obtain 3-(ethylthio)-4-(3-methyl-6-(trifluoromethyl)-3H-imidazo[4,5-b]pyridin-2-yl)-1H-pyrazol-5-amine (720 mg, 2.1 mmol, 78% yield). 1H-NMR (400 MHz, DMSO-D6) δ 12.01 (s, 1H), 8.66 (s, 1H), 8.37 (s, 1H), 5.75 (s, 2H), 3.77 (s, 3H), 2.88 (q, J=6.8 Hz, 2H), 1.15 (t, J=6.8 Hz, 3H); ESI MS (m/z) 343.00 (MH)$^+$.

e) Step-5: 2-(Ethylthio)-3-(3-methyl-6-(trifluoromethyl)-3H-imidazo[4,5-b]pyridin-2-yl)pyrazolo[1,5-a]pyrimidin-7(4H)-one To a stirred solution of 3-(ethylthio)-4-(3-methyl-6-(trifluoromethyl)-3H-imidazo[4,5-b]pyridin-2-yl)-1H-pyrazol-5-amine (550 mg, 1.61 mmol) along with its un-cyclized intermediate in acetic acid (5 mL), methyl 3,3-dimethoxypropanoate (0.34 mL, 2.41 mmol) was added. The reaction mixture was heated at 100° C. for 6 h. The reaction mixture was cooled to 25° C. and concentrated under reduced pressure to strip of acetic acid. Water (20 mL) was added to the above concentrated reaction mixture and the reaction mixture were extracted thrice with ethyl acetate (25 mL). The ethyl acetate layer was washed with water (50 mL), dried over anhydrous sodium sulfate and concentrated under reduced pressure to obtain the crude product. The crude product was purified by flash column chromatography on silica gel using 5% methanol in dichloromethane as an eluent to obtain 2-(ethylthio)-3-(3-methyl-6-(trifluoromethyl)-3H-imidazo[4,5-b]pyridin-2-yl)pyrazolo[1,5-a]pyrimidin-7(4H)-one (375 mg, 0.95 mmol, 59% yield). $^1$H-NMR (400 MHz, DMSO-d6) δ 12.40 (s, 1H), 8.80 (q, J=0.9 Hz, 1H), 8.56 (dd, J=2.1, 0.6 Hz, 1H), 7.84 (d, J=7.3 Hz, 1H), 5.87 (d, J=7.3 Hz, 1H), 3.77 (s, 3H), 3.16 (q, J=7.3 Hz, 2H), 1.32 (t, J=7.3 Hz, 3H); ESI MS (m/z) 395.00(M–H)+.

f) Step-6: 2-(7-Bromo-2-(ethylthio)pyrazolo[1,5-a]pyrimidin-3-yl)-3-methyl-6-(trifluoromethyl)-3H-imidazo[4,5-b]pyridine To a stirred solution of 2-(ethylthio)-3-(3-methyl-6-(trifluoromethyl)-3H-imidazo[4,5-b]pyridin-2-yl)pyrazolo[1,5-a]pyrimidin-7(4H)-one (1.05 g, 2.66 mmol) in acetonitrile (28 mL), potassium carbonate (1.10 g, 7.99 mmol) and phosphorus oxybromide (2.29 g, 7.99 mmol) were added at 25° C. The reaction mixture was further heated at 95° C. for 4 h. The reaction mixture was cooled to 0° C. The reaction mixture was diluted with ice-water mixture (50 mL). The pH of the reaction mixture was adjusted to 7-8 using slow addition of saturated aqueous sodium bicarbonate solution. The reaction mixture was extracted thrice with ethyl acetate (50 mL). The ethyl acetate layer was washed with water (50 mL), dried over anhydrous sodium sulfate and concentrated under reduced pressure to obtain the crude product. The crude product was purified by flash column chromatography on silica gel using 50% ethyl acetate in hexane as an eluent to obtain 2-(7-bromo-2-(ethylthio)pyrazolo[1,5-a]pyrimidin-3-yl)-3-methyl-6-(trifluoromethyl)-3H-imidazo[4,5-b]pyridine (980 mg, 2.14 mmol, 80% yield). $^1$H-NMR (400 MHz, DMSO-d6) δ 8.77 (t, J=1.1 Hz, 1H), 8.55 (d, J=1.5 Hz, 1H), 8.48 (d, J=4.6 Hz, 1H), 7.65 (d, J=4.6 Hz, 1H), 3.92 (s, 3H), 3.25 (q, J=7.3 Hz, 2H), 1.40 (t, J=7.3 Hz, 3H); ESI MS (m/z) 456.95, 458.95 (MH; Br$^{79,81}$)+ g) Step-7: 2-(7-(3-Chloro-5-fluorophenyl)-2-(ethylthio)pyrazolo[1,5-a]pyrimidin-3-yl)-3-methyl-6-(trifluoromethyl)-3H-imidazo[4,5-b]pyridine To a solution of 2-(7-bromo-2-(ethylthio)pyrazolo[1,5-a]pyrimidin-3-yl)-3-methyl-6-(trifluoromethyl)-3H-imidazo[4,5-b]pyridine (170 mg, 0.37 mmol) and (3-chloro-5-fluorophenyl)boronic acid (78 mg, 0.446 mmol) in a mixture of tetrahydrofuran (4 mL) and water (2 mL), sodium carbonate (197 mg, 1.86 mmol) was added. The reaction mixture was thoroughly deoxygenated by subjecting to vacuum/nitrogen cycles three times. The tetrakis(triphenylphosphine)palladium(0) (12.9 mg, 0.01 mmol) was added to the reaction mixture and was heated at 85° C. for 4 h. After completion of the reaction, the reaction mixture was cooled to 25° C. and filtered through a pad of celite. The filtrate was concentrated under reduced pressure and the crude product was purified by flash column chromatography on silica gel using 20% ethyl acetate in hexane as an eluent to obtain 2-(7-(3-chloro-5-fluorophenyl)-2-(ethylthio)pyrazolo[1,5-a]pyrimidin-3-yl)-3-methyl-6-(trifluoromethyl)-3H-imidazo[4,5-b]pyridine (120 mg, 0.24 mmol, 64% yield). $^1$H-NMR (400 MHz, DMSO-d6) δ 8.77-8.79 (m, 2H), 8.55 (d, J=1.5 Hz, 1H), 8.23 (d, J=1.5 Hz, 1H), 8.10 (dq, J=9.7, 1.2 Hz, 1H), 7.79 (dt, J=8.8, 2.1 Hz, 1H), 7.55 (d, J=4.6 Hz, 1H), 3.96 (s, 3H), 3.16 (q, J=7.3 Hz, 2H), 1.40 (t, J=7.2 Hz, 3H); ESI MS (m/z) 506.95, 508.95 (MH; Cl$^{35,37}$)+.

Example-12: Synthesis of 3-(7-(3,5-dichlorophenyl)-2-(ethylsulfonyl)pyrazolo[1,5-a]pyrimidin-3-yl)-6-(trifluoromethyl)-[1,2,4]triazolo[4,3-a]pyridine (Compound No. 111)

a) Step-1: 2-Hydrazineyl-5-(trifluoromethyl)pyridine

To a stirred solution of 2-chloro-5-(trifluoromethyl)pyridine (10.0 g, 55.1 mmol) in ethanol, hydrazine hydrate (5.18 g, 123 mmol) was added. The resulting reaction mixture was stirred at 90° C. for 16 h. The reaction mixture was cooled to 25° C. and concentrated under reduced pressure to strip of ethanol. Water (50 mL) was added to the above concentrated reaction mixture and the reaction mixture were extracted thrice with ethyl acetate (200 mL), dried over anhydrous sodium sulfate and concentrated under reduced pressure to obtain 2-hydrazinyl-5-(trifluoromethyl)pyridine (8.50 g, 48.00 mmol, 87% yield). $^1$H-NMR (400 MHz, DMSO-d6) δ 8.25 (d, J=0.7 Hz, 2H), 7.68 (dd, J=9.0, 2.4 Hz, 1H), 6.78 (d, J=9.0 Hz, 1H), 4.32 (s, 2H); ESI MS (m/z) 178.10 (MH)$^+$.

b) Step-2: 7-(3,5-Dichlorophenyl)-2-(ethylthio)-N'-(5-(trifluoromethyl)pyridin-2-yl)pyrazolo[1,5-a]pyrimidine-3-carbohydrazide To a stirred solution of 2-hydrazinyl-5-(trifluoromethyl)pyridine (0.80 g, 4.52 mmol) in N,N-dimethylformamide (8 mL), 7-(3,5-dichlorophenyl)-2-(ethylthio)pyrazolo[1,5-a]

pyrimidine-3-carboxylic acid (1.66 g, 4.52 mmol), 1-(3-dimethylaminopropyl)-3-ethylcarbodiimide hydrochloride (1.29 g, 6.77 mmol), 1-hydroxybenzotriazole (0.91 g, 6.77 mmol) and N,N-diisopropylethylamine (1.75 mL, 13.55 mmol) were added at 0° C. The reaction mixture was stirred at 25° C. for 16 h under nitrogen atmosphere. After completion of the reaction, water (20 mL) was added to the reaction mixture and the resulting precipitate was filtered and dried under reduced pressure to obtain 7-(3,5-dichlorophenyl)-2-(ethylthio)-N'-(5-(trifluoromethyl)pyridin-2-yl)pyrazolo[1,5-a]pyrimidine-3-carbohydrazide (1.2 g, 2.27 mmol, 50% yield). $^1$H-NMR (400 MHz, DMSO-d6) δ 9.78 (s, 1H), 9.39 (s, 1H), 8.83 (dd, J=11.9, 4.6 Hz, 1H), 8.42 (d, J=20.2 Hz, 1H), 8.24-8.29 (m, 2H), 7.91-7.99 (m, 1H), 7.84 (dd, J=8.9, 2.1 Hz, 1H), 7.58-7.61 (m, 1H), 6.77 (d, J=8.7 Hz, 1H), 3.09 (q, J=7.2 Hz, 2H), 1.40 (t, J=7.2 Hz, 3H); ESI MS (m/z) 527.25 (MH)$^+$.

c) Step-3: 3-(7-(3,5-Dichlorophenyl)-2-(ethylthio) pyrazolo[1,5-a]pyrimidin-3-yl)-6-(trifluoromethyl)-[1,2,4]triazolo[4,3-a]pyridine To 7-(3,5-Dichlorophenyl)-2-(ethylthio)-N'-(5-(trifluoromethyl)pyridin-2-yl)pyrazolo[1,5-a]pyrimidine-3-carbohydrazide (1 g, 1.90 mmol), phosphoryl chloride (3 mL) was added and the resulting reaction mixture was heated at 90° C. for 6 h. The reaction mixture was cooled at 25° C. and concentrated under reduced pressure. The reaction mixture was further cooled to 0° C. and the resulting mass was treated with saturated sodium bicarbonate solution to make the pH basic (pH 9). The resulting mixture was extracted thrice with ethyl acetate (50 mL). The combined ethyl acetate layers were dried over anhydrous sodium sulphate and concentrated under reduced to obtain the crude product. The crude product was purified by column chromatography on silica gel using 25% ethyl acetate in hexane as an eluent to obtain 3-(7-(3,5-dichlorophenyl)-2-(ethylthio)pyrazolo[1,5-a]pyrimidin-3-yl)-6-(trifluoromethyl)-[1,2,4]triazolo[4,3-a]pyridine (500 mg, 0.98 mmol, 52% yield). $^1$H-NMR (400 MHz, DMSO-d6) δ 9.09 (d, J=1.0 Hz, 1H), 8.72 (d, J=4.4 Hz, 1H), 8.32 (d, J=2.0 Hz, 2H), 8.09 (d, J=9.8 Hz, 1H), 7.96 (t, J=2.0 Hz, 1H), 7.68 (dd, J=9.7, 1.6 Hz, 1H), 7.56-7.58 (m, 1H), 3.17 (q, J=7.3 Hz, 2H), 1.42 (t, J=7.3 Hz, 3H); ESI MS (m/z) 508.70 (MH)+.

d) Step-4: 3-(7-(3,5-Dichlorophenyl)-2-(ethylsulfonyl)pyrazolo[1,5-a]pyrimidin-3-yl)-6-(trifluoromethyl)-[1,2,4]triazolo[4,3-a]pyridine To a solution of 3-(7-(3,5-dichlorophenyl)-2-(ethylthio) pyrazolo[1,5-a]pyrimidin-3-yl)-6-(trifluoromethyl)-[1,2,4] triazolo[4,3-a]pyridine (0.35 g, 0.68 mmol) in dichloromethane (8 mL), m-chloroperbenzoic acid (0.58 g, 2.06 mmol, 60%) was added at 0° C. The resulting reaction mixture was stirred at 25° C. for 16 h. The reaction mixture was diluted with dichloromethane (20 mL) and washed twice with aqueous saturated sodium bicarbonate (20 mL), followed by water (10 mL). The combined organic layers were dried over sodium sulphate and concentrated under reduced pressure to obtain the crude product. The crude product was purified by column chromatography on silica gel using 30% ethyl acetate in hexane as an eluent to obtain 3-(7-(3,5-dichlorophenyl)-2-(ethylsulfonyl)pyrazolo[1,5-a]pyrimidin-3-yl)-6-(trifluoromethyl)-[1,2,4]triazolo[4,3-a]pyridine (210 mg, 0.388 mmol, 56% yield). $^1$H-NMR (400 MHz, DMSO-d6) δ 8.90 (d, J=4.4 Hz, 2H), 8.24 (d, J=1.7 Hz, 2H), 8.15 (d, J=9.5 Hz, 1H), 8.01 (t, J=2.0 Hz, 1H), 7.82 (d, J=4.6 Hz, 1H), 7.74 (dd, J=9.7, 1.6 Hz, 1H), 3.62 (q, J=7.3 Hz, 2H), 1.27 (t, J=7.5 Hz, 3H); ESI MS (m/z) 540.90 (MH)+.

Example 13: Synthesis of (7-(3,5-dichlorophenyl)-3-(3-methyl-6-(trifluoromethyl)-3H-imidazo[4,5-b]pyridin-2-yl)pyrazolo[1,5-a]pyrimidin-2-yl)(ethyl)(imino)-$\lambda^6$-sulfanone (Compound No. 135)

To a stirred solution of 2-(7-(3,5-dichlorophenyl)-2-(ethylthio)pyrazolo[1,5-a]pyrimidin-3-yl)-3-methyl-6-(trifluoromethyl)-3H-imidazo[4,5-b]pyridine (312 mg, 0.60 mmol) and ammonium carbamate (140 mg, 1.79 mmol) in methanol (6 mL), iodobenzene diacetate (384 mg, 1.19 mmol) was added at 0° C. The resulting reaction mixture was stirred at 25° C. for 16 h. The reaction mixture was concentrated under reduced pressure. The crude residue was diluted with water (20 mL) and the mixture was extracted thrice with ethyl acetate (50 mL). The ethyl acetate layer was washed with water (30 mL), dried over anhydrous sodium sulfate and concentrated under reduced pressure to obtain the crude product. The crude product was purified by preparative HPLC to obtain (7-(3,5-dichlorophenyl)-3-(3-methyl-6-(trifluoromethyl)-3H-imidazo[4,5-b]pyridin-2-yl)pyrazolo[1,5-a]pyrimidin-2-yl)(ethyl)(imino)$\lambda^6$-sulfanone (110 mg, 0.2 mmol, 44% yield). 1H-NMR (400 MHz, DMSO-d6) δ 8.90 (d, J=4.4 Hz, 1H), 8.84 (d, J=1.2 Hz, 1H), 8.62 (t, J=1.1 Hz, 1H), 8.25 (d, J=2.0 Hz, 2H), 7.98 (t, J=2.0 Hz, 1H), 7.75 (d, J=4.4 Hz, 1H), 4.80 (s, 1H), 3.81 (s, 3H), 3.49-3.56 (m, 2H), 1.28 (t, J=7.5 Hz, 3H); ESI MS (m/z) 554.00 (MH)+.

The following compounds (Table-1) were obtained using analogue procedures as described in the schemes 1-23 or in the examples.

TABLE 1

| Compd No. | Compound Name | Analytical Data |
|---|---|---|
| 1 | 2-(1-(3,5-Dichlorophenyl)-2-(ethylsulfonyl)indolizin-3-yl)-3-methyl-6-(trifluoromethyl)-3H-imidazo[4,5-b]pyridine | $^1$H-NMR (400 MHz, DMSO-d6) δ 8.92 (t, J = 2.2 Hz, 1H), 8.71 (t, J = 2.2 Hz, 1H), 8.15-8.17 (m, 1H), 7.68-7.74 (m, 3H), 7.52-7.55 (m, 1H), 7.16-7.20 (m, 1H), 6.93-6.99 (m, 1H), 3.79 (s, 3H), 3.05 (dtd, J = 63.8, 14.5, 7.3 Hz, 2H), 0.89-1.1 (m, 3H); ESI-MS (m/z) 553.90, (MH)+ |
| 2 | 2-(2-(Ethylsulfonyl)imidazo[1,2-a]pyridin-3-yl)-3-methyl-6-(trifluoromethyl)-3H-imidazo[4,5-b]pyridine | $^1$H-NMR (400 MHz, DMSO-d6) δ 8.93-8.93 (m, 1H), 8.73 (dd, J = 2.1, 0.6 Hz, 1H), 8.47 (dt, J = 7.0, 1.1 Hz, 1H), 7.94 (dt, J = 9.2, 1.1 Hz, 1H), 7.68 (ddd, J = 9.0, 6.8, 1.2 Hz, 1H), 7.22 (td, J = 6.9, 1.1 Hz, 1H), 3.86 (s, 3H), 3.49-3.52 (q, J = 6.8 Hz, 2H), 1.15-1.24 (t, J = 7.6 Hz, 3H); ESI MS (m/z) 409.95 (MH)+. |
| 3 | 6-(1-Bromo-2-(ethylsulfonyl)indolizin-3-yl)-7-methyl-3-(trifluoromethyl)-7H-imidazo[4,5-c]pyridazine | $^1$H-NMR (400 MHz, DMSO-d6) δ (9.34 (s, 1H), 8.35-8.42 (m, 2H), 7.90-7.96 (m, 1H), 7.56-7.73 (m, 1H), 7.22 (td, J = 6.9, 1.1 Hz, 1H), 3.94 (s, 3H), 3.52 (q, J = 7.4 Hz, 2H), 1.18 (t, J = 7.4 Hz, 3H); ESI MS (m/z) 410.00 (MH)+. |

TABLE 1-continued

| Compd No. | Compound Name | Analytical Data |
|---|---|---|
| 4 | 2-(2-(Ethylsulfonyl)imidazo[1,2-a]pyridin-3-yl)-5-(trifluoromethyl)benzo[d]oxazole | $^1$H-NMR (400 MHz, DMSO-d6) δ 9.49-9.53 (m, 1H), 8.38-8.40 (m, 1H), 8.14 (dd, J = 14.3, 8.4 Hz, 1H), 8.05 (dt, J = 9.0, 1.2 Hz, 1H), 7.87-7.91 (m, 1H), 7.80 (ddd, J = 9.0, 6.8, 1.2 Hz, 1H), 7.51 (td, J = 7.0, 1.3 Hz, 1H), 3.73-3.79 (q, J = 7.2 Hz, 2H), 1.31 (t, J = 6.8 Hz, 3H); ESI MS (m/z) 395.90 (MH)+. |
| 5 | 2-(2-(Ethylsulfonyl)-7-(trifluoromethyl)indolizin-3-yl)-3-methyl-6-(trifluoromethyl)-3H-imidazo[4,5-b]pyridine | $^1$H-NMR (400 MHz, DMSO-d6) δ (9.32 (s, 1H), 8.34-8.36 (m, 2H), 8.26 (d, J = 6.7 Hz, 1H), 7.45 (s, 1H), 7.10 (dd, J = 7.5, 2.0 Hz, 1H), 3.81 (s, 3H), 3.36-3.41 (m, 2H), 1.11 (t, J = 7.3 Hz, 3H); ESI MS (m/z) 477.00 (MH)+. |
| 6 | 2-(8-(3,5-Dichlorophenyl)-2-(ethylsulfonyl)indolizin-3-yl)-3-methyl-6-(trifluoromethyl)-3H-imidazo[4,5-b]pyridine | $^1$H-NMR (400 MHz, DMSO-d6) δ 8.93 (s, 1H), 8.73 (s, 1H), 8.22 (d, J = 7.1 Hz, 1H), 7.81 (s, 3 H), 7.27 (d, J = 6.8 Hz, 1H), 6.99-7.13 (m, 2H), 3.73 (s, 3H), 3.40 (q, J = 7.2 Hz, 2H), 1.11 (t, J = 7.3 Hz, 3H); ESI-MS (m/z) 553.15, (MH)+. |
| 7 | 2-(1-(3,5-Dichlorophenyl)-2-(ethylsulfonyl)-7-(trifluoromethyl)indolizin-3-yl)-3-methyl-6-(trifluoromethyl)-3H-imidazo[4,5-b]pyridine | $^1$H-NMR (400 MHz, DMSO-d6) δ (8.94-8.95 (m, 1H), 8.74 (d, J = 1.5 Hz, 1H), 8.38 (d, J = 7.6 Hz, 1H), 7.72-7.87 (m, 4H), 7.16 (dd, J = 7.5, 1.8 Hz, 1H), 3.78 (s, 3H), 2.90-3.10( m, 2H), 0.86-1.01 (t, J = 7.6 Hz, 3H); ESI MS (m/z) 621.00, (MH)+ |
| 8 | 2-(6-(3,5-Dichlorophenyl)-2-(ethylsulfonyl)indolizin-3-yl)-3-methyl-6-(trifluoromethyl)-3H-imidazo[4,5-b]pyridine | $^1$H-NMR (400 MHz, DMSO-d6) δ 8.92-8.93 (m, 1H), 8.71-8.71 (m, 1H), 8.55 (d, J = 0.7 Hz, 1H), 7.90-7.94 (m, 1H), 7.73-7.77 (m, 2H), 7.62 (m, 1H), 7.53 (dd, J = 9.4, 1.6 Hz, 1H), 7.01-7.28 (m, 1H), 3.75 (s, 3H), 3.33-3.42 (m, 2H), 1.15 (t, J = 6.2 Hz, 3H); ESI MS (m/z) 553.00, (MH)+. |
| 9 | 2-(2-(Ethylthio)-5,7-dimethylpyrazolo[1,5-a]pyrimidin-3-yl)-3-methyl-6-(trifluoromethyl)-3H-imidazo[4,5-b]pyridine | $^1$H-NMR (400 MHz, CDCl3) δ 8.64 (d, J = 1.2 Hz, 1H), 8.31 (d, J = 1.5 Hz, 1H), 6.65 (d, J = 0.7 Hz, 1H), 4.02 (s, 3H), 3.29 (q, J = 7.4 Hz, 2H), 2.79 (d, J = 0.7 Hz, 3H), 2.57 (s, 3H), 1.46 (t, J = 7.3 Hz, 3H); ESI MS (m/z) 407.10 (MH)+. |
| 10 | 2-(2-(Ethylsulfonyl)-5,7-dimethylpyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.84 (s, 1H), 8.61 (d, J = 2.0 Hz, 1H), 7.36 (d, J = 1.0 Hz, 1H), 3.78 (s, 3H), 3.73 (q, J = 7.3 Hz, 2H), 2.83 (s, 3H), 2.57 (s, 3 H), 1.25 (t, J = 7.3 Hz, 3 H); ESI MS (m/z) 439.25 (MH)+. |
| 11 | 2-(2-(Ethylthio)-5,7-dimethylpyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.13 (s, 1H), 8.18 (s, 1H), 7.06 (d, J = 0.6 Hz, 1H), 4.00 (s, 3H), 3.21 (q, J = 7.3 Hz, 2H), 2.75 (s, 3H), 2.53 (d, J = 2.1 Hz, 3H), 1.36 (t, J = 7.3 Hz, 3H) ; ESI MS (m/z) 406.90 (MH)+. |
| 12 | 2-(2-(Ethylsulfonyl)-5,7-dimethylpyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.24 (s, 1H), 8.26 (s, 1H), 7.37 (d, J = 1.0 Hz, 1H), 3.89 (s, 3H), 3.73 (q, J = 7.4 Hz, 2H), 2.83 (s, 3H), 2.57 (s, 3H), 1.26 (t, J = 7.5 Hz, 3H) ; ESI MS (m/z) 439.05 (MH)+. |
| 13 | 2-(2-(Ethylthio)-5,7-dimethylpyrazolo[1,5-a]pyrimidin-3-yl)-5-((trifluoromethyl)thio)benzo[d]oxazole | $^1$H-NMR (400 MHz, DMSO-d6) δ 8.12 (d, J = 2.0 Hz, 1H), 7.93-7.95 (m, 1H), 7.68 (dd, J = 8.4, 1.8 Hz, 1H), 7.13 (d, J = 1.1 Hz, 1H), 3.28 (q, J = 7.3 Hz, 2H), 2.74 (d, J = 0.7 Hz, 3H), 2.65 (s, 3H), 1.45 (t, J = 7.3 Hz, 3H); ESI MS (m/z) 425.05 (MH)+. |
| 14 | 2-(2-(Ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.27 (dd, J = 7.1, 1.7 Hz, 1H), 8.77 (s, 1H), 8.71 (q, J = 2.0 Hz, 1H), 8.54 (s, 1H), 7.21 (dd, J = 7.0, 4.3 Hz, 1H), 3.92 (d, J = 18.6 Hz, 3H), 3.23 (q, J = 7.3 Hz, 2H), 1.38 (t, J = 7.3 Hz, 3H); ESI MS (m/z) 379.25 (MH)+. |
| 15 | 2-(2-(Ethylsulfonyl)-5,7-dimethylpyrazolo[1,5-a]pyrimidin-3-yl)-5-((trifluoromethyl)sulfonyl)benzo[d]oxazole | $^1$H-NMR (400 MHz, DMSO-d6) δ 8.67 (d, J = 2.0 Hz, 1H), 8.31 (d, J = 8.6 Hz, 1H), 8.18-8.20 (m, 1H), 7.43 (d, J = 1.0 Hz, 1H), 3.91 (q, J = 7.4 Hz, 2H), 2.80 (d, J = 0.7 Hz, 3H), 2.67 (s, 3H), 1.31 (t, J = 7.3 Hz, 3H) ; ESI MS (m/z) 489.25 (MH)+. |
| 16 | 2-(2-(Ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.50 (dd, J = 7.2, 1.6 Hz, 1H), 8.87 (dd, J = 4.0, 1.6 Hz, 1H), 8.84 (q, J = 0.9 Hz, 1H), 8.61 (dd, J = 2.1, 0.7 Hz, 1H), 7.51 (dd, J = 7.1, 4.2 Hz, 1H), 3.79 (s, 3H), 3.75 (q, J = 7.3 Hz, 2H), 1.21-1.26 (m, 3H); ESI MS (m/z) 411.15 (MH)+. |
| 17 | 2-(2-(Ethylthio)pyrazolo[1,5-a]pyrimidin-3-yl)-5-((trifluoromethyl)thio)benzo[d]oxazole | $^1$H-NMR (400 MHz, DMSO-d6) δ 9.27-9.29 (m, 1H), 8.82-8.83 (m, 1H), 8.13 (d, J = 3.4 Hz, 1H), 7.95 (dd, J = 8.4, 1.3 Hz, 1H), 7.69 (dt, J = 8.5, 1.7 Hz, 1H), 7.26-7.30 (m, 1H), 3.28 (t, J = 7.3 Hz, 2H), 1.43 (t, J = 7.3 Hz, 3H); ESI MS (m/z) 396.95 (MH)+. |
| 18 | 2-(2-(Ethylsulfonyl)pyrazolo[1,5-a]pyrimidin-3-yl)-5-((trifluoromethyl)sulfonyl)benzo[d]oxazole | $^1$H-NMR (400 MHz, DMSO-d6) δ 9.53 (dd, J = 7.1, 1.7 Hz, 1H), 9.05 (dd, J = 4.2, 1.5 Hz, 1H), 8.67 (s, 1H), 8.32 (d, J = 8.8 Hz, 1H), 8.20 (d, J = 8.3 Hz, 1H), 7.59 (dd, J = 7.1, 4.2 Hz, 1H), 3.95 (q, J = 7.3 Hz, 2H), 1.30 (t, J = 7.3 Hz, 3H); ESI MS (m/z) 411.15 (MH)+. |
| 19 | 2-(2-(Ethylthio)-7-(4-fluorophenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ (8.77 (q, J = 0.9 Hz, 1H), 8.75 (d, J = 4.4 Hz, 1H), 8.54-8.54 (m, 1H), 8.29-8.33 (m, 2H), 7.49-7.53 (m, 2H), 7.43 (d, J = 4.6 Hz, 1H), 3.97 (s, 3H), 3.17 (q, J = 7.3 Hz, 2H), 1.36 (t, J = 7.3 Hz, 3H); ESI MS (m/z) 473.00 (MH)+. |

TABLE 1-continued

| Compd No. | Compound Name | Analytical Data |
|---|---|---|
| 20 | 2-(2-(Ethylthio)-7-(4-fluorophenyl)pyrazolo[1,5-a]pyrimidin-3-yl)-3-methyl-6-(trifluoromethyl)-3H-imidazo[4,5-c]pyridine | $^1$H-NMR (400 MHz, CHLOROFORM-D) δ (8.92 (s, 1H), 8.61 (d, J = 4.4 Hz, 1H), 8.21 (s, 1H), 8.17 (dd, J = 8.9, 5.3 Hz, 2H), 7.31 (t, J = 8.7 Hz, 2H), 7.02 (d, J = 4.4 Hz, 1H), 4.07 (s, 3H), 3.26 (q, J = 7.4 Hz, 2H), 1.46 (t, J = 7.5 Hz, 3H); ESI MS (m/z) 473.35 (MH)+. |
| 21 | 2-(2-(Ethylsulfonyl)-7-(4-fluorophenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ (9.23 (s, 1H), 8.90 (d, J = 4.4 Hz, 1H), 8.25-8.28 (m, 3H), 7.69 (d, J = 4.4 Hz, 1H), 7.56 (t, J = 8.9 Hz, 2H), 3.92 (s, 3H), 3.72 (q, J = 7.4 Hz, 2H), 1.26 (t, J = 7.3 Hz, 3H) ; ESI MS (m/z) 504.90 (MH)+. |
| 22 | 2-(2-(Ethylthio)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.27 (dd, J = 6.8, 1.7 Hz, 1H), 9.14 (s, 1H), 8.70 (dd, J = 4.3, 1.6 Hz, 1H), 8.19 (d, J = 0.7 Hz, 1H), 7.21 (dd, J = 6.8, 4.2 Hz, 1H), 4.01 (s, 3H), 3.22 (q, J = 7.3 Hz, 2H), 1.32-1.38 (m, 3H); ESI MS (m/z) 378.90 (MH)+. |
| 23 | 2-(2-(Ethylsulfonyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.50 (dd, J = 7.1, 1.7 Hz, 1H), 9.22 (s, 1H), 8.87 (q, J = 2.0 Hz, 1H), 8.25 (d, J = 0.7 Hz, 1H), 7.51 (dd, J = 7.2, 4.0 Hz, 1H), 3.90 (s, 3H), 3.74 (q, J = 7.4 Hz, 2H), 1.24 (t, J = 7.5 Hz, 3H) ESI MS (m/z) 411.05 (MH)+. |
| 24 | 2-(7-(3,5-Dichlorophenyl)-2-(ethylthio)pyrazolo[1,5-a]pyrimidin-3-yl)-3-methyl-6-(trifluoromethyl)-3H-imidazo[4,5-c]pyridine | $^1$H-NMR (400 MHz, CHLOROFORM-D) δ 8.94 (s, 1H), 8.64 (d, J = 4.4 Hz, 1H), 8.22 (s, 1H), 8.07 (d, J = 2.0 Hz, 2H), 7.62 (t, J = 1.8 Hz, 1H), 7.06 (d, J = 4.4 Hz, 1H), 4.08 (s, 3H), 3.27 (q, J = 7.3 Hz, 2H), 1.51 (t, J = 7.5 Hz, 3H); ESI MS (m/z) 522.70 (MH)+. |
| 25 | 2-(2-(Ethylsulfonyl)-7-(4-fluorophenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ (8.90 (d, J = 4.6 Hz, 1H), 8.85 (d, J = 1.5 Hz, 1H), 8.63 (d, J = 1.5 Hz, 1H), 8.25-8.28 (m, 2H), 7.69 (d, J = 4.6 Hz, 1H), 7.53-7.59 (m, 2H), 3.81 (s, 3H), 3.73 (q, J = 7.4 Hz, 2H), 1.26 (t, J = 7.3 Hz, 3H); ESI MS (m/z) 505.10 (MH)+. |
| 26 | 2-(7-(3,5-Dichlorophenyl)-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.94 (d, J = 4.6 Hz, 1H), 8.86 (d, J = 1.5 Hz, 1H), 8.64 (d, J = 1.5 Hz, 1H), 8.22 (d, J = 1.8 Hz, 2H), 7.99 (t, J = 1.8 Hz, 1H), 7.79 (d, J = 4.3 Hz, 1H), 3.81 (s, 3H), 3.71 (q, J = 7.4 Hz, 2H), 1.27 (t, J = 7.3 Hz, 3H) ; ESI MS (m/z) 555.00 (MH)+. |
| 27 | 2-(2-(Ethylthio)-7-(4-(trifluoromethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.77 (t, J = 2.3 Hz, 2H), 8.55 (d, J = 1.5 Hz, 1H), 8.36 (dd, J = 6.7, 2.1 Hz, 2H), 7.66 (d, J = 7.9 Hz, 2H), 7.47 (d, J = 4.6 Hz, 1H), 3.97 (s, 3H), 3.16 (q, J = 7.3 Hz, 2H), 1.35 (t, J = 7.3 Hz, 3H); ESI MS (m/z) 539.20 (MH)$^+$. |
| 28 | 2-(2-(Ethylthio)-7-(4-(trifluoromethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.16 (d, J = 2.4 Hz, 1H), 8.76-8.78 (m, 1H), 8.35-8.37 (m, 2H), 8.20 (d, J = 2.3 Hz, 1H), 7.67 (d, J = 8.8 Hz, 2H), 7.47 (d, J = 4.6 Hz, 1H), 4.04 (s, 3H), 3.16 (q, J = 7.4 Hz, 2H), 1.35 (t, J = 7.3 Hz, 3H); ESI MS (m/z) 538.80 (MH)$^+$. |
| 29 | 2-(2-(Ethylsulfonyl)-7-(4-(trifluoromethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.93 (d, J = 4.4 Hz, 1H), 8.86 (d, J = 1.2 Hz, 1H), 8.63 (d, J = 2.0 Hz, 1H), 8.31 (dd, J = 6.8, 2.2 Hz 2H) 7.70-7.73 (m, 3H) 3.81 (s 3H) 3.73 (q J = 7.4 Hz, 2H), 1.24-1.29 (m, 3H) ; ESI MS (m/z) 571.25 (MH)$^+$. |
| 30 | 2-(2-(Ethylsulfonyl)-7-(4-(trifluoromethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.24 (s, 1H), 8.93 (d, J = 4.4 Hz, 1H), 8.31 (dt, J = 9.5, 2.5 Hz, 2H), 8.27 (d, J = 1.0 Hz, 1H), 7.70-7.73 (m, 3H), 3.92 (s, 3H), 3.72 (q, J = 7.3 Hz, 2H), 1.22-1.27 (m, 3H) ; ESI MS (m/z) 570.80 (MH)$^+$. |
| 31 | 2-(2-(Ethylthio)-7-(4-(trifluoromethoxy)phenyl)pyrazolo[1,5-a]pyrimidin-3-yl)-5-((trifluoromethyl)thio)benzo[d]oxazole | $^1$H-NMR (400 MHz, CHLOROFORM-D) δ 8.82 (d, J = 4.4 Hz, 1H), 8.17-8.23 (m, 3H), 7.71 (d, J = 8.3 Hz, 1H), 7.52-7.62 (m, 1H), 7.45 (d, J = 8.1 Hz, 2H), 7.00-7.08 (m, 1H), 3.30 (q, J = 7.4 Hz, 2H), 1.51 (t, J = 7.3 Hz, 3H); ESI MS (m/z) 557.15 (MH)+. |
| 32 | 2-(2-(Ethylsulfonyl)-7-(4-(trifluoromethoxy)phenyl)pyrazolo[1,5-a]pyrimidin-3-yl)-5-((trifluoromethyl)sulfonyl)benzo[d]oxazole | $^1$H-NMR (400 MHz, DMSO-d6) δ 9.10 (d, J = 4.6 Hz, 1H), 8.70 (d, J = 1.8 Hz, 1H), 8.34 (d, J = 8.9 Hz, 1H), 8.26-8.28 (m, 2H), 8.22 (dd, J = 8.7, 1.7 Hz, 1H), 7.80 (d, J = 4.3 Hz, 1H), 7.70 (d, J = 7.9 Hz, 2H), 3.92 (q, J = 7.3 Hz, 2H), 1.30 (t, J = 7.3 Hz, 3H) ; ESI MS (m/z) 620.95 (MH)+. |
| 33 | 2-(2-(Ethylthio)-7-(4-fluorophenyl)pyrazolo[1,5-a]pyrimidin-3-yl)-5-((trifluoromethyl)thio)benzo[d]oxazole | $^1$H-NMR (400 MHz, DMSO-d6) δ 8.87 (d, J = 4.6 Hz, 1H), 8.26-8.30 (m, 2H), 8.14 (d, J = 1.7 Hz, 1H), 7.97 (d, J = 8.3 Hz, 1H), 7.70 (dd, J = 8.3, 1.7 Hz, 1H), 7.48-7.52 (m, 3H), 3.22 (q, J = 7.3 Hz, 2H), 1.42 (t, J = 7.3 Hz, 3H); ESI MS (m/z) 491.30 (MH)+. |
| 34 | 2-(2-(Ethylsulfonyl)-7-(4-fluorophenyl)pyrazolo[1,5-a]pyrimidin-3-yl)-5-((trifluoromethyl)sulfonyl)benzo[d]oxazole | $^1$H-NMR (400 MHz, CHLOROFORM-D) δ 9.04 (d, J = 4.4 Hz, 1H), 8.62 (d, J = 1.7 Hz, 1H), 8.11-8.22 (m, 3H), 7.99 (d, J = 8.6 Hz, 1H), 7.34-7.39 (m, 3H), 3.67-3.88 (m, 2H), 1.53-1.75 (m, 3H) ; ESI MS (m/z) 555.00 (MH)+. |
| 35 | 2-(7-(4-Chlorophenyl)-2-(ethylthio)pyrazolo[1,5-a]pyrimidin-3-yl)-3-methyl-6- | $^1$H-NMR (400 MHz, DMSO-d6) δ 9.16 (s, 1H), 8.76 (d, J = 4.6 Hz, 1H), 8.25 (dt, J = 9.1, 2.3 Hz, 2H), 8.21 (d, J = 0.9 Hz, 1H), 7.74 (dd, J = 6.7, 1.8 Hz, 2H), 7.45 (d, J = 4.6 Hz, 1H), |

TABLE 1-continued

| Compd No. | Compound Name | Analytical Data |
|---|---|---|
| | (trifluoromethyl)-3H-imidazo[4,5-c]pyridine | 4.04 (s, 3H), 3.16 (q, J = 7.3 Hz, 2H), 1.35 (t, J = 7.3 Hz, 3H); ESI MS (m/z) 488.75 (MH)+. |
| 36 | 2-(7-(4-Chlorophenyl)-2-(ethylthio)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.75-8.77 (m, 2H), 8.55 (s, 1H), 8.25 (d, J = 8.6 Hz, 2H), 7.74 (d, J = 8.6 Hz, 2H), 7.45 (d, J = 4.3 Hz, 1H), 3.97 (s, 3H), 3.16 (q, J = 7.2 Hz, 2H), 1.36 (t, J = 7.3 Hz, 3H); ESI MS (m/z) 489.00 (MH)+. |
| 37 | 2-(7-(4-Chlorophenyl)-2-(ethylsulfonyl)pyrazolo[1,5-a]pyrimidin-3-yl)-3-methyl-6-(trifluoromethyl)-3H-imidazo[4,5-c]pyridine | ¹H-NMR (400 MHz, DMSO-d6) δ 9.23 (s, 1H), 8.91 (d, J = 4.6 Hz, 1H), 8.27 (s, 1H), 8.20 (dt, J = 9.1, 2.3 Hz, 2H), 7.78 (dt, J= 9.1, 2.3 Hz, 2H), 7.71 (d, J = 4.6 Hz, 1H), 3.91 (s, 3H), 3.72 (q, J = 7.3 Hz, 2H), 1.22-1.27 (m, 3H) ; ESI MS (m/z) 520.95 (MH)+. |
| 38 | 2-(7-(4-Chlorophenyl)-2-(ethylthio)pyrazolo[1,5-a]pyrimidin-3-yl)-5-((trifluoromethyl)thio)benzo[d]oxazole | ¹H-NMR (400 MHz, DMSO-d6) δ 8.87 (d, J = 4.6 Hz, 1H), 8.23 (dd, J = 6.7, 2.1 Hz, 2H), 8.14 (d, J = 1.7 Hz, 1H), 7.97 (d, J = 8.3 Hz, 1H), 7.69-7.74 (m, 3H), 7.52 (d, J = 4.6 Hz, 1H), 3.22 (q, J = 7.3 Hz, 2H), 1.41 (q, J = 7.3 Hz, 3H); ESI MS (m/z) 506.90 (MH)+. |
| 39 | 2-(7-(4-Chlorophenyl)-2-(ethylsulfonyl)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.91 (d, J = 4.6 Hz, 1H), 8.85 (d, J = 1.5 Hz, 1H), 8.63 (d, J = 1.8 Hz, 1H), 8.19-8.22 (m, 2H), 7.78 (dd, J = 6.7, 2.1 Hz, 2H), 7.71 (d, J = 4.3 Hz, 1H), 3.81 (s, 3H), 3.72 (q, J = 7.3 Hz, 2H), 1.26 (t, J = 7.3 Hz, 3H) ; ESI MS (m/z) 520.75 (MH)+. |
| 40 | 2-(7-(4-Chlorophenyl)-2-(ethylsulfonyl)pyrazolo[1,5-a]pyrimidin-3-yl)-5-((trifluoromethyl)sulfonyl)benzo[d]oxazole | ¹H-NMR (400 MHz, DMSO-d6) δ 9.08 (d, J = 4.6 Hz, 1H), 8.69 (d, J = 1.5 Hz, 1H), 8.33 (d, J = 8.9 Hz, 1H), 8.21 (dd, J = 8.6, 1.8 Hz, 1H), 8.16-8.18 (m, 2H), 7.76-7.79 (m, 3H), 3.90 (q, J = 7.3 Hz, 2H), 1.31 (t, J = 7.3 Hz, 3H) ; ESI MS (m/z) 571.00 (MH)+. |
| 41 | 2-(7-(3,5-Dichlorophenyl)-2-(ethylsulfonyl)pyrazolo[1,5-a]pyrimidin-3-yl)-3-methyl-6-(trifluoromethyl)-3H-imidazo[4,5-c]pyridine | ¹H-NMR (400 MHz, DMSO-d6) δ (9.24 (s, 1H), 8.94 (d, J = 4.6 Hz, 1H), 8.27 (s, 1H), 8.22 (d, J = 1.8 Hz, 2H), 8.00 (t, J = 1.8 Hz, 1H), 7.80 (d, J = 4.3 Hz, 1H), 3.91 (s, 3H), 3.70 (q, J = 7.4 Hz, 2H), 1.27 (t, J = 7.3 Hz, 3H) ; ESI MS (m/z) 554.95 (MH)+. |
| 42 | 2-(7-(3,5-Dichlorophenyl)-2-(ethylthio)pyrazolo[1,5-a]pyrimidin-3-yl)-5-((trifluoromethyl)thio)benzo[d]oxazole | ¹H-NMR (400 MHz, DMSO-d6) δ 8.92 (d, J = 4.4 Hz, 1H), 8.30 (d, J = 2.0 Hz, 2H), 8.17 (d, J = 1.7 Hz, 1H), 7.99 (d, J = 8.3 Hz, 1H), 7.96 (t, J = 2.0 Hz, 1H), 7.65-7.74 (m, 2H), 3.23 (q, J = 7.3 Hz, 2H), 1.48 (t, J = 7.2 Hz, 3H); ESI MS (m/z) 540.95 (MH)+. |
| 43 | 2-(7-(3,5-Dichlorophenyl)-2-(ethylsulfonyl)pyrazolo[1,5-a]pyrimidin-3-yl)-5-((trifluoromethyl)sulfonyl)benzo[d]oxazole | ¹H-NMR (400 MHz, DMSO-d6) δ 9.12 (d, J = 4.4 Hz, 1H), 8.69 (d, J = 1.7 Hz, 1H), 8.34 (d, J = 8.6 Hz, 1H), 8.22 (dd, J = 8.7, 1.8 Hz, 1H), 8.19 (d, J = 2.0 Hz, 2H), 7.99 (t, J = 1.8 Hz, 1H), 7.87 (d, J = 4.6 Hz, 1H), 3.89 (q, J = 7.4 Hz, 2H), 1.33 (t, J = 7.5 Hz, 3H) ; ESI MS (m/z) 605.00 (MH)+. |
| 44 | 2-(2-(Ethylthio)-5-phenylpyrazolo[1,5-a]pyrimidin-3-yl)-3-methyl-6-(trifluoromethyl)-3H-imidazo[4,5-c]pyridine | ¹H-NMR (400 MHz, DMSO-d6) δ 9.32 (d, J = 7.3 Hz, 1H), 8.77 (d, J = 1.2 Hz, 1H), 8.54 (d, J = 1.5 Hz, 1H), 8.25-8.27 (m, 2H), 7.83 (d, J = 7.3 Hz, 1H), 7.56 (t, J = 3.2 Hz, 3H), 4.05 (s, 3H), 3.24 (q, J = 7.3 Hz, 2H), 1.39 (t, J = 7.3 Hz, 3H); ESI MS (m/z) 455(MH)+ |
| 45 | 2-(2-(Ethylthio)-5-phenylpyrazolo[1,5-a]pyrimidin-3-yl)-3-methyl-6-(trifluoromethyl)-3H-imidazo[4,5-c]pyridine | ¹H-NMR (400 MHz, DMSO-d6) δ 9.32 (d, J = 7.3 Hz, 1H), 9.17 (s, 1H), 8.26-8.29 (m, 2H), 8.20 (d, J = 1.0 Hz, 1H), 7.83 (d, J = 7.3 Hz, 1H), 7.54-7.57 (m, 3H), 4.13 (s, 3H), 3.23 (q, J = 7.3 Hz, 2H), 1.38 (t, J = 7.3 Hz, 3H); ESI MS (m/z) 455.05(MH)+ |
| 46 | 2-(2-(Ethylsulfonyl)-5-phenylpyrazolo[1,5-a]pyrimidin-3-yl)-3-methyl-6-(trifluoromethyl)-3H-imidazo[4,5-d]pyridine | ¹H-NMR (400 MHz, DMSO-d6) δ 9.56 (d, J = 7.6 Hz, 1H), 8.86 (d, J = 1.5 Hz, 1H), 8.63 (d, J = 1.5 Hz, 1H), 8.23 (dd, J = 8.1, 1.7 Hz, 2H), 8.14 (d, J = 7.6 Hz, 1H), 7.56 (dd, J = 13.9, 6.1 Hz, 3H), 3.89 (s, 3H), 3.82 (q, J = 7.4 Hz, 2H), 1.27 (t, J = 7.3 Hz, 3H); ESI MS (m/z) 487.15(MH)+ |
| 47 | 2-(2-(Ethylsulfonyl)-5-phenylpyrazolo[1,5-a]pyrimidin-3-yl)-3-methyl-6-(trifluoromethyl)-3H-imidazo[4,5-d]pyridine | ¹H-NMR (400 MHz, DMSO-d6) δ 9.55 (d, J = 7.3 Hz, 1H), 9.25 (s, 1H), 8.25 (t, J = 6.7 Hz, 3H), 8.14 (d, J = 7.6 Hz, 1H), 7.52-7.59 (m, 3H), 4.00 (s, 3H), 3.82 (q, J = 7.3 Hz, 2H), 1.27 (t, J = 7.3 Hz, 3H); ESI MS (m/z) 487.2(MH)+ |
| 48 | 2-(6-Chloro-2-(ethylthio)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 9.72 (d, J = 2.2 Hz, 1H), 8.77 (d, J = 2.2 Hz, 2H), 8.54 (d, J = 1.5 Hz, 1H), 3.91 (s, 3H), 3.22 (q, J = 7.3 Hz, 2H), 1.37 (t, J = 7.3 Hz, 3H); ESI MS (m/z) 412.90(MH)+ |
| 49 | 2-(2-(Ethylthio)-6-phenylpyrazolo[1,5-a]pyrimidin-3-yl)-3-methyl-6-(trifluoromethyl)-3H-imidazo[4,5-b]pyridine | ¹H-NMR (400 MHz, DMSO-d6) δ 9.66 (d, J = 2.1 Hz, 1H), 9.12 (d, J = 2.4 Hz, 1H), 8.77 (d, J = 1.2 Hz, 1H), 8.54 (t, J = 1.1 Hz, 1H), 7.90-7.92 (m, 2H), 7.54 (t, J = 7.5 Hz, 2H), 7.44-7.48 (m, 1H), 3.99 (s, 3H), 3.25 (q, J = 7.3 Hz, 2H), 1.39 (t, J = 7.3 Hz, 3H); ESI MS (m/z) 455.60(MH)+ |
| 50 | 2-(6-Chloro-2-(ethylsulfonyl)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 9.99 (d, J = 2.4 Hz, 1H), 8.90 (dd, J = 39.0, 1.8 Hz, 2H), 8.62 (d, J = 1.5 Hz, 1H), 3.71-3.78 (m, 5H), 1.24 (t, J = 7.3 Hz, 3H); ESI MS (m/z) 445.20 (MH)+ |
| 51 | 2-(2-(Ethylthio)-5-(4-(trifluoromethoxy)phenyl)pyrazolo | ¹H-NMR (400 MHz, DMSO-d6) δ 9.36 (d, J = 7.3 Hz, 1H), 9.16 (s, 1H), 8.40 (d, J = 9.0 Hz, 2H), 8.20 (d, J = 0.7 Hz, 1H), |

TABLE 1-continued

| Compd No. | Compound Name | Analytical Data |
|---|---|---|
| | [1,5-a]pyrimidin-3-yl)-3-methyl-6-(trifluoromethyl)-3H-imidazo[4,5-c]pyridine | 7.86 (d, J = 7.3 Hz, 1H), 7.53 (d, J = 8.1 Hz, 2H), 4.11 (s, 3H), 3.24 (q, J = 7.3 Hz, 2H), 1.39 (t, J = 7.5 Hz, 3H); ESI MS (m/z) 539.3(MH)+ |
| 52 | 2-(6-Chloro-2-(ethylthio)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.73 (d, J = 2.1 Hz, 1H), 9.15 (s, 1H), 8.78 (d, J = 2.4 Hz, 1H), 8.20 (s, 1H), 3.99 (s, 3H), 3.21 (q, J = 7.3 Hz, 2H), 1.36 (t, J = 7.3 Hz, 3H); ESI MS (m/z) 412.90(MH)+ |
| 53 | 2-(6-Chloro-2-(ethylsulfonyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.99 (d, J = 2.2 Hz, 1H), 9.22 (s, 1H), 8.95 (d, J = 2.2 Hz, 1H), 8.26 (s, 1H), 3.89 (s, 3H), 3.74 (q, J = 7.4 Hz, 2H), 1.24 (t, J = 7.3 Hz, 3H); ESI MS (m/z) 445.05(MH)+ |
| 54 | 2-(2-(Ethylsulfonyl)-6-phenylpyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.89 (d, J = 2.2 Hz, 1H), 9.28 (d, J = 2.3 Hz, 1H), 8.86 (d, J = 2.1 Hz, 1H), 8.63 (d, J = 2.7 Hz, 1H), 7.92-7.94 (m, 2H), 7.52-7.60 (m, 3H), 3.83 (s, 3H), 3.77 (q, J = 7.4 Hz, 2H), 1.27 (t, J = 7.5 Hz, 3H); ESI MS (m/z) 487.15(MH)+ |
| 55 | 2-(2-(Ethylthio)-5-(4-(trifluoromethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.36 (d, J = 7.3 Hz, 1H), 8.78 (t, J = 1.1 Hz, 1H), 8.55 (d, J = 1.5 Hz, 1H), 8.37-8.40 (m, 2H), 7.86 (d, J = 7.3 Hz, 1H), 7.54 (d, J = 7.9 Hz, 2H), 4.03 (s, 3H), 3.24 (q, J = 7.3 Hz, 2H), 1.39 (t, J = 7.3 Hz, 3H); ESI MS (m/z) 539.15(MH)+ |
| 56 | 2-(2-(Ethylsulfonyl)-5-(4-(trifluoromethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.60 (d, J = 7.3 Hz, 1H), 9.24 (s, 1H), 8.36-8.38 (m, 2H), 8.27 (d, J = 1.0 Hz, 1H), 8.16 (d, J = 7.6 Hz, 1H), 7.52 (d, J = 8.1 Hz, 2H), 3.99 (s, 3H), 3.82 (q, J = 7.4 Hz, 2H), 1.27 (t, J = 7.3 Hz, 3H); ESI MS (m/z) 571.1(MH)+ |
| 57 | 2-(2-(Ethylthio)-5-(4-fluorophenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.32 (d, J = 7.3 Hz, 1H), 8.77 (t, J = 1.1 Hz, 1H), 8.54 (t, J = 1.1 Hz, 1H), 8.31-8.35 (m, 2H), 7.82 (d, J = 7.6 Hz, 1H), 7.39 (t, J = 8.8 Hz, 2H), 4.03 (s, 3H), 3.23 (q, J = 7.3 Hz, 2H), 1.38 (t, J = 7.3 Hz, 3H); ESI MS (m/z) 473.3(MH)+ |
| 58 | 2-(6-(4-Chlorophenyl)-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.70 (d, J = 2.1 Hz, 1H), 9.11 (d, J = 2.1 Hz, 1H), 8.77 (s, 1H), 8.54 (d, J = 1.8 Hz, 1H), 7.94 (d, J = 8.6 Hz, 2H), 7.60 (d, J = 8.6 Hz, 2H), 3.98 (s, 3H), 3.25 (q, J = 7.3 Hz, 2H), 1.39 (t, J = 7.3 Hz, 3H); ESI MS (m/z) 488.95(MH)+ |
| 59 | 2-(2-(Ethylsulfonyl)-5-(4-(trifluoromethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.60 (d, J = 7.6 Hz, 1H), 8.86 (t, J = 1.0 Hz, 1H), 8.64 (d, J = 2.0 Hz, 1H), 8.34-8.37 (m, 2H), 8.16 (d, J = 7.6 Hz, 1H), 7.53 (d, J = 8.1 Hz, 2H), 3.89 (s, 3H), 3.82 (q, J = 7.3 Hz, 2H), 1.27 (t, J = 7.5 Hz, 3H); ESI MS (m/z) 571.6(MH)+ |
| 60 | 2-(2-(Ethylthio)-5-(4-fluorophenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ (9.32 (d, J = 7.3 Hz, 1H), 9.16 (s, 1H), 8.33-8.37 (m, 2H), 8.20 (d, J = 1.0 Hz, 1H), 7.83 (d, J = 7.3 Hz, 1H), 7.36-7.40 (m, 2H), 4.11 (s, 3H), 3.23 (q, J = 7.3 Hz, 2H), 1.38 (t, J = 7.3 Hz, 3H); ESI MS (m/z) 473.3(MH)+ |
| 61 | 2-(2-(Ethylsulfonyl)-5-(4-fluorophenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ (9.56 (d, J = 7.6 Hz, 1H), 9.24 (s, 1H), 8.31-8.34 (m, 2H), 8.27 (d, J = 1.0 Hz, 1H), 8.14 (d, J = 7.6 Hz, 1H), 7.34-7.40 (m, 2H), 3.99 (s, 3H), 3.81 (q, J = 7.4 Hz, 2H), 1.27 (t, J = 7.3 Hz, 3H); ESI MS (m/z) 505.05(MH)+ |
| 62 | 2-(2-(Ethylsulfonyl)-5-(4-fluorophenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ (9.56 (d, J = 7.3 Hz, 1H), 8.86 (q, J = 0.9 Hz, 1H), 8.63-8.63 (m, 1H), 8.31 (ddd, J = 12.2, 5.4, 3.2 Hz, 2H), 8.14 (d, J = 7.6 Hz, 1H), 7.36-7.40 (m, 2H), 3.88 (s, 3H), 3.82 (q, J = 7.3 Hz, 2H), 1.27 (t, J = 7.5 Hz, 3H); ESI MS (m/z) 505.3(MH)+ |
| 63 | 2-(6-(4-Chlorophenyl)-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.93 (d, J = 2.1 Hz,1H), 9.27 (d, J = 2.0 Hz, 1H), 8.86 (t, J = 1.1 Hz, 1H), 8.63 (t, J = 0.9 Hz, 1H), 7.96 (dt, J = 9.1, 2.3 Hz, 2H), 7.65 (dt, J = 9.1, 2.4 Hz, 2H), 3.82 (s, 3H), 3.77 (q, J = 7.4 Hz, 2H), 1.26 (t, J = 7.3 Hz, 3H); ESI MS (m/z) 520.95(MH)+ |
| 64 | 2-(2-(Ethylthio)-6-phenylpyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.66 (d, J = 2.1 Hz, 1H), 9.16 (s, 1H), 9.11 (d, J = 2.1 Hz, 1H), 8.20 (d, J = 0.9 Hz, 1H), 7.90-7.92 (m, 2H), 7.54 (t, J = 7.5 Hz, 2H), 7.44-7.48 (m, 1H), 4.06 (s, 3H), 3.25 (q, J = 7.3 Hz, 2H), 1.39 (t, J = 7.3 Hz, 3H); ESI MS (m/z) 455.10(MH)+ |
| 65 | 2-(5-(3,5-Dichlorophenyl)-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.41 (d, J = 7.3 Hz, 1H), 8.77 (q, J = 1.0 Hz, 1H), 8.55-8.55 (m, 1H), 8.26 (d, J = 2.0 Hz, 2H), 7.95 (d, J = 7.3 Hz, 1H), 7.83 (t, J = 2.0 Hz, 1H), 4.00 (s, 3H), 3.24 (q, J = 7.3 Hz, 2H), 1.39 (t, J = 7.3 Hz, 3H); ESI MS (m/z) 520.90(MH) |
| 66 | 2-(2-(Ethylsulfonyl)-6-phenylpyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.89 (d, J = 2.2 Hz, 1H), 9.27 (d, J = 2.2 Hz, 1H), 9.24 (s, 1H), 8.27 (d, J = 0.7 Hz, 1H), 7.92-7.94 (m, 2H), 7.57-7.61 (m, 2H), 7.50-7.54 (m, 1H), 3.94 (s, 3H), 3.76 (q, J = 7.4 Hz, 2H), 1.26 (t, J = 7.5 Hz, 3H); ESI MS (m/z) 487.30(MH)+ |

TABLE 1-continued

| Compd No. | Compound Name | Analytical Data |
|---|---|---|
| 67 | 2-(5-(3,5-Dichlorophenyl)-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.65 (d, J = 7.3 Hz, 1H), 8.86 (s, 1H), 8.64 (d, J = 2.0 Hz, 1H), 8.23-8.26 (m, 3H), 7.85 (t, J = 1.8 Hz, 1H), 3.86 (s, 3H), 3.81 (q, J = 7.3 Hz, 2H), 1.26 (t, J = 7.3 Hz, 3H); ESI MS (m/z) 555.00(MH)+ |
| 68 | 2-(5-(3,5-Dichlorophenyl)-2-(ethylthio)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.40 (d, J = 7.3 Hz,1H), 9.20 (s, 1H), 8.27 (d, J = 2.0 Hz, 2H), 8.20 (d, J = 0.7 Hz, 1H), 7.95 (d, J = 7.3 Hz, 1H), 7.83 (t, J = 2.0 Hz, 1H), 4.09 (s, 3H), 3.24 (q, J = 7.3 Hz, 2H), 1.38 (t, J = 7.3 Hz, 3H); ESI MS (m/z) 520.90(MH)+ |
| 69 | 2-(5-(3,5-Dichlorophenyl)-2-(ethylsulfonyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.65 (t, J = 3.8 Hz,1H), 9.26 (s, 1H), 8.28 (d, J = 0.6 Hz, 1H), 8.24-8.25 (m, 3H), 7.86 (t, J = 1.8 Hz, 1H), 3.97 (s, 3H), 3.80 (q, J = 7.4 Hz, 2H), 1.26 (t, J = 7.3 Hz, 3H); ESI MS (m/z) 555.05(MH)+ |
| 70 | 2-(6-Bromo-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.76 (d, J = 2.0 Hz, 1H), 8.79 (d, J = 2.2 Hz, 1H), 8.76 (d, J = 1.2 Hz, 1H), 8.54 (d, J = 2.0 Hz, 1H), 3.91 (s, 3H), 3.21 (q, J = 7.3 Hz, 2H), 1.36 (t, J = 7.3 Hz, 3H); ; ESI MS (m/z) 458.90(MH)+ |
| 71 | 2-(6-Bromo-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 10.03 (d, J = 2.0 Hz, 1H), 8.96 (d, J = 2.2 Hz, 1H), 8.85 (t, J = 1.0 Hz, 1H), 8.62-8.63 (m, 1H), 3.78 (s, 3H), 3.74 (q, J = 7.3 Hz, 2H), 1.24 (t, J = 7.3 Hz, 3H);ESI MS (m/z) 490.75(MH)+ |
| 72 | 2-(6-(3,5-dichlorophenyl)-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.78 (d, J = 2.4 Hz, 1H), 9.15 (d, J = 2.2 Hz, 1H), 8.77 (d, J = 2.0 Hz, 1H), 8.54 (d, J = 1.5 Hz, 1H), 8.04 (d, J = 2.1 Hz, 2H), 7.68 (t, J = 1.8 Hz, 1H), 3.97 (s, 3H), 3.25 (q, J = 7.4 Hz, 2H), 1.40 (t, J = 7.3 Hz, 3H); ESIMS (m/z) 523.00(MH)+ |
| 73 | 2-(6-(4-Chlorophenyl)-2-(ethylthio)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.70 (d, J = 2.1 Hz, 1H), 9.16 (s, 1H), 9.11 (d, J = 2.1 Hz, 1H), 8.20 (s, 1H), 7.94 (d, J = 8.6 Hz, 2H), 7.60 (d, J = 8.6 Hz, 2H), 4.05 (s, 3H), 3.25 (q, J = 7.3 Hz, 2H), 1.39 (t, J = 7.3 Hz, 3H); ESI MS (m/z) 489.15(MH)+ |
| 74 | 2-(6-(4-Chlorophenyl)-2-(ethylsulfonyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.93 (d, J = 1.8 Hz, 1H), 9.24-9.27 (m, 2H), 8.27 (s, 1H), 7.96 (d, J = 8.6 Hz, 2H), 7.66 (d, J = 8.6 Hz, 2H), 3.93 (s, 3H), 3.76 (q, J = 7.3 Hz, 2H), 1.26 (t, J = 7.3 Hz, 3H); ESI MS(m/z) 520.95(MH)+ |
| 75 | 2-(2-(Ethylthio)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.35 (d, J = 7.3 Hz, 1H), 9.16 (s, 1H), 8.38 (d, J = 9.0 Hz, 2H), 8.21 (d, J = 1.0 Hz, 1H), 7.84 (d, J = 7.3 Hz, 1H), 7.45 (d, J = 9.0 Hz, 2H), 6.72-6.98 (m,1H), 4.11 (s, 3H), 3.24 (q, J = 7.3 Hz, 2H), 1.39 (t, J = 7.3 Hz,3H); ESI MS (m/z) 571.00(MH)+ |
| 76 | 2-(6-(3,5-Dichlorophenyl)-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 10.01 (d, J = 2.1 Hz, 1H), 9.31 (d, J = 2.2 Hz, 1H), 8.86 (s, 1H), 8.64 (s, 1H), 8.07 (d, J = 2.0 Hz, 2H), 7.77 (t, J = 1.8 Hz, 1H), 3.82 (s, 3H), 3.76 (q, J = 7.3 Hz, 2H), 1.27 (t, J = 7.3 Hz, 3H); ESI MS (m/z) 555.00(MH)+ |
| 77 | 2-(2-(Ethylthio)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.35 (d, J = 7.3 Hz, 1H), 8.77 (d, J = 1.2 Hz, 1H), 8.54 (d, J = 1.5 Hz, 1H), 8.37 (d, J = 8.8 Hz, 2H), 7.84 (d, J = 7.3 Hz, 1H), 7.46 (d, J = 8.8 Hz, 2H), 6.72-6.98 (m, 1H),4.03 (s, 3H), 3.24 (q, J = 7.3 Hz, 2H), 1.38 (t, J = 7.3 Hz, 3H); ESI MS(m/z) 571.11(MH)+ |
| 78 | 2-(2-(Ethylsulfonyl)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.59 (d, J = 7.3 Hz, 1H), 9.24 (s, 1H), 8.34-8.37 (m,2H), 8.27 (d, J = 0.7 Hz, 1H), 8.15 (d, J = 7.6 Hz, 1H), 7.44 (d, J = 8.8 Hz, 2H), 6.71-6.97 (m, 1H), 3.99 (s, 3H), 3.81 (q, J = 7.3 Hz, 2H), 1.27 (t, J = 7.3 Hz, 3H); ESI MS (m/z) 603.50(MH)+ |
| 79 | 2-(2-(Ethylsulfonyl)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ (9.59 (d, J = 7.3 Hz, 1H), 8.86 (d, J = 1.5 Hz, 1H), 8.64 (d, J = 1.5 Hz, 1H), 8.34 (dd, J = 6.8, 2.2 Hz, 2H), 8.15 (d, J = 7.6 Hz, 1H), 7.45 (d, J = 8.8 Hz, 2H),6.71-6.97 (m, 1H), 3.89 (s, 3H), 3.82 (q, J = 7.4 Hz, 2H), 1.27 (t, J = 7.4 Hz, 3H); ESI MS (m/z) 603.05(MH)+ |
| 80 | 2-(6-(3,5-Dichlorophenyl)-2-(ethylthio)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.80 (d, J = 2.1 Hz, 1H), 9.16 (d, J = 2.1 Hz, 2H), 8.20 (d, J = 0.9 Hz, 1H), 8.06 (d, J = 1.8 Hz, 2H), 7.69 (t, J = 1.8 Hz, 1H), 4.05 (s, 3H), 3.25 (q, J = 7.3 Hz, 2H), 1.40 (t, J = 7.3 Hz, 3H); ESI MS (m/z) 523.00(MH)+ |
| 81 | 2-(6-(3,5-Dichlorophenyl)-2-(ethylsulfonyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 10.01 (d, J = 2.1 Hz, 1H), 9.31 (d, J = 2.4 Hz, 1H), 9.24 (s, 1H), 8.27 (d, J = 0.9 Hz, 1H), 8.07 (d, J = 1.8 Hz, 2H), 7.77 (t, J = 1.8 Hz, 1H), 3.93 (s, 3H), 3.76 (q, J = 7.3 Hz, 2H), 1.26 (t, J = 7.3 Hz, 3H); ESI MS (m/z) 554.90(MH)+ |
| 82 | 2-(2-(Ethylthio)-6-(4-(trifluoromethoxy)phenyl)pyrazolo[1,5-a]pyrimidin-3-yl)-3-methyl-6- | $^1$H-NMR (400 MHz, DMSO-d6) δ 9.71 (d, J = 2.4 Hz, 1H), 9.11 (d, J = 2.4 Hz, 1H), 8.77 (d, J = 1.5 Hz, 1H), 8.54 (d, J = 1.5 Hz, 1H), 8.02-8.05 (m, 2H), 7.54 (d, J = 7.9 Hz, 2H), 3.98 |

TABLE 1-continued

| Compd No. | Compound Name | Analytical Data |
|---|---|---|
| | (trifluoromethyl)-3H-imidazo[4,5-b]pyridine | (s, 3H), 3.25 (q, J = 7.3 Hz, 2H), 1.39 (t, J = 7.3 Hz, 3H); ESI MS(m/z) 539.15(MH)+ |
| 83 | 2-(2-(Ethylsulfonyl)-6-(4-(trifluoromethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.93 (d, J = 2.1 Hz, 1H), 9.27 (d, J = 2.1 Hz, 1H), 8.86 (d, J = 1.2 Hz, 1H), 8.63 (d, J = 1.5 Hz, 1H), 8.03-8.06 (m, 2H), 7.59 (d, J = 7.9 Hz, 2H), 3.83 (s, 3H), 3.71-3.79 (m,2H), 1.27 (t, J = 7.5 Hz, 3H); ESI MS (m/z) 570.90(MH)+ |
| 84 | 2-(5-(4-Chlorophenyl)-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.34 (d, J = 7.6 Hz, 1H), 8.77 (d, J = 1.5 Hz, 1H), 8.54 (d, J = 1.5 Hz, 1H), 8.28 (d, J = 8.8 Hz, 2H), 7.84 (d, J = 7.6 Hz, 1H), 7.62 (d, J = 8.8 Hz, 2H), 4.02 (s, 3H), 3.24 (q, J = 7.3 Hz, 2H), 1.38 (t, J = 7.5 Hz, 3H); ESIMS (m/z) 488.95(MH)+ |
| 85 | 2-(5-(4-Chlorophenyl)-2-(ethylthio)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.34 (d, J = 7.3 Hz, 1H), 9.16 (s, 1H), 8.30 (dt, J = 9.2, 2.4 Hz, 2H), 8.20 (d, J = 1.0 Hz, 1H), 7.84 (d, J = 7.6 Hz, 1H), 7.61 (dt, J = 9.1, 2.3 Hz, 2H), 4.10 (s, 3H),3.23 (q, J = 7.3 Hz, 2H), 1.38 (t, J = 7.3 Hz, 3H);ESIMS (m/z) 489.05(MH)+ |
| 86 | 2-(2-(Ethylthio)-6-(4-(trifluoromethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.71 (d, J = 2.1 Hz, 1H), 9.16 (s, 1H), 9.12 (d, J = 2.1 Hz, 1H), 8.20 (s, 1H), 8.04 (d, J = 8.6 Hz, 2H), 7.54 (d, J = 7.9 Hz, 2H), 4.06 (s, 3H), 3.25 (q, J = 7.3 Hz, 2H), 1.39 (t, J = 7.3 Hz, 3H); ESI MS (m/z) 538.30(MH)+ |
| 87 | 2-(2-(Ethylthio)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ (8.76 (d, J = 4.6 Hz, 2H), 8.55 (d, J = 1.5 Hz, 1H), 8.35 (dd, J = 6.7, 2.1 Hz, 2H), 7.58 (d, J = 8.9 Hz, 2H), 7.46 (d, J = 4.6 Hz, 1H), 6.76-7.02 (m, 1H), 3.97 (s, 3H), 3.17 (q, J = 7.3 Hz, 2H), 1.35 (t, J = 7.3 Hz, 3H); ESIMS (m/z) 570.90(MH)+ |
| 88 | 2-(5-(4-Chlorophenyl)-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.58 (d, J = 7.3 Hz, 1H), 8.86 (t, J = 1.0 Hz, 1H), 8.64 (t, J = 1.1 Hz, 1H), 8.24-8.27 (m, 2H), 8.15 (d, J = 7.6 Hz, 1H), 7.60-7.63 (m, 2H), 3.88 (s, 3H), 3.81 (q, J = 7.3 Hz, 2H), 1.27 (t, J = 7.3 Hz, 3H);ESI MS (m/z) 520.90(MH)+ |
| 89 | 2-(5-(4-Chlorophenyl)-2-(ethylsulfonyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.58 (d, J = 7.3 Hz, 1H), 9.25 (s, 1H), 8.26-8.28 (m, 3H), 8.15 (d, J = 7.6 Hz, 1H), 7.61 (d, J = 8.8 Hz, 2H), 3.98 (s, 3H), 3.81 (q, J = 7.3 Hz, 2H), 1.26 (t, J = 7.5 Hz, 3H); ESI MS (m/z) 520.95(MH)+ |
| 90 | 2-(2-(Ethylsulfonyl)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.92 (d, J = 4.4 Hz, 1H), 8.86 (t, J = 1.0 Hz, 1H), 8.63 (t, J = 1.1 Hz, 1H), 8.27-8.30 (m, 2H), 7.72 (d, J = 4.6 Hz, 1H), 7.62 (d, J = 8.8 Hz, 2H), 6.76-7.04 (m, 1H), 3.81 (s, 3H), 3.73 (q, J = 7.4 Hz, 2H), 1.26 (t, J = 7.3 Hz, 3H); ESIMS (m/z) 602.95(MH)+ |
| 91 | 2-(2-(Ethylsulfonyl)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.24 (s, 1H), 8.90-8.93 (m, 1H), 8.27-8.31 (m, 3H), 7.68-7.73 (m, 1H), 7.62 (d, J = 8.9 Hz, 2H), 6.76-7.04 (m, 1H), 3.91 (d, J = 9.5 Hz, 3H), 3.72 (q, J = 7.4 Hz, 2H), 1.26 (t, J = 7.3 Hz, 3H); ESI MS (m/z) 603.15(MH)+ |
| 92 | 3-(7-(3,5-Dichlorophenyl)-2-(ethylthio)pyrazolo[1,5-a]pyrimidin-3-yl)-7-(trifluoromethyl)-[1,2,4]triazolo[4,3-a]pyridine | $^1$H-NMR (400 MHz, DMSO-d6) δ 8.72 (d, J = 4.4 Hz, 1H), 8.66 (d, J = 7.3 Hz, 1H), 8.49 (s, 1H), 8.32 (d, J = 2.0 Hz, 2H), 7.96 (t, J = 2.0 Hz, 1H), 7.57 (d, J = 4.4 Hz, 1H), 7.30 (dd, J = 7.3, 1.7 Hz, 1H), 3.17 (q, J = 7.3 Hz, 2H), 1.41 (t, J = 7.3 Hz, 3H); ESI MS(m/z) 508.85(MH)+ |
| 93 | 2-(2-(Ethylthio)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.16 (s, 1H), 8.76 (d, J = 4.6 Hz,1H), 8.32-8.35 (m, 2H), 8.21 (d, J = 0.7 Hz, 1H), 7.58 (d, J = 9.0 Hz, 2H), 7.46 (d, J = 4.6 Hz, 1H), 6.76-7.02 (m, 1H), 4.04 (s, 3H), 3.17 (q, J = 7.3 Hz, 2H), 1.35 (t, J = 7.3 Hz, 3H); ESIMS (m/z) 571.10(MH)+ |
| 94 | 3-(7-(3,5-Dichlorophenyl)-2-(ethylsulfonyl)pyrazolo[1,5-a]pyrimidin-3-yl)-7-(trifluoromethyl)-[1,2,4]triazolo[4,3-a]pyridine | $^1$H-NMR (400 MHz, DMSO-d6) δ 8.90 (d, J = 4.4 Hz, 1H), 8.55 (s, 1H), 8.47 (d, J = 7.3 Hz, 1H), 8.23 (d, J = 2.0 Hz, 2H), 8.01 (t, J = 2.0 Hz, 1H), 7.81 (d, J = 4.4 Hz, 1H), 7.35 (dd, J = 7.3, 1.7 Hz, 1H), 3.64 (q, J = 7.3 Hz, 2H), 1.27 (t, J = 7.3 Hz, 3H); ESI MS(m/z) 540.80(MH)+ |
| 95 | 2-(2-(Ethylthio)-6-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.69 (t, J = 1.2 Hz, 1H), 9.11 (d, J = 2.1 Hz, 1H), 8.77 (s, 1H), 8.54 (s, 1H), 8.01 (d, J = 8.6 Hz, 2H), 7.45 (d, J = 8.3 Hz, 2H), 6.71-6.98 (m, 1H), 3.98 (s, 3H), 3.25 (q, J = 7.2 Hz, 2H), 1.39 (t, J = 7.3 Hz, 3H); ESI MS (m/z) 570.85(MH)+ |
| 96 | 2-(2-(Ethylsulfonyl)-6-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 9.92 (d, J = 2.2 Hz, 1H), 9.27 (d, J = 2.2 Hz, 1H), 8.86 (d, J = 1.5 Hz, 1H), 8.63 (d, J = 2.0 Hz, 1H), 8.03 (dd, J = 6.6, 2.2 Hz, 2H), 7.50 (d, J = 8.8 Hz, 2H), 6.73-6.99 (m, 1H), 3.83 (s, 3H), 3.77 (q, J = 7.3 Hz, 2H), 1.27 (t, J = 7.3 Hz, 3H); ESI MS (m/z) 602.80(MH)+ |
| 97 | 2-(7-(3-Chlorophenyl)-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.77 (d, J = 4.3 Hz, 2H), 8.55 (d, J = 1.8 Hz, 1H), 8.36 (d, J = 1.8 Hz, 1H), 8.14 (d, J = 7.6 Hz, 1H), 7.74 (d, J = 8.3 Hz, 1H), 7.69 (t, J = 7.9 Hz, 1H), 7.49 (d, J = 4.6 Hz, 1H), 3.97 (s, 3H), 3.16 (q, J = 7.3 Hz, 2H), 1.39 (t, J = 7.3 Hz, 3H); ESI MS (m/z) 488.95(MH)+ |

TABLE 1-continued

| Compd No. | Compound Name | Analytical Data |
|---|---|---|
| 98 | 2-(7-(3,5-Difluorophenyl)-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.77-8.79 (m, 2H), 8.55 (d, J = 1.5 Hz, 1H), 8.00-8.05 (m, 2H), 7.62 (tt, J = 9.2, 2.4 Hz, 1H), 7.53-7.55 (m, 1H), 3.96 (s, 3H), 3.09-3.20 (q, J = 7.6 Hz, 1H), 1.38 (t, J = 7.6 Hz, 3H); ESI MS (m/z) 490.75(MH)+ |
| 99 | 2-(7-(3-Chlorophenyl)-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.92 (d, J = 4.4 Hz, 1H), 8.85 (s, 1H), 8.63 (s, 1H), 8.25 (t, J = 1.8 Hz, 1H), 8.12 (d, J = 7.6 Hz, 1H), 7.77-7.79 (m, 1H), 7.70-7.74 (m, 2H), 3.81 (s, 3H), 3.71 (q, J = 7.4 Hz, 2H), 1.27 (t, J = 7.3 Hz, 3H); ESI MS (m/z) 521.05(MH)+ |
| 100 | 2-(2-(Ethylsulfonyl)-6-(4-(trifluoromethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.93 (d, J = 2.1 Hz, 1H), 9.27 (d, J = 2.1 Hz, 1H), 9.24 (s, 1H), 8.27 (d, J = 0.9 Hz, 1H), 8.05 (dd, J = 6.7, 2.1 Hz, 2H), 7.59 (d, J = 7.9 Hz, 2H), 3.94 (s, 3H), 3.76 (q, J = 7.3 Hz, 2H), 1.26 (t, J = 7.3 Hz, 3H); ESI MS (m/z) 570.95(MH)+ |
| 101 | 2-(7-(3,5-Difluorophenyl)-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.95 (d, J = 4.4 Hz, 1H), 8.86(d, J = 1.2 Hz, 1H), 8.64 (d, J = 2.0 Hz, 1H), 7.96-7.98 (m, 2H), 7.79 (d, J = 4.4 Hz, 1H), 7.64-7.70 (m, 1H), 3.81 (s, 3H), 3.73 (q, J = 7.3 Hz, 2H), 1.27 (t, J = 7.3 Hz, 3H); ESI MS (m/z) 522.80(MH)+ |
| 102 | 2-(7-(3-Chloro-5-fluorophenyl)-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ (8.77-8.79 (m, 2H), 8.55 (d, J = 1.5 Hz, 1H), 8.23 (d, J = 1.5 Hz, 1H), 8.10 (dq, J = 9.7, 1.2 Hz, 1H), 7.79 (dt, J = 8.8, 2.1 Hz, 1H), 7.55 (d, J = 4.6 Hz, 1H), 3.96 (s, 3H), 3.16 (q, J = 7.3 Hz, 2H), 1.40 (t, J = 7.2 Hz, 3H); ESI MS (m/z) 506.95(MH)+ |
| 103 | 2-(7-(3-Chloro-5-fluorophenyl)-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.95 (d, J = 4.6 Hz, 1H), 8.86 (d, J = 1.2 Hz, 1H), 8.64 (d, J = 1.8 Hz, 1H), 8.12 (d, J = 1.8 Hz, 1H), 8.06 (dq, J = 9.5, 1.3 Hz, 1H), 7.84 (dt, J = 8.7, 2.1 Hz, 1H), 7.79 (d, J = 4.6 Hz, 1H), 3.81 (s, 3H), 3.72 (q, J = 7.3 Hz, 2H), 1.27 (t, J = 7.3 Hz, 3H); ESI MS (m/z)540.06 |
| 104 | 2-(7-(3,4-Dichlorophenyl)-2-(ethylsulfonyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.93 (d, J = 4.4 Hz, 1H), 8.86 (d, J = 1.5 Hz, 1H), 8.63 (d, J = 2.0 Hz, 1H), 8.46 (d, J = 2.2 Hz, 1H), 8.16 (dd, J = 8.6, 2.2 Hz, 1H), 7.99 (d, J = 8.3 Hz, 1H), 7.77 (d, J = 4.4 Hz, 1H), 3.82 (d, J = 7.3 Hz, 3H), 3.72 (q, J =7.4 Hz, 2H), 1.27 (t, J = 7.3 Hz, 3H); ESI MS (m/z) 554.75(MH)+ |
| 105 | 7-(3,5-Dichlorophenyl)-2-(ethylthio)-3-(1-methyl-5-(trifluoromethyl)-1H-benzo[d]imidazol-2-yl)pyrazolo[1,5-a]pyrimidine | $^1$H-NMR (400 MHz, DMSO-d6) δ 8.74 (d, J = 4.4 Hz, 1H), 8.31 (d, J = 2.0 Hz, 2H), 8.05 (s, 1H), 7.94 (t, J = 2.0 Hz, 1H), 7.85 (d, J = 8.6 Hz, 1H), 7.63 (d, J = 8.6 Hz, 1H), 7.53 (d, J = 4.4 Hz, 1H), 3.89 (s, 3H), 3.14 (q, J = 7.3 Hz, 2H), 1.40 (t, J = 7.2 Hz, 3H); ESI MS (m/z) 521.80(MH)+ |
| 106 | 2-(Ethylthio)-3-(1-methyl-5-(trifluoromethyl)-1H-benzo[d]imidazol-2-yl)pyrazolo[1,5-a]pyrimidine | $^1$H-NMR (400 MHz, DMSO-d6) δ 9.24 (dd, J = 7.1, 1.7 Hz, 1H), 8.66 (q, J = 2.0 Hz, 1H), 8.04 (s, 1H), 7.83 (d, J = 8.6 Hz, 1H), 7.62 (dd, J = 8.6, 1.2 Hz, 1H), 7.17 (dd, J = 6.8, 4.2 Hz, 1H), 3.86 (s, 3H), 3.20 (q, J = 7.3 Hz, 2H), 1.36 (t, J = 7.3 Hz, 3H); ESI MS (m/z) 377.70(MH)+ |
| 107 | 7-(3,5-Dichlorophenyl)-2-(ethylsulfonyl)-3-(1-methyl-5-(trifluoromethyl)-1H-benzo[d]imidazol-2-yl)pyrazolo[1,5-a]pyrimidine | $^1$H-NMR (400 MHz, DMSO-d6) δ 8.91 (d, J = 4.4 Hz, 1H), 8.22 (d, J = 2.0 Hz, 2H), 8.09 (s, 1H), 7.99 (t, J = 1.8 Hz, 1H), 7.90 (d, J = 8.3 Hz, 1H), 7.77 (d, J = 4.4 Hz, 1H), 7.68-7.70 (m, 1H), 3.78 (s, 3H), 3.71 (q, J = 7.3 Hz, 2H), 1.26 (t, J = 7.3 Hz, 3H); ESI MS (m/z) 555.85(MH)+ |
| 108 | 2-(Ethylsulfonyl)-3-(1-methyl-5-(trifluoromethyl)-1H-benzo[d]imidazol-2-yl)pyrazolo[1,5-a]pyrimidine | $^1$H-NMR (400 MHz, DMSO-d6) δ 9.48 (dd, J = 7.1, 1.7 Hz, 1H), 8.84 (q, J = 2.0 Hz, 1H), 8.08 (s, 1H), 7.89 (d, J = 8.6 Hz, 1H), 7.68 (d, J = 10.3 Hz, 1H), 7.49 (q, J = 3.7 Hz, 1H), 3.72-3.77 (m, 5H), 1.23 (t, J = 7.3 Hz, 3H); ESI MS (m/z) 409.70(MH)+ |
| 109 | 2-(2-(Ethylsulfonyl)-6-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ (9.91 (dd, J = 11.1, 2.3 Hz, 1H), 9.24-9.28(m, 2H), 8.27 (d, J = 1.0 Hz, 1H), 8.03 (dt, J = 9.5, 2.5 Hz, 2H), 7.50 (d, J = 8.8 Hz, 2H), 6.86 (tt, J = 51.9, 3.0 Hz,1H), 3.94 (s, 3H), 3.76 (q, J = 7.4 Hz, 2H), 1.27 (t, J = 7.3 Hz,3H); ESI MS (m/z) 603.00(MH)+ |
| 110 | 3-(7-(3,5-Dichlorophenyl)-2-(ethylthio)pyrazolo[1,5-a]pyrimidin-3-yl)-6-(trifluoromethyl)-[1,2,4]triazolo[4,3-a]pyridine | $^1$H-NMR (400 MHz, DMSO-d6) δ 9.09 (d, J = 1.0 Hz, 1H), 8.72 (d, J = 4.4 Hz, 1H), 8.32 (d, J = 2.0 Hz, 2H), 8.09 (d, J = 9.8 Hz, 1H), 7.96 (t, J = 2.0 Hz, 1H), 7.68 (dd, J = 9.7, 1.6 Hz, 1H), 7.56-7.58(m, 1H), 3.17 (q, J = 7.3 Hz, 2H), 1.42 (t, J = 7.3 Hz, 3H); ESI MS (m/z) 508.70(MH)+ |
| 111 | 3-(7-(3,5-Dichlorophenyl)-2-(ethylsulfonyl)pyrazolo[1,5-a]pyrimidin-3-yl)-6-(trifluoromethyl)-[1,2,4]triazolo[4,3-a]pyridine | $^1$H-NMR (400 MHz, DMSO-d6) δ 8.90 (d, J = 4.4 Hz, 2H), 8.24 (d, J = 1.7 Hz, 2H), 8.15 (d, J = 9.5 Hz, 1H), 8.01 (t, J = 2.0 Hz, 1H), 7.82 (d, J = 4.6 Hz, 1H), 7.74 (dd, J = 9.7, 1.6 Hz, 1H), 3.62 (q, J = 7.3 Hz, 2H), 1.27 (t, J = 7.5 Hz, 3H); ESI MS (m/z) 540.90(MH)+ |
| 112 | 2-(7-(2,3-Dichlorophenyl)-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.82 (d, J = 4.3 Hz, 1H), 8.78 (d, J = 1.2 Hz, 1H), 8.55 (d, J = 1.8 Hz, 1H), 7.95 (dd, J = 7.9, 1.5 Hz, 1H), 7.75 (dd, J = 7.6, 1.5 Hz, 1H), 7.64 (t, J = 7.9 Hz,1H), 7.37 (d, J = 4.3 Hz, 1H), 3.99 (s, 3H), 2.98 (q, J = 7.3 Hz,2H), 1.24 (t, J = 7.3 Hz, 3H); ESI MS (m/z) 524.75(MH)+ |
| 113 | 2-(2-(Ethylthio)-7-phenylpyrazolo[1,5-a]pyrimidin-3- | $^1$H-NMR (400 MHz, DMSO-d6) δ (8.74-8.77 (m, 2H), 8.54 (d, J = 1.8 Hz, 1H), 8.20-8.23 (m, 2H), 7.64-7.67 (m, 3H), 7.42 (d, |

TABLE 1-continued

| Compd No. | Compound Name | Analytical Data |
|---|---|---|
| | yl)-3-methyl-6-(trifluoromethyl)-3H-imidazo | J = 4.6 Hz, 1H), 3.97 (s, 3H), 3.16 (q, J = 7.3 Hz, 2H), 1.34-1.38 (t, J = 7.3 Hz, 3H); ESI MS (m/z) 455.10(MH)+ |
| 114 | 2-(7-(2,3-Dichlorophenyl)-2-(ethylsulfonyl)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 9.01 (d, J = 4.3 Hz, 1H), 8.87 (d, J = 1.2 Hz, 1H), 8.64 (d, J = 1.5 Hz, 1H), 8.00 (dd, J = 8.1, 1.7 Hz, 1H), 7.78 (dd, J = 7.6, 1.5 Hz, 1H), 7.67-7.71 (m, 2H), 3.83 (s, 3H), 3.68 (q, J = 7.3 Hz, 2H), 1.20 (t, J = 7.5 Hz, 3H); ESI MS (m/z) 554.85(MH)+ |
| 115 | 2-(2-(Ethylsulfonyl)-7-phenylpyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.91 (d, J = 4.3 Hz, 1H), 8.85 (d, J = 1.2 Hz, 1H), 8.63 (d, J = 1.5 Hz, 1H), 8.16-8.19 (m,2H), 7.66-7.70 (m, 4H), 3.82 (s, 3H), 3.72 (q, J = 7.3 Hz, 2H), 1.26 (t, J = 7.5 Hz, 3H); ESI MS (m/z)486.75(MH)+ |
| 116 | 2-(7-(4-Chloro-3-fluorophenyl)-2-(ethylthio)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.78 (d, J = 4.4 Hz, 2H), 8.55 (s, 1H), 8.35 (dd, J = 10.8, 2.0 Hz, 1H), 8.11 (dd, J = 8.4, 1.8 Hz, 1H), 7.91 (t, J = 8.2 Hz, 1H), 7.52 (d, J = 4.6 Hz, 1H), 3.96 (s, 3H), 3.17 (q, J = 7.3 Hz, 2H), 1.37 (t, J = 7.3 Hz, 3H); ESI MS(m/z) 506.70(MH)+ |
| 117 | 2-(7-(3,5-Dichlorophenyl)-2-(ethylthio)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.78 (d, J = 4.6 Hz, 2H), 8.55 (d, J = 2.2 Hz,1H), 8.31 (d, J = 2.0 Hz, 2H), 7.95 (t, J = 1.8 Hz, 1H), 7.57 (d, J = 4.4 Hz, 1H), 3.96 (s, 3H), 3.15 (q, J = 7.3 Hz, 2H), 1.41 (t, J = 7.2 Hz, 3H); ESI MS (m/z) 522.90(MH)+ |
| 118 | 2-(7-(4-Chloro-3-fluorophenyl)-2-(ethylsulfonyl)pyrazolo[1,5-a]pyrimidin-3-yl)-3-methyl-6-(trifluoromethyl)-3H-imidazo[4,5-b]pyridine | ¹H-NMR(400 MHz, DMSO-d6) δ 8.94 (d, J = 4.4 Hz, 1H), 8.86 (t, J = 1.1 Hz, 1H), 8.63-8.64 (m, 1H), 8.28 (dd, J = 10.5, 2.0 Hz, 1H), 8.07 (dd, J = 8.4, 1.3 Hz, 1H), 7.96 (t, J = 8.1 Hz, 1H), 7.77 (d, J = 4.4 Hz, 1H), 3.81 (s, 3H), 3.73 (q, J = 7.4 Hz, 2H), 1.26 (t, J = 7.5 Hz, 3H); ESI MS (m/z)539.05(MH)+ |
| 119 | 2-(7-(4-Chloro-3-fluorophenyl)-2-(ethylthio)pyrazolo[1,5-a]pyrimidin-3-yl)-3-methyl-6-(trifluoromethyl)-3H-imidazo[4,5-c]pyridine | ¹H-NMR (400 MHz, DMSO-d6) δ (9.18 (s, 1H), 8.80 (d, J = 4.4 Hz,1H), 8.37 (dd, J = 10.8, 2.0 Hz, 1H), 8.23 (d, J = 1.0 Hz, 1H), 8.12-8.14 (m,1H), 7.93 (t, J = 8.1 Hz, 1H), 7.54 (d, J = 4.6 Hz, 1H), 4.05 (s, 3H), 3.19 (q, J = 7.3 Hz, 2H), 1.39 (t, J = 7.3 Hz, 3H); ESI MS (m/z) 507.00(MH; |
| 120 | 2-(7-(2,4-Dichlorophenyl)-2-(ethylthio)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.81 (d, J = 4.3 Hz, 1H), 8.77 (d, J = 1.2 Hz, 1H), 8.55 (d, J = 1.5 Hz, 1H), 7.97 (d, J = 1.8 Hz, 1H), 7.82 (d, J = 8.3 Hz, 1H), 7.72 (dd, J = 8.4, 2.0 Hz, 1H), 7.34 (d, J = 4.3 Hz, 1H), 3.98-4.03 (m, 3H), 3.01 (q, J = 7.3 Hz, 2H), 1.26 (t, J = 7.3 Hz, 3H); ESI MS (m/z) 522.75(MH)+ |
| 121 | 2-(7-(2,4-Dichlorophenyl)-2-(ethylsulfonyl)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.99 (d, J = 4.2 Hz, 1H), 8.86 (d, J = 1.2 Hz, 1H), 8.63 (d, J = 2.0 Hz, 1H), 8.01 (d, J = 2.0 Hz, 1H), 7.84 (d, J = 8.3 Hz, 1H), 7.77 (dd, J = 8.3, 2.0 Hz, 1H), 7.67 (d, J = 4.4 Hz, 1H), 3.82 (s, 3H), 3.67 (q, J = 7.3 Hz, 2H), 1.20 (t, J = 7.5 Hz, 3H); ESI MS(m/z) 555.00(MH)+; |
| 122 | 2-(7-(2,4-Dichlorophenyl)-2-(ethylthio)pyrazolo[1,5-a]pyrimidin-3-yl)-3-methyl-6-(trifluoromethyl)-3H-imidazo[4,5-c]pyridine | ¹H-NMR (400 MHz, DMSO-d6) δ 9.17 (s, 1H), 8.81 (d, J = 4.4 Hz,1H), 8.20 (s, 1H), 7.97 (d, J = 2.0 Hz, 1H), 7.82 (d, J = 8.3 Hz, 1H), 7.72 (dd, J = 8.3, 2.2 Hz, 1H), 7.35 (d, J = 4.4 Hz, 1H), 4.05 (s, 3H), 3.01 (q, J = 7.3 Hz, 2H), 1.25 (t, J = 7.2 Hz, 3H); ESI MS (m/z) 522.95(MH)+, |
| 123 | 2-(7-(3-Chloro-5-fluorophenyl)-2-(ethylthio)pyrazolo[1,5-a]pyrimidin-3-yl)-3-methyl-6-(trifluoromethyl)-3H-imidazo[4,5-c]pyridine | ¹H-NMR (400 MHz, DMSO-d6) δ 9.16 (s, 1H), 8.79 (d, J = 4.6 Hz,1H), 8.22 (d, J = 7.9 Hz, 2H), 8.10 (dt, J = 9.6, 1.8 Hz, 1H), 7.80 (dt, J = 8.7, 2.1 Hz, 1H), 7.56 (d, J = 4.6 Hz, 1H), 4.03 (s, 3H), 3.16 (q, J = 7.2 Hz, 2H), 1.40 (t, J = 7.3 Hz, 3H); ESI MS (m/z) 506.95(MH)+ |
| 124 | 2-(7-(3-Chloro-5-fluorophenyl)-2-(ethylsulfonyl)pyrazolo[1,5-a]pyrimidin-3-yl)-3-methyl-6-(trifluoromethyl)-3H-imidazo[4,5-c]pyridine | ¹H-NMR (400 MHz, DMSO-d6) δ 9.26 (s, 1H), 8.97 (d, J = 4.4 Hz,1H), 8.29 (d, J = 0.7 Hz, 1H), 8.14 (d, J = 1.5 Hz, 1H), 8.06-8.09 (m, 1H), 7.86 (dt, J = 8.7, 2.1 Hz, 1H), 7.82 (d, J = 4.4 Hz, 1H), 3.93 (s, 3H), 3.73 (q, J = 7.3 Hz, 2H), 1.29 (t, J = 7.3 Hz, 3H); ESI MS (m/z) 539.05(MH)+ |
| 125 | 2-(7-(3,5-Bis(trifluoromethyl)phenyl)-2-(ethylthio)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.93 (s, 2H), 8.83 (d, J = 4.4 Hz, 1H), 8.78 (d, J = 1.2 Hz, 1H), 8.55 (d, J = 2.0 Hz, 1H), 8.44 (s, 1H), 7.72 (d, J = 4.4 Hz, 1H), 3.97 (s, 3H), 3.14 (q, J = 7.3 Hz, 2H), 1.38 (t, J = 7.2 Hz, 3H); ESI MS (m/z) 591.05(MH)+ |
| 126 | 2-(2-(Ethylthio)-7-(3-(trifluoromethyl)phenyl)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.79 (d, J = 4.6 Hz, 1H), 8.77 (q, J = 0.9 Hz, 1H), 8.74 (d, J = 1.5 Hz, 1H), 8.55 (d, J = 1.5 Hz, 1H), 8.42 (d, J = 8.1 Hz, 1H), 8.04 (d, J = 8.1 Hz, 1H), 7.90 (t, J = 7.8 Hz, 1H), 7.56 (d, J = 4.6 Hz, 1H), 3.97 (s, 3H), 3.15 (q, J = 7.3 Hz, 2H), 1.37 (t, J = 7.3 Hz, 3H); ESI MS (m/z) 523.00(MH)+ |
| 127 | 2-(2-(Ethylthio)-7-(3-fluorophenyl)pyrazolo[1,5-a]pyrimidin-3-yl)-3-methyl-6-(trifluoromethyl)-3H-imidazo[4,5-b]pyridine | ¹H-NMR (400 MHz, DMSO-d6) δ 8.77 (t, J = 2.3 Hz, 2H), 8.55 (d, J = 1.5 Hz, 1H), 8.13 (dt, J = 10.4, 2.1 Hz, 1H), 8.05 (dd, J = 6.7, 1.2 Hz, 1H), 7.71 (td, J = 7.9, 6.1 Hz, 1H), 7.48-7.55 (m,2H), 3.97 (s, 3H), 3.16 (q, J = 7.3 Hz, 2H), 1.37 (t, J = 7.3 Hz, 3H); ESI MS (m/z) 472.75(MH)+ |
| 128 | 2-(7-(3,5-Bis(trifluoromethyl)phenyl)-2-(ethylsulfonyl)pyrazolo[1,5-a]pyrimidin-3-yl)-3-methyl-6- | ¹H-NMR (400 MHz, DMSO-d6) δ 8.99 (d, J = 4.3 Hz, 1H), 8.86 (d, J = 1.2 Hz, 1H), 8.84 (s, 2H), 8.64 (d, J = 1.5 Hz, 1H), 8.48 (s, 1H), 7.94 (d, J = 4.3 Hz, 1H), 3.82 (s, 3H), 3.68 (q, J = 7.3 Hz, 2H), 1.28 (t, J = 7.3 Hz, 3H); ESI MS (m/z) |

TABLE 1-continued

| Compd No. | Compound Name | Analytical Data |
|---|---|---|
|  | (trifluoromethyl)-3H-imidazo[4,5-b]pyridine | 623.00(MH)+ |
| 129 | 2-(2-(ethylsulfonyl)-7-(3-(trifluoromethyl)phenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.95 (d, J = 4.4 Hz, 1H), 8.86 (t, J = 1.1 Hz, 1H), 8.63-8.64 (m, 1H), 8.55 (s, 1H), 8.43 (d, J = 7.8 Hz, 1H), 8.07 (d, J = 7.8 Hz, 1H), 7.94 (t, J = 7.8 Hz,1H), 7.80 (d, J = 4.4 Hz, 1H), 3.82 (s, 3H), 3.70 (q, J = 7.3 Hz,2H), 1.27 (t, J = 7.3 Hz, 3H); ESI MS (m/z) 555.00(MH)+ |
| 130 | 2-(2-(Ethylsulfonyl)-7-(3-fluorophenyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.93 (d, J = 4.4 Hz, 1H), 8.86 (dd, J= 2.1, 0.6 Hz, 1H), 8.63 (q, J = 0.9 Hz, 1H), 8.04-8.08 (m, 1H), 8.01-8.03 (m, 1H), 7.72-7.78 (m, 2H), 7.55-7.60 (m, 1H), 3.81 (s, 3H), 3.73 (q, J = 7.3 Hz, 2H), 1.27 (t, J = 7.5 Hz,3H); ESI MS (m/z) 504.80(MH)+ |
| 131 | 2-(2-(Ethylthio)-7-methylpyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.75 (q, J = 0.9 Hz, 1H), 8.59 (d, J = 4.4 Hz, 1H), 8.53 (dd, J = 2.1, 0.6 Hz, 1H), 7.17 (dd, J = 4.4, 1.0 Hz, 1H), 3.93 (s, 3H), 3.24 (q, J = 7.3 Hz, 2H), 2.81 (d, J = 0.7 Hz, 3H), 1.38 (t, J = 7.3 Hz, 3H); ESI MS (m/z) 393.05(MH)+ |
| 132 | 2-(2-(Ethylthio)-7-(3-fluorophenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.16 (s, 1H), 8.77 (d, J = 4.4 Hz,1H), 8.21 (s, 1H), 8.13 (d, J = 9.8 Hz, 1H), 8.05 (d, J = 8.3 Hz, 1H), 7.71 (dd, J = 14.2, 8.1 Hz, 1H), 7.49-7.56 (m, 2H), 4.04 (s, 3H), 3.16 (q, J = 7.3 Hz, 2H), 1.37 (t, J = 7.3 Hz, 3H); ESI MS (m/z) 473.10(MH)+ |
| 133 | 2-(2-(Ethylsulfonyl)-7-methylpyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.84 (q, J = 0.9 Hz, 1H), 8.76 (d, J = 4.4 Hz, 1H), 8.61 (dd, J = 2.1, 0.6 Hz, 1H), 7.46 (dd, J= 4.4, 1.0 Hz, 1H), 3.72-3.78 (m, 5H), 2.88 (d, J = 0.7 Hz,3H), 1.26 (t, J = 7.3 Hz, 3H); ESI MS (m/z) 425.05MH)+ |
| 134 | 2-(2-(Ethylthio)-7-(3-(trifluoromethyl)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.16 (s, 1H), 8.79 (d, J = 4.6 Hz,1H), 8.74 (s, 1H), 8.42 (d, J = 7.8 Hz, 1H), 8.21 (d, J = 0.7 Hz, 1H), 8.04 (d, J = 7.8 Hz, 1H), 7.91 (t, J = 7.8 Hz, 1H), 7.56 (d, J = 4.4 Hz, 1H), 4.05 (s, 3H), 3.15 (q, J = 7.3 Hz, 2H), 1.37 (t, J = 7.2 Hz, 3H); ESI MS(m/z) 523.10(MH)+ |
| 135 | (7-(3,5-Dichlorophenyl)-3-(3-methyl-6-(trifluoromethyl)-3H-imidazo[4,5-b]pyridin-2-yl)pyrazolo[1,5-a]pyrimidin-2-yl)(ethyl)(imino)-λ$^6$-sulfanone | $^1$H-NMR (400 MHz, DMSO-d6) δ 8.90 (d, J = 4.4 Hz, 1H), 8.84 (d, J = 1.2 Hz,1H), 8.62 (t, J = 1.1 Hz, 1H), 8.25 (d, J = 2.0 Hz, 2H), 7.98 (t, J = 2.0 Hz, 1H), 7.75 (d, J = 4.4 Hz, 1H), 4.80 (s,1H), 3.81 (s, 3H), 3.49-3.56 (m, 2H), 1.28 (t, J = 7.5 Hz,3H); ESI MS (m/z) 554.00(MH)+ |
| 136 | 2-(2-(Ethylsulfonyl)-7-(3-(trifluoromethyl)phenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.24 (s, 1H), 8.95 (d, J = 4.4 Hz,1H), 8.55 (s, 1H), 8.42 (d, J = 7.8 Hz, 1H), 8.27 (d, J = 0.7 Hz, 1H), 8.08 (d, J = 8.1 Hz, 1H), 7.94 (t, J = 7.8 Hz, 1H), 7.80 (d, J = 4.4 Hz, 1H), 3.92 (s, 3H), 3.69 (q, J = 7.3 Hz, 2H), 1.27 (t, J = 7.3 Hz, 3H); ESI MS(m/z) 555.05(MH)+ |
| 137 | 2-(2-(Ethylsulfonyl)-7-(3-fluorophenyl)pyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.24 (s, 1H), 8.93 (d, J = 4.4 Hz, 1H), 8.27 (d, J = 1.0 Hz, 1H), 8.01-8.07 (m, 2H), 7.72-7.78 (m,2H), 7.55-7.63 (m, 1H), 3.92 (s, 3H), 3.72 (q, J = 7.4 Hz, 2H), 1.26 (t, J = 7.3 Hz, 3H); ESI MS (m/z) 505.00(MH)+ |
| 138 | 2-(2-(Ethylthio)-7-methylpyrazolo[1,5-a]pyrimidin-3-yl)-3-methyl-6-(trifluoromethyl)-3H-imidazo[4,5-c]pyridine | $^1$H-NMR (400 MHz, DMSO-d6) δ 9.14 (s, 1H), 8.59 (d, J = 4.4 Hz, 1H), 8.19 (d, J = 1.0 Hz, 1H), 7.17 (dd, J = 4.4, 0.7 Hz, 1H), 4.00 (s, 3H), 3.24 (q, J = 7.3 Hz, 2H), 2.81 (s, 3H), 1.38 (t, J = 7.3 Hz, 3H); ESI MS (m/z)393.00(MH)+ |
| 140 | 2-(7-(3-Chloro-4-fluorophenyl)-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.78 (d, J = 4.6 Hz, 2H), 8.56-8.59 (m,2H), 8.26 (qd, J = 4.4, 2.3 Hz, 1H), 7.75 (t, J = 8.9 Hz, 1H), 7.52 (d, J = 4.6 Hz, 1H), 3.98 (s, 3H), 3.18 (q, J = 7.3 Hz, 2H), 1.41 (t, J = 7.3 Hz, 3H); ESI MS (m/z) 506.90(MH)+ |
| 141 | 2-(2-(Ethylthio)-5,7-bis(trifluoromethyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.82 (d, J = 1.2 Hz, 1H), 8.63 (t, J = 1.1 Hz, 1H), 8.22 (s, 1H), 3.93 (s, 3H), 3.27 (q, J = 7.2 Hz, 2H), 1.42 (t, J = 7.3 Hz, 3H); ESI MS (m/z) 515.05(MH)+ |
| 142 | 2-(2-(Ethylsulfonyl)-5,7-bis(trifluoromethyl)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.90 (d, J = 1.2 Hz, 1H), 8.69 (d, J = 1.5 Hz, 1H), 8.64 (s, 1H), 3.76-3.82 (m, 5H), 1.26 (t, J = 7.3 Hz, 3H); ESI MS (m/z) 546.95(MH)+ |
| 143 | 2-(Ethylthio)-3-(3-methyl-6-(trifluoromethyl)-3H-imidazo[4,5-b]pyridin-2-yl)pyrazolo[1,5-a]pyrimidin-7(4H)-one | $^1$H-NMR (400 MHz, DMSO-d6) δ 12.40 (s, 1H), 8.80 (q, J = 0.9 Hz, 1H), 8.56 (dd, J = 2.1, 0.6 Hz, 1H), 7.84 (d, J = 7.3 Hz, 1H), 5.87 (d, J = 7.3 Hz, 1H), 3.77 (s, 3H), 3.16 (q, J = 7.3 Hz, 2H), 1.32 (t, J = 7.3 Hz, 3H); ESI MS (m/z) 395.00(M-H)+ |
| 144 | 2-(7-Bromo-2-(ethylthio)pyrazolo[1,5-a]pyrimidin-3-yl)-3-methyl-6-(trifluoromethyl)-3H-imidazo[4,5-b]pyridine | $^1$H-NMR (400 MHz, DMSO-d6) δ 8.77 (t, J = 1.1 Hz, 1H), 8.55 (d, J = 1.5 Hz, 1H), 8.48 (d, J = 4.6 Hz, 1H), 7.65 (d, J = 4.6 Hz, 1H), 3.92 (s, 3H), 3.25 (q, J = 7.3 Hz, 2H), 1.40 (t, J = 7.3 Hz, 3H); ESI MS (m/z) 456.95(MH)+; |

*Compound names generated using Chemdraw Professional 18.1

The following compounds (Table-2) can be obtained using analogue procedures as described in the schemes 1-23 or in the examples.

TABLE 2

| Sr. No | Compound Name |
| --- | --- |
| 145 | 2-(Ethylsulfonyl)-N-methyl-3-(7-(trifluoromethyl)-[1,2,4]triazolo[1,5-c]pyrimidin-2-yl)pyrazolo[1,5-a]pyrimidin-7-amine |
| 146 | 6-(8-(4-Chloro-3-fluorophenyl)-2-(ethylsulfonyl)indolizin-3-yl)-7-methyl-3-(trifluoromethyl)-7H-imidazo[4,5-c]pyridazine |
| 147 | 2-(2-(Ethylsulfonyl)-7-(5-methyl-3-(trifluoromethyl)-1H-pyrazol-1-yl)pyrazolo[1,5-a]pyrimidin-3-yl)-3-methyl-6-(trifluoromethyl)-3H-imidazo[4,5-b]pyridine |
| 148 | 2-(Ethylthio)-N-methyl-3-(3-methyl-6-(trifluoromethyl)-3H-imidazo[4,5-b]pyridin-2-yl)pyrazolo[1,5-a]pyrimidin-7-amine |
| 149 | 2-(2-(Ethylsulfonyl)-7-(3-fluorophenoxy)pyrazolo[1,5-a]pyrimidin-3-yl)-3-methyl-6-(trifluoromethyl)-3H-imidazo[4,5-b]pyridine |
| 150 | 6-(8-(4-Chloro-3-fluorophenyl)-2-(ethylsulfonyl)imidazo[1,2-a]pyridin-3-yl)-7-methyl-3-(trifluoromethyl)-7H-imidazo[4,5-c]pyridazine |
| 151 | 2-(6-(3,5-Dichlorophenyl)-2-(ethylsulfonyl)pyrazolo[1,5-a]pyrimidin-3-yl)-6-(trifluoromethyl)imidazo[1,2-a]pyrazine |
| 152 | 4-(2-(Ethylsulfonyl)-3-(7-methyl-3-(trifluoromethyl)-7H-imidazo[4,5-c]pyridazin-6-yl)indolizin-8-yl)-2-fluorobenzonitrile |
| 153 | 2-(8-(Cyclopropylmethyl)-2-(ethylsulfonyl)imidazo[1,2-a]pyridin-3-yl)-3-methyl-6-(trifluoromethyl)-3H-imaidazo[4,5-b]pyridine |
| 154 | 2-(7-(4-Chloro-1H-pyrazol-1-yl)-2-(ethylsulfonyl)pyrazolo[1,5-a]pyrimidin-3-yl)-3-methyl-6-(trifluoromethyl)-3H-imidazo[4,5-b]pyridine |
| 155 | 2-(2-(Ethylsulfonyl)-7-(5-methyl-1H-1,2,4-triazol-1-yl)pyrazolo[1,5-a]pyrimidin-3-yl)-3-methyl-6-(trifluoromethyl)-3H-imidazo[4,5-b]pyridine |
| 156 | 2-(2-(Ethylsulfonyl)-7-(1-methyl-1H-pyrazol-5-yl)pyrazolo[1,5-a]pyrimidin-3-yl)-3-methyl-6-(trifluoromethyl)-3H-imidazo[4,5-b]pyridine |
| 157 | 2-(2-(Ethylsulfonyl)-7-(1-methyl-3-(trifluoromethyl)-1H-pyrazol-5-yl)pyrazolo[1,5-a]pyrimidin-3-yl)-3-methyl-6-(trifluoromethyl)-3H-imidazo[4,5-b]pyridine |
| 158 | 2-(7-Cyclopropyl-2-(ethylsulfonyl)pyrazolo[1,5-a]pyrimidin-3-yl)-6-(trifluoromethyl)-[1,2,4]triazolo[1,5-a]pyrazine |
| 159 | 2-(2-(Ethylsulfonyl)-7-(1-methyl-3-(trifluoromethyl)-1H-pyrazol-5-yl)pyrazolo[1,5-a]pyrazine (trifluoromethyl)imidazo[1,2-c]pyrimidine |
| 160 | 4-(2-(Ethylsulfonyl)-3-(7-(trifluoromethyl)imidazo[1,2-a]pyridin-2-yl)pyrazolo[1,5-a]pyrimidin-7-yl)morpholine |
| 161 | 2-(7-(4-Chloro-3-fluorophenyl)-2-(ethylsulfonyl)pyrazolo[1,5-a]pyrimidin-3-yl)-7-(trifluoromethyl)-[1,2,4]triazolo[1,5-c]pyrimidine |
| 162 | 2-(2-(Ethylsulfonyl)-7-(1H-1,2,4-triazol-1-yl)pyrazolo[1,5-a]pyrimidin-3-yl)-7-(trifluoromethyl)-[1,2,4]triazolo[1,5-c]pyrimidine |
| 163 | 2-(2-(Ethylsulfonyl)-5,7-bis(trifluoromethyl)pyrazolo[1,5-a]pyrimidin-3-yl)-3-methyl-6-(trifluoromethyl)-3H-imidazo[4,5-b]pyridine |
| 164 | 6-(1-Bromo-2-(ethylsulfonyl)-8-methylindolizin-3-yl)-7-methyl-3-(trifluoromethyl)-7H-imidazo[4,5-c]pyridazine |
| 165 | 6-(8-Bromo-2-(ethylsulfonyl)indolizin-3-yl)-3-(difluoromethyl)-7-methyl-7H-imidazo[4,5-c]pyridazine |
| 166 | 2-(2-(Ethylsulfonyl)-7-methoxypyrazolo[1,5-a]pyrimidin-3-yl)-3-methyl-6-(trifluoromethyl)-3H-imidazo[4,5-b]pyridine |
| 167 | 2-(2-(Ethylsulfonyl)-7-(methylthio)pyrazolo[1,5-a]pyrimidin-3-yl)-3-methyl-6-(trifluoromethyl)-3H-imidazo[4,5-b]pyridine |
| 168 | 2-(Ethylsulfonyl)-3-(3-methyl-6-(trifluoromethyl)-3H-imidazo[4,5-b]pyridin-2-yl)pyrazolo[1,5-a]pyrimidine-7(4H)-thione |
| 169 | 2-(2-(Ethylsulfonyl)-7-(1,1,2,2-tetrafluoroethoxy)pyrazolo[1,5-a]pyrimidin-3-yl)-3-methyl-6-(trifluoromethyl)-3H-imidazo[4,5-b]pyridine |
| 170 | 2-(7-Ethoxy-2-(ethylsulfonyl)pyrazolo[1,5-a]pyrimidin-3-yl)-6-(trifluoromethyl)imidazo[1,2-a]pyrazine |
| 171 | Diethyl((2-(ethylsulfonyl)-3-(6-(trifluoromethyl)imidazo[1,2-a]pyrazin-2-yl)pyrazolo[1,5-a]pyrimidin-7-yl)imino)-16-sulfanone |
| 172 | 2-(Ethylsulfonyl)-N,N-dimethyl-3-(3-methyl-6-(trifluoromethyl)-3H-imidazo[4,5-b]pyridin-2-yl)imidazo[1,2-a]pyridin-8-amine |
| 173 | 6-(2-(Ethylsulfonyl)-7-(5-(trifluoromethyl)pyridin-2-yl)pyrazolo[1,5-a]pyrimidin-3-yl)-7-methyl-3-(trifluoromethyl)-7H-imidazo[4,5-c]pyridazine |
| 174 | 2-(7-(4-Chloro-3-fluorophenyl)-2-(ethylsulfonyl)pyrazolo[1,5-a]pyrimidin-3-yl)-3,5-dimethyl-6-(trifluoromethyl)-3,5-dihydro-4H-imidazo[4,5-c]pyridin-4-one |
| 175 | 2-(2-(Ethylsulfonyl)-7-(3-(trifluoromethyl)-1H-1,2,4-triazol-1-yl)pyrazolo[1,5-a]pyrimidin-3-yl)-3,5-dimethyl-6-(trifluoromethyl)-3,5-dihydro-4H-imidazo[4,5-c]pyridin-4-one |
| 176 | 2-(7-(3-Chloro-5-fluorophenyl)-2-(ethylsulfonyl)pyrazolo[1,5-a]pyrimidin-3-yl)-6-(trifluoromethyl)-[1,2,4]triazolo[1,5-a]pyrazine |
| 177 | 2-(7-(3,5-Dichlorophenyl)-2-(ethylsulfonyl)pyrazolo[1,5-a]pyrimidin-3-yl)-7-(trifluoromethyl)imidazo[1,2-c]pyrimidine |
| 178 | 2-(7-(4-Chloro-3-fluorophenyl)-2-(ethylsulfonyl)pyrazolo[1,5-a]pyrimidin-3-yl)-6-methyl-7-(trifluoromethyl)-[1,2,4]triazolo[1,5-c]pyrimidin-5(6H)-one |
| 179 | 2-(7-(5-Chloropyridin-2-yl)-2-(ethylsulfonyl)pyrazolo[1,5-a]pyrimidin-3-yl)-6-(trifluoromethyl)-[1,2,4]triazolo[1,5-a]pyridine |
| 180 | 2-(2-(Ethylsulfonyl)-7-(5-methyl-3-(trifluoromethyl)-1H-pyrazol-1- |

TABLE 2-continued

| Sr. No | Compound Name |
|---|---|
| | yl)pyrazolo[1,5-a]pyrimidin-3-yl)-6-methyl-7-(trifluoromethyl)-[1,2,4]triazolo[1,5-c]pyrimidine-5(6H)-one |
| 181 | 2-(2-(Ethylsulfonyl)-7-(3-(trifluoromethyl)-1H-1,2,4-triazol-1-yl)pyrazolo[1,5-a]pyrimidin-3-yl)-7-(trifluoromethyl)-[1,2,4]triazolo[1,5-c]pyrimidine |
| 182 | Ethyl(3-(3-methyl-6-(trifluoromethyl)-3H-imidazo[4,5-c]pyridin-2-yl)pyrazolo[1,5-a]pyrimidin-2-yl)(methylimino)-16-sulfanone |

Compound names generated using Chemdraw Professional 18.1

As described herein, the compounds of formula (I) show insecticidal activities which are exerted with respect to numerous insects which attacks on important agricultural crops. The compounds of the present invention were assessed for their activity as described in the following tests:

BIOLOGY EXAMPLES

Example A: *Helicoverpa armigera*

Diet incorporation method was used, in which the required quantity of test compounds were weighed and dissolved in a surfactant solution, kept on vortex for 90 min for proper mixing, then was diluted with water to the desired test concentrations. The solutions were incorporated into semi-synthetic diet when the temperature reached approximately 50° C. in the bioassay containers. The diet and solution was stirred thoroughly for properly mixing and then left to cool for 30 min. The solidified diet was cut into equal pieces, and then each piece was transferred into one cell of the bio-assay trays. A single third starved instar larva was released into each of these cells of the bioassay trays and each tray was covered with a lid. The bio-assay trays were kept under laboratory conditions at a temperature of 25° C. and relative humidity of 70%. Observations on dead, moribund and alive larvae were recorded at 96 h after the release of the larvae. Percent mortality was calculated by combining dead and moribund larvae and comparing the result to the one of the untreated control. The compounds 15 21 25 26 28 32 39 83 87 90 91 93 97 99 101 102 103 104 109 118 120 126 and 136 showed an activity higher than 70 percent mortality @ 300 PPM.

Example B: *Spodoptera litura*

Diet incorporation method was used, in which the required quantity of test compounds were weighed and dissolved in surfactant solution, kept on vortex for 90 min for proper mixing, then diluted with water to the desired test concentrations. The solutions were incorporated into semi-synthetic diet when the temperature reached approximately 50° C. in the bioassay containers. The diet and solution was stirred thoroughly for properly mixing and was left to cool for 30 min. The solidified diet was cut into equal pieces, and then each piece was transferred into one cell of the bio-assay trays. A single starved third instar larva was released into each of these cells of the bioassay trays and the tray was covered with a lid. The bio-assay trays were kept under laboratory conditions at a temperature of 25° C. and relative humidity of 70%. Observations on dead, moribund and alive larvae were recorded at 96 h after the release of the larvae. Percent mortality was calculated by combining dead and moribund larvae and comparing the result to the one of the untreated control. The compounds 15 21 25 26 37 63 83 87 90 93 101 103 118 126 129 and 134 showed an activity higher than 70 percent mortality @ 300 PPM.

Example C: *Plutella xylostella*

The leaf dip method was used for testing, wherein the required quantity of the compounds were weighed and dissolved in a surfactant solution, kept on a Vortex at 2000 rpm with zirconia beads for 90 min for proper mixing and then diluted with 0.01% Triton-X solution to the desired test concentration. Cabbage leaves were dipped in the solution for 10 seconds, shade dried for 20 min and then transferred to bioassay trays. A single second instar larva was released into each bioassay tray cell and the tray was covered with a lid. The bio-assay trays were kept under laboratory conditions at a temperature of 25° C. and relative humidity of 70%. Observations on dead, moribund and living larvae were recorded at 72 h after the release. Percent mortality was calculated by combining dead and moribund larvae and comparing the result to the one of the untreated control. The compounds 5 6 9 12 15 18 20 21 22 25 26 27 28 29 30 32 34 35 37 39 40 43 46 48 50 62 63 66 67 69 70 71 74 80 81 83 87 88 90 91 93 95 96 99 100 101 103 104 109 114 115 118 119 129 130 131 133 135 136 and 137 showed an activity higher than 70 percent mortality @ 300 PPM.

Example D: *Bemisia tabaci*

The leaf dip method was used for testing, wherein the required quantity of the test compounds were weighed and dissolved in surfactant solution, kepton a Vortex at 2000 rpm with zirconia beads for 90 min for proper mixing and then diluted with 0.01% Triton-X solution to the desired test concentration. Cotton leaves were dipped in the solution for 10 seconds, shade dried for 20 min and then the leaves were kept in glass units with the petiole dipped in water. Known numbers of freshly emerged adults were released and kept in the plant growth chamber at a temperature of 25° C. and relative humidity of 70%. Observations on dead, moribund and living adults were recorded at 72 h after the release. Percent mortality was calculated by combining dead and moribund adults and comparing the result to the one of the untreated control. The compound 22 and 119 showed an activity higher than 70 percent mortality @ 300 PPM.

Example E: *Myzus persicae*

The leaf dip method was used for testing, wherein the required quantity of the test compounds were weighed and dissolved in a surfactant solution, kept on a Vortex at 2000 rpm with zirconia beads for 90 min for proper mixing and then diluted with 0.01% Triton-X solution to the desired test concentration. Capsicum leaves were dipped in the solution for 10 seconds, shade dried for 20 min and then the leaves were kept in glass units with the petiole dipped in water. Known numbers of third instar nymphs were released into the glass units and then kept in the plant growth chambers at a temperature of 25° C. and relative humidity of 70%. Observations on dead, moribund and living nymphs were recorded at 72 h after the release. Percent mortality was calculated by combining dead and moribund nymphs and comparing the result to the one of the untreated control. The compounds 9 14 16 22 23 50 71 104 and 131 were showing efficacy higher than 70 percent mortality @ 300 PPM.

Example F: *Nilaparvata lugens*

Seedling dip method was used for screening, wherein the required quantity of the test compounds were weighed and dissolved in surfactant solution, kept on a Vortex at 2000 rpm with zirconia beads for 90 min for proper mixing, then diluted with 0.01% Triton-X solution to the desired test concentration. Paddy seedlings were dipped in the solution for 10 seconds, shade dried for 20 min and then transferred into glass tubes with the roots kept in water. Known numbers of third instar nymphs were released into the test tubes and the tubes were kept in the plant growth chamber at a temperature of 25° C. and relative humidity of 75%. Observations on dead, moribund and living nymphs were recorded at 72 h after the release. Percent mortality was calculated by combining dead and moribund nymphs and comparing the result to the one of the untreated control. The compounds 1422 and 63 showed an activity higher than 70 percent mortality @ 300 PPM.

Having described the invention with reference to certain preferred embodiments, other embodiments will become apparent to one skilled in the art from the consideration of the specification. It will be apparent to those skilled in the art that many modifications, both to materials and methods, may be practiced without departing from the scope of the invention.

The invention claimed is:
1. A compound of formula (I),

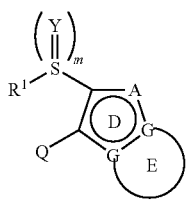

Formula (I)

wherein,
$R^1$ is selected from the group consisting of $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl and $C_3$-$C_8$-cycloalkyl-$C_1$-$C_6$-alkyl;

Y is independently selected from O or $NR^Y$;

$R^Y$ is selected from the group consisting of hydrogen, cyano, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_3$-$C_5$-cycloalkyl and $C_3$-$C_5$-cycloalkyl-$C_1$-$C_3$-alkyl;

A represents N or $CR^2$;

G represents N or C; provided that both G are not nitrogen simultaneously;

$R^2$ is selected from the group consisting of hydrogen, halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $CR^4{=}NR^5$, $NR^5R^6$, $S(O)_{0-2}R^7$, $C({=}O)R^8$, $S(O)_{0-1}R^9{=}NR^{10}$, $N{=}S(O)_{0-1}(R^9)_2$, $P({=}O)(OR')_2$, $Si(R')_3$, $C_6$-$C_{10}$-aryl, $C_7$-$C_{14}$-aralkyl and $C_3$-$C_{10}$-heterocyclyl; wherein each aliphatic group may be optionally substituted with one or more groups of $R^{2a}$ and cyclic groups of $R^2$ may be optionally substituted with one or more groups of $R^{2b}$;

$R^{2a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, $OR^4$, $CR^4{=}NR^5$, $NR^5R^6$, $S(O)_{0-2}R^7$, $C({=}O)R^8$, $S(O)_{0-1}R^9{=}NR^{10}$, $N{=}S(O)_{0-1}(R^9)_2$, $Si(R')_3$, $C_6$-$C_{10}$-aryl, $C_7$-$C_{14}$-aralkyl and $C_3$-$C_{10}$-heterocyclyl;

$R^{2b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $CR^4{=}NR^5$, $NR^5R^6$, $S(O)_{0-2}R^7$, $C({=}O)R^8$, $Si(R')_3$, $S(O)_{0-1}R^9{=}NR^{10}$ and $N{=}S(O)_{0-1}(R^9)_2$; or two $R^{2a}$ or two $R^{2b}$ substituents together with the atom to which they are attached or together with further atoms selected from the group consisting of C, N, O, S and optionally including 1 to 3 ring members selected from the group consisting of $C({=}O)$, $C({=}S)$, $S(O)_{0-2}$ and $Si(R')_2$, may form a 3- to 7-membered ring, which for its part may be substituted by one or more groups of $R^{2ab}$;

$R^{2ab}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $NR^5R^6$, $S(O)_{0-2}R^7$, $S(O)_{0-1}R^9{=}NR^{10}$, $N{=}S(O)_{0-1}(R^9)_2$, $Si(R')_3$, $C_6$-$C_{10}$-aryl, $C_7$-$C_{14}$-aralkyl and $C_3$-$C_{10}$-heterocyclyl;

Q is selected from the group consisting of Q1 to Q10:

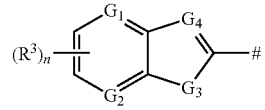

Q1

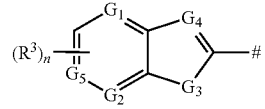

Q2

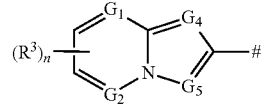

Q3

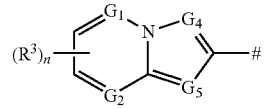

Q4

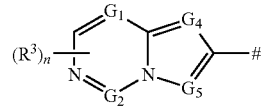

Q5

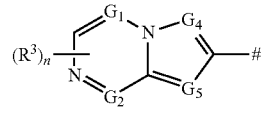

Q6

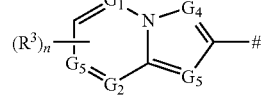

Q7

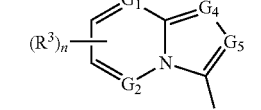

Q8

-continued

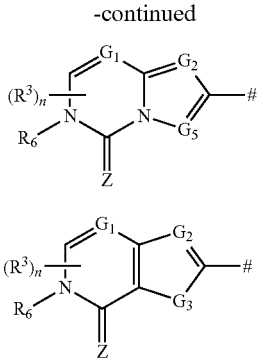

Q9

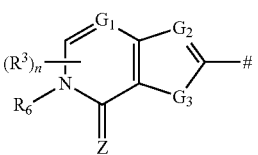

Q10 wherein # denotes the point of attachment to the ring D;
$G_1$, $G_2$, $G_4$ and $G_5$ independently represent N or $CR^3$; $G_3$ is $NR^6$, O, or S; Z is O or S; and n is an integer ranging from 0 to 4;

$R^3$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $CR^4$=$NR^5$, $NR^5R^6$, $S(O)_{0-2}R^7$, $C(=O)R^8$, $S(O)_{0-1}R^9$=$NR^{10}$, N=$S(O)_{0-1}$ $(R^9)_2$, $P(=O)(OR')_2$, $Si(R')_3$, $C_6$-$C_{10}$-aryl, $C_7$-$C_{14}$-aralkyl and $C_3$-$C_{10}$-heterocyclyl; wherein each aliphatic group may be optionally substituted with one or more groups of $R^{3a}$ and cyclic groups of $R^3$ may be optionally substituted with one or more groups of $R^{3b}$;

$R^{3a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, $OR^4$, $CR^4$=$NR^5$, $NR^5R^6$, $S(O)_{0-2}R^7$, $C(=O)R^8$, $S(O)_{0-1}R^9$=$NR^{10}$, N=$S(O)_{0-1}$ $(R^9)_2$, $Si(R')_3$, $C_6$-$C_{10}$-aryl, $C_7$-$C_{14}$-aralkyl and $C_3$-$C_{10}$-heterocyclyl;

$R^{3b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $C(R')_2$—$NR^5R^6$, $C(R')_2$—$OR^4$, $CR^4$=$NR^5$, $NR^5R^6$, $S(O)_{0-2}R^7$, $C(=O)R^8$, $S(O)_{0-1}R^9$=$NR^{10}$, N=$S(O)_{0-1}$ $(R^9)_2$, $Si(R')_3$, $C_6$-$C_{10}$-aryl, $C_7$-$C_{14}$-aralkyl and $C_3$-$C_{10}$-heterocyclyl;

two $R^{3a}$ or two $R^{3b}$ substituents together with the atom to which they are attached or together with further atoms selected from the group consisting of C, N, O, S and optionally including 1 to 3 ring members selected from the group consisting of C(=O), C(=S), S(O) m and $Si(R')_2$, may form a 3- to 7-membered ring, which for its part may be substituted by one or more groups of $R^{3ab}$; wherein $R^{3ab}$ is selected from the group consisting of hydrogen, halogen, cyano, $C_1$-$C_6$-alkyl, $C_1$-$C_6$-haloalkyl, $C_3$-$C_8$-cycloalkyl, $OR^4$, $NR^5R^6$, $S(O)_{0-2}R^7$;

two $R^3$ together with the atom to which they are attached or together with further atoms selected from the group consisting of C, N, O, S and optionally including 1 to 3 ring members selected from the group consisting of C(=O), C(=S), S(O) m and $Si(R')_2$ may form a three to seven membered ring, which for its part may be substituted by one or more groups selected from the group consisting of halogen, cyano, $R^{3c}$, $OR^{3c}$, $SR^{3c}$, $NR^{3c}_2$, $Si(R^{3c})_3$, $COOR^{3c}$, and $CONR^{3c}_2$;

$R^{3c}$ is selected from the group consisting of hydrogen, halogen, straight chain or branched chain $C_1$-$C_6$-alkyl and cyclic $C_{3-8}$-alkyl; wherein each group of $R^{3c}$ is optionally substituted by one or more halogen;

ring E represents a 5 or 6 membered heterocyclic ring fused with ring D; wherein ring E is optionally substituted by one or more groups of $R^{11}$;

$R^{11}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $CR^4$=$NR^5$, $NR^5R^6$, $S(O)_{0-2}R^7$, $C(=O)R^8$, $S(O)_{0-1}R^9$=$NR^{10}$, N=$S(O)_{0-1}$ $(R^9)_2$, $P(=O)(OR')_2$, $Si(R')_3$, $C_6$-$C_{10}$-aryl, $C_7$-$C_{14}$-aralkyl and $C_3$-$C_{10}$-heterocyclyl; wherein each aliphatic group may be optionally substituted with one or more groups of $R^{11a}$ and cyclic groups of $R^{11}$ may be optionally substituted with one or more groups of $R^{11b}$;

$R^{11a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, $OR^4$, $CR^4$=$NR^5$, $NR^5R^6$, $S(O)_{0-2}R^7$, $C(=O)R^8$, $S(O)_{0-1}R^9$=$NR^{10}$, N=$S(O)_{0-1}$ $(R^9)_2$, $Si(R')_3$, $C_6$-$C_{10}$-aryl, $C_7$-$C_{14}$-aralkyl and $C_3$-$C_{10}$-heterocyclyl;

$R^{11b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, $C(R')_2$—$NR^5R^6$, $C(R')_2$—$OR^4$, $CR^4$=$NR^5$, $NR^5R^6$, $S(O)_{0-2}R^7$, $C(=O)R^8$, $S(O)_{0-1}R^9$=$NR^{10}$, N=$S(O)_{0-1}$ $(R^9)_2$, $Si(R')_3$, $C_6$-$C_{10}$-aryl, $C_7$-$C_{14}$-aralkyl and $C_3$-$C_{10}$-heterocyclyl;

$R^4$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $S(O)_2R^7$, $Si(R')_3$, $C_6$-$C_{10}$-aryl, $C_7$-$C_{14}$-aralkyl and $C_3$-$C_{10}$-heterocyclyl; wherein each aliphatic group may be optionally substituted with $R^{4a}$ and cyclic groups of $R^4$ may be optionally substituted with one or more groups of $R^{4b}$;

$R^{4a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, OR', NR'R", $S(O)_{0-2}R'$, $C(=O)R'$, $Si(R')_3$, $C_6$-$C_{10}$-aryl, $C_7$-$C_{14}$-aralkyl and $C_3$-$C_{10}$-heterocyclyl;

$R^{4b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, OR', NR'R", $S(O)_{0-2}R'$, $C(=O)R'$, $Si(R')_3$, $C_6$-$C_{10}$-aryl, $C_7$-$C_{14}$-aralkyl and $C_3$-$C_{10}$-heterocyclyl;

$R^5$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, $OR^4$, NR'R", $S(O)_{0-2}R^7$, $C(=O)R^8$, $Si(R')_3$, $C_6$-$C_{10}$-aryl, $C_7$-$C_{14}$-aralkyl and $C_3$-$C_{10}$-heterocyclyl; wherein each aliphatic group may be optionally substituted with $R^{5a}$ and cyclic groups of $R^5$ may be optionally substituted with one or more groups of $R^{5b}$;

$R^{5a}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, OR', NR'R", $S(O)_{0-2}R'$, $C(=O)R'$, $Si(R')_3$, $C_6$-$C_{10}$-aryl, $C_7$-$C_{14}$-aralkyl and $C_3$-$C_{10}$-heterocyclyl;

$R^{5b}$ is selected from the group consisting of halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_8$-cycloalkyl, OR', NR'R", $S(O)_{0-2}R'$, $Si(R')_3$, $C(=O)R'$, $C_6$-$C_{10}$-aryl, $C_7$-$C_{14}$-aralkyl and $C_3$-$C_{10}$-heterocyclyl;

$R^6$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-cycloalkyl and $C(=O)R^8$;

R⁷ is selected from the group consisting of C₁-C₆-alkyl, C₂-C₆-alkenyl, C₂-C₆-alkynyl, C₁-C₆-haloalkyl, C₂-C₆-haloalkenyl, C₃-C₈-cycloalkyl, NR⁵R⁶, C₆-C₁₀-aryl, C₇-C₁₄-aralkyl and C₃-C₁₀-heterocyclyl; wherein each aliphatic group may be optionally substituted with one or more groups of R⁷ᵃ and cyclic groups of R⁷ may be optionally substituted with one or more groups of R⁷ᵇ;

R⁷ᵃ is selected from the group consisting of halogen, cyano, C₁-C₆-alkyl, C₂-C₆-alkenyl, C₂-C₆-alkynyl, C₁-C₆-haloalkyl, C₃-C₈-cycloalkyl, OR', NR'R'', S(O)₀₋₂R', C(=O)R', C₆-C₁₀-aryl, C₇-C₁₄-aralkyl and C₃-C₁₀-heterocyclyl;

R⁷ᵇ is selected from the group consisting of halogen, cyano, C₁-C₆-alkyl, C₂-C₆-alkenyl, C₂-C₆-alkynyl, C₁-C₆-haloalkyl, C₂-C₆-haloalkenyl, C₃-C₈-cycloalkyl, OR', NR'R'', S(O)₀₋₂R', C(=O)R', C₆-C₁₀-aryl, C₇-C₁₄-aralkyl and C₃-C₁₀-heterocyclyl;

R⁸ is selected from the group consisting of hydrogen, C₁-C₆-alkyl, C₂-C₆-alkenyl, C₂-C₆-alkynyl, C₁-C₆-haloalkyl, C₂-C₆-haloalkenyl, C₃-C₈-cycloalkyl, OR⁴, NR⁵R⁶, N=S(O)₀₋₁(R⁹)₂, C₆-C₁₀-aryl, C₇-C₁₄-aralkyl and C₃-C₁₀-heterocyclyl; wherein each aliphatic group may be optionally substituted with one or more groups of R⁸ᵃ and cyclic groups of R⁸ may be optionally substituted with one or more groups of R⁸ᵇ;

R⁸ᵃ is selected from the group consisting of halogen, cyano, C₁-C₆-alkyl, C₂-C₆-alkenyl, C₂-C₆-alkynyl, C₁-C₆-haloalkyl, C₃-C₈-cycloalkyl, OR', NR'R'', S(O)₀₋₂R', C(=O)R', C₆-C₁₀-aryl, C₇-C₁₄-aralkyl and C₃-C₁₀-heterocyclyl;

R⁸ᵇ is selected from the group consisting of halogen, cyano, C₁-C₆-alkyl, C₂-C₆-alkenyl, C₂-C₆-alkynyl, C₁-C₆-haloalkyl, C₂-C₆-haloalkenyl, C₃-C₈-cycloalkyl, OR', NR'R'', S(O)₀₋₂R', C(=O)R', C₆-C₁₀-aryl, C₇-C₁₄-aralkyl and C₃-C₁₀-heterocyclyl;

R⁹ is selected from the group consisting of C₁-C₆-alkyl, C₂-C₆-alkenyl, C₂-C₆-alkynyl, C₁-C₆-haloalkyl, C₂-C₆-haloalkenyl, C₃-C₈-cycloalkyl and C(=O)R⁸;

R¹⁰ is selected from the group consisting of hydrogen, cyano, C₁-C₆-alkyl, C₂-C₆-alkenyl, C₂-C₆-alkynyl, C₁-C₆-haloalkyl, C₂-C₆-haloalkenyl, C₃-C₈-cycloalkyl, Si(R')₃, S(O)₀₋₂R⁷ and C(=O)R⁸;

R' is selected from the group consisting of halogen, cyano, R'', OR'', N(R'')₂, S(O)₀₋₂R'', C(=O)R'', C(=O)OR'' and C(=O)N(R'')₂R⁸;

R'' is selected from the group consisting of hydrogen, C₁-C₆-alkyl, C₂-C₆-alkenyl, C₂-C₆-alkynyl, C₁-C₆-haloalkyl and C₃-C₈-cycloalkyl; wherein each may be optionally substituted with halogen;

each group of R¹ to R¹¹, R²ᵃ, R²ᵇ, R²ᵃᵇ, R³ᵃ, R³ᵇ, R³ᵃᵇ, R³ᶜ, R⁴ᵃ, R⁴ᵇ, R⁵ᵃ, R⁵ᵇ, R⁷ᵃ, R⁷ᵇ, R⁸ᵃ and R⁸ᵇ may be optionally substituted by one or more groups selected from the group consisting of halogen, cyano, R', OR', SR', N(R')₂, COOR' and CON(R')₂;

"m" is an integer ranging from 0 to 2;

or agrochemically acceptable salts, isomers/structural isomers, stereo-isomers, diastereoisomers, enantiomers, tautomers, polymorphs, metal complexes or N-oxides thereof.

2. The compound of formula (I) according to claim 1, wherein Q is selected from the group consisting of Q1a to Q10b:

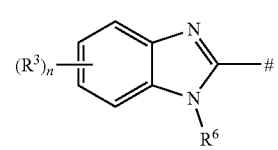
Q1a

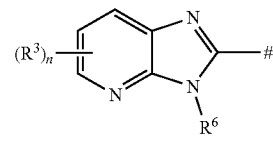
Q1b

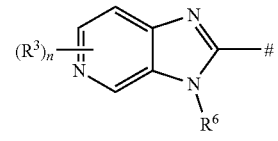
Q1c

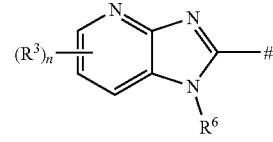
Q1d

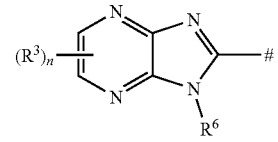
Q1e

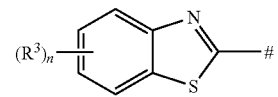
Q1f

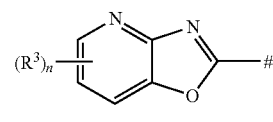
Q1g

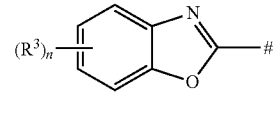
Q1h

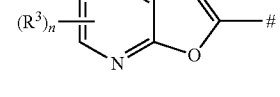
Q1i

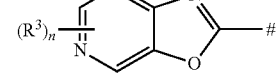
Q1j

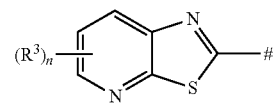
Q1k

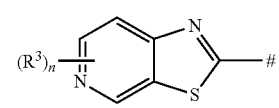
Q1l

-continued

Q2a 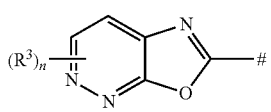

Q2b 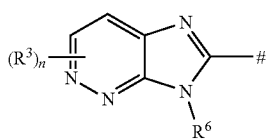

Q2c 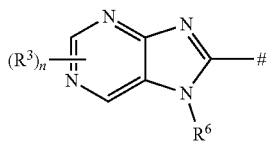

Q2d 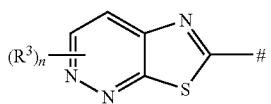

Q3a 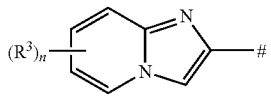

Q4a 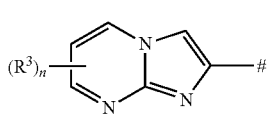

Q4b 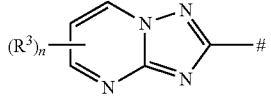

Q5a 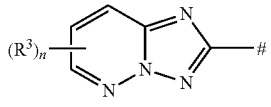

Q5b 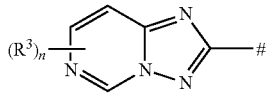

Q5c 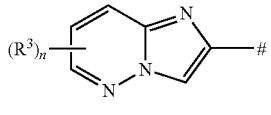

Q5d 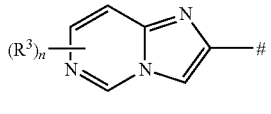

Q6a 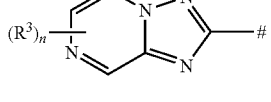

Q6b 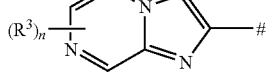

-continued

Q7a 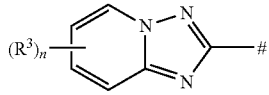

Q8a 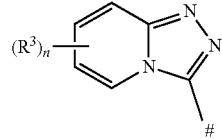

Q9a 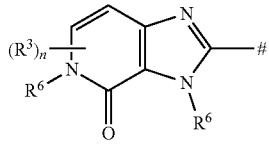

Q9b 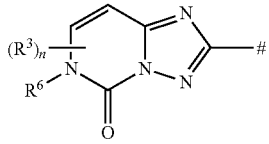

Q10a 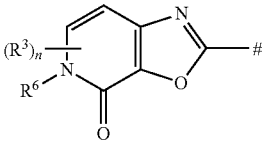

Q10b 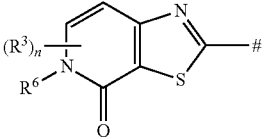

wherein, # denotes the point of attachment to the ring D, $R^6$ is selected from the group consisting of hydrogen, $C_1$-$C_6$-alkyl, and cyclic $C_{3-10}$-alkyl; wherein each group of $R^6$ is optionally substituted by one or more halogen and "n" is an integer ranging from 0 to 4.

3. The compound of formula (I) according to claim 1, wherein fused ring DE is selected from the group consisting of DE-1 to DE-15;

DE-1 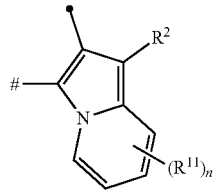

DE-2 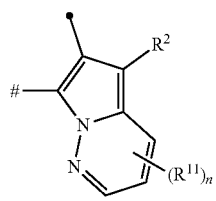

-continued
DE-3
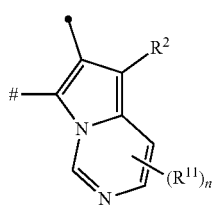
DE-4
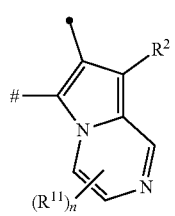
DE-5
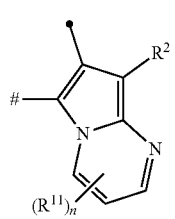
DE-6
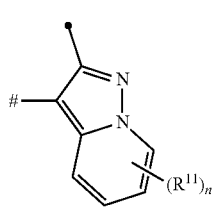
DE-7
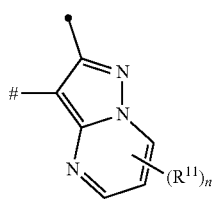
DE-8
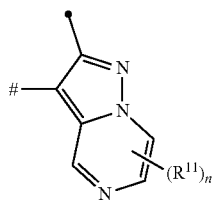
DE-9
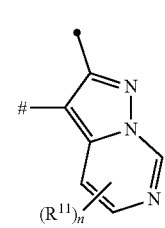
-continued
DE-10
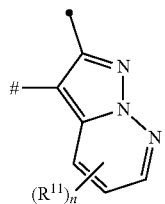
DE-11
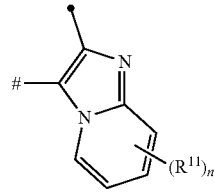
DE-12
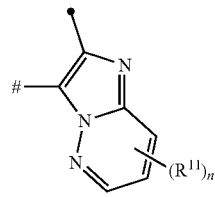
DE-13
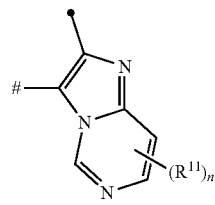
DE-14
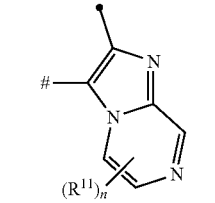
DE-15
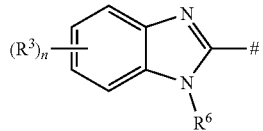
wherein, # denotes the point of attachment to the ring Q and ● denotes the point of attachment to the group —S(Y)$_m$R$^1$ and "n" is an integer ranging from 0 to 4.
4. The compound of formula (I) according to claim 1, wherein Q is selected from Q1a, Q1b, Q1c, Q1h, Q2b, Q3a, Q5b, Q5d, Q6a, Q6b, Q7a, Q8a, Q9a or Q9b;
Q1a -continued Q1b 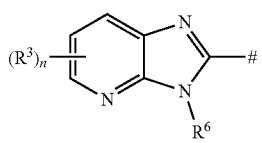

Q1c 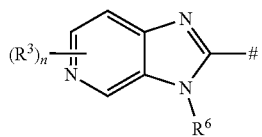

Q1h 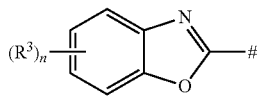

Q2b 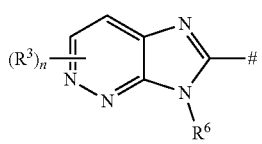

Q3a 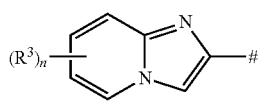

Q5b 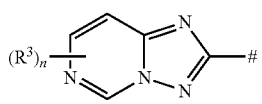

Q5d 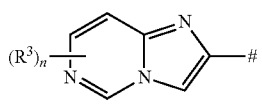

Q6a 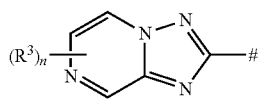

Q6b 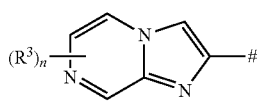

Q7a 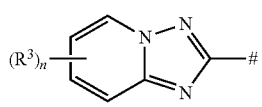

Q8a 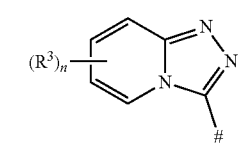

Q9a 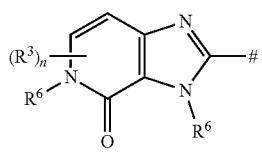

-continued

Q9b 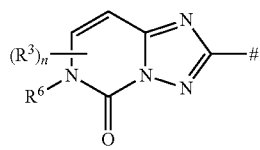

wherein, # denotes the point of attachment to the ring D;
R$^3$ is selected from the group consisting of halogen, cyano, C$_1$-C$_6$-alkyl, C$_1$-C$_6$-haloalkyl, C$_3$-C$_8$-cycloalkyl and S(Y)$_{0-2}$R$^7$;
R$^6$ is selected from the group consisting of hydrogen, C$_1$-C$_6$-alkyl and C$_3$-C$_{10}$-cycloalkyl;
fused rings D and E are selected from the group consisting of DE-1 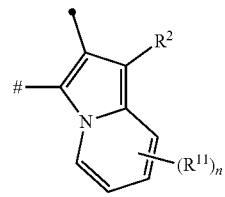

DE-7 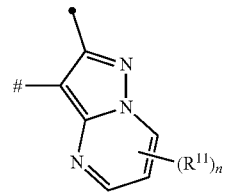

DE-11 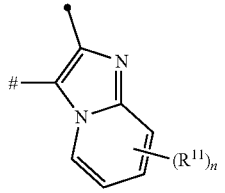

wherein, # denotes the point of attachment to the ring Q and ● denotes the point of attachment to the group —S(Y)$_m$R$^1$;
R$^2$ is selected from the group consisting of halogen, cyano, C$_1$-C$_6$-alkyl, C$_1$-C$_6$-haloalkyl, C$_3$-C$_8$-cycloalkyl, C$_6$-C$_8$-aryl, C$_7$-C$_9$-aralkyl and C$_3$-C$_6$-heterocyclyl; wherein each aliphatic group may be optionally substituted with one or more groups of R$^{2a}$ and cyclic groups of R$^2$ may be optionally substituted with one or more groups of R$^{2b}$;
"m" is an integer ranging from 0 to 2;
"n" is an integer ranging from 0 to 4;
R$^{11}$ is selected from the group consisting of halogen, cyano, C$_1$-C$_6$-alkyl, C$_1$-C$_6$-haloalkyl, C$_3$-C$_8$-cycloalkyl, OR$^4$, NR$^5$R$^6$, C$_6$-C$_{10}$-aryl, C$_7$-C$_{14}$-aralkyl and C$_3$-C$_{10}$-heterocyclyl; wherein each aliphatic group may be optionally substituted with one or more groups of R$^{11a}$ and cyclic groups of R$^{11}$ may be optionally substituted with one or more groups of R$^{11b}$.

5. The compound of formula (I) according to claim 1, wherein said compound of formula (I) is selected from 2-(1-(3,5-dichlorophenyl)-2-(ethylsulfonyl) indolizin-3-yl)-

3-methyl-6-(trifluoromethyl)-3H-imidazo[4,5-b]pyridine; 2-(2-(ethylsulfonyl) imidazo[1,2-a]pyridin-3-yl)-3-methyl-6-(trifluoromethyl)-3H-imidazo[4,5-b]pyridine; 6-(1-bromo-2-(ethylsulfonyl) indolizin-3-yl)-7-methyl-3-(trifluoromethyl)-7H-imidazo[4,5-c]pyridazine; 2-(2-(ethylsulfonyl) imidazo[1,2-a]pyridin-3-yl)-5-(trifluoromethyl)benzo[d]oxazole; 2-(2-(ethylsulfonyl)-7-(trifluoromethyl) indolizin-3-yl)-3-methyl-6-(trifluoromethyl)-3H-imidazo[4,5-b]pyridine; 2-(8-(3,5-dichlorophenyl)-2-(ethylsulfonyl) indolizin-3-yl)-3-methyl-6-(trifluoromethyl)-3H-imidazo[4,5-b]pyridine; 2-(1-(3,5-dichlorophenyl)-2-(ethylsulfonyl)-7-(trifluoromethyl) indolizin-3-yl)-3-methyl-6-(trifluoromethyl)-3H-imidazo[4,5-b]pyridine; 2-(6-(3,5-dichlorophenyl)-2-(ethylsulfonyl) indolizin-3-yl)-3-methyl-6-(trifluoromethyl)-3H-imidazo[4,5-b]pyridine; 2-(2-(ethylthio)-5,7-dimethylpyrazolo[1,5-a]pyrimidin-3-yl)-3-methyl-6-(trifluoromethyl)-3H-imidazo[4,5-b]pyridine; 2-(2-(ethylsulfonyl)-5,7-dimethylpyrazolo[1,5-a]pyrimidin-3-yl)-3-methyl-6-(trifluoromethyl)-3H-imidazo[4,5-b]pyridine; 2-(2-(ethylthio)-5,7-dimethylpyrazolo[1,5-a]pyrimidin-3-yl)-3-methyl-6-(trifluoromethyl)-3H-imidazo[4,5-c]pyridine; 2-(2-(ethylsulfonyl)-5,7-dimethylpyrazolo[1,5-a]pyrimidin-3-yl)-3-methyl-6-(trifluoromethyl)-3H-imidazo[4,5-c]pyridine; 2-(2-(ethylthio)-5,7-dimethylpyrazolo[1,5-a]pyrimidin-3-yl)-5-((trifluoromethyl)thio)benzo[d]oxazole; 2-(2-(ethylthio)pyrazolo[1,5-a]pyrimidin-3-yl)-3-methyl-6-(trifluoromethyl)-3H-imidazo[4,5-b]pyridine; 2-(2-(ethylsulfonyl)-5,7-dimethylpyrazolo[1,5-a]pyrimidin-3-yl)-5-((trifluoromethyl)sulfonyl)benzo[d]oxazole; 2-(2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)pyrazolo[1,5-a]pyrimidin-3-yl)-5-((trifluoromethyl)thio)benzo[d]oxazole; 2-(2-(ethylsulfonyl)pyrazolo[1,5-a]pyrimidin-3-yl)-5-((trifluoromethyl)sulfonyl)benzo[d]oxazole; 2-(2-(ethylthio)-7-(4-fluorophenyl)pyrazolo[1,5-a]pyrimidin-3-yl)-3-methyl-6-(trifluoromethyl)-3H-imidazo[4,5-b]pyridine; 2-(2-(ethylthio)-7-(4-fluorophenyl)pyrazolo[1,5-a]pyrimidin-3-yl)-3-methyl-6-(trifluoromethyl)-3H-imidazo[4,5-c]pyridine; 2-(2-(ethylsulfonyl)-7-(4-fluorophenyl)pyrazolo[1,5-a]pyrimidin-3-yl)-3-methyl-6-(trifluoromethyl)-3H-imidazo[4,5-c]pyridine; 2-(2-(ethylthio)pyrazolo[1,5-a]pyrimidin-3-yl)-3-methyl-6-(trifluoromethyl)-3H-imidazo[4,5-c]pyridine; 2-(2-(ethylsulfonyl)pyrazolo[1,5-a]pyrimidin-3-yl)-3-methyl-6-(trifluoromethyl)-3H-imidazo[4,5-c]pyridine; 2-(7-(3,5-dichlorophenyl)-2-(ethylthio)pyrazolo[1,5-a]pyrimidin-3-yl)-3-methyl-6-(trifluoromethyl)-3H-imidazo[4,5-c]pyridine; 2-(2-(ethylsulfonyl)-7-(4-fluorophenyl)pyrazolo[1,5-a]pyrimidin-3-yl)-3-methyl-6-(trifluoromethyl)-3H-imidazo[4,5-b]pyridine; 2-(7-(3,5-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)-7-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylthio)-7-(4-(trifluoromethoxy)phenyl)pyrazolo[1,5-a]pyrimidin-3-yl)-3-methyl-6-(trifluoromethyl)-3H-imidazo[4,5-c]pyridine; 2-(2-(ethylsulfonyl)-7-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-7-(4-(trifluoromethoxy)phenyl)pyrazolo[1,5-a]pyrimidin-3-yl)-3-methyl-6-(trifluoromethyl)-3H-imidazo[4,5-c]pyridine; 2-(2-(ethylthio)-7-(4-(trifluoromethoxy)phenyl)pyrazolo[1,5-a]pyrimidin-3-yl)-5-((trifluoromethyl)thio)benzo[d]oxazole; 2-(2-(ethylsulfonyl)-7-(4-(trifluoromethoxy)phenyl) pyrazolo[1,5-a]pyrimidin-3-yl)-5-((trifluoromethyl)sulfonyl)benzo[d]oxazole; 2-(2-(ethylthio)-7-(4-fluorophenyl)pyrazolo[1,5-a]pyrimidin-3-yl)-5-((trifluoromethyl)thio)benzo[d]oxazole; 2-(2-(ethylsulfonyl)-7-(4-fluorophenyl)pyrazolo[1,5-a]pyrimidin-3-yl)-5-((trifluoromethyl)sulfonyl)benzo[d]oxazole; 2-(7-(4-chlorophenyl)-2-(ethylthio)pyrazolo[1,5-a]pyrimidin-3-yl)-3-methyl-6-(trifluoromethyl)-3H-imidazo[4,5-c]pyridine; 2-(7-(4-chlorophenyl)-2-(ethylthio)pyrazolo[1,5-a]pyrimidin-3-yl)-3-methyl-6-(trifluoromethyl)-3H-imidazo[4,5-b]pyridine; 2-(7-(4-chlorophenyl)-2-(ethylsulfonyl)pyrazolo[1,5-a]pyrimidin-3-yl)-3-methyl-6-(trifluoromethyl)-3H-imidazo[4,5-c]pyridine; 2-(7-(4-chlorophenyl)-2-(ethylthio)pyrazolo[1,5-a]pyrimidin-3-yl)-5-((trifluoromethyl)thio)benzo[d]oxazole; 2-(7-(4-chlorophenyl)-2-(ethylsulfonyl)pyrazolo[1,5-a]pyrimidin-3-yl)-3-methyl-6-(trifluoromethyl)-3H-imidazo[4,5-b]pyridine; 2-(7-(4-chlorophenyl)-2-(ethylsulfonyl)pyrazolo[1,5-a]pyrimidin-3-yl)-5-((trifluoromethyl)sulfonyl)benzo[d]oxazole; 2-(7-(3,5-dichlorophenyl)-2-(ethylsulfonyl)pyrazolo[1,5-a]pyrimidin-3-yl)-3-methyl-6-(trifluoromethyl)-3H-imidazo[4,5-c]pyridine; 2-(7-(3,5-dichlorophenyl)-2-(ethylthio)pyrazolo[1,5-a]pyrimidin-3-yl)-5-((trifluoromethyl)thio)benzo[d]oxazole; 2-(7-(3,5-dichlorophenyl)-2-(ethylsulfonyl)pyrazolo[1,5-a]pyrimidin-3-yl)-5-((trifluoromethyl)sulfonyl)benzo[d]oxazole; 2-(2-(ethylthio)-5-phenylpyrazolo[1,5-a]pyrimidin-3-yl)-3-methyl-6-(trifluoromethyl)-3H-imidazo[4,5-c]pyridine; 2-(2-(ethylthio)-5-phenylpyrazolo[1,5-a]pyrimidin-3-yl)-3-methyl-6-(trifluoromethyl)-3H-imidazo[4,5-c]pyridine; 2-(2-(ethylsulfonyl)-5-phenylpyrazolo[1,5-a]pyrimidin-3-yl)-3-methyl-6-(trifluoromethyl)-3H-imidazo[4,5-b]pyridine; 2-(2-(ethylsulfonyl)-5-phenylpyrazolo[1,5-a]pyrimidin-3-yl)-3-methyl-6-(trifluoromethyl)-3H-imidazo[4,5-c]pyridine; 2-(6-chloro-2-(ethylthio)pyrazolo[1,5-a]pyrimidin-3-yl)-3-methyl-6-(trifluoromethyl)-3H-imidazo[4,5-b]pyridine; 2-(2-(ethylthio)-6-phenylpyrazolo[1,5-a]pyrimidin-3-yl)-3-methyl-6-(trifluoromethyl)-3H-imidazo[4,5-b]pyridine; 2-(6-chloro-2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)-5-(4-(trifluoromethoxy)phenyl)pyrazolo[1,5-a]pyrimidin-3-yl)-3-methyl-6-(trifluoromethyl)-3H-imidazo[4,5-c]pyridine; 2-(6-chloro-2-(ethylthio)pyrazolo[1,5-a]pyrimidin-3-yl)-3-methyl-6-(trifluoromethyl)-3H-imidazo[4,5-c]pyridine; 2-(6-chloro-2-(ethylsulfonyl)pyrazolo[1,5-a]pyrimidin-3-yl)-3-methyl-6-(trifluoromethyl)-3H-imidazo[4,5-c]pyridine; 2-(2-(ethylsulfonyl)-6-phenylpyrazolo[1,5-a]pyrimidin-3-yl)-3-methyl-6-(trifluoromethyl)-3H-imidazo[4,5-b]pyridine; 2-(2-(ethylthio)-5-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-5-(4-(trifluoromethoxy)phenyl)pyrazolo[1,5-a]pyrimidin-3-yl)-3-methyl-6-(trifluoromethyl)-3H-imidazo[4,5-c]pyridine; 2-(2-(ethylthio)-5-(4-fluorophenyl)pyrazolo[1,5-a]pyrimidin-3-yl)-3-methyl-6-(trifluoromethyl)-3H-imidazo[4,5-b]pyridine; 2-(6-(4-chlorophenyl)-2-(ethylthio)pyrazolo[1,5-a]pyrimidin-3-yl)-3-methyl-6-(trifluoromethyl)-3H-imidazo[4,5-b]pyridine; 2-(2-(ethylsulfonyl)-5-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylthio)-5-(4-fluorophenyl)pyrazolo[1,5-a]pyrimidin-3-yl)-3-methyl-6-(trifluoromethyl)-3H-imidazo[4,5-c]pyridine; 2-(2-(ethylsulfonyl)-5-(4-fluorophenyl)pyrazolo[1,5-a]pyrimidin-3-yl)-3-methyl-6-(trifluoromethyl)-3H-imidazo[4,5-c]pyridine; 2-(2-(ethylsulfonyl)-5-(4- fluorophenyl)pyrazolo[1,5-a]pyrimidin-3-yl)-3-methyl-6-(trifluoromethyl)-3H-imidazo[4,5-b]pyridine; 2-(6-(4-chlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)-6-phenylpyrazolo[1,5-a]pyrimidin-3-yl)-3-methyl-6-(trifluoromethyl)-3H-imidazo[4,5-c]pyridine; 2-(5-(3,5-dichlorophenyl)-2-(ethylthio)pyrazolo[1,5-a]pyrimidin-3-yl)-3-methyl-6-(trifluoromethyl)-3H-imidazo[4,5-b]pyridine; 2-(2-(ethylsulfonyl)-6-phenylpyrazolo[1,5-a]pyrimidin-3-yl)-3-methyl-6-(trifluoromethyl)-3H-imidazo[4,5-c]pyridine; 2-(5-(3,5-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(5-(3,5-dichlorophenyl)-2-(ethylthio)pyrazolo[1,5-a]pyrimidin-3-yl)-3-methyl-6-(trifluoromethyl)-3H-imidazo[4,5-c]pyridine; 2-(5-(3,5-dichlorophenyl)-2-(ethylsulfonyl)pyrazolo[1,5-a]pyrimidin-3-yl)-3-methyl-6-(trifluoromethyl)-3H-imidazo[4,5-c]pyridine; 2-(6-bromo-2-(ethylthio)pyrazolo[1,5-a]pyrimidin-3-yl)-3-methyl-6-(trifluoromethyl)-3H-imidazo[4,5-b]pyridine; 2-(6-bromo-2-(ethylsulfonyl)pyrazolo[1,5-a]pyrimidin-3-yl)-3-methyl-6-(trifluoromethyl)-3H-imidazo[4,5-b]pyridine; 2-(6-(3,5-dichlorophenyl)-2-(ethylthio)pyrazolo[1,5-a]pyrimidin-3-yl)-3-methyl-6-(trifluoromethyl)-3H-imidazo[4,5-b]pyridine; 2-(6-(4-chlorophenyl)-2-(ethylthio)pyrazolo[1,5-a]pyrimidin-3-yl)-3-methyl-6-(trifluoromethyl)-3H-imidazo[4,5-c]pyridine; 2-(6-(4-chlorophenyl)-2-(ethylsulfonyl)pyrazolo[1,5-a]pyrimidin-3-yl)-3-methyl-6-(trifluoromethyl)-3H-imidazo[4,5-c]pyridine; 2-(2-(ethylthio)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 2-(6-(3,5-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylthio)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 2-(2-(ethylsulfonyl)-5-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(6-(3,5-dichlorophenyl)-2-(ethylthio)pyrazolo[1,5-a]pyrimidin-3-yl)-3-methyl-6-(trifluoromethyl)-3H-imidazo[4,5-c]pyridine; 2-(6-(3,5-dichlorophenyl)-2-(ethylsulfonyl)pyrazolo[1,5-a]pyrimidin-3-yl)-3-methyl-6-(trifluoromethyl)-3H-imidazo[4,5-c]pyridine; 2-(2-(ethylthio)-6-(4-(trifluoromethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-6-(4-(trifluoromethoxy)phenyl)pyrazolo[1,5-a]pyrimidin-3-yl)-3-methyl-6-(trifluoromethyl)-3H-imidazo[4,5-b]pyridine; 2-(5-(4-chlorophenyl)-2-(ethylthio)pyrazolo[1,5-a]pyrimidin-3-yl)-3-methyl-6-(trifluoromethyl)-3H-imidazo[4,5-b]pyridine; 2-(5-(4-chlorophenyl)-2-(ethylthio)pyrazolo[1,5-a]pyrimidin-3-yl)-3-methyl-6-(trifluoromethyl)-3H-imidazo[4,5-c]pyridine; 2-(2-(ethylthio)-6-(4-(trifluoromethoxy)phenyl)pyrazolo[1,5-a]pyrimidin-3-yl)-3-methyl-6-(trifluoromethyl)-3H-imidazo[4,5-c]pyridine; 2-(2-(ethylthio)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(5-(4-chlorophenyl)-2-(ethylsulfonyl)pyrazolo[1,5-a]pyrimidin-3-yl)-3-methyl-6-(trifluoromethyl)-3H-imidazo[4,5-b]pyridine; 2-(5-(4-chlorophenyl)-2-(ethylsulfonyl)pyrazolo[1,5-a]pyrimidin-3-yl)-3-methyl-6-(trifluoromethyl)-3H-imidazo[4,5-c]pyridine; 2-(2-(ethylsulfonyl)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 3-(7-(3,5-dichlorophenyl)-2-(ethylthio)pyrazolo[1,5-a]pyrimidin-3-yl)-7-(trifluoromethyl)-[1,2,4]triazolo[4,3-a]pyridine; 2-(2-(ethylthio)-7-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 3-(7-(3,5-dichlorophenyl)-2-(ethylsulfonyl)pyrazolo[1,5-a]pyrimidin-3-yl)-7-(trifluoromethyl)-[1,2,4]triazolo[4,3-a]pyridine; 2-(2-(ethylthio)-6-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(2-(ethylsulfonyl)-6-(4-(1,1,2,2-tetrafluoroethoxy)phenyl)pyrazolo[1,5-a]pyrimidin-3-yl)-3-methyl-6-(trifluoromethyl)-3H-imidazo[4,5-b]pyridine; 2-(7-(3-chlorophenyl)-2-(ethylthio)pyrazolo[1,5-a]pyrimidin-3-yl)-3-methyl-6-(trifluoromethyl)-3H-imidazo[4,5-b]pyridine; 2-(7-(3,5-difluorophenyl)-2-(ethylthio)pyrazolo[1,5-a]pyrimidin-3-yl)-3-methyl-6-(trifluoromethyl)-3H-imidazo[4,5-b]pyridine; 2-(7-(3-chlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylsulfonyl)-6-(4-(trifluoromethoxy)phenyl)pyrazolo[1,5-a]pyrimidin-3-yl)-3-methyl-6-(trifluoromethyl)-3H-imidazo[4,5-c]pyridine; 2-(7-(3,5-difluorophenyl)-2-(ethylsulfonyl)pyrazolo[1,5-a]pyrimidin-3-yl)-3-methyl-6-(trifluoromethyl)-3H-imidazo[4,5-b]pyridine; 2-(7-(3-chloro-5-fluorophenyl)-2-(ethylthio)pyrazolo[1,5-a]pyrimidin-3-yl)-3-methyl-6-(trifluoromethyl)-3H-imidazo[4,5-b]pyridine; 2-(7-(3-chloro-5-fluorophenyl)-2-(ethylsulfonyl)pyrazolo[1,5-a]pyrimidin-3-yl)-3-methyl-6-(trifluoromethyl)-3H-imidazo[4,5-b]pyridine; 2-(7-(3,4-dichlorophenyl)-2-(ethylsulfonyl)pyrazolo[1,5-a]pyrimidin-3-yl)-3-methyl-6-(trifluoromethyl)-3H-imidazo[4,5-b]pyridine; 7-(3,5-dichlorophenyl)-2-(ethylthio)-3-(1-methyl-5-(trifluoromethyl)-1H-benzo[d]imidazol-2-yl)pyrazolo[1,5-a]pyrimidine; 2-(ethylthio)-3-(1-methyl-5-(trifluoromethyl)-1H-benzo[d]imidazol-2-yl)pyrazolo[1,5-a]pyrimidine; 7-(3,5-dichlorophenyl)-2-(ethylsulfonyl)-3-(1-methyl-5-(trifluoromethyl)-1H-benzo[d]imidazol-2-yl)pyrazolo[1,5-a]pyrimidine; 2-(ethylsulfonyl)-3-(1-methyl-5-(trifluoromethyl)-1H-benzo[d]imidazol-2-yl)pyrazolo[1,5-a]pyrimidine; 2-(2-(ethylsulfonyl)-6-(4-(1,1,2,2-tetrafluoroethoxy)phenyl)pyrazolo[1,5-a]pyrimidin-3-yl)-3-methyl-6-(trifluoromethyl)-3H-imidazo[4,5-c]pyridine; 3-(7-(3,5-dichlorophenyl)-2-(ethylthio)pyrazolo[1,5-a]pyrimidin-3-yl)-6-(trifluoromethyl)-[1,2,4]triazolo[4,3-a]pyridine; 3-(7-(3,5-dichlorophenyl)-2-(ethylsulfonyl)pyrazolo[1,5-a]pyrimidin-3-yl)-6-(trifluoromethyl)-[1,2,4]triazolo[4,3-a]pyridine; 2-(7-(2,3-dichlorophenyl)-2-(ethylthio)pyrazolo[1,5-a]pyrimidin-3-yl)-3-methyl-6-(trifluoromethyl)-3H-imidazo[4,5-b]pyridine; 2-(2-(ethylthio)-7-phenylpyrazolo[1,5-a]pyrimidin-3-yl)-3-methyl-6-(trifluoromethyl)-3H-imidazo[4,5-b]pyridine; 2-(7-(2,3-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylsulfonyl)-7-phenylpyrazolo[1,5-a]pyrimidin-3-yl)-3-methyl-6-(trifluoromethyl)-3H-imidazo[4,5-b]pyridine; 2-(7-(4-chloro-3-fluorophenyl)-2-(ethylthio)pyrazolo[1,5-a]pyrimidin-3-yl)-3-methyl-6-(trifluoromethyl)-3H-imidazo[4,5-b]pyridine; 2-(7-(3,5-dichlorophenyl)-2-(ethylthio)pyrazolo[1,5-a]pyrimidin-3-yl)-3-methyl-6-(trifluoromethyl)-3H-imidazo[4,5-b]pyridine; 2-(7-(4-chloro-3-fluorophenyl)-2-(ethylsulfonyl)pyrazolo[1,5-a]

pyrimidin-3-yl)-3-methyl-6-(trifluoromethyl)-3H-imidazo[4,5-b]pyridine; 2-(7-(4-chloro-3-fluorophenyl)-2-(ethylthio)pyrazolo[1,5-a]pyrimidin-3-yl)-3-methyl-6-(trifluoromethyl)-3H-imidazo[4,5-c]pyridine; 2-(7-(2,4-dichlorophenyl)-2-(ethylthio)pyrazolo[1,5-a]pyrimidin-3-yl)-3-methyl-6-(trifluoromethyl)-3H-imidazo[4,5-b]pyridine; 2-(7-(2,4-dichlorophenyl)-2-(ethylsulfonyl)pyrazolo[1,5-a]pyrimidin-3-yl)-3-methyl-6-(trifluoromethyl)-3H-imidazo[4,5-b]pyridine; 2-(7-(2,4-dichlorophenyl)-2-(ethylthio)pyrazolo[1,5-a]pyrimidin-3-yl)-3-methyl-6-(trifluoromethyl)-3H-imidazo[4,5-c]pyridine; 2-(7-(3-chloro-5-fluorophenyl)-2-(ethylthio)pyrazolo[1,5-a]pyrimidin-3-yl)-3-methyl-6-(trifluoromethyl)-3H-imidazo[4,5-c]pyridine; 2-(7-(3-chloro-5-fluorophenyl)-2-(ethylsulfonyl)pyrazolo[1,5-a]pyrimidin-3-yl)-3-methyl-6-(trifluoromethyl)-3H-imidazo[4,5-c]pyridine; 2-(7-(3,5-bis(trifluoromethyl)phenyl)-2-(ethylthio)pyrazolo[1,5-a]pyrimidin-3-yl)-3-methyl-6-(trifluoromethyl)-3H-imidazo[4,5-b]pyridine; 2-(2-(ethylthio)-7-(3-(trifluoromethyl)phenyl)pyrazolo[1,5-a]pyrimidin-3-yl)-3-methyl-6-(trifluoromethyl)-3H-imidazo[4,5-b]pyridine; 2-(2-(ethylthio)-7-(3-fluorophenyl)pyrazolo[1,5-a]pyrimidin-3-yl)-3-methyl-6-(trifluoromethyl)-3H-imidazo[4,5-b]pyridine; 2-(7-(3,5-bis(trifluoromethyl)phenyl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylsulfonyl)-7-(3-(trifluoromethyl)phenyl)pyrazolo[1,5-a]pyrimidin-3-yl)-3-methyl-6-(trifluoromethyl)-3H-imidazo[4,5-b]pyridine; 2-(2-(ethylsulfonyl)-7-(3-fluorophenyl)pyrazolo[1,5-a]pyrimidin-3-yl)-3-methyl-6-(trifluoromethyl)-3H-imidazo[4,5-b]pyridine; 2-(2-(ethylthio)-7-methylpyrazolo[1,5-a]pyrimidin-3-yl)-3-methyl-6-(trifluoromethyl)-3H-imidazo[4,5-b]pyridine; 2-(2-(ethylthio)-7-(3-fluorophenyl)pyrazolo[1,5-a]pyrimidin-3-yl)-3-methyl-6-(trifluoromethyl)-3H-imidazo[4,5-c]pyridine; 2-(2-(ethylsulfonyl)-7-methylpyrazolo[1,5-a]pyrimidin-3-yl)-3-methyl-6-(trifluoromethyl)-3H-imidazo[4,5-b]pyridine; 2-(2-(ethylthio)-7-(3-(trifluoromethyl)phenyl)pyrazolo[1,5-a]pyrimidin-3-yl)-3-methyl-6-(trifluoromethyl)-3H-imidazo[4,5-c]pyridine; (7-(3,5-dichlorophenyl)-3-(3-methyl-6-(trifluoromethyl)-3H-imidazo[4,5-b]pyridin-2-yl) pyrazolo[1,5-a]pyrimidin-2-yl)(ethyl)(imino)-□6-sulfanone; 2-(2-(ethylsulfonyl)-7-(3-(trifluoromethyl)phenyl)pyrazolo[1,5-a]pyrimidin-3-yl)-3-methyl-6-(trifluoromethyl)-3H-imidazo[4,5-c]pyridine; 2-(2-(ethylsulfonyl)-7-(3-fluorophenyl)pyrazolo[1,5-a]pyrimidin-3-yl)-3-methyl-6-(trifluoromethyl)-3H-imidazo[4,5-c]pyridine; 2-(2-(ethylthio)-7-methylpyrazolo[1,5-a]pyrimidin-3-yl)-3-methyl-6-(trifluoromethyl)-3H-imidazo[4,5-c]pyridine; 2-(7-(3-chloro-4-fluorophenyl)-2-(ethylthio)pyrazolo[1,5-a]pyrimidin-3-yl)-3-methyl-6-(trifluoromethyl)-3H-imidazo[4,5-b]pyridine; 2-(2-(ethylthio)-5,7-bis(trifluoromethyl)pyrazolo[1,5-a]pyrimidin-3-yl)-3-methyl-6-(trifluoromethyl)-3H-imidazo[4,5-b]pyridine; 2-(2-(ethylsulfonyl)-5,7-bis(trifluoromethyl) pyrazolo[1,5-a]pyrimidin-3-yl)-3-methyl-6-(trifluoromethyl)-3H-imidazo[4,5-b]pyridine; 2-(ethylthio)-3-(3-methyl-6-(trifluoromethyl)-3H-imidazo[4,5-b]pyridin-2-yl) pyrazolo[1,5-a]pyrimidin-7 (4H)-one; 2-(7-bromo-2-(ethylthio)pyrazolo[1,5-a]pyrimidin-3-yl)-3-methyl-6-(trifluoromethyl)-3H-imidazo[4,5-b]pyridine; 2-(ethylsulfonyl)-N-methyl-3-(7-(trifluoromethyl)-[1,2,4]triazolo[1,5-c]pyrimidin-2-yl) pyrazolo[1,5-a]pyrimidin-7-amine; 6-(8-(4-chloro-3-fluorophenyl)-2-(ethylsulfonyl)indolizin-3-yl)-7-methyl-3-(trifluoromethyl)-7H-imidazo[4,5-c]pyridazine; 2-(2-(ethylsulfonyl)-7-(5-methyl-3-(trifluoromethyl)-1H-pyrazol-1-yl) pyrazolo[1,5-a]pyrimidin-3-yl)-3-methyl-6-(trifluoromethyl)-3H-imidazo[4,5-b]pyridine; 2-(ethylthio)-N-methyl-3-(3-methyl-6-(trifluoromethyl)-3H-imidazo[4,5-b]pyridin-2-yl) pyrazolo[1,5-a]pyrimidin-7-amine; 2-(2-(ethylsulfonyl)-7-(3-fluorophenoxy) pyrazolo[1,5-a]pyrimidin-3-yl)-3-methyl-6-(trifluoromethyl)-3H-imidazo[4,5-b]pyridine; 6-(8-(4-chloro-3-fluorophenyl)-2-(ethylsulfonyl) imidazo[1,2-a]pyridin-3-yl)-7-methyl-3-(trifluoromethyl)-7H-imidazo[4,5-c]pyridazine; 2-(6-(3,5-dichlorophenyl)-2-(ethylsulfonyl)pyrazolo[1,5-a]pyrimidin-3-yl)-6-(trifluoromethyl) imidazo[1,2-a]pyrazine; 4-(2-(ethylsulfonyl)-3-(7-methyl-3-(trifluoromethyl)-7H-imidazo[4,5-c]pyridazin-6-yl)indolizin-8-yl)-2-fluorobenzonitrile; 2-(8-(cyclopropylmethyl)-2-(ethylsulfonyl) imidazo[1,2-a]pyridin-3-yl)-3-methyl-6-(trifluoromethyl)-3H-imidazo[4,5-b]pyridine; 2-(7-(4-chloro-1H-pyrazol-1-yl)-2-(ethylsulfonyl)pyrazolo[1,5-a]pyrimidin-3-yl)-3-methyl-6-(trifluoromethyl)-3H-imidazo[4,5-b]pyridine; 2-(2-(ethylsulfonyl)-7-(5-methyl-1H-1,2,4-triazol-1-yl) pyrazolo[1,5-a]pyrimidin-3-yl)-3-methyl-6-(trifluoromethyl)-3H-imidazo[4,5-b]pyridine; 2-(2-(ethylsulfonyl)-7-(1-methyl-1H-pyrazol-5-yl) pyrazolo[1,5-a]pyrimidin-3-yl)-3-methyl-6-(trifluoromethyl)-3H-imidazo[4,5-b]pyridine; 2-(2-(ethylsulfonyl)-7-(1-methyl-3-(trifluoromethyl)-1H-pyrazol-5-yl) pyrazolo[1,5-a]pyrimidin-3-yl)-3-methyl-6-(trifluoromethyl)-3H-imidazo[4,5-b]pyridine; 2-(7-cyclopropyl-2-(ethylsulfonyl)pyrazolo[1,5-a]pyrimidin-3-yl)-6-(trifluoromethyl)-[1,2,4]triazolo[1,5-a]pyrazine; 2-(2-(ethylsulfonyl)-7-(1-methyl-3-(trifluoromethyl)-1H-pyrazol-5-yl) pyrazolo[1,5-a]pyrimidin-3-yl)-7-(trifluoromethyl) imidazo[1,2-c]pyrimidine; 4-(2-(ethylsulfonyl)-3-(7-(trifluoromethyl)imidazo[1,2-a]pyridin-2-yl) pyrazolo[1,5-a]pyrimidin-7-yl)morpholine; 2-(7-(4-chloro-3-fluorophenyl)-2-(ethylsulfonyl)pyrazolo[1,5-a]pyrimidin-3-yl)-7-(trifluoromethyl)-[1,2,4]triazolo[1,5-c]pyrimidine; 2-(2-(ethylsulfonyl)-7-(1H-1,2,4-triazol-1-yl) pyrazolo[1,5-a]pyrimidin-3-yl)-7-(trifluoromethyl)-[1,2,4]triazolo[1,5-c]pyrimidine; 2-(2-(ethylsulfonyl)-5,7-bis(trifluoromethyl) pyrazolo[1,5-a]pyrimidin-3-yl)-3-methyl-6-(trifluoromethyl)-3H-imidazo[4,5-b]pyridine; 6-(1-bromo-2-(ethylsulfonyl)-8-methylindolizin-3-yl)-7-methyl-3-(trifluoromethyl)-7H-imidazo[4,5-c]pyridazine; 6-(8-bromo-2-(ethylsulfonyl)indolizin-3-yl)-3-(difluoromethyl)-7-methyl-7H-imidazo[4,5-c]pyridazine; 2-(2-(ethylsulfonyl)-7-methoxypyrazolo[1,5-a]pyrimidin-3-yl)-3-methyl-6-(trifluoromethyl)-3H-imidazo[4,5-b]pyridine; 2-(2-(ethylsulfonyl)-7-(methylthio)pyrazolo[1,5-a]pyrimidin-3-yl)-3-methyl-6-(trifluoromethyl)-3H-imidazo[4,5-b]pyridine; 2-(ethylsulfonyl)-3-(3-methyl-6-(trifluoromethyl)-3H-imidazo[4,5-b]pyridin-2-yl)pyrazolo[1,5-a]pyrimidine-7 (4H)-thione; 2-(2-(ethylsulfonyl)-7-(1,1,2,2-tetrafluoroethoxy) pyrazolo[1,5-a]pyrimidin-3-yl)-3-methyl-6-(trifluoromethyl)-3H-imidazo[4,5-b]pyridine; 2-(7-ethoxy-2-(ethylsulfonyl)pyrazolo[1,5-a]pyrimidin-3-yl)-6-(trifluoromethyl) imidazo[1,2-a]pyrazine; diethyl((2-(ethylsulfonyl)-3-(6-(trifluoromethyl) imidazo[1,2-a]pyrazin-2-yl) pyrazolo[1,5-a]pyrimidin-7-yl)imino)-16-sulfanone; 2-(ethylsulfonyl)-N, N-dimethyl-3-(3-methyl-6-(trifluoromethyl)-3H-imidazo[4,5-b]pyridin-2-yl) imidazo[1,2-a]pyridin-8-amine; 6-(2-(ethylsulfonyl)-7-(5-(trifluoromethyl) pyridin-2-yl) pyrazolo[1,5-a]pyrimidin-3-yl)-7-methyl-3-(trifluoromethyl)-7H-imidazo[4,5-c]pyridazine; 2-(7-(4-chloro-3-fluorophenyl)-2-(ethylsulfonyl)pyrazolo[1,5-a]pyrimidin-3-yl)-3,5-dimethyl-6-(trifluoromethyl)-3,5-dihydro-4H-imidazo[4,5-c]pyridin-4-one; 2-(2-(ethylsulfonyl)-7-(3-(trifluoromethyl)-1H-1,2,4-triazol-1-yl) pyrazolo[1,5-a]pyrimidin-3-yl)-3,5-dimethyl-6-(trifluoromethyl)-3,5- dihydro-4H-imidazo[4,5-c]pyridin-4-one; 2-(7-(3-chloro-5-fluorophenyl)-2-(ethylsulfonyl)pyrazolo[1,5-a]pyrimidin-3-yl)-6-(trifluoromethyl)-[1,2,4]triazolo[1,5-a]pyrazine; 2-(7-(3,5-dichlorophenyl)-2-(ethylsulfonyl)pyrazolo[1,5-a]pyrimidin-3-yl)-7-(trifluoromethyl) imidazo[1,2-c]pyrimidine; 2-(7-(4-chloro-3-fluorophenyl)-2-(ethylsulfonyl)pyrazolo[1,5-a]pyrimidin-3-yl)-6-methyl-7-(trifluoromethyl)-[1,2,4]triazolo[1,5-c]pyrimidin-5 (6H)-one; 2-(7-(5-chloropyridin-2-yl)-2-(ethylsulfonyl)pyrazolo[1,5-a]pyrimidin-3-yl)-6-(trifluoromethyl)-[1,2,4]triazolo[1,5-a]pyridine; 2-(2-(ethylsulfonyl)-7-(5-methyl-3-(trifluoromethyl)-1H-pyrazol-1-yl) pyrazolo[1,5-a]pyrimidin-3-yl)-6-methyl-7-(trifluoromethyl)-[1,2,4]triazolo[1,5-c]pyrimidin-5 (6H)-one; 2-(2-(ethylsulfonyl)-7-(3-(trifluoromethyl)-1H-1,2,4-triazol-1-yl) pyrazolo[1,5-a]pyrimidin-3-yl)-7-(trifluoromethyl)-[1,2,4]triazolo[1,5-c]pyrimidine; ethyl(3-(3-methyl-6-(trifluoromethyl)-3H-imidazo[4,5-c]pyridin-2-yl) pyrazolo[1,5-a]pyrimidin-2-yl)(methylimino)-16-sulfanone.

6. A composition for controlling or preventing insects and/or mite pests comprising a biologically effective amount of compound of formula (I) or agronomically acceptable salts, isomers/structural isomers, stereo-isomers, diastereoisomers, enantiomers, tautomers, polymorphs, metal complexes or N-oxides thereof according to claim 1 and at least one additional component selected from the group consisting of surfactants and auxiliaries.

7. The composition according to claim 6, wherein said composition additionally comprises at least one additional biological active compatible compound selected from fungicides, insecticides, nematicides, acaricides, biopesticides, herbicides, plant growth regulators, antibiotics, fertilizers or nutrients.

8. The composition according to claim 6, wherein said biologically effective amount of compound of formula (I) ranges from 0.1% to 99% by weight with respect to the total weight of the composition.

9. A combination comprising a biologically effective amount of the compound according to claim 1 and at least one additional biological active compatible compound selected from fungicides, insecticides, nematicides, acaricides, biopesticides, herbicides, plant growth regulators, antibiotics, fertilizers and nutrients.

10. A method of combating insects and mite pests comprising contacting the insects and mite pests, their habitat, breeding ground, food supply, plant, seed, soil, area, material or environment in which the insect and mite pests are growing or may grow, or the materials, plants, seeds, soils, surfaces or spaces to be protected from pest attack or infestation with a biologically effective amount of compound of formula (I) or salts, metal complexes, N-oxides, isomers, polymorphs, composition or combination thereof according to claim 1.

11. A method for protecting crops from attack or infestation by insects and mite pests comprises contacting the crop with a biologically effective amount of the compound or salts, metal complexes, N-oxides, isomers, polymorphs, composition or combination thereof according to claim 1.

12. The method according to claim 10, wherein said method comprises applying effective dosages of compound of formula (I) in amounts ranging from 1 gai to 5000 gai per hectare in agricultural or horticultural crops.

13. A method for the protection of seeds, plants and plant parts from soil insects and of the seedlings roots and shoots from soil and foliar insects comprising contacting the seeds before sowing and/or after pre-germination with the compound of formula (I) or salts, metal complexes, N-oxides, isomers, polymorphs, composition or combination thereof according to claim 1.

14. A method for combating insects and mite pests in agricultural crops, horticultural crops, household and vector control and parasites on animals, comprising:
applying the compound of formula (I) or salts, metal complexes, N-oxides, isomers, polymorphs, composition or combination thereof according to claim 1.

15. The method according 14, wherein said agricultural crops are cereals, corn, sorghum, bajra, rice, soybean, oil seeds and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers, other vegetables and ornamentals.

16. A combination comprising a seed and a compound of formula (I) or salts, metal complexes, N-oxides, isomers, polymorphs, composition or combination thereof according to claim 1, wherein the amount of compound of formula (I) in said seed ranging from about 0.0001% to about 1% by weight.

17. The composition of claim 8, wherein the biologically effective amount of the compound of formula (I) ranges from 5% to 50% by weight with respect to the total weight of the composition.

* * * * *